(12) United States Patent
Gallo et al.

(10) Patent No.: US 7,994,278 B1
(45) Date of Patent: Aug. 9, 2011

(54) BIOLOGICALLY ACTIVE POLYPEPTIDES DERIVED FROM A NOVEL EARLY STAGE PREGNANCY FACTOR DESIGNATED MATERNIN (MA)

(75) Inventors: Robert C. Gallo, Bethesda, MD (US); Joseph Bryant, Baltimore, MD (US); Yanto Lundardi-Iskandar, Gaithersburg, MD (US)

(73) Assignee: Nobel Biosciences LLC, Gaithersburg, MD (US)

( * ) Notice: Subject to any disclaimer, the term of this patent is extended or adjusted under 35 U.S.C. 154(b) by 1276 days.

(21) Appl. No.: 09/632,831

(22) Filed: Aug. 4, 2000

Related U.S. Application Data

(60) Provisional application No. 60/147,825, filed on Aug. 6, 1999, provisional application No. 60/188,777, filed on Mar. 13, 2000.

(51) Int. Cl.
*A61K 38/00* (2006.01)
*A61K 38/04* (2006.01)

(52) U.S. Cl. .................. 530/324; 530/326; 530/329

(58) Field of Classification Search .................. None
See application file for complete search history.

(56) References Cited

U.S. PATENT DOCUMENTS

| | | | |
|---|---|---|---|
| 4,161,519 A | 7/1979 | Talwar | |
| 4,201,770 A | 5/1980 | Stevens | 424/177 |
| 4,400,316 A | 8/1983 | Katsuragi et al. | |
| 4,689,222 A | 8/1987 | McMichael | |
| 4,691,006 A | 9/1987 | Stevens | |
| 4,692,332 A | 9/1987 | McMichael | |
| 4,713,366 A | 12/1987 | Stevens | |
| 4,714,680 A | 12/1987 | Civin et al. | |
| 4,762,913 A | 8/1988 | Stevens | |
| 4,767,842 A | 8/1988 | Stevens | |
| 4,780,312 A | 10/1988 | Talwar | |
| 4,855,285 A | 8/1989 | Stevens | |
| 4,880,626 A | 11/1989 | McMichael | |
| 4,966,753 A | 10/1990 | McMichael | |
| 5,004,681 A | 4/1991 | Boyse et al. | |
| 5,061,620 A | 10/1991 | Tsukamoto et al. | |
| 5,141,867 A | 8/1992 | Ivanoff et al. | |
| 5,192,553 A | 3/1993 | Boyse et al. | |
| 5,380,668 A | 1/1995 | Herron | |
| 5,445,968 A | 8/1995 | Blithe et al. | |
| 5,451,527 A | 9/1995 | Sarin et al. | |
| 5,494,899 A | 2/1996 | Kincade et al. | |
| 5,508,261 A | 4/1996 | Moyle et al. | |
| 5,610,136 A | 3/1997 | McMichael | |
| 5,614,612 A | 3/1997 | Haigwood et al. | |
| 5,635,599 A | 6/1997 | Pastan et al. | |
| 5,677,275 A | 10/1997 | Lunardi-Iskandar et al. | |
| 5,700,781 A | 12/1997 | Harris | |
| 5,811,390 A | 9/1998 | Bourinbaiar | 514/8 |
| 5,877,148 A | 3/1999 | Lunardi-Iskandar et al. | |
| 5,877,159 A | 3/1999 | Powell et al. | |
| 5,968,513 A | 10/1999 | Gallo et al. | |
| 5,997,871 A | 12/1999 | Gallo et al. | |
| 6,013,857 A | 1/2000 | Deboer et al. | |
| 6,156,952 A | 12/2000 | Bryant et al. | |
| 6,319,504 B1 * | 11/2001 | Gallo et al. | 424/198.1 |
| 6,331,610 B1 * | 12/2001 | Bourinbaiar | 530/324 |
| 6,583,109 B1 * | 6/2003 | Gallo et al. | 514/3.8 |
| 6,620,416 B1 * | 9/2003 | Gallo et al. | 424/278.1 |
| 6,699,656 B2 * | 3/2004 | Gallo et al. | 435/5 |

FOREIGN PATENT DOCUMENTS

| | | |
|---|---|---|
| EP | 0 049 898 B2 | 4/1982 |
| EP | 0 142 387 A1 | 5/1985 |
| EP | 0 211 411 A2 | 2/1987 |
| EP | 0323769 | 11/1988 |
| JP | 04300896 | 10/1992 |
| WO | WO 86/04241 | 7/1986 |
| WO | WO 87/03487 | 6/1987 |
| WO | WO 90/02759 | 3/1990 |
| WO | WO9108228 | 6/1991 |
| WO | WO 91/09872 | 7/1991 |
| WO | WO 91/16921 | 11/1991 |
| WO | WO 92/22654 | 12/1992 |
| WO | WO9222568 | 12/1992 |
| WO | WO 94/20859 | 9/1994 |
| WO | WO 94/24148 | 10/1994 |
| WO | WO 96/04008 | 2/1996 |
| WO | WO97/49373 | 12/1997 |
| WO | WO 97/49418 | 12/1997 |
| WO | WO9749373 | 12/1997 |
| WO | WO99/06438 | 2/1999 |
| WO | WO9906438 | 2/1999 |
| WO | WO9925849 | 5/1999 |

OTHER PUBLICATIONS

Morgan, F. J., et al., 1975, The amino acid sequence of human chorionic gonadotropin: The alpha subunit and beta subunit, J. Biol. Chem. 250(13):5247-5258.*
Gait, M. J., and J. Karn, 1995, Progress in anti-HIV structure-based drug design, TIBTECH 13:430-438.*
Hirsch, M. S., et al., 1998, Antiretroviral drug resistance testing in adults with HIV infection: Implications for clinical management, JAMA 279(24):1984-1991.*
Bodey, B., et al., 2000, Genetically engineered monoclonal antibodies for direct anti-neoplastic treatment and cancer cell specific delivery of chemotherapeutic agents, Curr. Pharm. Desgin 6:261-276.*

(Continued)

*Primary Examiner* — Jeffrey Parkin
(74) *Attorney, Agent, or Firm* — Foley & Lardner LLP

(57) ABSTRACT

The invention relates to therapeutic polypeptides isolated from beta-human chorionic gonadotropin (β-hCG) found in human early pregnancy urine, now synthetically produced and designated Maternin. The therapeutic polypeptides and their functional equivalents are useful in treating and/or preventing various medical conditions. Examples of therapeutic effects of the therapeutic polypeptides include anti-HIV, anti-cancer, anti-wasting, prohematopoietic (e.g., anemias, radiation-mediated bone marrow damage, and trauma-mediated blood loss), and anti-angiogenic effects. The invention also provides pharmaceutical compositions comprising the therapeutic polypeptides, as well as methods for using the therapeutic polypeptides, functional equivalents and/or pharmaceutical compositions in the treatment and/or prevention of such medical conditions.

20 Claims, 57 Drawing Sheets

OTHER PUBLICATIONS

Lesniak, M. S., et al., 2001, Drug delivery to tumors of the central nervous system, Curr. Neurol. Neurosci. Reports 1:210-216.*
Alfthan et al. (1992) Cancer Res. 52: 4628-4633.
Bagshawe (1992) Acta Oncol. 31: 99-106.
Bidart, J-M et al., "Human Chorionic Gonadotropin Molecular Forms, Detection, and Clinical Implications." TEM 4:285 (1993).
Birken, S. et al., "Structure of the Human Chorionic Gonadotropin .beta.-Subunit Fragment from Pregnancy Urine." Endocrinology 123:572 (1988).
Bourinbaiar, A.S. et al., "Pregnancy hormones, estrogen and progesterone, prevent HIV-1 synthesis in monocytes but not in lymphocytes." FEBS Letters 302:206 (1992).
Chen, W. et al., "Recombinant Carbohydrate Variant of Human Choriogonadotropin .beta.-Subunit (hCG.beta.) Descarboxyl Terminus (115-145)." Journal of Biological Chemistry 266:6246 (1991).
Cole, L.A., et al., "The Deactivation of hCG by Nicking and Dissociation" Journal of Clinical Endocrinology and Metabolism 76:704 (1993).
Cole Laurence A. et al., "The Heterogeneity of Human Chorionic Gonadotropin (hCG). III. The Occurrence and Biological and Immunological Activities of Nicked hCG." Endocrinology 129:1559 (1991).
Curti, Critical Reviews in Oncology/Hematology, vol. 14, pp. 29-39, 1993.
Danforth, D.N., Jr., M.D., "How Subsequent Pregnancy Affects Outcome in Women with a Prior Breast Cancer." Oncology 5:23 (1991).
Elford et al. (1993) AIDS 7: 1667-1671.
Freireich, E.J. et al., "Quantitative Comparison of Toxicity of Anticancer Agents in Mouse, Rat, Hamster, Dog, Monkey, and Man." Cancer Chemotherapy Reports 50:219 (1966).
Hirabayashi, M., M.D., "Early Gastric Cancer and a Concomitant Pregnancy", The American Surgeon 53:730 (1987).
Huang, J. et al., "Amino/Carboxyl-terminal Deletion Mutants of Human Choriogonadotropin .beta.." The Journal of Biological Chemistry 268:9311 (1993).
Huang, J. et al., "Mutagenesis of the 'determinant loop' region of human choriogonadotropin .beta.." Molecular and Cellular Endocrinology 90:211 (1993).
Jain, Scientific American, pp. 58-65, Jul. 1994.
Kumar, S. et al., "Necrosis and Inhibition of Growth of Human Lung Tumor by Anti-.alpha.-Human Chorionic Gonadotropin Antibody." J. Natl Cancer Inst. 84:42 (1992).
Loosfelt, H. et al., "Cloning and Sequencing of Porcine LH-hCG Receptor cDNA: Variants Lacking Transmembrane Domain." Science 245:525 (1989).
Mann et al, Scand. J. Clin. Lab. Invest. , Suppl. vol. 216, pp. 97-104, 1993.
Marcillac et al. (1992) Cancer Res. 52: 3901-3907.
McFarland, K.C. et al., "Lutropin-Choriogonadotropin Receptor: An Unusual Member of the G Protein-Coupled Receptor Family." Science 245:494 (1989).
Nakhai, B. et al., "Over-expression and characterization of recombinant beta subunit of the human chorionic gonadotropin hormone synthesized in insect cells infected with a genetically engineered baculovirus." Indian Journal of Biochemistry & Biophysics 29:315 (1992).
Northfeldt et al. (1991) Hematology/Oncology Clinics of North America 5: 297-310.
Ozturk, M. et al., "Ectopic .beta.-Human Chorionic Gonadotropin Production by a Human Hepatoma Cell Line (FOCUS): Isolation and Immunochemical Characterization." Endocrinology 120:559 (1987).
Ozturk, M. et al., "Physiological Studies of Human Chorionic Gonadotropin (hCG), .alpha.hCG, and .beta.hCG as Measured by Specific Monoclonal Immunoradiometric Assays." Endocrinology 120:549 (1987).
Ross et al., Immunology Today, vol. 11, No. 6, 1990.
Siemen, Rodent Tumor Models in Experimental Cancer Therapy, Edited by Kallman, Pergamon Press, pp. 12-15, 1987.
Sridhar, P. et al., "Differential secretion and glycosylation of recombinant human chorionic gonadotropin (.beta.hCG) synthesized using different promoters in the baculovirus expression vector system." Gene (Netherlands) 131:261 (1993).

Stenman et al. (1993) Scand. J. Clin. Lab. Invest. Suppl. 216: 42-78.
Strickland et al. in Luteinizing hormone action and receptors, M. Ascoli, Ed., CRC Press, Boca Raton FL, 1985, p. 1.
Trott, Rodent Tumor Models in Experimental Cancer Therapy, Edited by Kallman, Pergramon Press, pp. 6-11, 1987.
Ward et al. in Reproduction in Domestic Animals, 4th ed., Cuppos, PT, ed., pp. 25-80, Academic Press, NY (1991).
Wass, M. et al., "Response of lymphocytes from cancer patients to human ★chorionic★ gonadotrophin", Lancet (England) 1:8004:171 (1977).
Yano, T. et al., "Inhibition of human epithelial ovarian cancer cell growth in vitro by agonistic and antagonistic analogues of luteinizing hormone-releasing hormone." Proc. Natl. Acad. Sci. USA 91:1701 (1994).
Fink, et al., Amino Acid Sequence Elucidation of Human Acrosin-Trypsin Inhibitor (HUSI-II) Reveals that Kazal-type Proteinase Inhibitors are Structurally Related to β-subunits of Glycoprotein Hormones, FEBs Letters, vol. 270, No. 1, 2, p. 222-224.
Birken, Steven, et al. "Structure of the Human Chorionic Gonadotropin β-Subunit Fragment from Pregnancy Urine." Endocrinology, vol. 123, 1988, pp. 572-583.
Abrams et al., 1983, J. Cell. Biochem. Supply A:53.
Aizawa and Tavassoli, 1986, Int. J. Cell Cloning 4:464-471.
Andrews et al., 1986, Blood 67;842-845.
Andrews et al., 1986, Blood 68;1030-1035.
Ballem et al., 1987, J. Clin. Invest. 80:33-40.
Ballem et al., 1992, New Eng. J. Med 327:1779-1784.
Barre-Sinoussi et al., 1983 Science 220:868-870.
Bauman et al., 1986, J. Cell Physiol. 128:133-142.
Bellet et al., 1984, Endocrinology 115:330-336.
Berchtold and Wenger, 1993, Blood 81:1246-1250.
Bidart et al., 1987, Mol. Immunology 24:339-345.
Bidart et al., 1987, J. Biol. Chem. 262:15483-15489.
Bidart et al., 1990, Science 248:736-739.
Blazevic et al., 1995, AIDS Res. Hum. Retroviruses 11:1335-1342.
Bodger, et al., 1983, Blood 61:1006-1010.
Bolognesi, 1993, Semin. Immunol. 5:203-214.
Bourinbaiar and Nagorny, 1992, FEMS Microbiol. Lett. 96:27-30.
Bourinbaiar and Nagorny, 1992, FEBS Microbiol. Lett. 309:82-84.
Bourinbaiar and Lee-Huang, 1995, Immunol. Lett. 44:13-17.
Braunstein et al., 1978, J. Clin. Endocrinology and Metabolism 47:326-332.
Broxmeyer et al., 1984, J. Clin Invest. 73:939-953.
Broxmeyer, 1983, CRC Critical Reviews in Oncology/Hemoatology 1:227-257.
Broxmeyer, 1982, J. Clin Invest. 69:632-642.
Busch et al., 1987, Blut 54:179-188.
Cain et al., 1986, Transplantation 41:22-25.
Cao et al., 1982, J. Med. Genet. 19:81-87.
Caraux et al., 1985, J. Immun. 134:835-840.
Chak et al., 1988, J. Clin. Oncol. 6:863-867.
Chen et al., 1992, AIDS 6;533-539.
"Chorionic Gonadotropin," U.S. Pharmacopia (USP23).
Clavel et al., 1986, Science, 233-343-346.
Cocchi et al., 1995, Science, 270-1811-1815.
Cole, L.A. "The heterogeneity of human gonadotropin (hCG). III. The occurrence and biological and immunological activities of nicked hCG," Endocrinology, Sep. 1991, 129 (3):1559-1567.
Cole, L.A. et al., "The biological and clinical significance of nicks in human chorionic gonadotropin and its free beta-subunit," Yale J Biol Med Nov.-Dec. 1991; 64 (6):627-37.
Cole, Laurence A. "hCG, Its Free Subunits and Its Metabolites—Roles in Pregnancy and Trophoblastic Disease," Journal of Reproductive Medicine, Jan. 1998, 43 (1): 3-10.
Creighton, 1993, Proteins, Structures and Molecular Principles (W.H. Freeman & Co., New York) pp. 34-49.
Daar et al., Nat'l Acad Sci USA 87:6574-6579.
Daffos, et al., 1983, am. J. Obstst. Gynecol. 146:985-987.
Daffos, et al., 1985, am. J. Obstst. Gynecol. 153:655-660.
Dalgleish et al., 1984, Nature 312: 763-767.
De et al., 1997, J. Clin. Invest. 99:1484-1491.
Delli-Bovi et al., 1986, Cancer Res. 46:6333-6338.
Deshmukh et al., 1994, J. Clin. Immunol. 14:162-168.

Dexter et al., 1977, J. Cell. Physiol. 91:335-344.
Dickie et al, 1991, Virology, 185:109-119.
Dirnhofer, S. et al., "Functional and immunological relevance of the COOH-terminal extension of human chorionic gonadotropin beta: implications for the WHO birth control vaccine," FASEB J Nov. 1993; 7(14):1381-1385.
Dirnhofer et al. 1994, J. Endocrinology 141:153-162.
Emerson et al., 1985, J. Clin. Invest. 76:1286-1290.
Ensoli et al., 1989, Science 243:223-226.
Erickson, 1990, Science 249:527-533.
Evans et al., 1991, J. Immunotherapy 10:39-50.
Ferrero et al., 1983, Proc Natl. Acad. Sci. USA 80:4114-4118.
Ferrero et al., 1986, Cancer Res. 46:975-980.
Franks et al., 1995, Pediatric Res. 37:56-63.
Friedman-Kien et al., 1981, J. Am. Acad. Dermatol. 5:468-473.
Gallo et al., 1984, Science 224:500-503.
Gelmann et al., 1987, Am. J. Med. 82:456-462.
Geller et al., 1985, Archs. Path. Lab. Met. 109:138-145.
Gill et al., 1990, Am. J. Clin. Oncol. 13:315-319.
Gill et al., 1991, Am. J. Med. 90:427-433.
Gill et al., 1994, AIDS, 8: 1695-1699.
Gill et al., 1996, New Eng. J. Med. 335 :1261-1269.
Goldman et al., 1980, Br. J. Haematol. 45:223-231.
Guyader et al., 1987, Nature 326:662-669.
Hammerskjold & Rekosh. 1989. Biochem E Biophysica Acta. 989:269-280.
Harris, 1995, Lancet 346:118-119.
Hermans, 1995, AIDS Res. Hum. Retroviruses S:96.
Hermans et al., 1995, Cell. Mol. Biol. 3:357-364.
Hershko et al., 1979, Lancet 1:945-947.
Heymsfield et al., Am. J. Clin. Nutr. 36:Oct. 1982, p. 680-690.
Hirokawa et al., 1982, Clin. Immunol. Immunopathol. 22:297-304.
Ho, H.H. et al., "Characterization of human chorionic gonadotropin peptide variants with a radio-receptor assay using recombinant human luteinizing hormone/chorionic gonadotropin receptors," Early Pregnancy Sep. 1997, 3 (3):204-12.
Huang and Terstappen, 1992, Nature 360:745-749.
Juttner et al., 1985, Br. J. Haematol. 61:739-745.
Kahn et al., 1990, am. Ann. Med. 112:254-261.
Kardana et al.: B. J. Cancer 1993 67:686-692.
Kardana, A. et al., "Human chorionic gonadotropin beta-subunit nicking enzymes in pregnancy and cancer patient serum," J Clin Endocrinol Metab, Sep. 1994, 79 (3):761-7.
Katz et al., 1985, Leukemia Res. 9:191-198.
Katz et al., 1986, Leukemia Res. 10:961-971.
Keating et al., 1984, Blood 64:1159-1162.
Kestler et al, 990, Science 248:1109-1112.
Keutmann et al., 1987, Proc. Natl. Acad. Sci. USA 84:2038-2042.
Keutmann et al., 1988, Biochemistry 27:8939-8944.
Klatzmann et al., 1984, Nature 312:767-768.
Kobata, Akira et al., "Structure, pathology and function of the N-linked sugar chains of human chorionic gonadotropin," Biochemica et Biophysica Acta 1455 (1999) 315-326.
Kodo et al., 1984, J. Clin. Invest. 73:1377-1384.
Kopp et al., 1993, AIDS Res. Hum. Retroviruses 9:267-275.
Korbling et al., 1986, Blood 67:529-532.
Kornyei et al., 1993, Biol. Reprod. 49:1149-1157.
Kotler et al., Am. J. Clin. Nutr. 1985 42: 1255-65.
Kotler and Grunfeld, *AIDS Wasting Syndrome*, 229-275.
Kotler et al., Am. J. Clin. Nutr. 1989; 50: 444-447.
Krown et al., 1990, Ann. Intern. Med. 112:812-821.
Lajtha, 1979, Differentiation 14:23-34.
Lajtha, 1979, Blood Cells 5:447-455.
Lapthorn et al., 1994, Nature 369:455-461.
Leary et al., 1987, Blood 69:953-956.
Letvin et al., 1990, J. AIDS 3;1023-1040.
Longhi et al., 1986, J. Immunol. Meth. 92:89-95.
Lord and Spooncer, 1986, Lymphokine Res. 5:59-72.
Louache et al., 1992, Blood 180:2991-2999.
Lu et al., 1983, Blood 61:250-256.
Lunardi-Iskandar et al., J. Natl. Cancer Inst 87(13) 974-981.
Lunardi-Iskandar et al., 1989, J. Clin. Invest. 83:610-615.
Lunardi-Iskandar et al., 1989, Leukemia Res. 13:573-581.
Lunardi-Iskandar et al., 1995, Nature 375:64-68.
Maddon et al., 1986, Cell 47:333-348.
Martin, 1991, *Basic and Chemical Endocrinology* (Appleton & Lange, East Norwalk) pp. 543-567.
Masood et al., 1984, AIDS Res. Hum. Retroviruses 10:969-976.
Mastrangelo et al., 1996, "Gene therapy for human cancer; an essay for clinicians", Sem. Oncology 23:4-21.
McDougal et al., 1986, Science, 231:382-385.
Merrifield, 1963, J. Amer. Chem. Soc. 85:2149-2156.
Mitsuya et al., 1991, Science 249:1533-1544.
Mitsuya et al., FASEB 1991, 2369-2381.
Moore et al., 1980, Blood 55:682-690.
Nakamura et al., 1988, Science 242:426-430.
Nicola et al., 1980, J. Cell. Physiol. 103:217-237.
Nijhof et al., 1983, J. Cell. Biol. 96:386-392.
Nicola et al., 1981, Blood 58:376-386.
Nijhof et al., 1984, Exp. Cell. Res. 155:583-587.
Nothdurft et al., 1977, Scand. J. Haematol. 19:470-481.
Ochs et al., 1981, Pediatr. Res. 15:601.
Ott et al., Am J Clin Nutr 1993; 57:15-19.
Paige et al., 1981, J. Exp. Med. 153:154-165.
Paul, 1994, Cell 82:177-182.
Perelson et al., 1966, Science 15:1582-1586.
Pierce et al, 1991, Rev. Biochem., 50:465-495.
Pillow et at., 1966, New Eng. J. Med. 275:94-97.
Policastro et al., 1983, "The β subunit of human chorionic gonadotropin is encoded by multiple genes", J. Biol. Chem. 258:11492-11499.
Popescu et al., 1995, JNCI 88:450-454.
Popovic et al., 1984, Science 224:497-500.
Prummer et al., 1985, Exp. Hematol. 13:891-898.
Puisieux et al., 1990, Endocrinology 126:687-694.
Raghavacher et al., 1983, J. Cell. Biochem. Suppl. 7A:78.
Reiffers et al., 1986, Exp. Hematol. 14:312-315.
Reisner et al., 1978, Proc. Natl. Acad. Sci. USA 75:2933-2936.
Reisner et al., 1982, Blood 59:360-363.
Riddell et al., 1996, "T-cell mediated rejection of gene-modified HIV-specific cytotoxic T lymphocytes in HIV-infected patients", Nat. Med. 2:216-222.
Robak et al., 1985, Leukemia Res. 9:1023-1029.
Rodeck, 1984, *Prenatal Diagnosis* (Royal College of Obstetricians and Gynaecologists, London).
Russo and Russo, Cancer Letters 1995 90: 81-89.
Ryan et al., 1988, FASEB J. 2:2661-2669.
Salahuddin et al., 1988, Science 242:430-433.
Sarpel et al., 1979, Exp. Hematol. 7:113-120.
Schall, 1991, Cytokine 3:165-183.
Schooley et al., 1990, ann. Int. Med. 112:247-253.
Sherman, 1992, J. Mol. Endocrinol. 6:951-959.
1996 Sigma Product Catalogue, p. 1134.
Siegal et al., 1990, Cancer 65:492-498.
Smith et al., 1987, Science 238:1704-1707.
Smith and Broxmeyer, 1986, Br. J. Haematol. 63:29-34.
Stevens et al., 1986, Immunol. Lett. 12:11-18.
Strauss et al., 1986, Exp Hematol. 14:935-945.
Strauss et al., 1986, Exp. Hematol. 14:878-886.
Strauss et al., 1986, Exp. Hematol. 14:935-945.
Terstappen et al., 1992, Leukemia 6:993-1000.
Thomas et al., 1972, Lancet 1(745):284-289.
Tilly et al., 1986, Lancet, Jul. 19 pp. 154-155.
To and Juttner, 1987, Br. J. Haematol. 66:285-288.
Torres et al., 1987, Immunol. Inv. 16:607-618.
Touraine, 1983, Birth Defects 19:139-142.
Triozzi et al., 1994, Int. J. Oncol. 5:1447-1453.
Tulunay et al., 1975, Proc. Natl. Acad. Sci USA 72:4100-4104.
Valenti, 1973, Am. J. Obstet. Gynecol. 115:851-853.
Van Gemen et al., 1994, J. Virol. Methods 49:157-168.
Varmus et al., 1988, Science 240:1427-1439.
Vaslin et al., 1994, AIDS Res. Hum. Retroviruses 10:1241-1250.
Vickery et al., 1983, J. Parasitol. 69:478-485.
Visser et al., 1984, J. Exp. Med. 59:1576-1590.
Ward et al, 1991, *Reproduction in Domestic Animals* (Academic Press, New York) pp. 25-80.

Weinroth et al., 1995, Infectious Agents and disease 4:76-94.
Whitlock and Witte, 1982, Proc. Natl. Acad. Sci. USA 79:3608-3612.
Williams et al., 1987, Exp. Hematol. 15:243-250.
Winchester et al., 1977, Proc. Natl. Acad. Sci. USA 7414012-4016.
Xia, 1993, J. Mol. Endocrinol., June 10:337-343.
Yarchoan et al., 1989, Proc. Vth Int. Conf. on AIDS, p. 564.
Yunis, 1983, Science 221:227-236.
James, John S. "New Approaches to HIV Treatment: Interview with Robert Gallo, M.D.," Aids Treatment News, Dec. 19, 1997, Issue 285, pp. 1-7 (www.immunet.org).
Iyer, K.S. et al., "Search for peptide immunogens of the beta-subunit of human chorionic gonadotropin (hCG) capable of eliciting hormone specific and neutralizing antisera. Identification of an undecapeptide eliciting hCG-specific antisera," Int J Pept Protein Res Feb. 1992: 39(2):137-44.
Hutchison, Clyde A., et al., "Mutagenesis at a Specific Position in a DNA Sequence," The Journal of Biological Chemistry Sep. 25, 1978, 253(18), pp. 6551-6560.
Van der Zee et al., "Synthetic Human Chorionic Gonadotripin-Related Oligopeptides Impair Early Innate Immune Responses to *Listeria monocytogenes* in Mice," *JID*, vol. 21, pp. 1072-1080 (2010).

Khan et al., "Amelioration of Renal Ischaemia-Reperfusion Injury by Synthetic Oligopeptides Related to Human Chorionic Gonadotropin," *Nephrol Dial Transplant*, vol. 24, pp. 2701-2708 (2009).
Kachra et al., "Low Molecular Weight Components But Not Dimeric HCG Inhibit Growth and Down-Regulate AP-1 Transcription Factor in Kaposi's Sarcoma Cells," *Endocrinology*, vol. 138, No. 9, pp. 4038-4041 (1997).
Gill et al., "Phase I Study of Human Chorionic Gonadotropin Given Subcutaneously to Patients with Acquired Immunodeficiency Syndrome-Related Mucocutaneous Kaposi's Sarcoma," *Journ. of the National Cancer Institute*, vol. 89, No. 23, pp. 1797-1802 (1997).
Lundardi-Iskandar et al., "Effects of a Urinary Factor from Women in Early Pregnancy of HIV-1, SIV and Associated Disease," *Nature Medicine*, vol. 4, pp. 428-434 (1998). [Abstract Only].
Hermans et al., "AIDS-related Kaposi's Sarcoma Patients with Visceral Manifestations, Response to Human Chorionic Gonadotropin Preparations," *J. Hum. Virol.*, vol. 1, No. 2, pp. 82-89 (1998). [Abstract Only].

\* cited by examiner

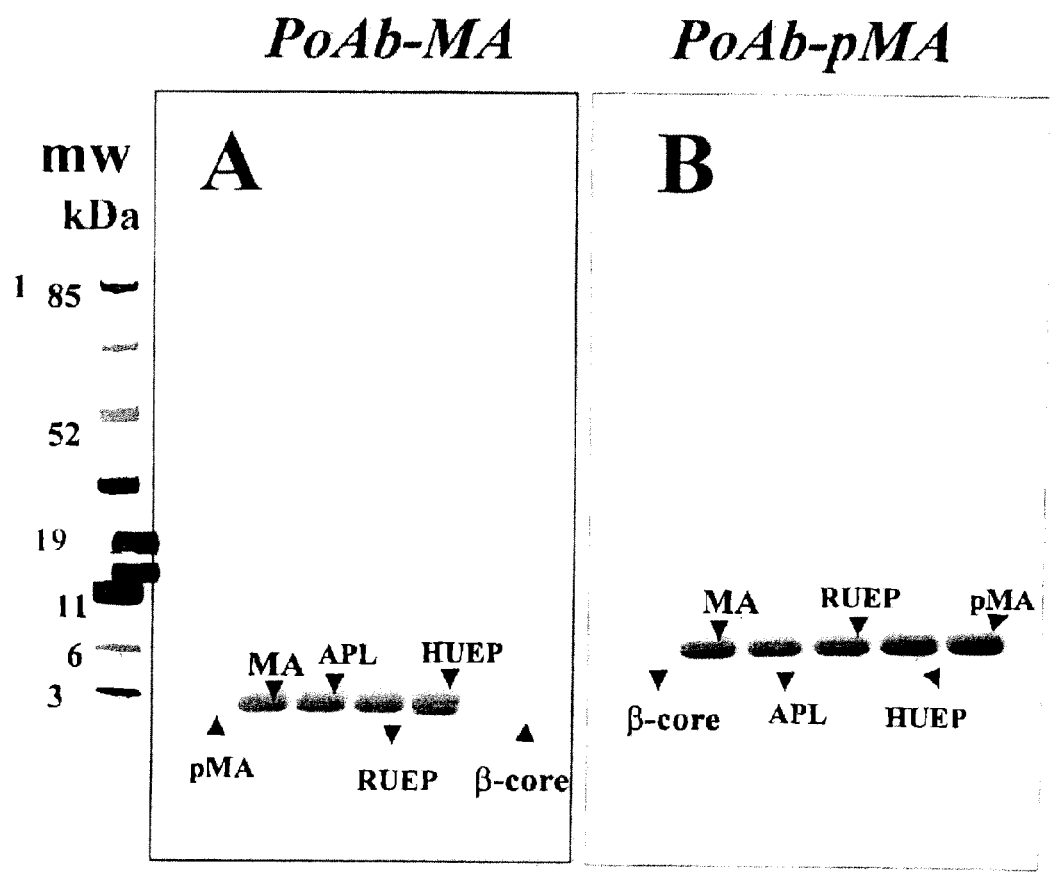
FIG. 2 A and B

*3D confocal microscopy showing normal nuclear morphology in human normal cells after hugh does of Maternin therapy*

*Human normal cells were treated with 2ug/ml of Maternin*

DOSES: rβhCG, αhCG, CR127: 2ug/DAILY/7 DAYS. CRUDE hCG: 300IU
CRUDE βhCG: 1ug/DAILY/7 DAYS, β-CORE: 2ug/DAILY/7 DAYS.
PBS, MA pMA & MAs 1, 2, OR 3 [SYNTHETIC PEPTIDES]:
200ng/DAILY/7 DAYS.

*Maternin Induces Apoptosis in Lewis Lung Carcinoma*

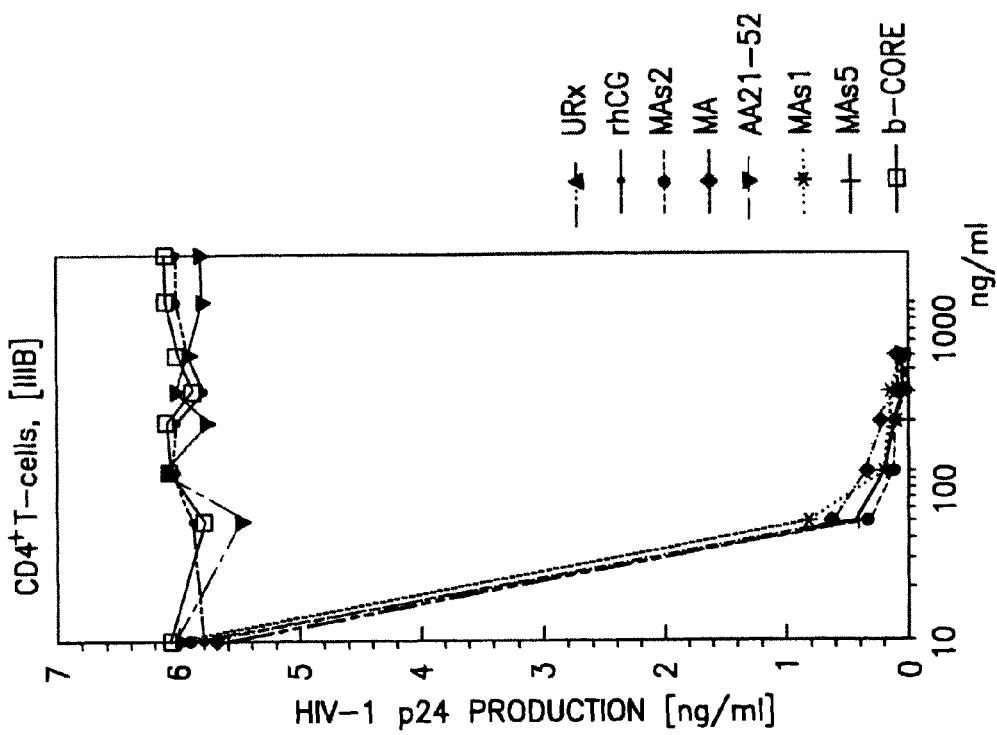
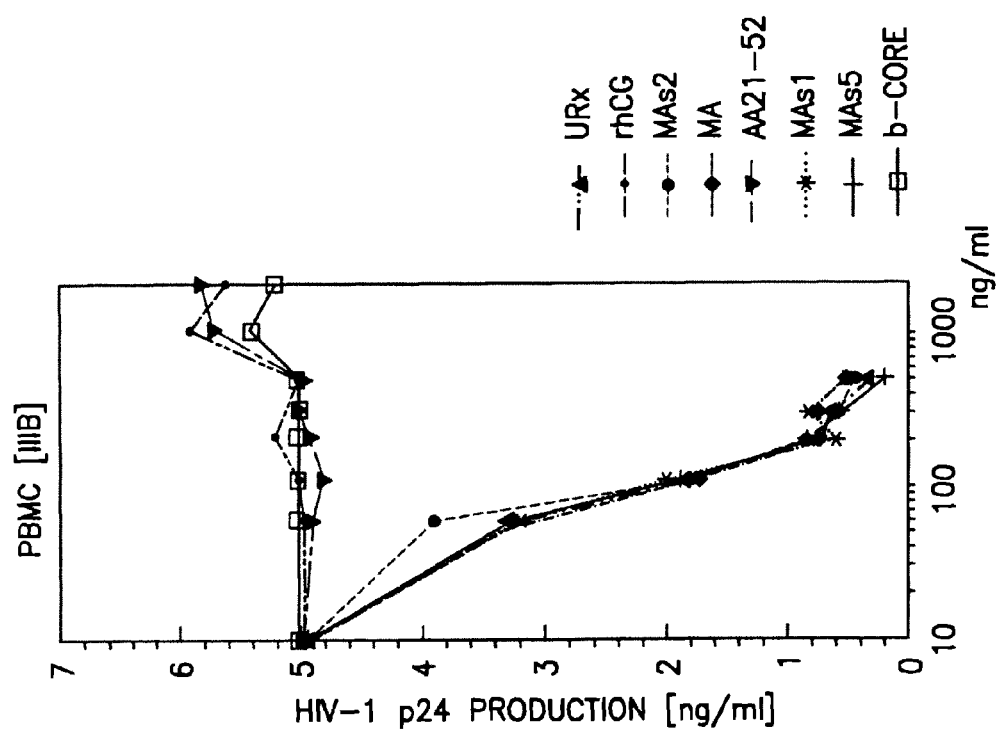
FIG. 7B
FIG. 7A

HIV-1 transgenic mice

Doses: CR127, rβhCG, AA 21-52
β-LH & β-core: 2 ug/daily/7 days
crude CG-10/APL: 300IU/daily/7 days
MA/MAs 1, 2 or pMA: 200 ng/daily/7 days

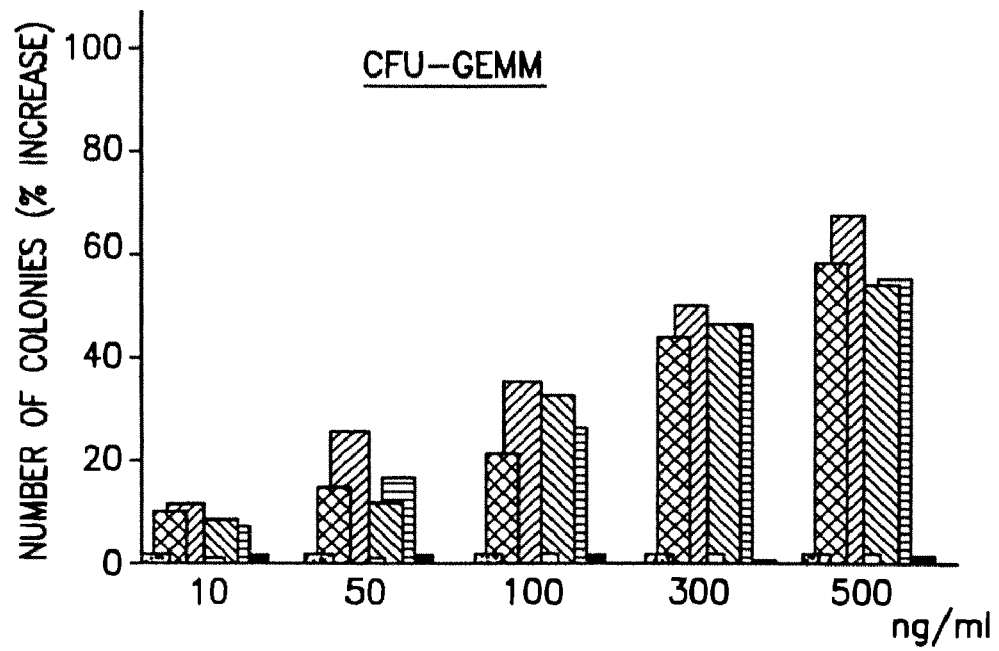
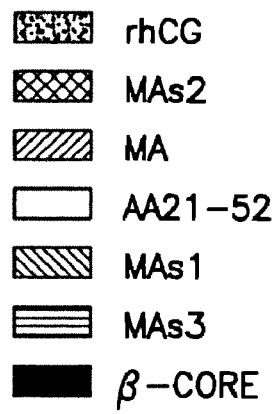
FIG.9A

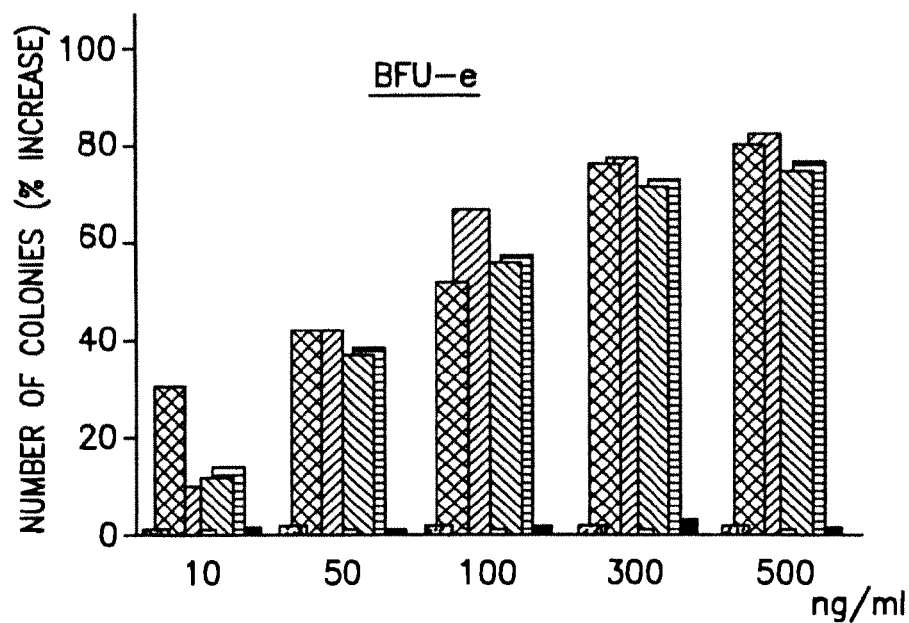
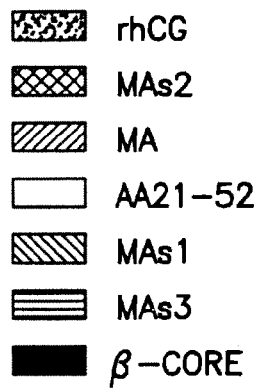
FIG.9B

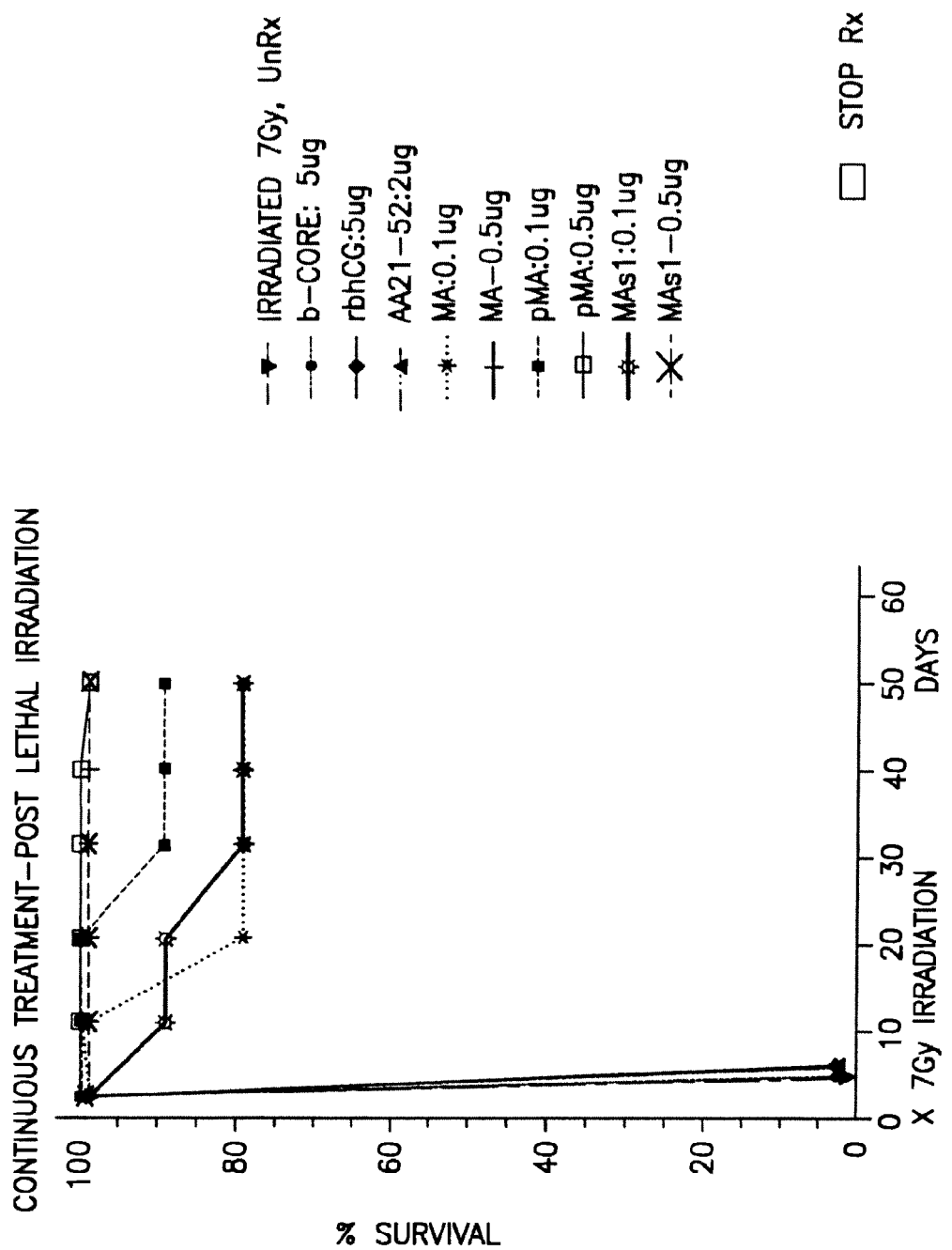

SEQUENCE LISTING

<160> NUMBER OF SEQ ID NOS: 51

<210> SEQ ID NO 1
<211> LENGTH: 145
<212> TYPE: PRT
<213> ORGANISM: Homo sapiens

<400> SEQUENCE: 1

```
Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145
```

<210> SEQ ID NO 2
<211> LENGTH: 35
<212> TYPE: PRT
<213> ORGANISM: Homo sapiens

<400> SEQUENCE: 2

Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
            20                  25                  30

Ser Cys Gln
        35

<210> SEQ ID NO 3
<211> LENGTH: 38
<212> TYPE: PRT
<213> ORGANISM: Homo sapiens

<400> SEQUENCE: 3

Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
            20                  25                  30

Ser Cys Gln Cys Ala Leu
        35

<210> SEQ ID NO 4
<211> LENGTH: 15
<212> TYPE: PRT
<213> ORGANISM: Homo sapiens

<400> SEQUENCE: 4

Val Arg Phe Glu Ser Ile Arg Leu Pro Gly Cys Pro Arg Gly Val
1               5                   10                  15

<210> SEQ ID NO 5
<211> LENGTH: 30
<212> TYPE: PRT
<213> ORGANISM: Homo sapiens

<400> SEQUENCE: 5

Asn Tyr Arg Asp Val Arg Phe Glu Ser Ile Arg Leu Pro Gly Cys Pro
1               5                   10                  15

Arg Gly Val Asn Pro Val Val Ser Tyr Ala Val Ala Leu Ser
            20                  25                  30

<210> SEQ ID NO 6
<211> LENGTH: 35
<212> TYPE: PRT
<213> ORGANISM: Homo sapiens

<400> SEQUENCE: 6

Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
            20                  25                  30

Ser Cys Gln
        35

<210> SEQ ID NO 7
<211> LENGTH: 7
<212> TYPE: PRT

```
<213> ORGANISM: Homo sapiens

<400> SEQUENCE: 7

Arg Leu Pro Gly Cys Pro Arg
1               5

<210> SEQ ID NO 8
<211> LENGTH: 6
<212> TYPE: PRT
<213> ORGANISM: Homo sapiens

<400> SEQUENCE: 8

Ala Pro Gly Cys Pro Gly
1               5

<210> SEQ ID NO 9
<211> LENGTH: 6
<212> TYPE: PRT
<213> ORGANISM: Homo sapiens

<400> SEQUENCE: 9

Leu Pro Gly Cys Pro Arg
1               5

<210> SEQ ID NO 10
<211> LENGTH: 6
<212> TYPE: PRT
<213> ORGANISM: Homo sapiens

<400> SEQUENCE: 10

Leu Pro Gly Cys Pro Gln
1               5

<210> SEQ ID NO 11
<211> LENGTH: 34
<212> TYPE: PRT
<213> ORGANISM: Homo sapiens

<400> SEQUENCE: 11

Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
            20                  25                  30

Ser Cys

<210> SEQ ID NO 12
<211> LENGTH: 36
<212> TYPE: PRT
<213> ORGANISM: Homo sapiens

<400> SEQUENCE: 12

Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
            20                  25                  30

Ser Cys Gln Cys
        35

<210> SEQ ID NO 13
<211> LENGTH: 37
<212> TYPE: PRT
<213> ORGANISM: Homo sapiens

<400> SEQUENCE: 13
```

```
Val Val Cys Asn Tyr Arg Asp Val Arg Phe Glu Ser Ile Arg Leu Pro
1               5                   10                  15

Gly Cys Pro Arg Gly Val Asn Pro Val Val Ser Tyr Ala Val Ala Leu
            20                  25                  30

Ser Cys Gln Cys Ala
            35

<210> SEQ ID NO 14
<211> LENGTH: 20
<212> TYPE: PRT
<213> ORGANISM: Homo sapiens

<400> SEQUENCE: 14

Val Val Cys Asn Tyr Arg Asp Val Arg Phe Glu Ser Ile Arg Leu Pro
1               5                   10                  15

Gly Cys Pro Arg
            20

<210> SEQ ID NO 15
<211> LENGTH: 32
<212> TYPE: PRT
<213> ORGANISM: Homo sapiens

<400> SEQUENCE: 15

Arg Pro Arg Cys Arg Pro Ile Asn Ala Thr Leu Ala Val Glu Lys Glu
1               5                   10                  15

Gly Cys Pro Val Cys Ile Thr Val Asn Thr Thr Ile Cys Ala Gly Tyr
            20                  25                  30

<210> SEQ ID NO 16
<211> LENGTH: 33
<212> TYPE: PRT
<213> ORGANISM: Homo sapiens

<400> SEQUENCE: 16

Arg Pro Arg Cys Arg Pro Ile Asn Ala Thr Leu Ala Val Glu Lys Glu
1               5                   10                  15

Gly Cys Pro Val Cys Ile Thr Val Asn Thr Thr Ile Cys Ala Gly Tyr
            20                  25                  30

Cys

<210> SEQ ID NO 17
<211> LENGTH: 34
<212> TYPE: PRT
<213> ORGANISM: Homo sapiens

<400> SEQUENCE: 17

Arg Pro Arg Cys Arg Pro Ile Asn Ala Thr Leu Ala Val Glu Lys Glu
1               5                   10                  15

Gly Cys Pro Val Cys Ile Thr Val Asn Thr Thr Ile Cys Ala Gly Tyr
            20                  25                  30

Cys Pro

<210> SEQ ID NO 18
<211> LENGTH: 35
<212> TYPE: PRT
<213> ORGANISM: Homo sapiens

<400> SEQUENCE: 18

Arg Pro Arg Cys Arg Pro Ile Asn Ala Thr Leu Ala Val Glu Lys Glu
1               5                   10                  15
```

```
Gly Cys Pro Val Cys Ile Thr Val Asn Thr Thr Ile Cys Ala Gly Tyr
            20                  25                  30

Cys Pro Thr
        35

<210> SEQ ID NO 19
<211> LENGTH: 13
<212> TYPE: PRT
<213> ORGANISM: Homo sapiens

<400> SEQUENCE: 19

Leu Gln Gly Val Leu Pro Ala Leu Pro Gln Val Val Cys
1               5                   10

<210> SEQ ID NO 20
<211> LENGTH: 14
<212> TYPE: PRT
<213> ORGANISM: Homo sapiens

<400> SEQUENCE: 20

Cys Leu Gln Gly Val Leu Pro Ala Leu Pro Gln Val Val Cys
1               5                   10

<210> SEQ ID NO 21
<211> LENGTH: 14
<212> TYPE: PRT
<213> ORGANISM: Homo sapiens

<400> SEQUENCE: 21

Cys Leu Gln Gly Arg Leu Pro Ala Leu Pro Arg Val Val Cys
1               5                   10

<210> SEQ ID NO 22
<211> LENGTH: 9
<212> TYPE: PRT
<213> ORGANISM: Homo sapiens

<400> SEQUENCE: 22

Cys Arg Leu Pro Gly Leu Pro Arg Cys
1               5

<210> SEQ ID NO 23
<211> LENGTH: 11
<212> TYPE: PRT
<213> ORGANISM: Homo sapiens

<400> SEQUENCE: 23

Thr Cys Asp Asp Pro Arg Phe Gln Asp Ser Ser
1               5                   10

<210> SEQ ID NO 24
<211> LENGTH: 169
<212> TYPE: PRT
<213> ORGANISM: Equine spp.

<400> SEQUENCE: 24

Met Glu Thr Leu Gln Gly Leu Leu Leu Trp Met Leu Leu Ser Val Gly
1               5                   10                  15

Gly Val Trp Ala Ser Arg Gly Pro Leu Arg Pro Leu Cys Arg Pro Ile
            20                  25                  30

Asn Ala Thr Leu Ala Ala Glu Lys Glu Ala Cys Pro Ile Cys Ile Thr
        35                  40                  45

Phe Thr Thr Ser Ile Cys Ala Gly Tyr Cys Pro Ser Met Val Arg Val
```

-continued

```
                 50                  55                  60
Met Pro Ala Ala Leu Pro Ala Ile Pro Gln Pro Val Cys Thr Tyr Arg
 65                  70                  75                  80

Glu Leu Arg Phe Ala Ser Ile Arg Leu Pro Gly Cys Pro Pro Gly Val
                 85                  90                  95

Asp Pro Met Val Ser Phe Pro Val Ala Leu Ser Cys His Cys Gly Pro
                100                 105                 110

Cys Gln Ile Lys Thr Thr Asp Cys Gly Val Phe Arg Asp Gln Pro Leu
                115                 120                 125

Ala Cys Ala Pro Gln Ala Ser Ser Ser Lys Asp Pro Pro Ser Gln
130                 135                 140

Pro Leu Thr Ser Thr Ser Thr Pro Thr Pro Gly Ala Ser Arg Arg Ser
145                 150                 155                 160

Ser His Pro Leu Pro Ile Lys Thr Ser
                165

<210> SEQ ID NO 25
<211> LENGTH: 141
<212> TYPE: PRT
<213> ORGANISM: Ovis spp.

<400> SEQUENCE: 25

Met Glu Met Leu Gln Gly Leu Leu Trp Leu Leu Leu Gly Val Ala
 1               5                  10                  15

Gly Val Trp Ala Ser Arg Gly Pro Leu Arg Pro Leu Cys Gln Pro Ile
                 20                  25                  30

Asn Ala Thr Leu Ala Ala Glu Lys Glu Ala Cys Pro Val Cys Ile Thr
                 35                  40                  45

Phe Thr Thr Ser Ile Cys Ala Gly Tyr Cys Leu Ser Met Lys Gln Val
 50                  55                  60

Leu Pro Val Ile Leu Pro Pro Met Pro Gln Arg Val Cys Thr Tyr His
 65                  70                  75                  80

Glu Leu Arg Phe Ala Ser Val Arg Leu Pro Gly Cys Pro Pro Gly Val
                 85                  90                  95

Asp Pro Met Val Ser Phe Pro Val Ala Leu Ser Cys His Cys Gly Pro
                100                 105                 110

Cys Arg Leu Ser Ser Thr Asp Cys Gly Gly Pro Arg Thr Gln Pro Leu
                115                 120                 125

Ala Cys Asp His Pro Pro Leu Pro Asp Ile Leu Phe Leu
130                 135                 140

<210> SEQ ID NO 26
<211> LENGTH: 141
<212> TYPE: PRT
<213> ORGANISM: Suidae

<400> SEQUENCE: 26

Met Glu Met Leu Gln Gly Leu Leu Trp Leu Leu Leu Ser Val Ala
 1               5                  10                  15

Gly Val Trp Ala Ser Arg Gly Pro Leu Arg Pro Leu Cys Arg Pro Ile
                 20                  25                  30

Asn Ala Thr Leu Ala Ala Glu Asn Glu Ala Cys Pro Val Cys Ile Thr
                 35                  40                  45

Phe Thr Thr Ser Ile Cys Ala Gly Tyr Cys Pro Ser Met Val Arg Val
 50                  55                  60

Leu Pro Ala Ala Leu Pro Pro Val Pro Gln Pro Val Cys Thr Tyr Arg
 65                  70                  75                  80
```

-continued

Glu Leu Ser Phe Ala Ser Ile Arg Leu Pro Gly Cys Pro Pro Gly Val
                85                  90                  95

Asp Pro Thr Val Ser Phe Pro Val Ala Leu Ser Cys His Cys Gly Pro
            100                 105                 110

Cys Arg Leu Ser Ser Asp Cys Gly Gly Pro Arg Ala Gln Pro Leu
        115                 120                 125

Ala Cys Asp Arg Pro Leu Leu Pro Gly Leu Leu Phe Leu
130                 135                 140

<210> SEQ ID NO 27
<211> LENGTH: 138
<212> TYPE: PRT
<213> ORGANISM: Canis familiaris

<400> SEQUENCE: 27

Leu Gln Gly Leu Leu Leu Trp Leu Leu Leu Ser Val Gly Gly Val Trp
1               5                   10                  15

Ala Ser Arg Gly Pro Leu Arg Pro Leu Cys Arg Pro Ile Asn Ala Thr
                20                  25                  30

Leu Ala Ala Glu Asn Glu Ala Cys Pro Val Cys Ile Thr Phe Thr Thr
            35                  40                  45

Thr Ile Cys Ala Gly Tyr Cys Pro Ser Met Val Arg Val Leu Pro Ala
    50                  55                  60

Ala Leu Pro Pro Val Pro Gln Pro Val Cys Thr Tyr His Glu Leu His
65                  70                  75                  80

Phe Ala Ser Ile Arg Leu Pro Gly Cys Pro Pro Gly Val Asp Pro Met
                85                  90                  95

Val Ser Phe Pro Val Ala Leu Ser Cys Arg Cys Gly Pro Cys Arg Leu
            100                 105                 110

Ser Asn Ser Asp Cys Gly Gly Pro Arg Ala Gln Ser Leu Ala Cys Asp
        115                 120                 125

Arg Pro Leu Leu Pro Gly Leu Leu Phe Leu
    130                 135

<210> SEQ ID NO 28
<211> LENGTH: 141
<212> TYPE: PRT
<213> ORGANISM: Bovidae

<400> SEQUENCE: 28

Met Glu Met Phe Gln Gly Leu Leu Leu Trp Leu Leu Leu Gly Val Ala
1               5                   10                  15

Gly Val Trp Ala Ser Arg Gly Pro Leu Arg Pro Leu Cys Gln Pro Ile
                20                  25                  30

Asn Ala Thr Leu Ala Ala Glu Lys Glu Ala Cys Pro Val Cys Ile Thr
            35                  40                  45

Phe Thr Thr Ser Ile Cys Ala Gly Tyr Cys Pro Ser Met Lys Arg Val
    50                  55                  60

Leu Pro Val Ile Leu Pro Pro Met Pro Gln Arg Val Cys Thr Tyr His
65                  70                  75                  80

Glu Leu Arg Phe Ala Ser Val Arg Leu Pro Gly Cys Pro Pro Gly Val
                85                  90                  95

Asp Pro Met Val Ser Phe Pro Val Ala Leu Ser Cys His Cys Gly Pro
            100                 105                 110

Cys Arg Leu Ser Ser Thr Asp Cys Gly Gly Pro Arg Thr Gln Pro Leu
        115                 120                 125

Ala Cys Asp His Pro Pro Leu Pro Asp Ile Leu Phe Leu
        130                 135                 140

<210> SEQ ID NO 29
<211> LENGTH: 141
<212> TYPE: PRT
<213> ORGANISM: Rattus norvegicus

<400> SEQUENCE: 29

Met Glu Arg Leu Gln Gly Leu Leu Leu Trp Leu Leu Leu Ser Pro Ser
1               5                   10                  15

Val Val Trp Ala Ser Arg Gly Pro Leu Arg Pro Leu Cys Arg Pro Val
            20                  25                  30

Asn Ala Thr Leu Ala Ala Glu Asn Glu Phe Cys Pro Val Cys Ile Thr
        35                  40                  45

Phe Thr Thr Ser Ile Cys Ala Gly Tyr Cys Pro Ser Met Val Arg Val
    50                  55                  60

Leu Pro Ala Ala Leu Pro Pro Val Pro Gln Pro Val Cys Thr Tyr Arg
65                  70                  75                  80

Glu Leu Arg Phe Ala Ser Val Arg Leu Pro Gly Cys Pro Pro Gly Val
                85                  90                  95

Asp Pro Ile Val Ser Phe Pro Val Ala Leu Ser Cys Arg Cys Gly Pro
            100                 105                 110

Cys Arg Leu Ser Ser Ser Asp Cys Gly Gly Pro Arg Thr Gln Pro Met
        115                 120                 125

Thr Cys Asp Leu Pro His Leu Pro Gly Leu Leu Phe
    130                 135                 140

<210> SEQ ID NO 30
<211> LENGTH: 143
<212> TYPE: PRT
<213> ORGANISM: Felis catus

<400> SEQUENCE: 30

Met Glu Met Leu Gln Gly Leu Leu Leu Trp Leu Leu Leu Leu Leu Asn
1               5                   10                  15

Val Gly Gly Val Trp Thr Ser Arg Glu Pro Leu Arg Pro Leu Cys Arg
            20                  25                  30

Pro Ile Asn Ala Thr Leu Ala Ala Glu Asn Glu Ala Cys Pro Val Cys
        35                  40                  45

Val Thr Phe Thr Thr Thr Ile Cys Ala Gly Tyr Cys Pro Ser Met Met
    50                  55                  60

Arg Val Leu Pro Ala Ala Leu Pro Pro Val Pro Gln Pro Val Cys Thr
65                  70                  75                  80

Tyr Arg Glu Leu Arg Phe Ala Ser Val Arg Leu Pro Gly Cys Pro Pro
                85                  90                  95

Gly Val Asp Pro Val Val Ser Phe Pro Val Ala Leu Ser Cys Arg Cys
            100                 105                 110

Gly Pro Cys Arg Leu Ser Ser Ser Asp Cys Gly Gly Pro Arg Ala Gln
        115                 120                 125

Pro Leu Ala Cys Asp Arg Pro Pro Leu Pro Gly Leu Leu Phe Leu
    130                 135                 140

<210> SEQ ID NO 31
<211> LENGTH: 141
<212> TYPE: PRT
<213> ORGANISM: Homo sapiens

<400> SEQUENCE: 31

```
Met Glu Met Leu Gln Gly Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
            115                 120                 125

Thr Cys Asp His Pro Gln Leu Ser Gly Leu Leu Phe Leu
            130                 135                 140

<210> SEQ ID NO 32
<211> LENGTH: 8
<212> TYPE: PRT
<213> ORGANISM: Homo sapiens

<400> SEQUENCE: 32

Ala Ala Pro Gly Cys Pro Ala Ala
1               5

<210> SEQ ID NO 33
<211> LENGTH: 4
<212> TYPE: PRT
<213> ORGANISM: Homo sapiens

<400> SEQUENCE: 33

Pro Ile Leu Pro
1

<210> SEQ ID NO 34
<211> LENGTH: 6
<212> TYPE: PRT
<213> ORGANISM: Homo sapiens

<400> SEQUENCE: 34

Leu Pro Gly Cys Arg Arg
1               5

<210> SEQ ID NO 35
<211> LENGTH: 4
<212> TYPE: PRT
<213> ORGANISM: Homo sapiens

<400> SEQUENCE: 35

Pro Gly Cys Pro
1

<210> SEQ ID NO 36
<211> LENGTH: 4
<212> TYPE: PRT
<213> ORGANISM: Homo sapiens

<400> SEQUENCE: 36
```

```
Pro Ala Leu Pro
1

<210> SEQ ID NO 37
<211> LENGTH: 6
<212> TYPE: PRT
<213> ORGANISM: Homo sapiens

<400> SEQUENCE: 37

Ala Pro Gly Cys Pro Ala
1               5

<210> SEQ ID NO 38
<211> LENGTH: 7
<212> TYPE: PRT
<213> ORGANISM: Homo sapiens

<400> SEQUENCE: 38

Ala Ala Gly Cys Ala Pro Arg
1               5

<210> SEQ ID NO 39
<211> LENGTH: 6
<212> TYPE: PRT
<213> ORGANISM: Homo sapiens

<400> SEQUENCE: 39

Ala Leu Gly Cys Leu Arg
1               5

<210> SEQ ID NO 40
<211> LENGTH: 6
<212> TYPE: PRT
<213> ORGANISM: Homo sapiens

<400> SEQUENCE: 40

Leu Pro Ala Ala Pro Arg
1               5

<210> SEQ ID NO 41
<211> LENGTH: 6
<212> TYPE: PRT
<213> ORGANISM: Homo sapiens

<400> SEQUENCE: 41

Leu Pro Arg Arg Pro Arg
1               5

<210> SEQ ID NO 42
<211> LENGTH: 6
<212> TYPE: PRT
<213> ORGANISM: Homo sapiens

<400> SEQUENCE: 42

Leu Pro Pro Pro Pro Arg
1               5

<210> SEQ ID NO 43
<211> LENGTH: 6
<212> TYPE: PRT
<213> ORGANISM: Homo sapiens

<400> SEQUENCE: 43

Cys Pro Ala Ala Pro Cys
1               5
```

```
<210> SEQ ID NO 44
<211> LENGTH: 6
<212> TYPE: PRT
<213> ORGANISM: Homo sapiens

<400> SEQUENCE: 44

Asn Pro Gly Cys Pro Arg
1               5

<210> SEQ ID NO 45
<211> LENGTH: 35
<212> TYPE: PRT
<213> ORGANISM: Homo sapiens

<400> SEQUENCE: 45

Gln Cys Ser Leu Ala Val Ala Tyr Ser Val Val Pro Asn Val Gly Arg
1               5                   10                  15

Pro Cys Gly Pro Leu Arg Ile Ser Glu Phe Arg Val Asp Arg Tyr Asn
                20                  25                  30

Cys Val Val
        35

<210> SEQ ID NO 46
<211> LENGTH: 29
<212> TYPE: PRT
<213> ORGANISM: Homo sapiens

<400> SEQUENCE: 46

Ser Tyr Ala Val Ala Leu Gln Arg Gly Val Asn Pro Val Cys Ala
1               5                   10                  15

Ala Asn Tyr Arg Asp Val Arg Phe Glu Ser Ile Arg Leu
                20                  25

<210> SEQ ID NO 47
<211> LENGTH: 31
<212> TYPE: PRT
<213> ORGANISM: Homo sapiens

<400> SEQUENCE: 47

Asn Tyr Arg Asp Val Arg Phe Glu Ser Ile Arg Leu Pro Gly Cys Pro
1               5                   10                  15

Arg Gly Val Asn Pro Val Val Ser Tyr Ala Val Ala Leu Ser Cys
                20                  25                  30

<210> SEQ ID NO 48
<211> LENGTH: 15
<212> TYPE: PRT
<213> ORGANISM: Homo sapiens

<400> SEQUENCE: 48

Arg Leu Pro Gly Cys Pro Arg Arg Leu Pro Gly Cys Pro Arg Cys
1               5                   10                  15

<210> SEQ ID NO 49
<211> LENGTH: 12
<212> TYPE: PRT
<213> ORGANISM: Homo sapiens

<400> SEQUENCE: 49

Asn Pro Val Val Ser Tyr Ala Val Ala Leu Ser Cys
1               5                   10

<210> SEQ ID NO 50
```

```
<211> LENGTH: 20
<212> TYPE: PRT
<213> ORGANISM: Homo sapiens

<400> SEQUENCE: 50

Val Arg Phe Glu Ser Ile Arg Leu Pro Gly Cys Pro Arg Gly Val Asn
1               5                   10                  15

Pro Val Val Ser
            20

<210> SEQ ID NO 51
<211> LENGTH: 97
<212> TYPE: DNA
<213> ORGANISM: Homo sapiens

<400> SEQUENCE: 51
catgaaatac cgtgatgtgc gttttgaaag cattcgtctg ccgggttgtc cgcgcggtgt      60
gaatccggtt gtgagctacg cggttgcgct gagctgc                              97
```

BIOLOGICALLY ACTIVE POLYPEPTIDES DERIVED FROM A NOVEL EARLY STAGE PREGNANCY FACTOR DESIGNATED MATERNIN (MA)

CROSS-REFERENCE TO RELATED APPLICATIONS

This application claims priority to provisional U.S. Patent Application No. 60/147,825, filed Aug. 6, 1999 and U.S. Patent Application No. 60/188,777, filed Mar. 13, 2000; the entire disclosure of these applications is incorporated herein by reference.

FEDERAL FUNDING

The research leading to at least one aspect of the invention described herein was made with the support of the U.S. government, under National Institute of Health Grant No. PO1CA78817. The U.S. government may have certain rights to aspects of the invention described herein.

FIELD OF THE INVENTION

The invention relates to therapeutic polypeptides useful in treating and/or preventing various medical conditions. Examples of therapeutic effects of the therapeutic polypeptides include anti-HIV, anti-cancer, anti-wasting, pro-hematopoietic (e.g., anemias, radiation or chemotherapy-mediated bone marrow damage, and trauma-mediated blood loss), anti-angiogenic and anti-inflammatory effects. The invention also provides pharmaceutical compositions comprising the therapeutic polypeptides, as well as methods for using the therapeutic polypeptides, functional equivalents and/or pharmaceutical compositions in the treatment and/or prevention of such medical conditions.

BACKGROUND OF THE INVENTION

This invention is the culmination of a lengthy research endeavor that began with an observation that a particular group of immunodeficient mice, inoculated with Kaposi's sarcoma (KS) cells, did not develop KS as expected. The researchers extracted KS cells from AIDS patients, grew the cells in vitro and then injected the cells into the immunodeficient mice, expecting the mice to develop KS. While most mice injected with the cells did develop KS, the researchers surprisingly identified a group of ten mice in which KS failed to develop.

In attempting to explain the failure of these mice to develop KS, the researchers first considered whether the anomaly was the result of a laboratory error, such as a failure to properly inject the mice. Closer observation revealed that all ten KS-negative mice were pregnant. A group of females and males had been mistakenly housed together. While the male mice had grown large malignant tumors, the females had only small tumors or no tumors at all. Further observation indicated that females with small tumors were in later stages of pregnancy, and those with no tumors were in early stages of pregnancy. Based on these collective observations, the researchers surmised that one or more factors produced in the early stages of pregnancy was responsible for impeding the development of KS lesions.

In the ensuing months, the group designed and executed a controlled study of the effects of pregnancy on KS. The results of the study were published in the May 4, 1995, issue of *Nature*.[1] In this study, the researchers injected KS cells into 24 female mice and 21 male mice. Four of the female mice were then caged with 2 males. All 4 females became pregnant. One month later, the males had developed large malignant tumors; and as expected, females in late stages of their pregnancy had developed smaller tumors, while newly pregnant females were tumor free.

These results confirmed the group's suspicions that a pregnancy-related factor was responsible for the inhibition of KS. The group noted that the pattern of no KS lesions in early stages of pregnancy and increasingly larger lesions at later stages of pregnancy inversely corresponds to the production of human chorionic gonadotropin (hCG). High levels of hCG are produced during early pregnancy, while lower levels are produced in later stages of pregnancy. The researchers investigated the anti-KS activity of crude commercial hCG preparations. These investigations revealed that some lots of some commercially available crude hCG preparations exhibited the same anti-KS effect seen in the pregnant mice.

In a related study published in the Oct. 24, 1996 issue of *The New England Journal of Medicine*,[2] the investigators tested hCG preparations on 30 human subjects. The results were compared with 6 others who were given a placebo. Twenty-four subjects received intralesional injections of preparations of hCG at doses of 250, 500, 1000, or 2000 international units (IU) three times a week for 2 weeks. In 5 of the 6 subjects who received the 2000 IU hCG dose, KS lesions shrank significantly or completely disappeared. Lesions in at least one subject in each of the 250, 500, and 1000 dose ranges also shrank or disappeared. This study provided further evidence that some lots of some commercial hCG preparations exhibit anti-KS effects. The results also demonstrated that certain crude commercial preparations of hCG can reduce or reverse symptoms of KS in humans.

In another related experiment, the researchers administered a 2000 IU hCG dose preparation to 6 subjects. These subjects were compared to six others who received a placebo. KS lesions shrank or completely disappeared in all 6 subjects receiving hCG, while none of the controls showed any change.

These results were further confirmed in a study published in the January/February 1998 issue of the *Journal of Human Virology*.[3] In this study, 13 subjects with advanced AIDS-KS and visceral KS were treated with a commercial hCG preparation known to have anti-KS effects. Of 12 subjects treated with the hCG preparation, 5 had a dramatic response to the therapy and overall tolerance to the treatment was excellent.

In addition to the surprising anti-KS properties revealed by this series of experiments, the group also observed that the hCG preparations had no toxic side effects, common in other anti-cancer therapeutics. In fact, some subjects reported increased energy, enhanced appetite and even weight gain, while the control group showed no such changes.

The variability of results among lots and sources of the hCG preparations led the group to conclude that the active factor, which was clearly present only in some lots from some sources, could not be hCG itself. And although the crude preparations produced some positive results, the variability in the crude preparations was not conducive to the development of a standard therapeutic protocol. The variability of results prevented an accurate determination of ideal dose, route or frequency of administration.

The group had made following observations:
even though the commercial preparations of hCG had a standardized amount of hCG, the observed activity varied from manufacturer to manufacturer and within a particular manufacturer's hCG preparations;
some of the commercial hCG preparations had no activity;

pure hCG (native purified and recombinant) had none of the observed activities;

when some commercial preparations of hCG were intentionally depleted of hCG activity, they maintained the previously observed activities; and mice do not have the genes for chorionic gonadotropin, but the observed activities were found in sera and the urine of mice in early pregnancy.

These observations led to the hypothesis that the activity of the hCG preparations is mediated by one or more molecules which co-purify with hCG in only some of the commercial preparations.

Next, the researchers tested fragments of hCG for therapeutic activity. A group of fragments from the β-chain of hCG (SEQ ID NO: 1) were identified which exhibited various anti-HIV, anti-cancer and pro-hematopoietic effects.[4] Among the peptides exhibiting such effects were the Satellin A1 peptide [β-hCG 45-57: Leu-Gln-Gly-Val-Leu-Pro-Ala-Leu-Pro-Gln-Val-Val-Cys (SEQ ID NO: 18); the Satellin A1 branched peptide: β-hCG 45-57 [Leu-Gln-Dab(Pro)-Val-Leu-Pro-Dab(Pro)-Leu-Pro-Gln-Val-Val-Cys (see SEQ ID NO: 18, for primary sequence), where "Dab" represents diaminobutyric acid, and Dab(Pro) indicates a proline peptide-bonded to the amino side chain of Dab], the Satellin A2 circularized peptide [β-hCG 45-57 with a cysteine residue added to the N-terminus, circularized via a disulfide bond between the cysteine residues: Cys-Leu-Gln-Gly-Val-Leu-Pro-Ala-Leu-Pro-Gln-Val-Val-Cys (SEQ ID NO: 19)], and the Satellin B peptide [β-hCG 109-119: Thr-Cys-Asp-Asp-Pro-Arg-Phe-Gln-Asp-Ser-Ser (SEQ ID NO: 22). Other β-hCG (SEQ ID NO: 1) peptide fragments demonstrating some degree of efficacy included the following: 109-145, 47-55, 48-56, 45-57 fused to 109-119, and 45-57 in combination with 109-119.

Although the already-discovered group of β-hCG fragments clearly were efficacious in treating KS and other conditions, it appeared that one or more factors remained to be discovered, i.e., the factor or factors which accounted for the higher degree of efficacy exhibited by the commercial hCG preparations. As discussed more fully in the detailed description of the invention, the present inventors have isolated two such highly active factors. The inventors have named these peptides "Maternin™" for the purpose of future commercialization, and the peptides are generically referred to herein as the MA peptides: MA (SEQ ID NO: 2) and pMA (SEQ ID NO: 3), which are the subject of the instant application.

Other researchers have investigated the use of preparations of heterodimeric hCG in the treatment of HIV. Such preparations have been shown to reduce the reverse transcriptase activity in HIV-1 infected lymphocytes and monocytes in culture[5] and to prevent transmission of HIV from lymphocytes to trophoblasts in vitro.[6] One researcher has proposed the use of doses of hCG below those necessary to induce a humoral immune response for treating of HIV infection.[7] Researchers have also reported that treatment with hCG improves T cell counts and physical symptoms in certain HIV infected subjects.[8] However, none of these researchers have successfully isolated novel, highly active peptides from commercial preparations of hCG or urine.

Additionally, the β-hCG (SEQ ID NO: 1) has been reported to reduce HIV production in lymphocytes at doses from 100 pg/ml to 100 μg/ml and in monocytes at doses up to approximately 10 μg/ml, with higher doses actually increasing the level of viral production in monocytes.[9] Lunardi-Iskandar et al.[10] reported that hCG, β-hCG (SEQ ID NO: 1), as well as a β-hCG carboxy-terminal peptides of amino acids 109-145 and 109-119 are efficacious in the treatment of Kaposi's Sarcoma. However, this work did not contemplate the presence of additional specific β-hCG-derived products with highly active anti-KS properties, or any of the other therapeutic effects for such products as described herein.

The inventors also previously identified fractions of early pregnancy urine with consistently potent therapeutic effects, such as anti-HIV, anti cancer, anti-wasting and pro-hematopoietic effects.[11] These effects were shown to be present in fractions of a source of native hCG or β-hCG. Particularly active fractions included material eluting from a gel filtration column with an apparent molecular weight of approximately 40 kD, 15 kD or 2-3 kD. The same peak fractions not only killed KS tumor cells but also inhibited HIV-1 replication in vitro, suppressed HIV-1 expression in HIV-1 transgenic mice, and inhibited the development of AIDS in $SIV_{MAC\ 251}$ infected macaques.[12] The instant invention is an extension of this work, and is the result of a lengthy and extensive program of experimentation directed towards identifying the one or more pharmacologically active constituents of early pregnancy urine.

Following our original report, several groups attempted to identify one or another of the molecules responsible for these activities. These reports were limited to in vitro studies showing some inhibition of KS cell growth in culture or of decreased HIV replication with some already well-known urinary products such as EDN RNase,[13] other RNases,[14] lysozyme,[15] and the native gylcosylated β-core of β-hCG[16] or with a putative purified hCG.[17] One group described some in vitro anti-KS activity with a low molecular weight fraction obtained from a crude hCG preparation, the chemical nature of which was not defined or further characterized.[18] Importantly, none of these reports showed in vivo results, and none showed the multiple effects described here. Moreover, with the exception of the hCG related products, none of these molecules are known to be relatively high during early pregnancy, and the report of positive results with native glycosylated β-core emphasized selective inhibition only of the growth of KS cells.[19]

In our earlier work[20] and confirmed in this report, we found no activity in vitro or in vivo in any of the various experimental systems described here with purified native glycosylated β-core, β-hCG, α-hCG, and/or hCG. Earlier and distinct from these in vitro studies, Russo and co-workers reported that a crude commercial hCG preparation (ProFasi, Organon) inhibited carcinogenesis induced by DMBA in rats.[21] As indicated, we have demonstrated that pure hCG has no effect on any tumor cell we have studied, and the crude ProFasi hCG was inactive.

4.1 Human Immunodeficiency Virus Therapy

The human immunodeficiency virus (HIV) is a member of the lentivirus family of retroviruses.[22] Retroviruses are small enveloped viruses containing a single-stranded RNA genome.

HIV has been implicated as the primary cause of acquired immune deficiency syndrome (AIDS),[23] a slowly progressing degenerative immunological disease. There are at least two distinct types of HIV: HIV-1[24] and HIV-2,[25] and a large amount of genetic heterogeneity exists within populations of each type.

In humans, HIV replication occurs predominantly in $CD4^+$ T lymphocyte populations. HIV infection leads to depletion of this cell type and eventually to immune incompetence, opportunistic infections, neurological dysfunctions, neoplastic growth, wasting and ultimately death.

The HIV viral particle comprises a viral core, composed in part of capsid proteins, together with the viral RNA genome and enzymes required for early replicative events. Myristylated Gag protein forms an outer shell around the viral core. This outer shell is, in turn, surrounded by a lipid membrane envelope derived from the infected cell membrane.

The HIV envelope surface glycoproteins are synthesized as a single 160 kilodalton precursor protein. A cellular protease cleaves the precursor during viral budding into two glycoproteins, gp41 and gp120. The gp41 component is a transmembrane glycoprotein. The gp120 component is an extracellular glycoprotein which remains non-covalently associated with gp41, possibly in a trimeric or multimeric form.[26]

HIV-associated diseases represent a major world health problem. Researchers attempting to develop anti-HIV drugs have focused various specific stages of the HIV life cycle as targets for therapeutic intervention.[27] For example, research efforts have targeted virally encoded reverse transcriptase (RT) as a point of attack for anti-HIV therapeutics. These efforts have resulted in a number of reverse-transcriptase-targeted drugs, including 2',3'-dideoxynucleoside analogs such as AZT, ddI, ddC, and d4T.[28]

The capacity of HIV to mutate has been a major obstacle in the search for a cure for HIV infection. Mutations can render effective drugs less effective, or even ineffective.

Moreover, it has become clear that the ability of drug-resistant strains of HIV to emerge is greatly diminished by the use of multi-drug treatment regimens. Multi-drug regimens are currently the preferred treatment for HIV-infected subjects. For example, combining anti-HIV compounds which target reverse transcriptase (e.g., azidothymidine (AZT), lamivudine (3TC), dideoxyinosine (ddI), dideoxycytidine (ddC)) with an HIV-1 protease inhibitor produces a far more potent effect (2 to 3 logs reduction) on viral load than monotherapy using a reverse transcriptase inhibitor alone (about 1 log reduction). Impressive results have been obtained using a combination of AZT, ddI, 3TC and ritonavir.[29]

Other researchers have sought to develop therapies which prevent HIV from entering its target cells. The focus of these efforts has been on CD4, the cell surface receptor for HIV. For example, researchers have found that recombinant soluble CD4 inhibits infection of CD4$^+$ T cells by some HIV-1 strains.[30] However, certain primary HIV-1 isolates are relatively less sensitive to inhibition by recombinant CD4.[31] In addition, clinical trials using recombinant soluble CD4 have produced inconclusive results.[32]

Researchers have also targeted late stages of HIV replication in the development of anti-HIV therapies. Late stages involve crucial virus-specific processing of certain viral proteins. This processing depends on the activity of a viral protease, and drugs are being developed which inhibit this protease.[33]

Chemokines produced by CD8$^+$ T cells have also been investigated as anti-HIV agents.[34] In particular, RANTES, MIP-1α and MIP-1β, are known to suppress HIV-1 p24 antigen production in cells infected with HIV-1 or HIV-2 isolates in vitro.[35]

Attention is also being given to the development of vaccines for the treatment of HIV infection. The HIV-1 envelope proteins (gp160, gp120, gp41) appear to be the major antigens for anti-HIV antibodies produced by AIDS patients,[36] and they may be the most promising antigen candidates for anti-HIV vaccine development. Various portions of gp160, gp120, and/or gp41 are also being tested for use as immunogenic targets for the host immune system.[37] Vaccines directed against HIV proteins are problematic because rapid viral mutation commonly renders such vaccines ineffective. Moreover, vaccines may be ineffective for individuals with active HIV infections.

4.2 Therapies for Hematopoietic Deficiencies

The morphologically recognizable and functionally capable cells circulating in blood include erythrocytes, neutrophilic, eosinophilic, and basophilic granulocytes, B-, T-, non B-, non T-lymphocytes, and platelets. These mature hematopoietic cells derive from and develop into morphologically recognizable dividing precursor cells for the respective lineages, such as erythroblasts for the erythrocyte series, myeloblasts, promyelocytes and myelocytes for the granulocyte series, and megakaryocytes for platelets. The precursor cells derive from more primitive cells that can simplistically be divided into two major subgroups: stem cells and progenitor cells.[38]

The definitions of stem and progenitor cells are operational and depend on functional, rather than on morphological, criteria. Stem cells have extensive self-renewal or self-maintenance capacity (a necessity since absence or depletion of these cells could result in the complete depletion of one or more cell lineages).[39] Pluripotential stem cells differentiate into several sub-lines of progenitor cells. These sub-lines typically have a more limited or completely eliminated self-renewal capacity. Progenitor cells ultimately produce morphologically recognizable precursor cells.[40]

A variety of infectious agents, genetic abnormalities and environmental factors can cause a deficiency in one or more hematopoietic cell types. For example, hematological deficiencies have been observed in HIV-1 infected individuals, including a reduction in CD4$^+$ T cells and cytopenias of one or more hematopoietic lineages.

HIV-related cytopenias are often associated with bone marrow morphologic abnormalities and deficient progenitor cell growth.[41] For example, idiopathic thrombocytopenic purpura (ITP), characterized by significant reduction in platelet numbers, often afflicts subjects infected with HIV.[42] The destruction of platelets appears to be mediated by platelet associated autoantibodies.[43] Management of ITP generally involves immunosuppression; consequently, treatment of ITP in HIV infected patients is complicated, since administration of immunosuppressive drugs is extremely detrimental to HIV-infected individuals.

Chemotherapy and radiation therapy are still the frontline methods used in the treatment of cancer and certain immunological disorders. It is well-known that these therapies cause a number of detrimental side-effects, such as pancytopenias or combinations of anemia, neutropenia and thrombocytopenia. The increase or replacement of hematopoietic cells is often crucial to the success of such treatments.[44]

Aplastic anemia is another serious condition characterized by hematopoietic deficiency. In the absence of stem cell therapy, aplastic anemias are commonly fatal. Without new stem cells, approximately 60-75% of individuals presenting with this disorder die within 12 months. The overall incidence of these diseases is approximately 25 new cases per million persons per year. No single pathogenic mechanism can account for all aplastic anemias; however, in most cases, provision of new hematopoietic stem cells is sufficient to allow permanent recovery.[45] Standard treatment involves bone marrow transplants; however, some subjects with aplastic anemia reject the transplanted marrow. This complication is particularly common among subjects who have been immunologically sensitized as a result of multiple therapeutic blood transfusions.

A common therapy for many hematological disorders, as well as the destruction of the endogenous hematopoietic cells caused by chemotherapy or radiotherapy, is bone marrow transplantation. However, the availability of bone marrow transplantation is restricted, since it is extremely rare to have perfectly matched (genetically identical) donors. Moreover, the complications of bone marrow incompatibility (e.g., host versus graft reaction and graft versus host disease) are often lethal. Even with closely matched family donors, the complications of partial mismatching cause substantial mortality and morbidity.

Researchers have also investigated the use of peripheral blood as a source of stem cells for hematopoietic reconstitution.[46] Promising results have been obtained for subjects with various leukemias[47] and subjects with lymphoma.[48] However, some studies using peripheral blood have failed to effect reconstitution.[49]

There is a need for methods which enable in vitro expansion of blood cells and for therapies which increase the production of hematopoietic cells in vivo and which reduce the need for reliance on bone marrow transplantation and/or blood transfusions.

4.3 Therapies for Wasting Syndromes

Wasting syndrome is generally characterized by a decrease in body mass of more than 10% from baseline body weight and a disproportionate loss of body mass with respect to body fat.[50] Wasting is distinguished from starvation, in which higher levels of body fat than body cell mass are depleted.[51] Wasting is associated with a variety of conditions, including HIV infection, other infectious diseases, sepsis, cancer, chronic cardiovascular disease and diarrhea.[52] Wasting is a significant factor in the mortality of subjects presenting with infections or cancer.

Current and potential therapies for wasting syndromes include nutritional support, appetite enhancers such as dronabinol and megestrol acetate, anabolic therapies, such as growth hormone, and cytokine inhibitors. However, nutritional support and appetite enhancers have the disadvantages that subjects tend to gain only fat and not overall body mass. Administration of growth hormone, and cytokine inhibitors are still being tested and may pose a risk of side effects.[53]

Treatment of wasting is critical to the survival and well-being of patients presenting with serious diseases such as cancer, chronic diarrhea and AIDS; accordingly, there is a need in the art for safe and effective therapies for wasting syndromes.

4.4 Cancer Therapy

A tumor (i.e., a neoplasm) is a mass resulting from abnormal, uncontrolled cell growth. Tumors can be benign or malignant. Benign tumors generally remain localized. The term "malignant" generally means that the tumor can invade and destroy neighboring body structures and spread to distant sites to cause death.[54]

Treatment options for cancer include, for example, surgery, chemotherapy and radiation treatment. Such options are commonly either ineffective or present serious side effects. Accordingly, there is a need for new drugs for use in the treatment of cancer.

Kaposi's Sarcoma (KS) is a rare type of cancer, the incidence of which is greatly increased in HIV infected subjects.[55] KS tumors are characterized by the presence of hyperplastic cells derived from vascular endothelial cells.[56] In some cases, neoplastic cells with chromosomal abnormalities are also present in the tumors.[57]

Currently available therapies for KS include radiotherapy, α-interferon and systemic chemotherapy.[58] However, hematological and non-hematological toxicities limit the prolonged use of chemotherapy and α-interferon in conjunction with anti-retroviral agents commonly used in the treatment of AIDS.[59] Thus, new anti-KS drugs are needed, preferably drugs which are also compatible with other AIDS therapeutics.

4.5 Anti-Angiogenesis

A variety of disease conditions, such as cancer, are currently treated using therapeutics which control angiogenesis. Angiogenesis is the formation of new blood vessels from existing capillaries. Angiogenesis is a pathological component of a number of diseases. For example, angiogenesis is necessary to enable tumors to grow beyond a few mm in size. Researchers have investigated a number of endogenous compounds thought to negatively-regulate angiogenesis, including angiostatin (a fragment of plasminogen), endostatin (a fragment of collagen), vasostatin (a fragment of kallikrein), and interferons α and β, and interleukin 12.[60] Other agents currently being considered include: SU5416 (a small-molecule angiogenesis inhibitor); IM862 (a naturally-occurring bipeptide and antiangiogenic agent); EMD121974 (a cyclic pentapeptide and a potent and selective inhibitor of alpha VB3); interferon-α 2B; ZD4190; SU6668 and PD 0173073.

SUMMARY OF THE INVENTION

The invention provides isolated MA peptides. The isolated MA peptides exhibit a variety of therapeutic effects, as more fully described in Sections 8 and 9. Examples of such therapeutic effects include anti-HIV effects, anti-cancer effects, anti-wasting effects, and pro-hematopoietic effects. Preferred MA peptides include:

MA (SEQ ID NO: 2); and
pMA (SEQ ID NO: 3).

Functional equivalents of the MA peptides are also provided by the invention. Preferred functional equivalants include:

$MA_{S1}$ (SEQ ID NO: 4);
$MA_{S2}$ (SEQ ID NO: 5);
$MA_{S3}$ (SEQ ID NO: 6);
$MA_{S5}$ (SEQ ID NO: 7);
$MA_{S9}$ (SEQ ID NO: 8);
$MA_{S10}$ (SEQ ID NO: 9);
$MA_{S11}$ (SEQ ID NO: 10);
β-hCG 55-88 (SEQ ID NO: 11);
β-hCG 55-90 (SEQ ID NO: 12);
β-hCG 55-91 (SEQ ID NO: 13);
β-hCG 55-74 (SEQ ID NO: 14);
β-hCG 6-37 (SEQ ID NO: 15);
β-hCG 6-38 (SEQ ID NO: 16);
β-hCG 6-39 (SEQ ID NO: 17); and
β-hCG 6-40 (SEQ ID NO: 18).

In one aspect, the functional equivalents consist of polypeptides which comprise within their amino acid sequences, the sequence of one or more MA peptides, and preferably exclude at least some β-hCG (SEQ ID NO: 1) amino acid residues contiguous to the MA peptide sequence.

In one embodiment of the invention, the functional equivalents are 5 to 38 amino acids in length and are truncations of any of the following peptides: MA (SEQ ID NO: 2); pMA (SEQ ID NO: 3); $MA_{S1}$ (SEQ ID NO: 4); $MA_{S2}$ (SEQ ID NO:

5); MA$_{S3}$ (SEQ ID NO: 6); MA$_{S5}$ (SEQ ID NO: 7); MA$_{S9}$ (SEQ ID NO: 8); MA$_{S10}$ (SEQ ID NO: 9); MA$_{S11}$ (SEQ ID NO: 10); β-hCG 55-88 (SEQ ID NO: 11); β-hCG 55-90 (SEQ ID NO: 12); β-hCG 55-91 (SEQ ID NO: 13); β-hCG 55-74 (SEQ ID NO: 14); β-hCG 6-37 (SEQ ID NO: 15); β-hCG 6-38 (SEQ ID NO: 16); β-hCG 6-39 (SEQ ID NO: 17); and β-hCG 6-40 (SEQ ID NO: 18). The truncations preferably result in peptides that are from 5 to 30 amino acid residues in length, more preferably from 5 to 20 amino acid residues in length, still more preferably from 5 to 15 amino acid residues in length, and ideally from 5 to 10 amino acid residues in length. In a related embodiment, the truncated polypeptides include peptides from the group consisting of MA (SEQ ID NO: 2); pMA (SEQ ID NO: 3); MA$_{S1}$ (SEQ ID NO: 4); MA$_{S2}$ (SEQ ID NO: 5); MA$_{S3}$ (SEQ ID NO: 6); MA$_{S5}$ (SEQ ID NO: 7); MA$_{S9}$ (SEQ ID NO: 8); MA$_{S10}$ (SEQ ID NO: 9); MA$_{S11}$ (SEQ ID NO: 10); β-hCG 55-88 (SEQ ID NO: 11); β-hCG 55-90 (SEQ ID NO: 12); β-hCG 55-91 (SEQ ID NO: 13); β-hCG 55-74 (SEQ ID NO: 14); β-hCG 6-37 (SEQ ID NO: 15); β-hCG 6-38 (SEQ ID NO: 16); β-hCG 6-39 (SEQ ID NO: 17); and β-hCG 6-40 (SEQ ID NO: 18) having 1, 2, 3, 4, 5 or 6 amino acid residues deleted from an amino terminus or carboxy terminus thereof. Moreover, the functional equivalents include polypeptides which comprise one or more of these truncated MA peptides.

The functional equivalents of the invention exclude full length human β-hCG (SEQ ID NO: 1).

The invention also provides pharmaceutical compositions comprising one or more therapeutic polypeptides and/or one or more functional equivalents of the invention. The pharmaceutical compositions are useful in the treatment of a variety of conditions as described more fully in Sections 8 and 9. Examples include HIV infection, cancer, wasting, and hematopoietic deficiencies.

Furthermore, the present invention provides an MA peptide isolated from early pregnancy urine consisting of the amino acid sequence of SEQ ID NO: 2 (MA). The invention also provides an MA peptide isolated from early pregnancy urine consisting of the amino acid sequence of SEQ ID NO: 3 (pMA).

In addition to the foregoing compositions and formulations, the invention provides methods for treating and/or preventing various medical conditions. Examples of conditions suitably treated and/or prevented according to the methods of the invention include HIV infection, cancer, wasting, hematopoietic deficiency, and pathological angiogenesis. The subject of the methods of the invention may be a human or other animal, preferably a mammal, such as a dog, cat, horse, sheep, cow or rat. The methods generally comprise administering to a subject in need thereof a pharmaceutically effective amount of one or more therapeutic polypeptides of the invention.

In one aspect of the invention, the condition treated is cancer. Examples of cancers which may be suitably treated according to the methods of the invention include brain cancer, breast cancer, lung cancer, pancreatic cancer, prostate cancer, renal cancer, and hematopoietic malignancies. The MA peptides may be used to treat any cancer for which the MA peptides have anti-cancer activity; cancers in addition to those described herein may readily be identified by those of skill in the art by screening the novel compounds of the invention using readily available assays. In a preferred aspect, the cancer is Kaposi's sarcoma. The therapeutic polypeptide(s) and/or functional equivalent(s) may also be administered in conjunction with another anti-cancer therapy, such as radiation therapy, anti-cancer chemotherapy, and/or anti-cancer vaccines.

In another aspect of the invention, the condition treated is a hematopoietic deficiency caused by radiation and/or chemical exposure. The radiation and/or chemical exposure may be associated with a medical therapy, such as anti-cancer therapy. The therapeutic polypeptide may be administered before, during or after the radiation and/or chemical exposure.

The invention also provides a rationally designed peptide exhibiting a therapeutic effect selected from the group consisting of anti-HIV effects, anti-cancer effects, anti-wasting effects, radioprotective effects, anti-angiogenic effects, anti-inflammatory effects and pro-hematopoietic effects, comprising at least one motif from each of the following groups: (a) SH3 and PDZ domain motifs; and (b) phosphorylation and myristoylation domain motifs.

In a preferred embodiment, the motifs are selected from SH3 domain motifs, PDZ domain motifs, phosphorylation domain motifs and myristoylation domain motifs as found in mammalian luteinizing hormone and/or mammalian chorionic gonadotropin.

In a more preferred embodiment, the motifs are selected from SH3 domain motifs, PDZ domain motifs, phosphorylation domain motifs and myristoylation domain motifs as found in a source selected from the group consisting of β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31).

Preferably no more than 20 amino acid residues separate the (a) motif from the (b) motif.

Preferably the (a) motif comprises an SH3 motif and the (b) motif comprises a phosphorylation motif. Moreover, it is also preferred that no more than 10 amino acid residues separate the SH3 motif from the phosphorylation motif, more preferably no more than 5 amino acid residues separate the SH3 motif from the phosphorylation motif, and ideally, the SH3 motif and the phosphorylation motif are immediately contiguous.

In a related embodiment, the (a) motif comprises an SH3 motif and the (b) motif comprises a myristoylation motif. Preferably no more than 15 amino acid residues separate the SH3 motif from the myristoylation motif, more preferably no more than 10 amino acid residues separate the SH3 motif from the myristoylation motif, and still more preferably no more than 5 amino acid residues separate the SH3 motif from the myristoylation motif. Ideally, the SH3 motif and the myristoylation motif are immediately contiguous.

The rationally designed peptide of the invention may suitably comprise more than one (a) motif and/or more than one (b) motif.

Motifs for inclusion in the rationally designed polypeptides of the invention are preferably selected from the following: (1) β-hCG 4-7, 50-53, 70-73, 124-129, 141-144, 30-33, 41-44, and 139-142; and (2) β-hCG 22-27, 47-52, 71-76, 66-68, 94-99, 109-112, and 120-122.

The (a) and (b) motifs may also be provided together in a continuous segment of a chorionic gonadotropin or leutenizing hormone amino acid sequence, e.g., β-hCG 6-37, 6-38, 6-39 and 6-40 (SEQ ID NOS: 13, 14, 15 and 16).

Preferred rationally designed peptides include β-hCG 1-39, 1-29, 1-35, 41-54, 66-76, 93-130, 93-131, 93-132, 93-135, 93-144, 93-145, 41-54 linked to 55-92, 41-54 linked to 59-89, or 41-54 linked to 55-76.

Preferred sources for motifs include HUSI-II polypeptide, β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31).

The rationally designed peptides are typically at least 5 and less than 100 amino acid residues in length, preferably at least 5 and less than 50 amino acid residues in length, more preferably at least 5 and less than 25 amino acid residues in length, still more preferably, at least 5 and less then 20 amino acid residues in length, and ideally at least 5 and less than 15 amino acid residues in length.

The invention also provides fragments of HUSI-II comprising an SH3 motif and flanking residues, preferably HUSI-II fragments 40-46, 40-60, 40-59, 40-58, 40-66, 40-67, 40-68.

In a related aspect, the invention provides a method for producing a peptide library for screening for a therapeutic effect (e.g., anti-HIV effects, anti-cancer effects, anti-wasting effects, radioprotective effects, anti-angiogenic effects, anti-inflammatory effects and pro-hematopoietic effects). The method generally comprises producing a set of rationally designed peptides, each peptide comprising at least one motif from each of the following groups (a) SH3 and PDZ domain motifs; and (b) phosphorylation and myristoylation domain motifs. The peptide library may be screened to identify peptides exhibiting the target therapeutic effect(s).

5.1 Definitions

A "therapeutically effective" amount or dose is an amount or dose which prevents or delays the onset or progression of an indicated disease or other adverse medical condition. The term also includes an amount sufficient to arrest or reduce the severity of an ongoing disease or other adverse medical condition, and also includes an amount necessary to enhance normal physiological functioning.

As used herein, "treatment" of a disease or other adverse medical condition, should be broadly interpreted based on the therapeutic effects described herein as variously including palliative, active, causal, conservative, medical, palliative, prophylactic, and/or symptomatic treatment, treatment designed to delay the onset or progression of the disease or other adverse medical condition, as well as treatment designed to arrest or reducing the severity of an ongoing disease or other adverse medical condition.

As used herein, a "pharmaceutically acceptable" component (such as a salt, carrier, excipient or diluent) of a formulation according to the present invention is a component which (1) is compatible with the other ingredients of the formulation in that it can be combined with the therapeutic polypeptides of the invention without eliminating the biological activity of the therapeutic polypeptides; and (2) is suitable for use in non-human animals or humans without undue adverse side effects (e.g., toxicity, irritation, and allergic response). Side effects are "undue" when their risk outweighs the benefit provided by the pharmaceutical composition.

As used herein, a "pharmaceutically acceptable" with reference to the degree of purity of a therapeutic polypeptide or nucleic acid indicates that the therapeutic polypeptide or nucleic acid (1) is free of contaminating materials that would eliminate the biological activity of the therapeutic polypeptide or nucleic acid; and (2) is free of contaminating materials that would render the therapeutic polypeptide or nucleic acid unsuitable for administration to non-human animals or humans by causing undue adverse side effects (e.g., toxicity, irritation, and allergic response). Side effects are "undue" when their risk outweighs the benefit provided by the therapeutic polypeptide or nucleic acid.

The term "substantially pure" when used in reference to a therapeutic polypeptide or nucleic acid is defined herein to mean a therapeutic polypeptide or nucleic acid that is substantially free from other contaminating proteins, nucleic acids, and other biologicals derived from an original source organism, recombinant DNA expression system, or from a synthetic procedure employed in the synthesis or purification of the therapeutic polypeptide of nucleic acid (e.g., chromatography reagents and polymers, such as acrylamide or agarose). Purity may be assayed by standard methods. Purity evaluation may be made on a mass or molar basis.

The term "functional equivalent" as used herein refers to a polypeptide sequence comprising a full-length MA peptide sequence, or comprising a fragment, analogue, derivative or truncation isoform of a full-length MA peptide. Functional equivalents also include, for example, an MA peptide in salt, complex, analogue, or derivative form, as well as a fragment, derivative or analogue of a native MA peptide. Functional equivalents retain some or all of the biological activity of the corresponding MA peptide. Functional equivalents exclude full-length β-hCG.

The word "transform" is broadly used herein to refer to introduction of an exogenous polynucleotide sequence into a prokaryotic or eukaryotic cell by any means known in the art (including for example, direct transmission of a polynucleotide sequence from a cell or virus particle, transmission by infective virus particles, and transmission by any known polynucleotide-bearing substance) resulting in a permanent or temporary alteration of genotype and in an immortal or non-immortal cell line.

The term "polypeptide" as used herein is intended to refer to amino acid sequences of any length, for example, the term specifically includes both peptides and proteins.

The terms "administer," "administration" and the like, as used herein with reference to a polypeptide, are intended to be inclusive of any means for delivering the polypeptide to a subject. For example, these terms are broadly inclusive of direct delivery of a polypeptide to a subject by conventional routes, as well as delivery of a prodrug which metabolizes in vivo to provide the polypeptide to a subject.

Panel A: shows an HPLC profile utilizing a SUPERDEX™ column (HR 10/30, cut-off 100-7000 Da) of the Pall-Filtron Microsep purified fraction.

Panel B: shows the results of SDS-PAGE elucidating peptides that generally ran with markers of about 4-6 kDa and 3-4 kDa.

Panel C: shows the results of mass spectroscopy using MALDI-TOF and an SA matrix.

Panel D: shows the sequence identity as confirmed by $MA_{S2}$ peptide synthesis with demonstrable reproducibility of bioactivities.

Figure 1A:
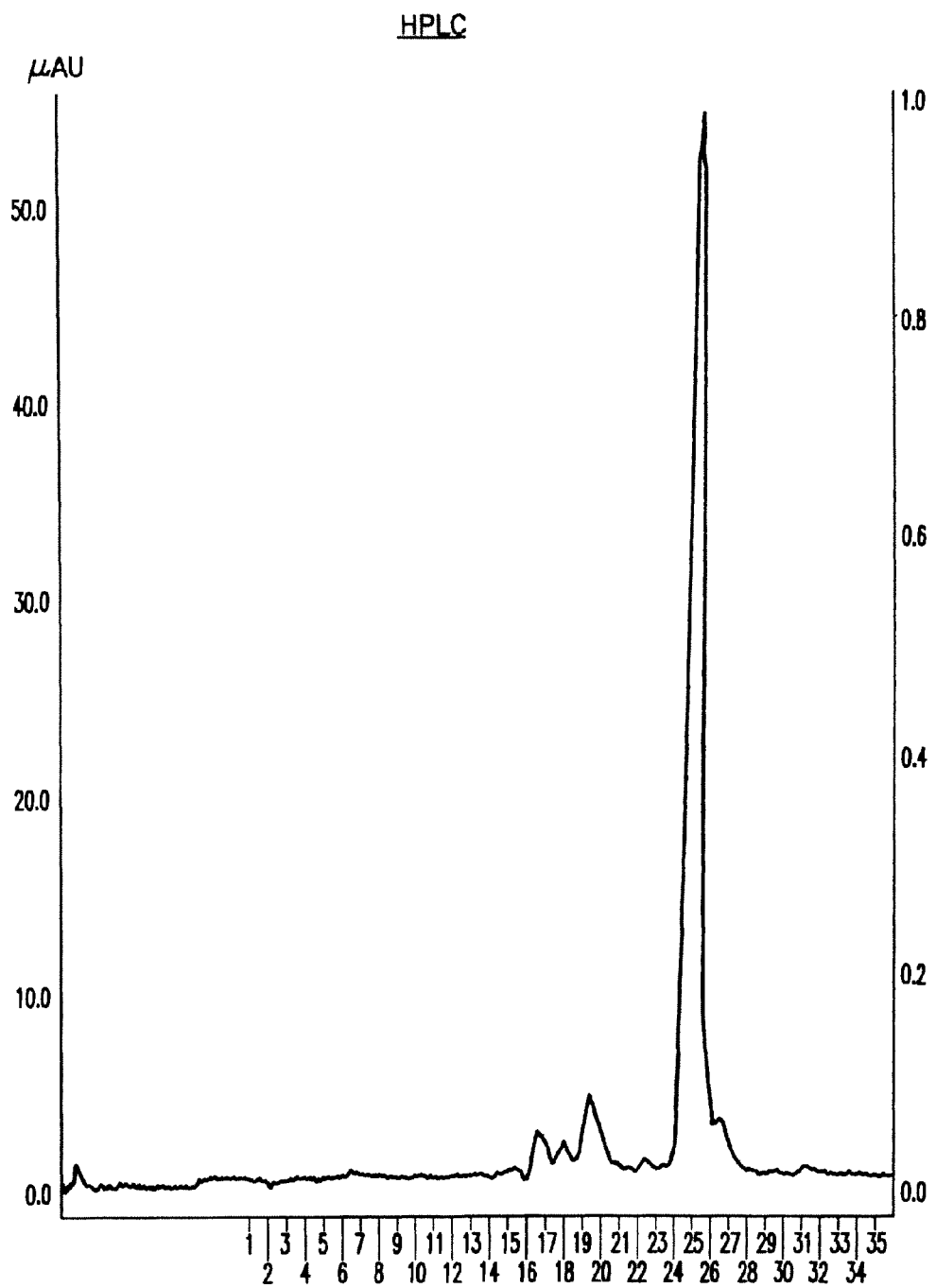
FIG. 1. Purification and identification of MA.
Figure 1B:
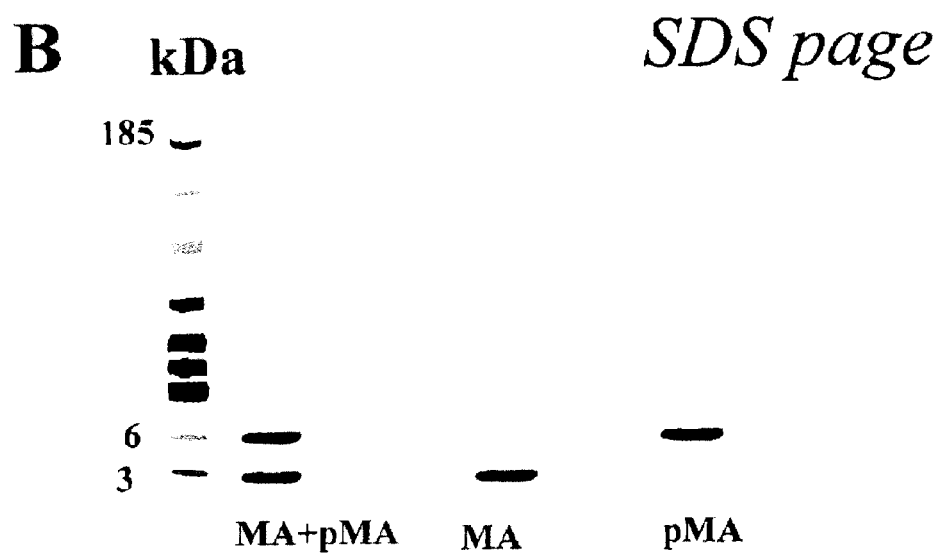
Figure 1C:
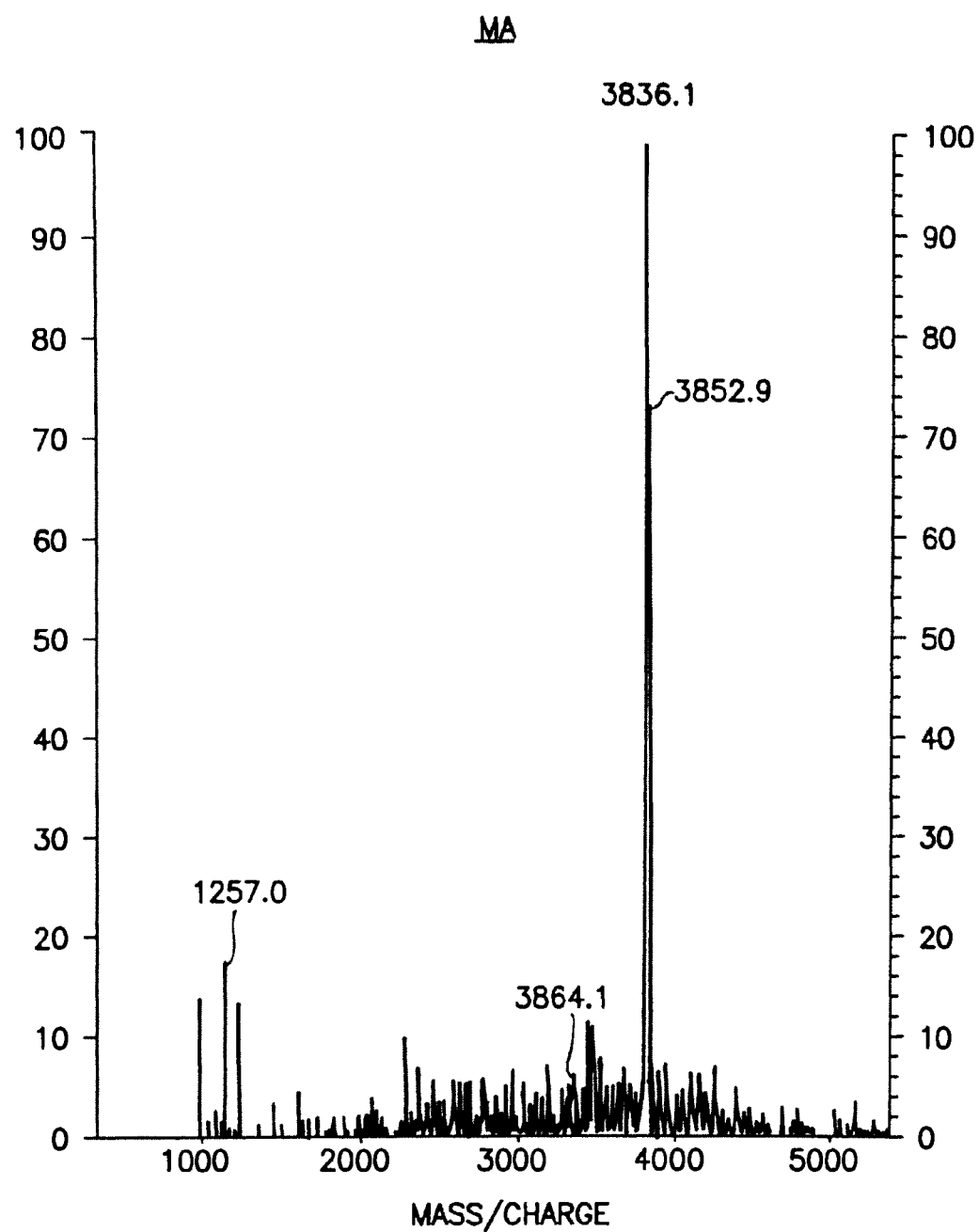
Figure 1D:
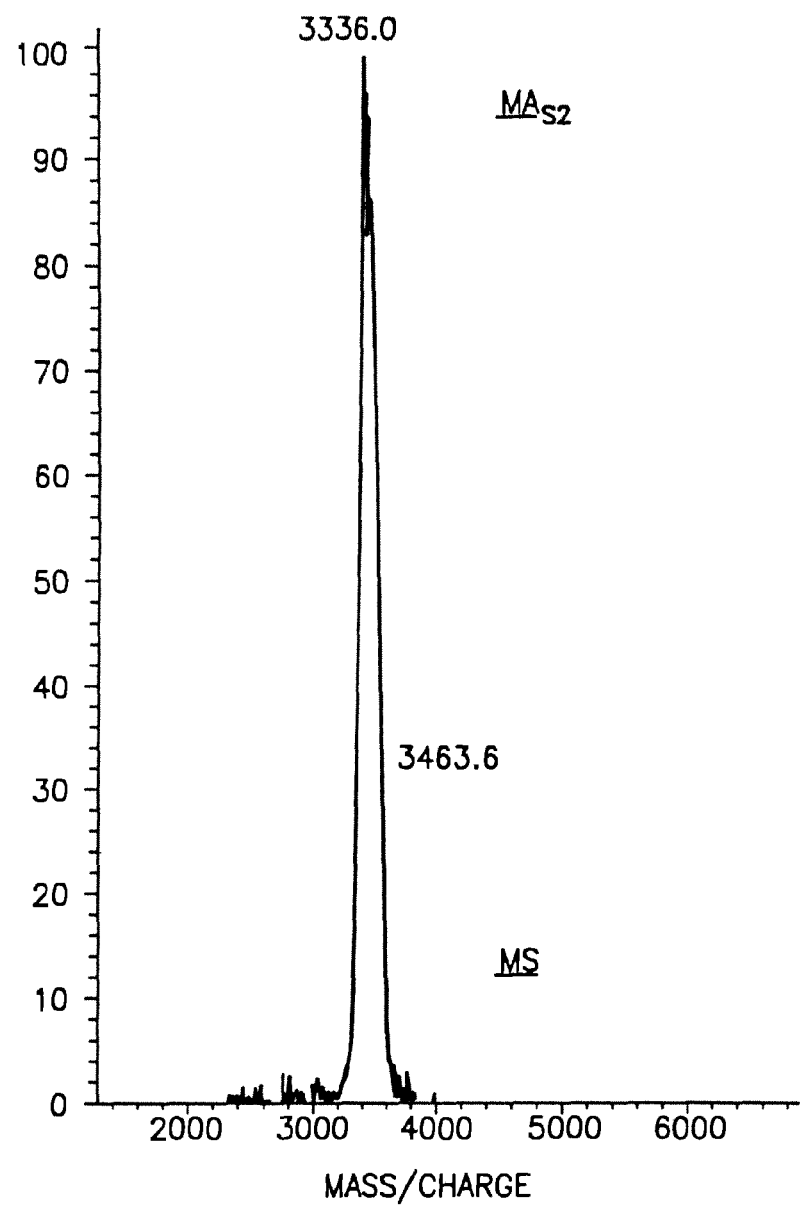
Figure 2C:
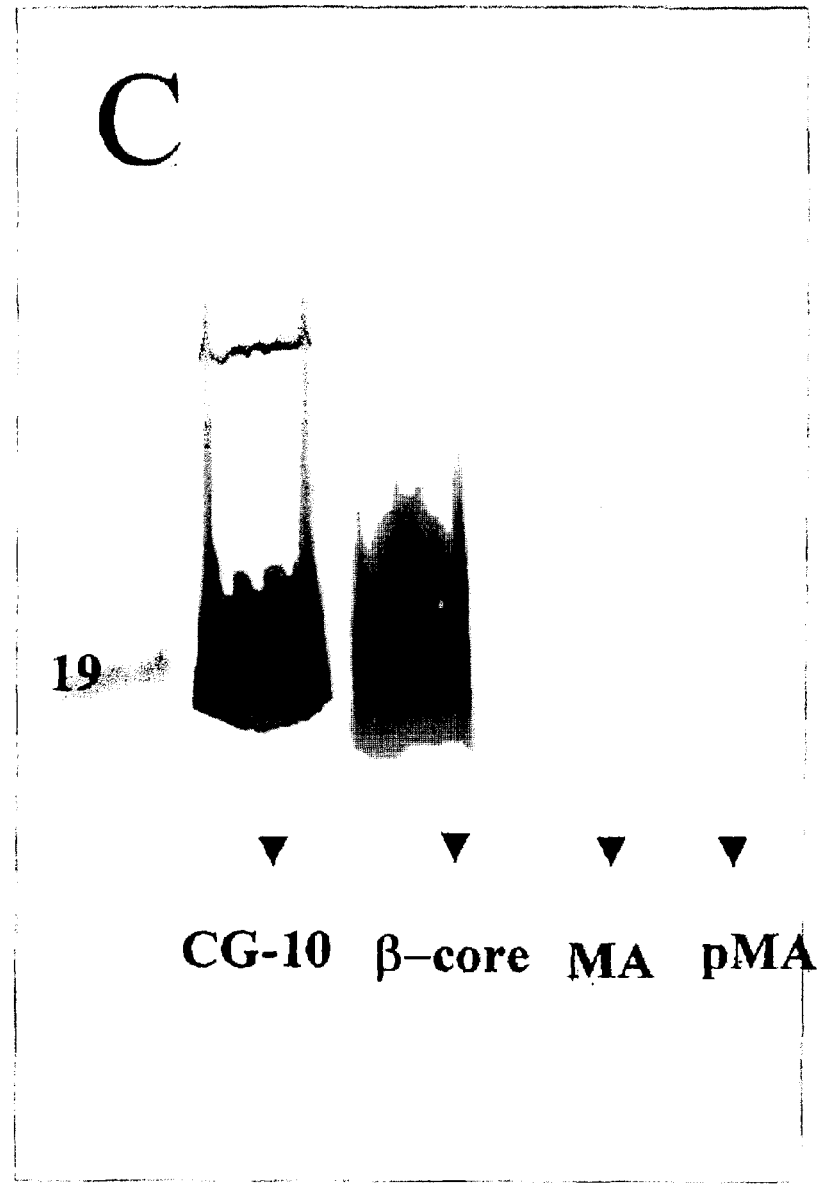

FIG. 2. Immunoblots of MA and pMA with monoclonal antibodies (MoAbs).

Panel A: Western blot analysis of MoAb to MA

Panel B: Western blot analysis of MoAb to pMA

Panel C: Western blot analysis of MoAB (B-210) to β-core

FIG. 3. Anti-tumor effects of native and synthetic MA on human tumor cells in vitro.

FIGS. 3A-3D Dose dependent inhibition of growth by MA as measured by colony formation assays. Assays were on day 7 with the indicated amount of test material added at time 0 (40).

Figures 3A, 3B:
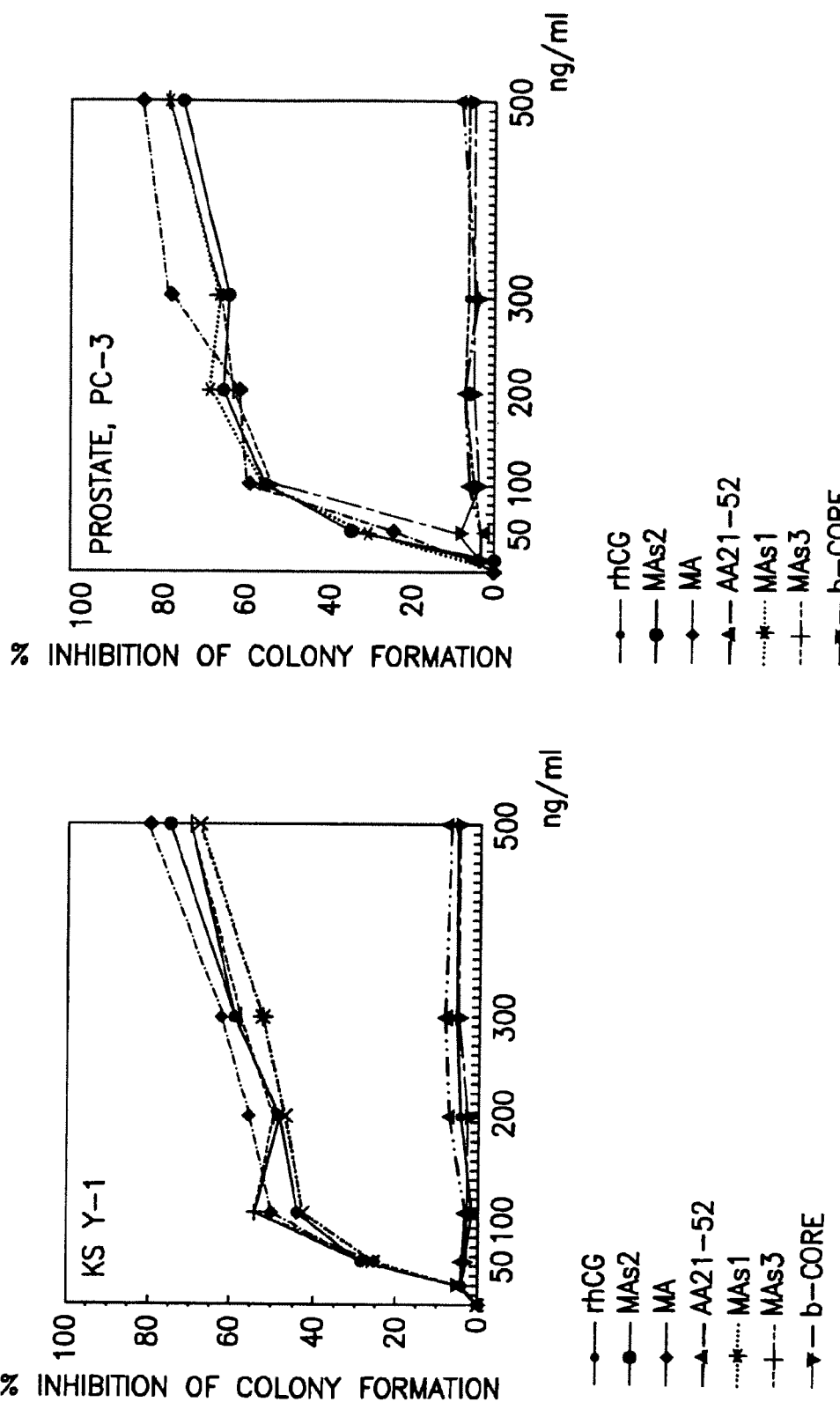

FIG. 3A: Kaposi sarcoma (KSY-1)

FIG. 3B: Prostate carcinoma cell line (PC4)

Figure 3D:
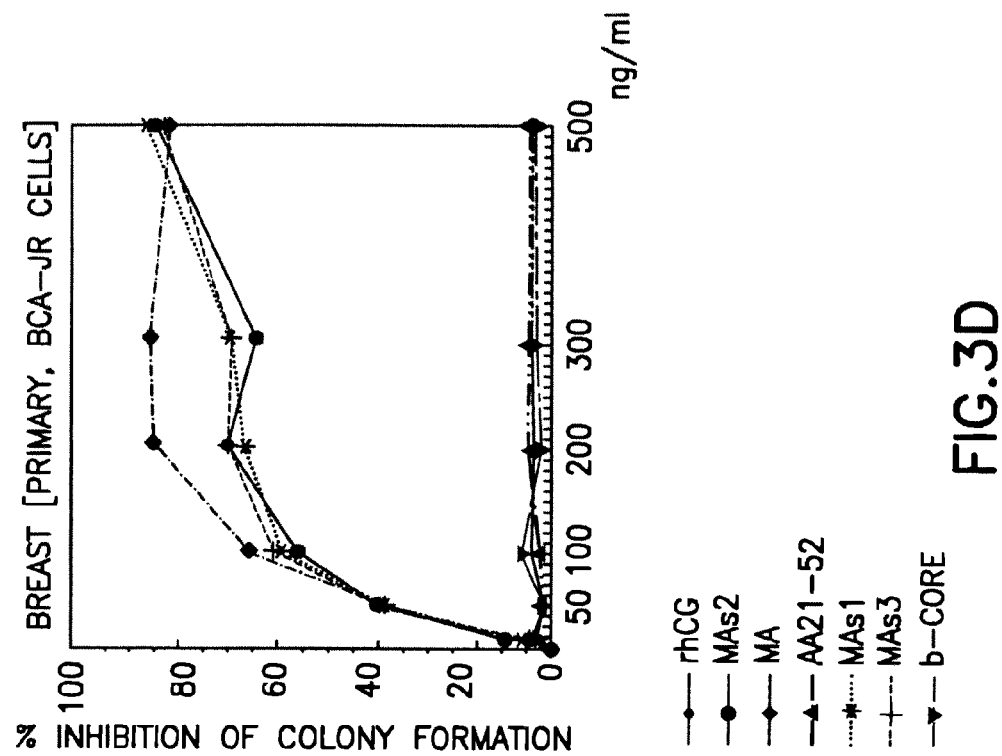
Figure 3C:
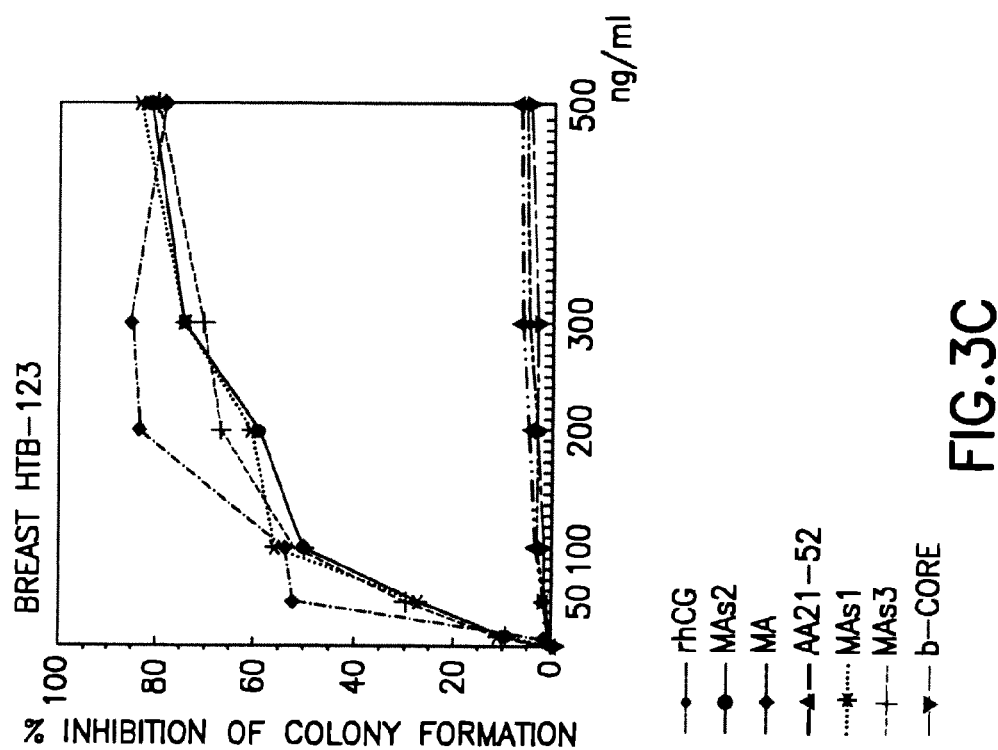

FIG. 3C: breast carcinoma cell line (HCB124)

FIG. 3D: primary breast cancer cells from biopsy of a intraductal breast carcinoma and cultured for 3 days.

FIGS. 3E-3H Dose dependent cell killing (apoptosis) by MA as measured by trypan blue exclusion and Annexin V staining (41).

Figure 3F:
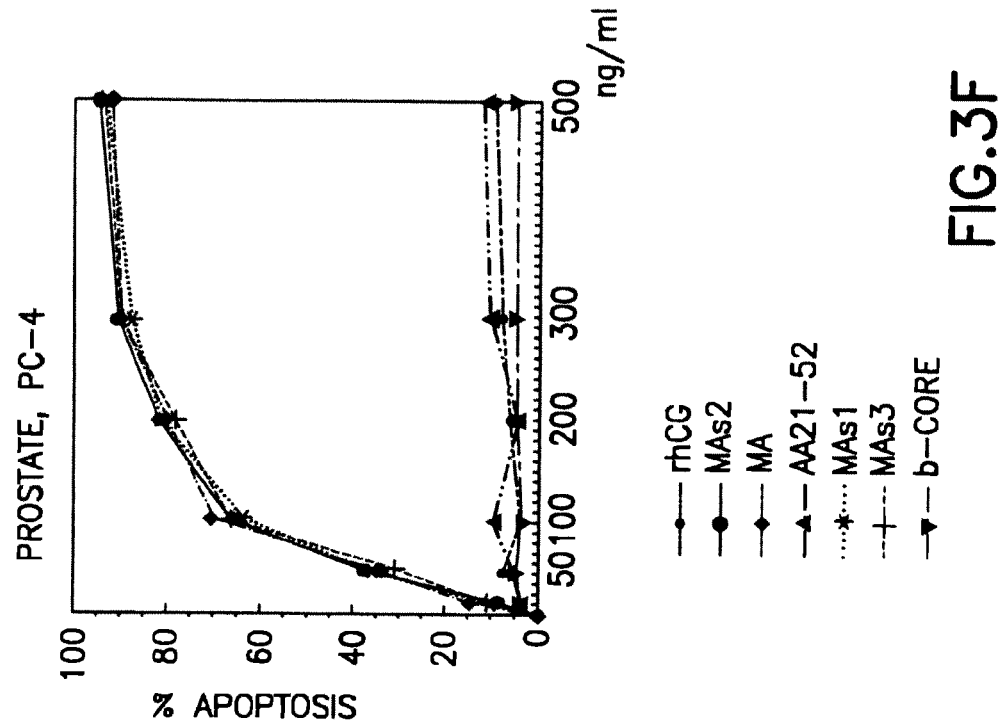
Figure 3E:
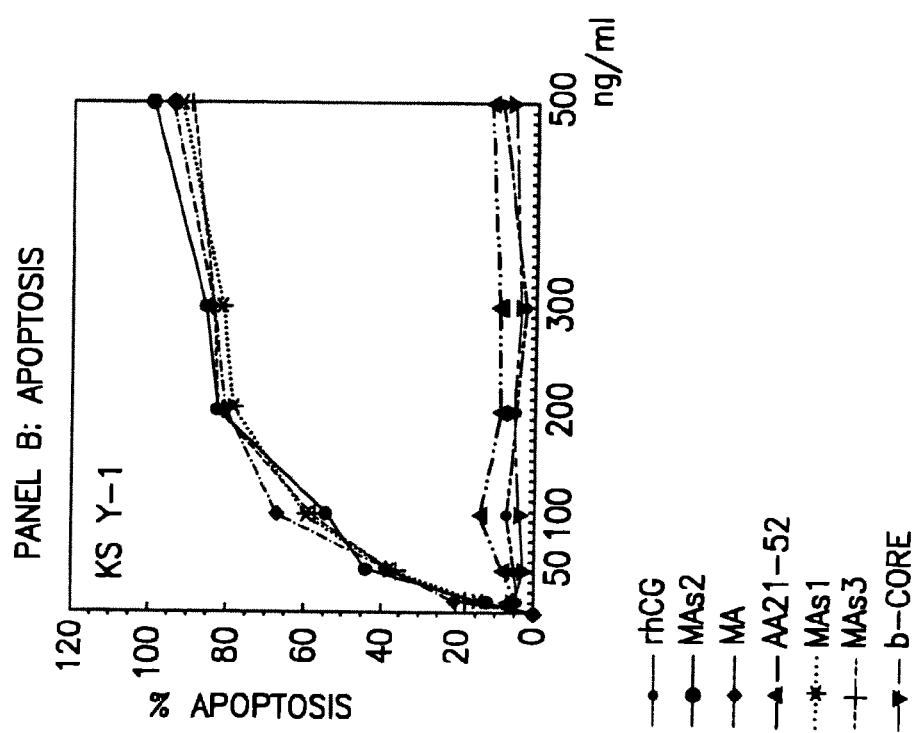

FIG. 3E: KSY-1 cells

FIG. 3F: Prostate carcinoma (PC3)

Figure 3H:
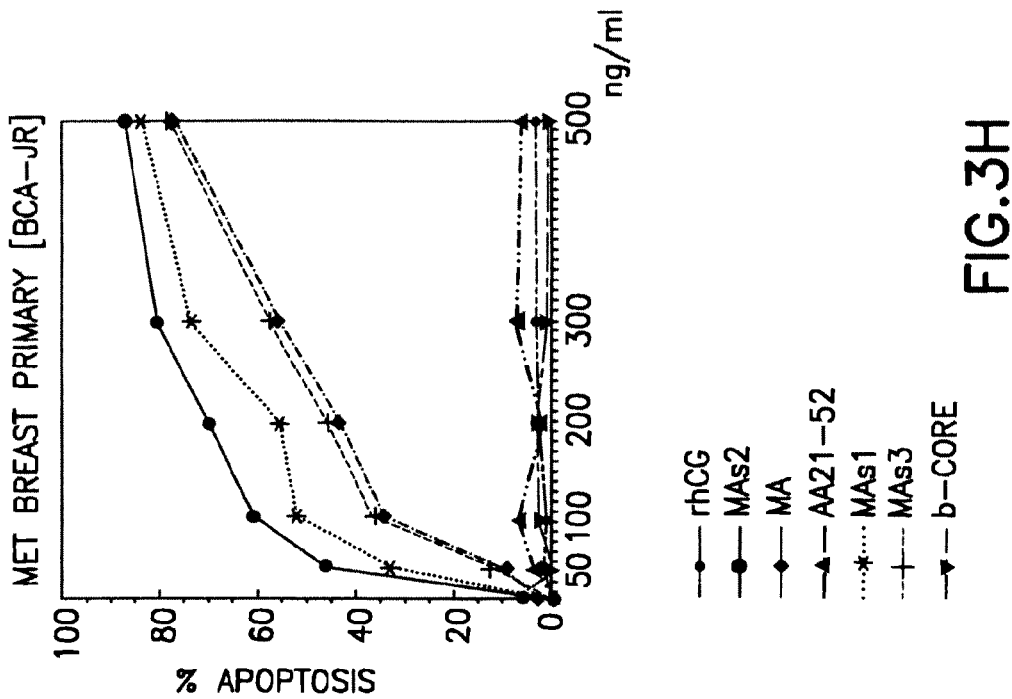
Figure 3G:
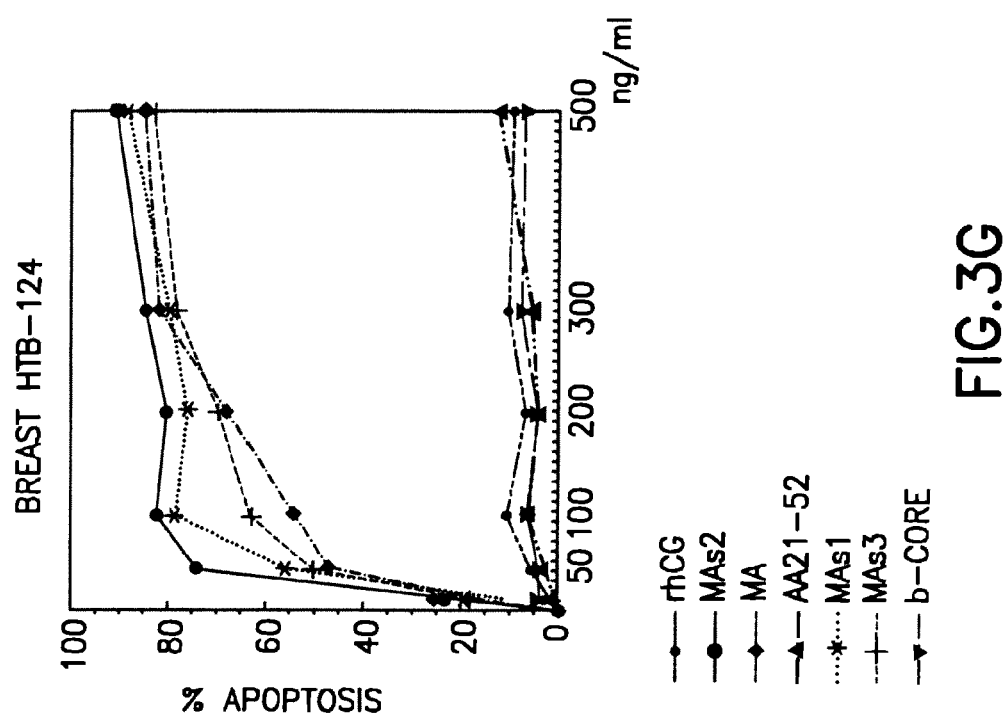
Figure 41:
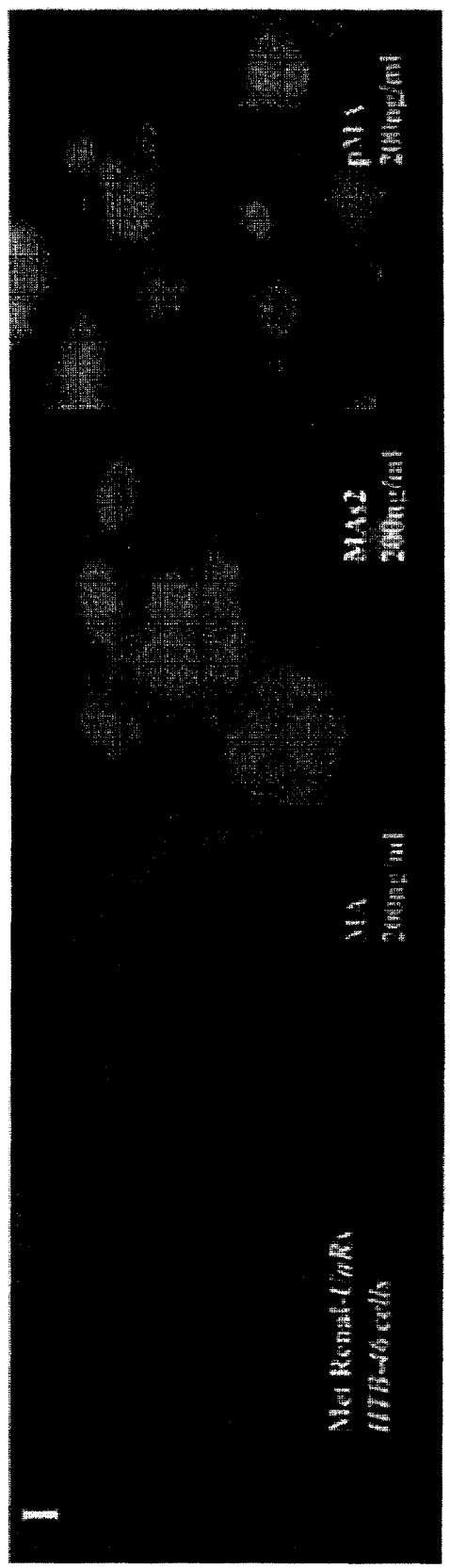

FIG. 3G: breast carcinoma (HTB 124)

FIG. 3H: Breast carcinoma (primary intraductal breast carcinoma biopsied tissue
 □CR127 is purified hCG.
 ▲AA 21-52 (control peptide)
 ◆MA
 *$MA_{S1}$
 ●$MA_{S2}$
 +$MA_{S3}$ FIG. 4. Three-dimensional confocal microscopic analysis showing selective induction of apoptosis of human neoplastic cells by MA.

is Panel A: Confocal microscopy results showing normal nuclear morphology in human normal cells following high doses of MA.

Panel B: Induction of apoptosis in KSY-1 cells.

Panels C and F: Induction of apoptosis in two prostate carcinoma cell lines.

Panel D: Induction of apoptosis in gliobastoma cells (HTB16).

Panel E: Induction of apoptosis in cell lines from carcinomas of the breast (HBT124).

Panel G: Induction of apoptosis in pancreatic cancer cells (CRL 1682).

Panel H: Induction of apoptosis in lung cancer cells (HTB-184).

Panel I: Induction of apoptosis in renal cancer cells (HTB-46).

Panels J and K: Representative examples using the prostate and breast carcinomas (PCANJ and BCAJR, respectively).

Figure 5A:
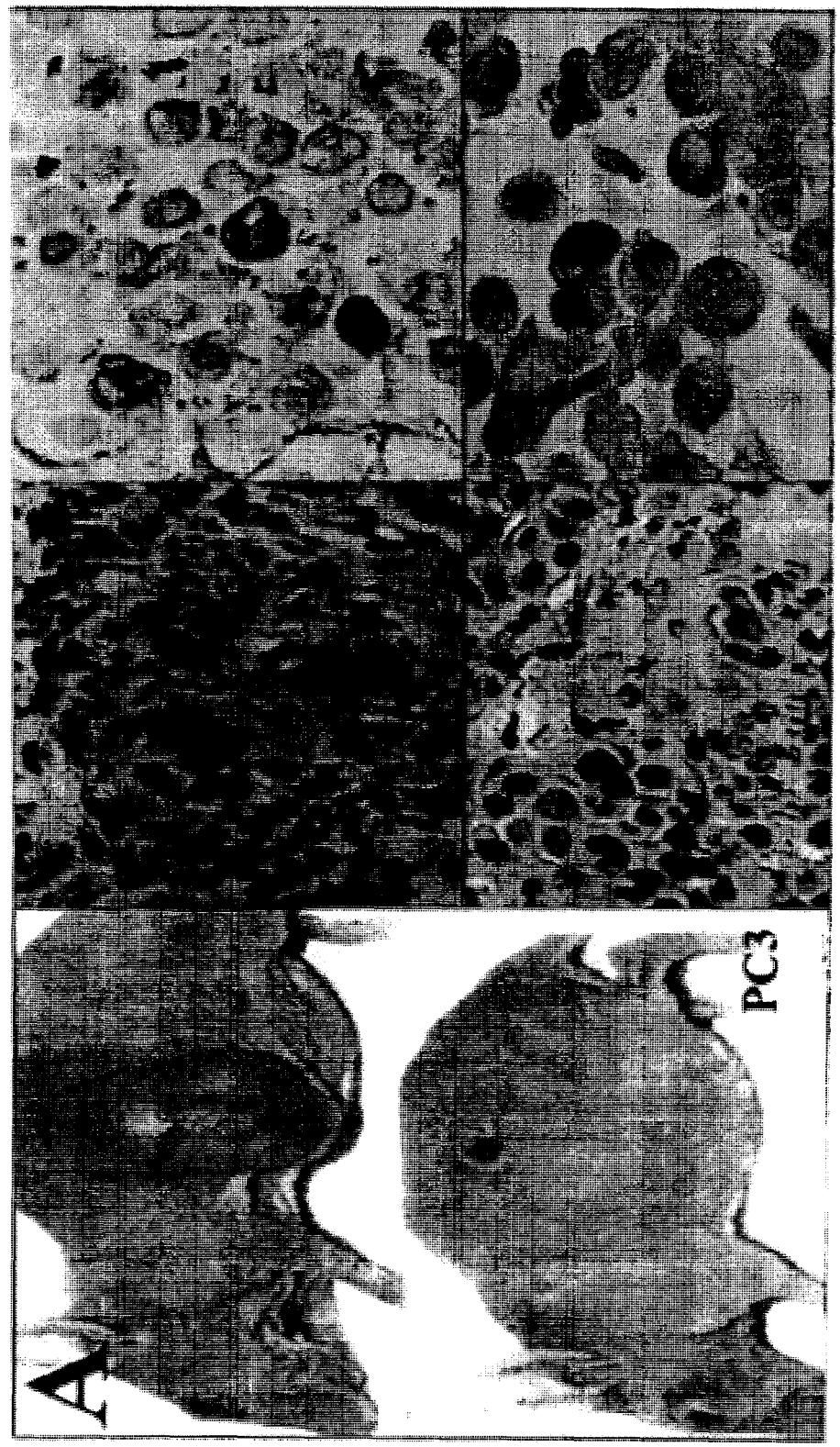
Figure 5B:
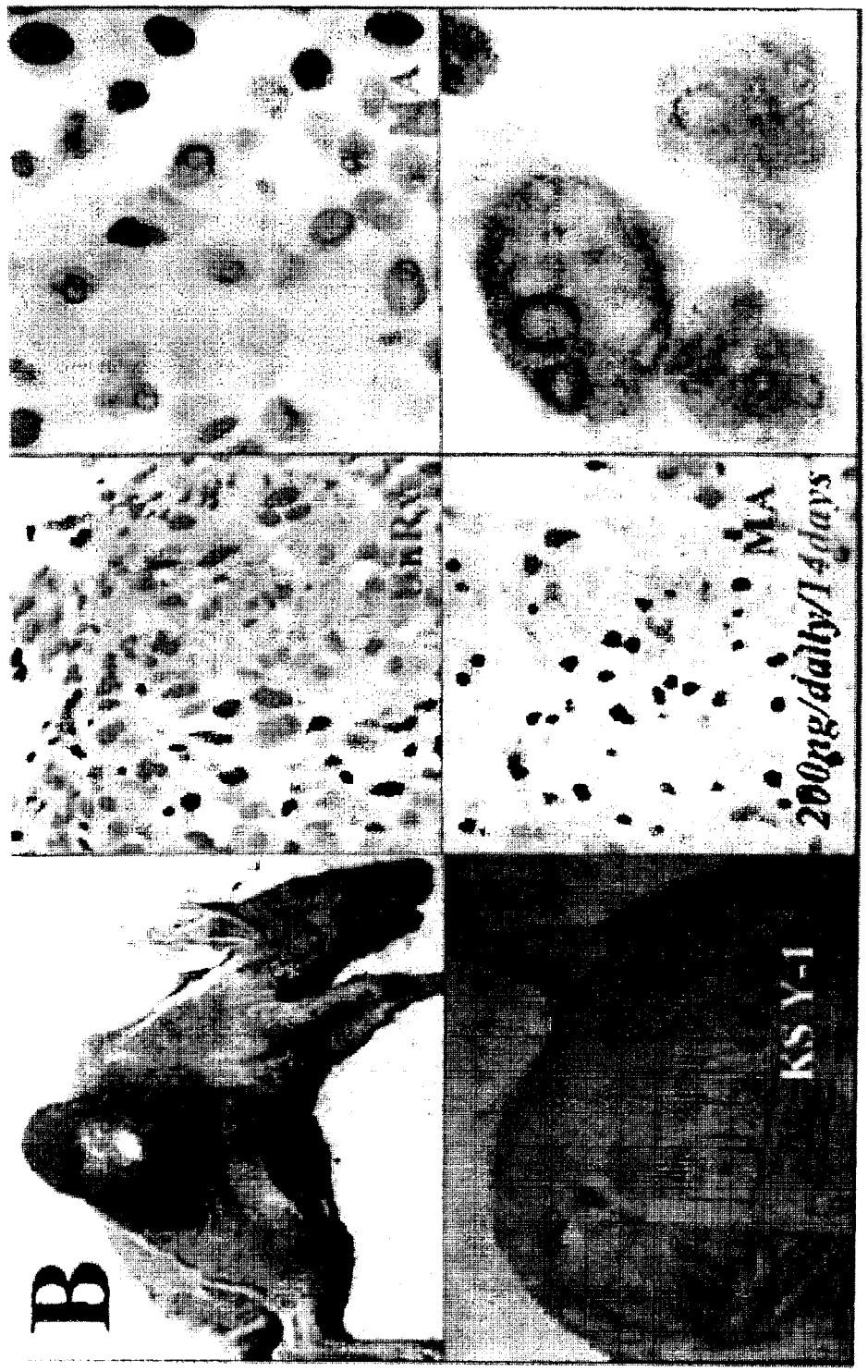
Figure 5C:
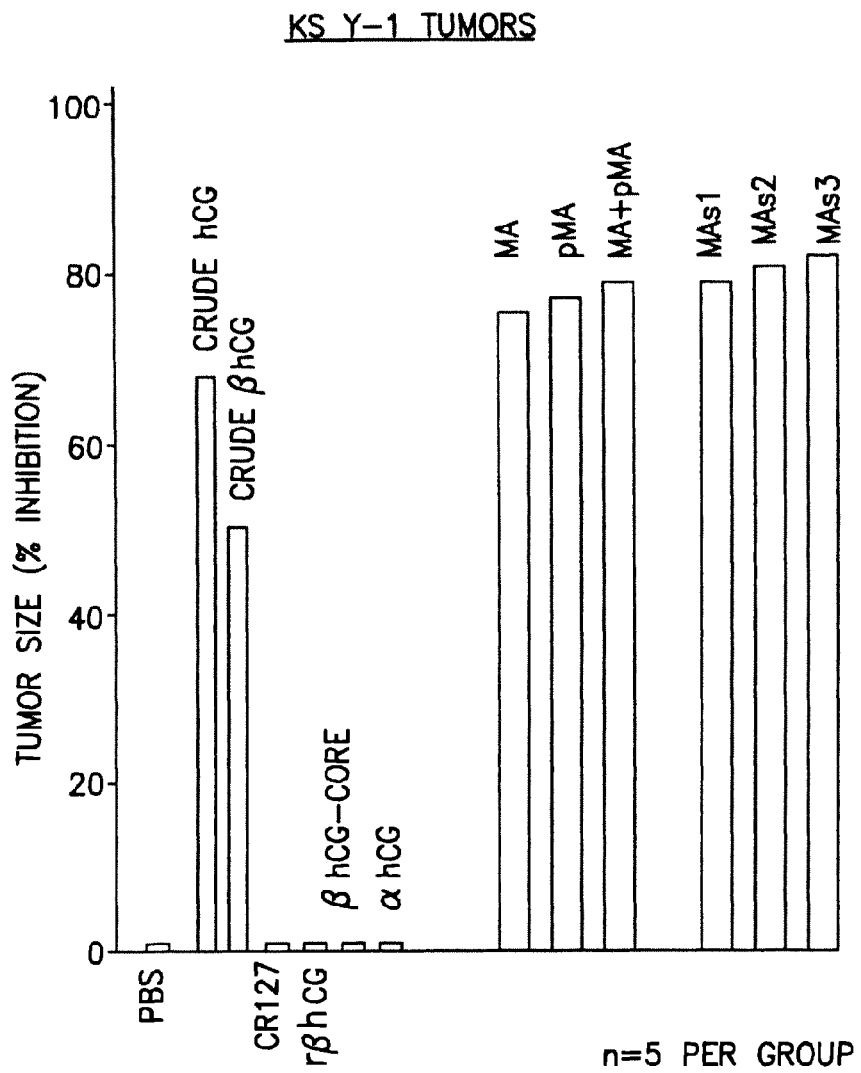
Figure 6A:
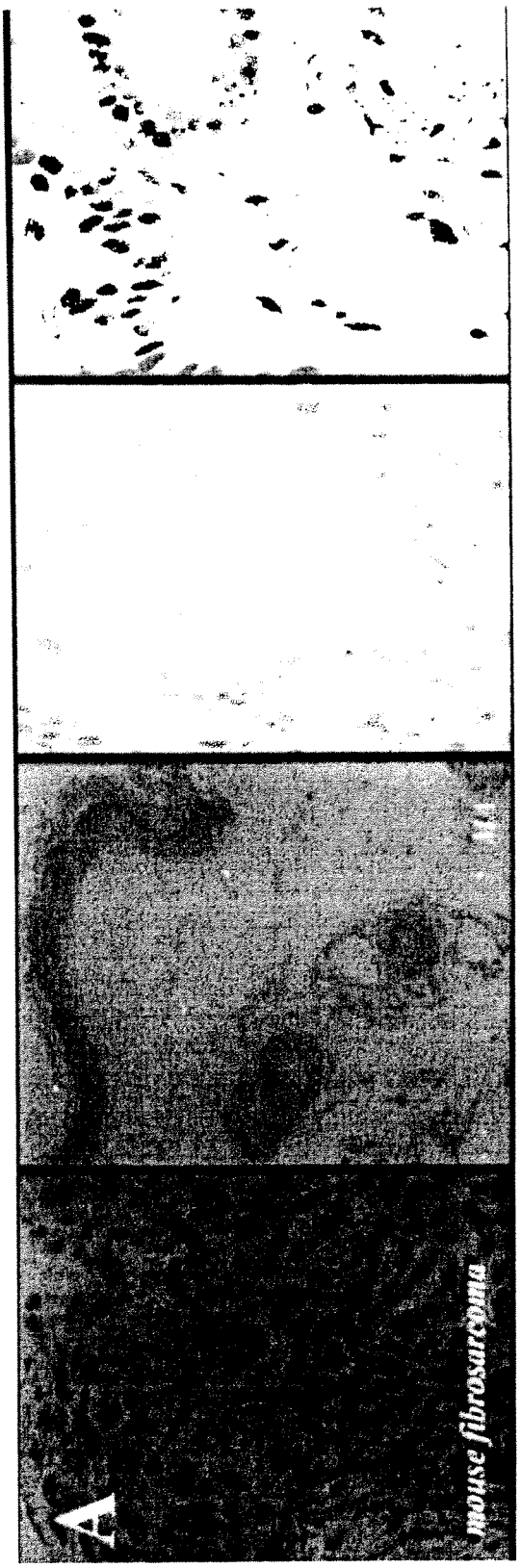
Figure 6B:
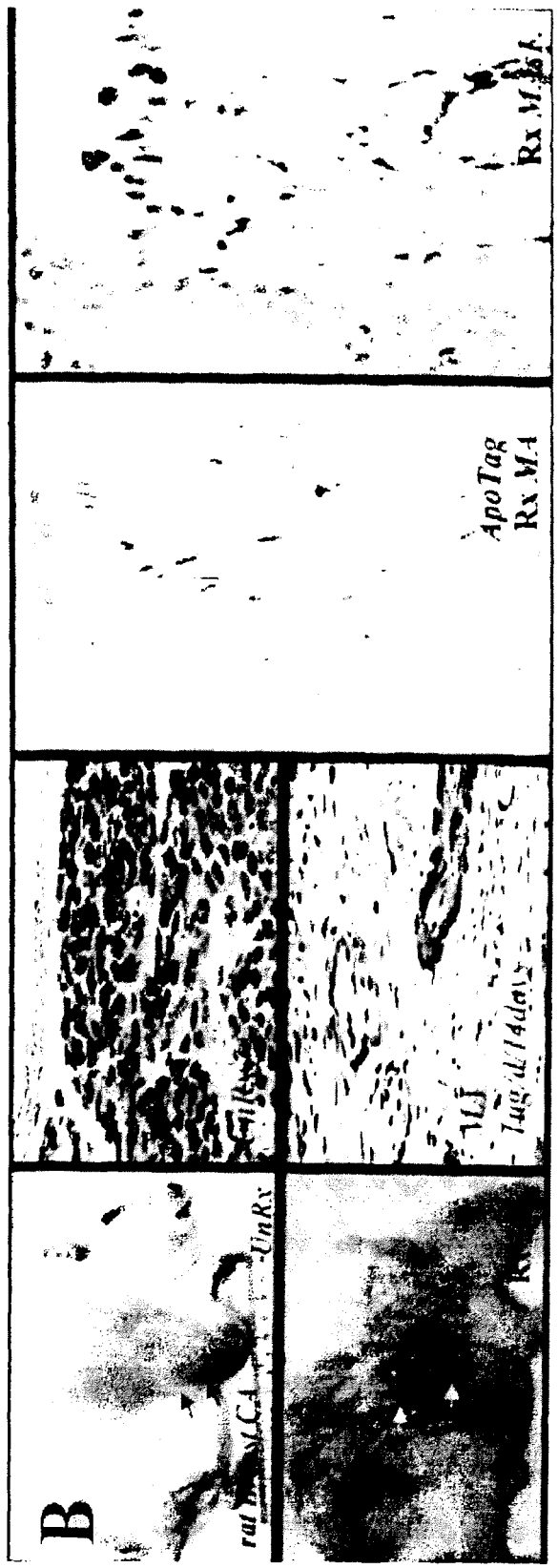
Figure 6C:
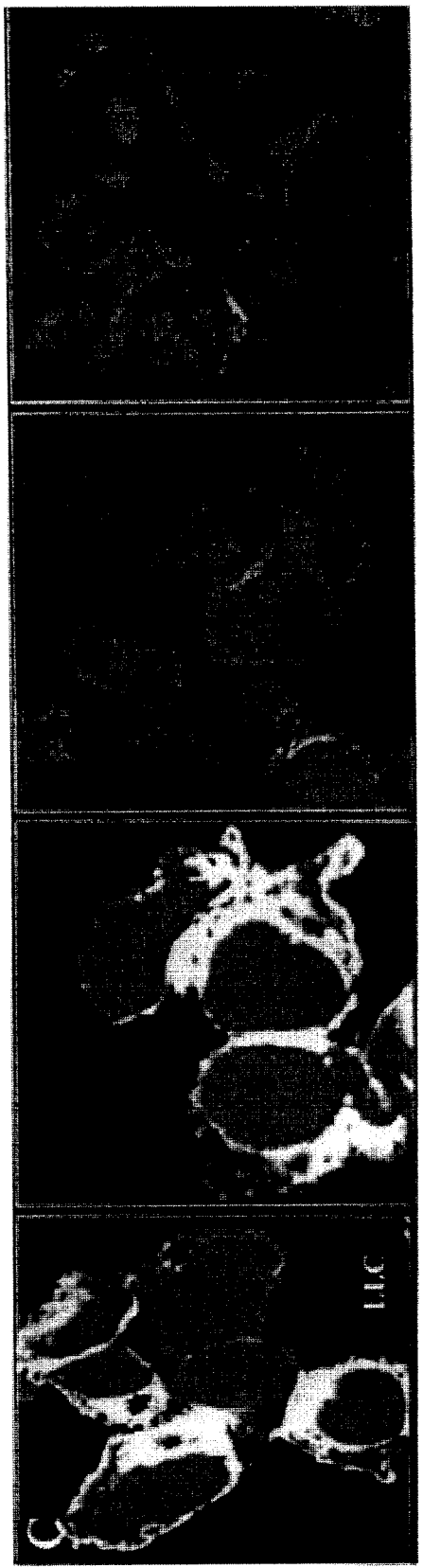
Figure 6D:

FIG. 5. Inhibition of development of tumors in immunodeficient mice transplanted with human cancer cells.

Panel A: Top left shows gross appearance of untreated prostate carcinoma tumor (PC3); top middle shows histological appearance of untreated tumor; top right shows MA histology of MA-treated tumor, showing hypocellularity and degenerative changes of remaining cells. Second row left shows gross appearance of MA-treated prostate carcinoma showing marked tumor regression; middle and right show histology of MA- and $MA_{S2}$-treated tumor showing hypocellularity and degenerative changes of the cells.

Panel B: Top left shows gross appearance of untreated KS tumor; top middle shows histology of untreated KS tumor; top right shows histology of MA-treated tumor showing dying cells. Bottom left shows mouse with KS tumor abolished after MA treatment; histology of MA-treated tumor showing dying cells; bottom right shows KS cells undergoing apoptosis after treatment with $MA_{S2}$. Brown color in cells of bottom right box is APO-TAG indicating apoptosis.

Panel C: Inhibition of tumor size by suboptimal doses (about 60 pMples) of MA (SEQ ID NO: 2); pMA (SEQ ID NO: 3); $MA_{S1}$ (SEQ ID NO: 4) and $MA_{S2}$ (SEQ ID NO: 5) in comparison with CR127, pure recombinant β-hCG, αhCG, and pure native glycosylated β-core, crude preparations of hCG (APL, Wyeth-Ayrest) and β-hCG (CG10, Sigma).

FIG. 6. Anti-tumor effects of MA peptides on spontaneous tumor growth in immunocompetent mice and rats.

Panel A: Results of treatment of mouse fibrosarcomas with MA for 2 weeks; left panel shows results with untreated cells; left center shows hemotoxin and eosin (H&E) staining in MA-treated cells showing hypocellularity; right center and right show TUNEL assays, indicating apoptosis.

Panel B: Results of treatment of one rat with a tumor of approximately 3×3 cm leading to complete tumor regression. Left top shows gross external appearance of massive carcinoma of the breast. Left bottom shows treated animal with tumor resolution. Center-left shows H&E staining in untreated mouse (top) and MA-treated mouse (below). Right and center-right show histological sections from MA- and $MA_{S1}$-treated rat, stained with APO-TAG to show apoptosis.

Panel C: Confocal microscopy of Lewis lung carcinoma cells untreated and after treatment with MA; from left-to-right shows untreated tumor cells, treatment with rβ-hCG (5 μg/ml), native MA (5 μg/ml), and $MA_{S1}$ (5 μg/ml).

Panel D: Confocal microscopy of B16 melanoma carcinoma cells untreated and after treatment with MA, under same conditions as Lewis lung carcinoma cells (Panel C).

Figure 7D:
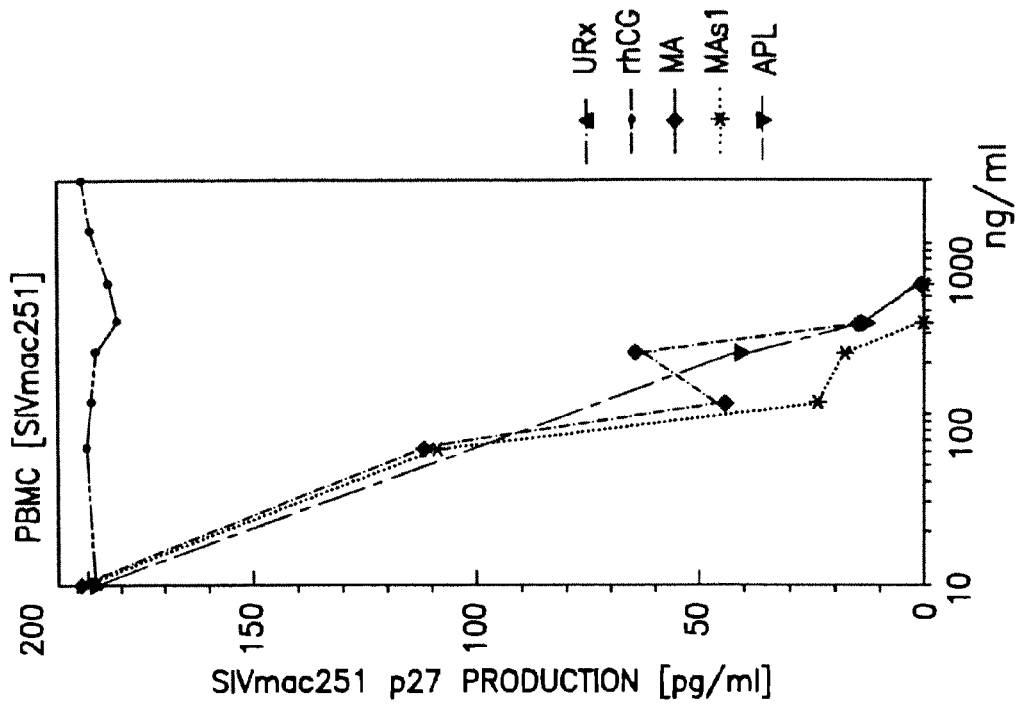
Figure 7C:
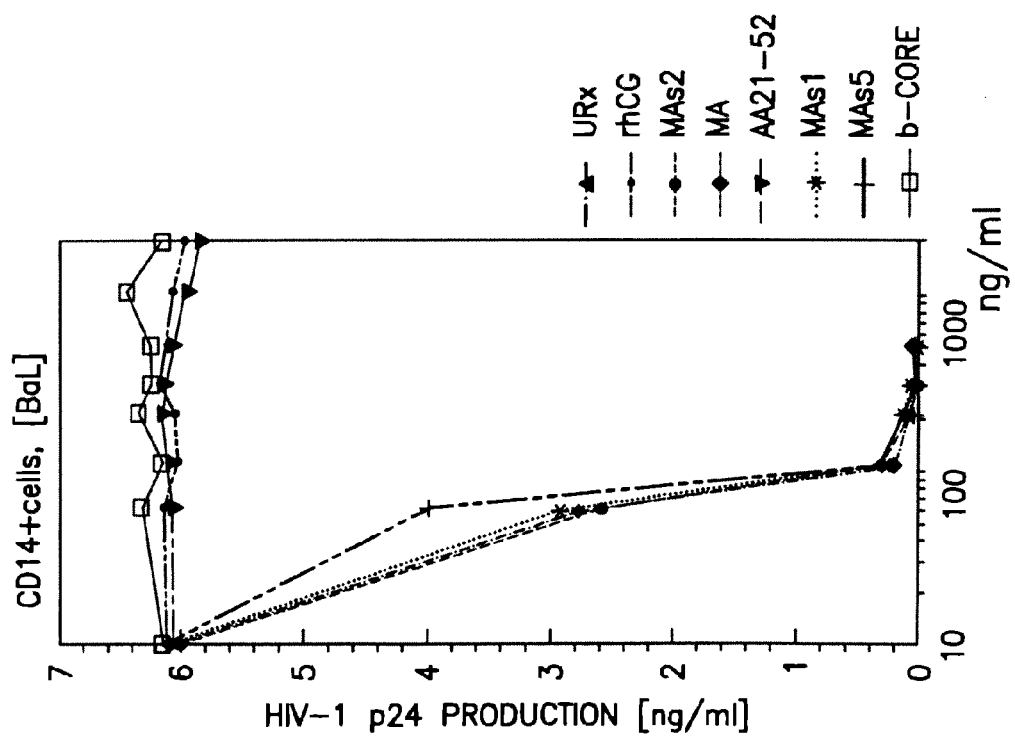

FIG. 7. Inhibition of HIV-1 and SIV replication by MA.

MA, $MA_{S1}$, $MA_{S2}$, and $MA_{S3}$ at approximately 30 to 100 nM inhibit HIV-1 (IIIB) infection of human PBMCs (Panel A); primary CDD4 T-cells (Panel B); HIV-1 Ba-L infection of primary macrophages (Panel C); and $SIV_{MAC\ 251}$ infection of rhesus macaque PBMCs (Panel D).

These cells were derived from PBMCs by enrichment techniques. There was no inhibition by similar concentrations of hCG (CR127) nor by control peptides AA 21-52. In addition, there was no effect of native glycosylated β-core, rβ-hCG, rα-hCG, and a variety of additional control peptides (not shown). MA also inhibited replication of primary HIV-1 isolates in PBMCs (not shown).
 CR127
 ▲AA 21-52 (control peptide)
 ▼untreated control
 ◆MA (native)
 *$MA_{S1}$
 ●$MA_{S2}$
 +$MA_{S3}$ Virus (MOI of 0.001) was added to $10^6$ cells in RPMI-1640 with 10% FCS. One hour later the various polypeptides were added once. The cells cultured for 3 days with 5 ug PHA and 20 i.m. of Il-2/ml at 37°, after which virus was estimated by determining p24 (HIV-1) or p27 (SIV) (Organon-Teknika). Importantly, no toxic side effects of MA occurred on the normal cells as determined by trypan blue, MTT, and 3TdR incorporation assays.

The results are expressed as a mean of triplicate samples with a less than 20% variation in the range of these values.

Figure 8A:
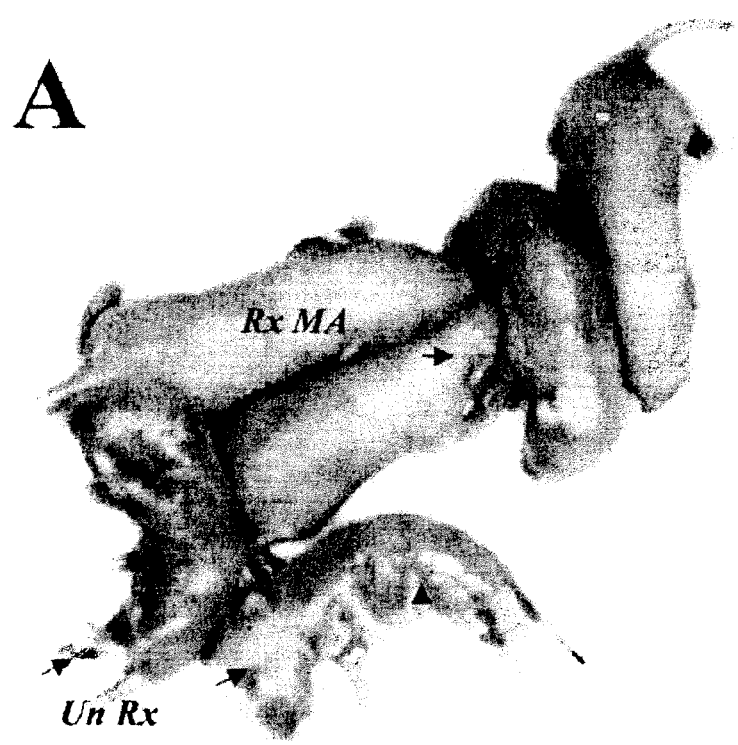
Figure 8B:
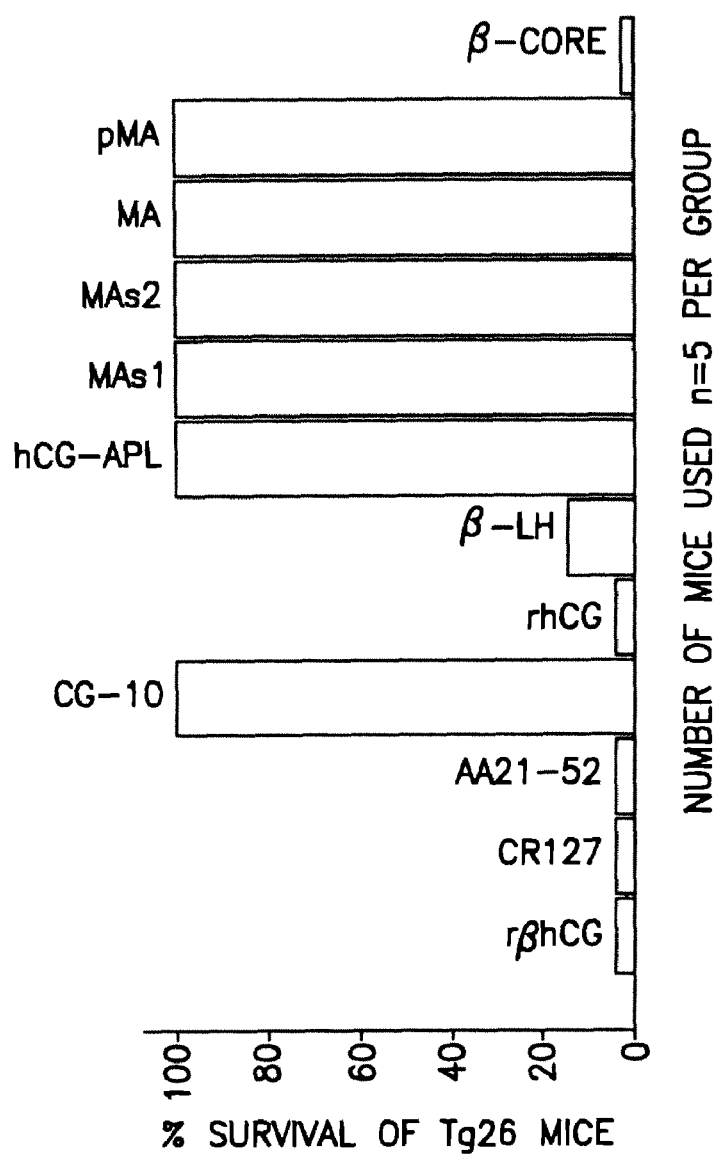
Figure 8C:
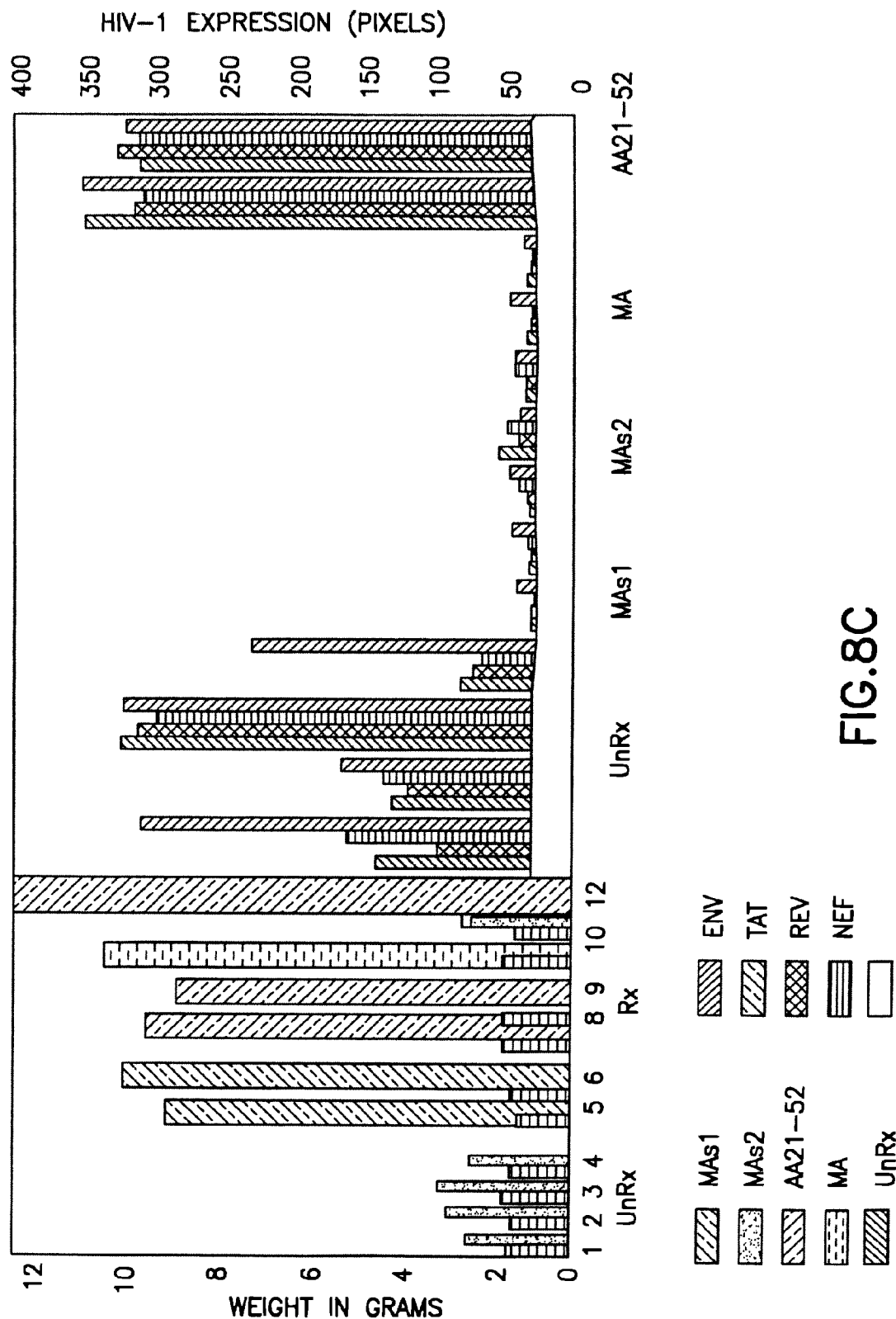

FIG. 8. MA represses HIV-1 gene expression in HIV-1 transgenic mice.

Panel A: Two untreated mice show hyperkeratosis and diminished size (red arrows). In contrast, transgenics breast feeding from mothers treated with native MA (200 ng) for 7 days show normal development.

Panel B: Shows % survival of MA peptide-treated mice as compared to controls.

Panel C: Shows weight gain of MA peptide-treated mice as compared to controls.

Figure 9C:
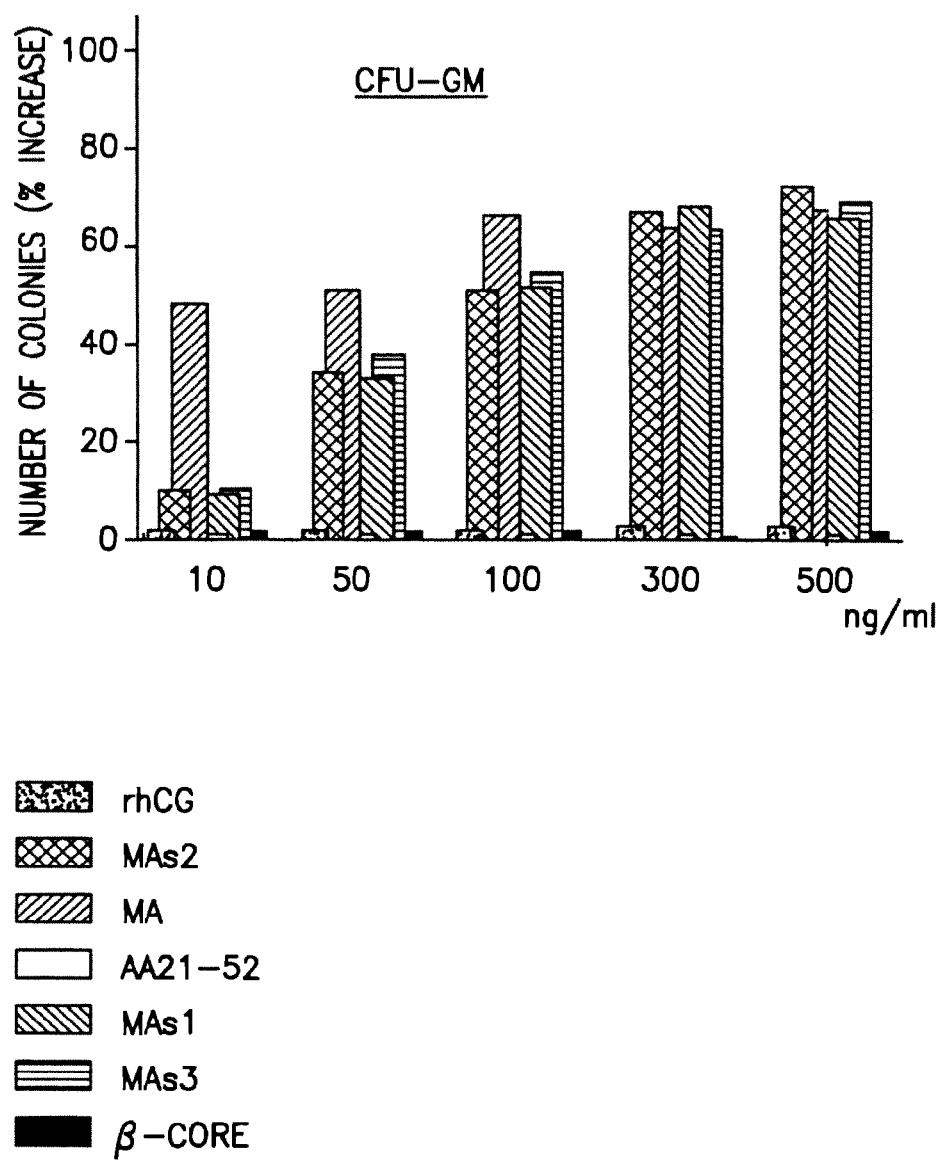
Figure 9D:
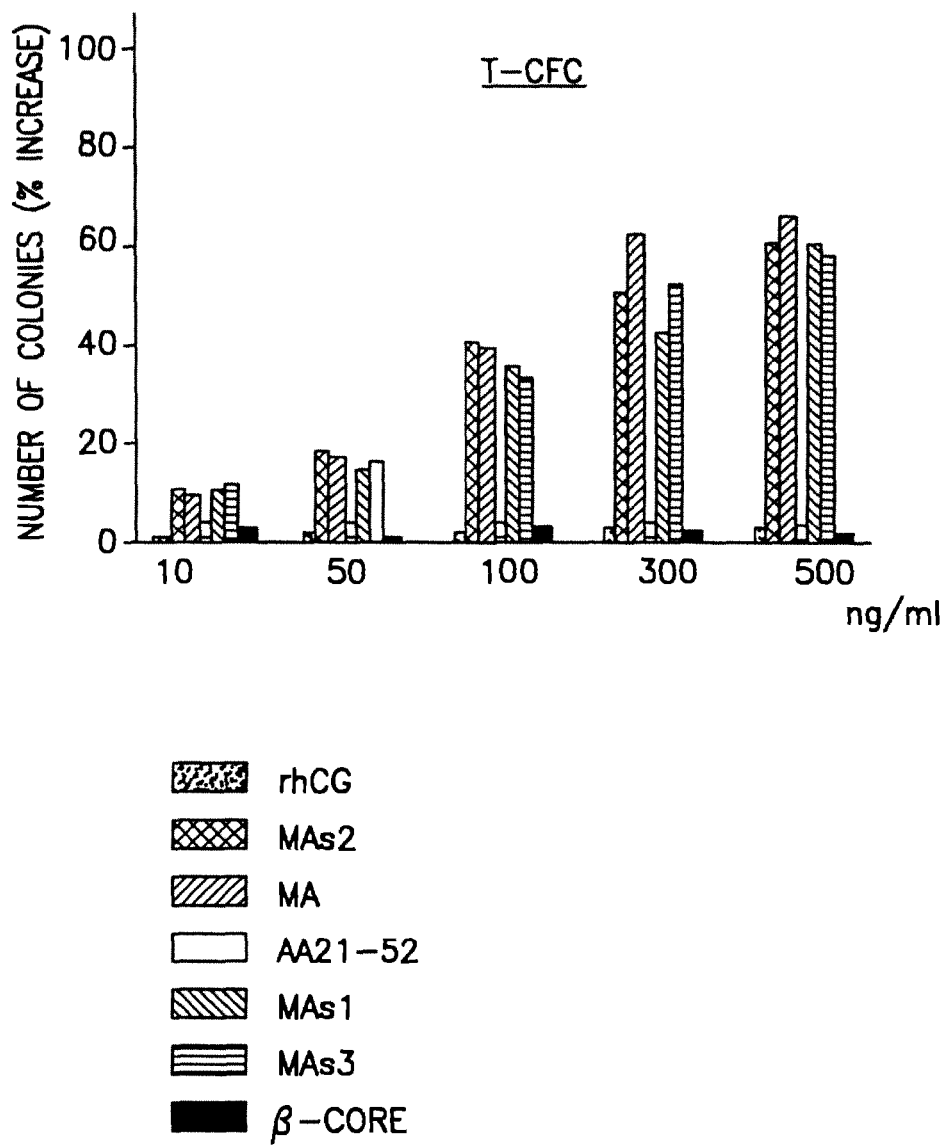

FIG. 9. Pro-hematopoietic effects of MA peptides in vitro using a human bone marrow derived culture.

Panel A: MA promotion of CFU-GEMM, which includes precursors of granulocytes, red blood cells, and macrophages.

Panel B: promotion of BFU-e, which are red blood cell precursors.

Panel C: shows promotion of CFU-GM, which include myeloid (granulocyte) and macrophage precursors.

Panel D: Promotion of T-CFC, which are cells capable of forming colonies of T-cells.

FIG. 10 shows the results of treatment of rats with MA before or after lethal irradiation.

Figure 10A:
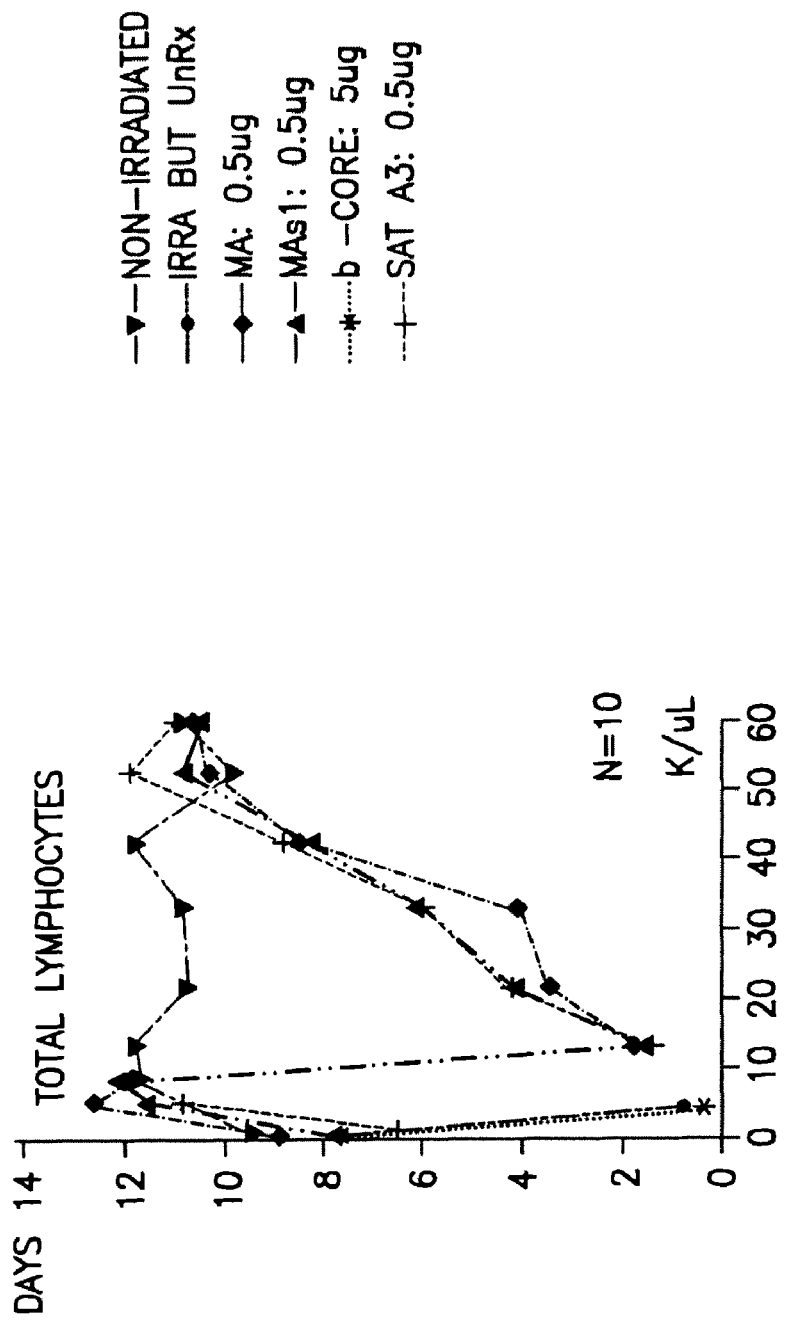
Figure 10C:
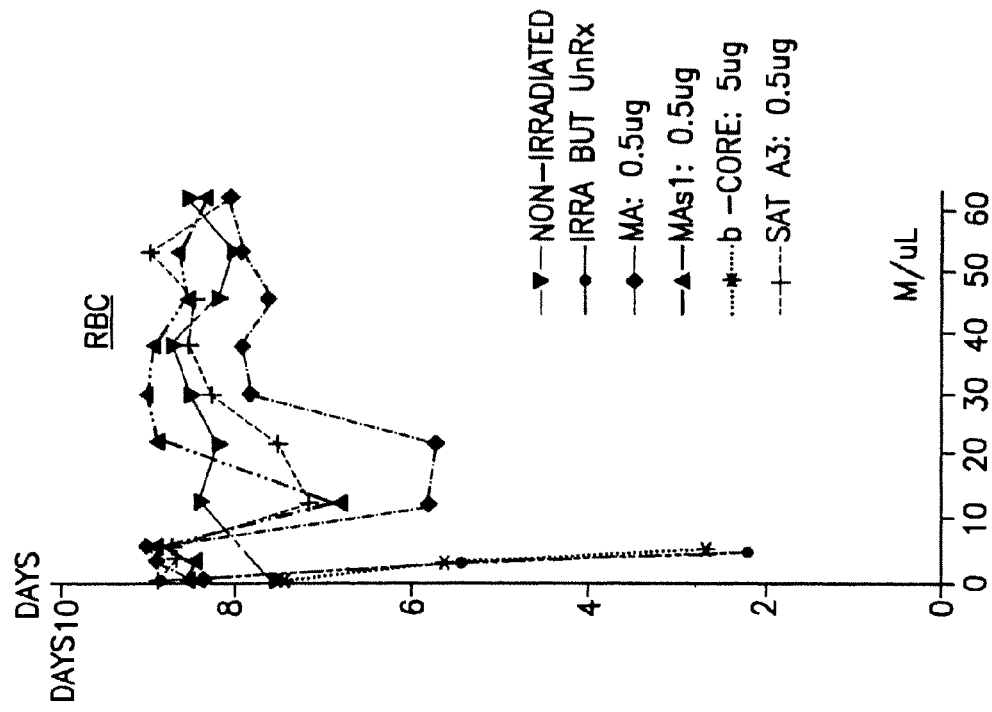
Figure 10B:
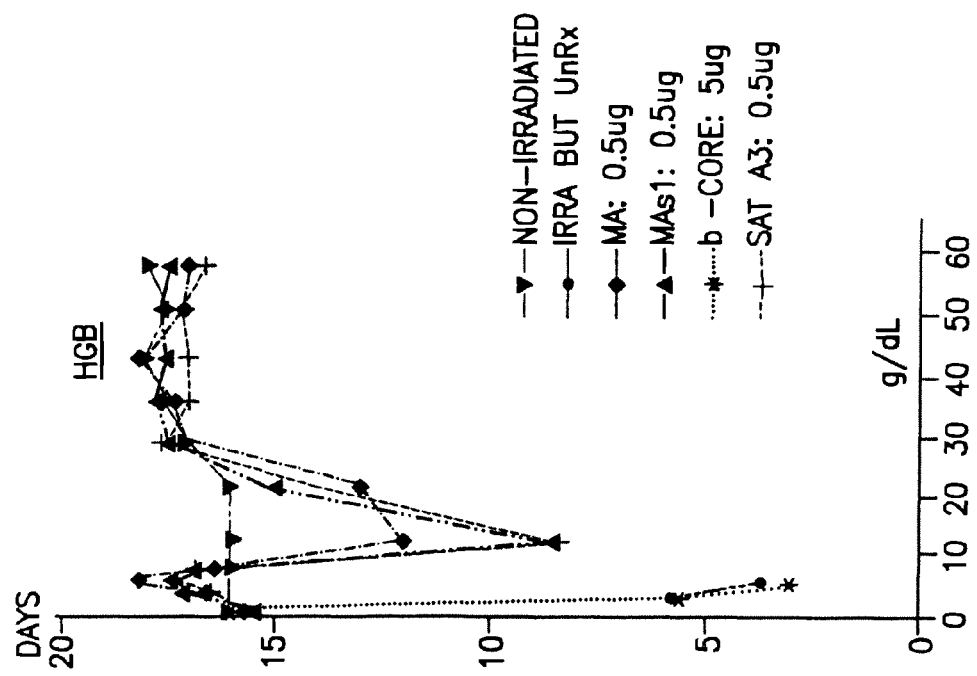
Figure 10D:
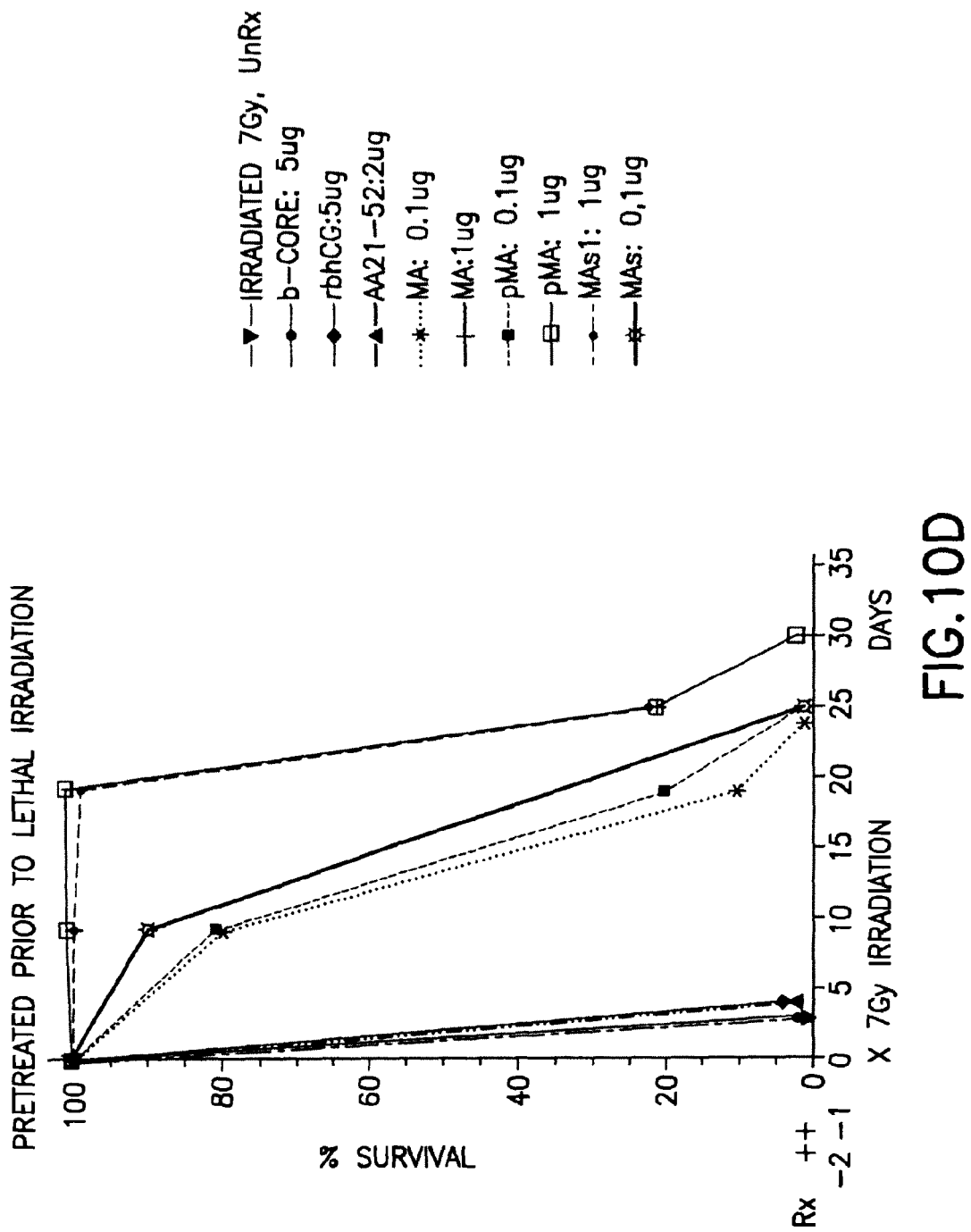

FIG. 10D: Survival of mice treated prior to irradiation.

FIG. 10E: Survival of mice treated during irradiation, with treatment maintained for 4 weeks following irradiation.

FIGS. 10A, 10B, and 10C: Hematopoietic recovery phase in these animals for total lymphocytes (10A), HGB (10B) and RBC (10C).

FIG. 11. Hematopoietic recovery of rats and monkeys.

Figure 11A:
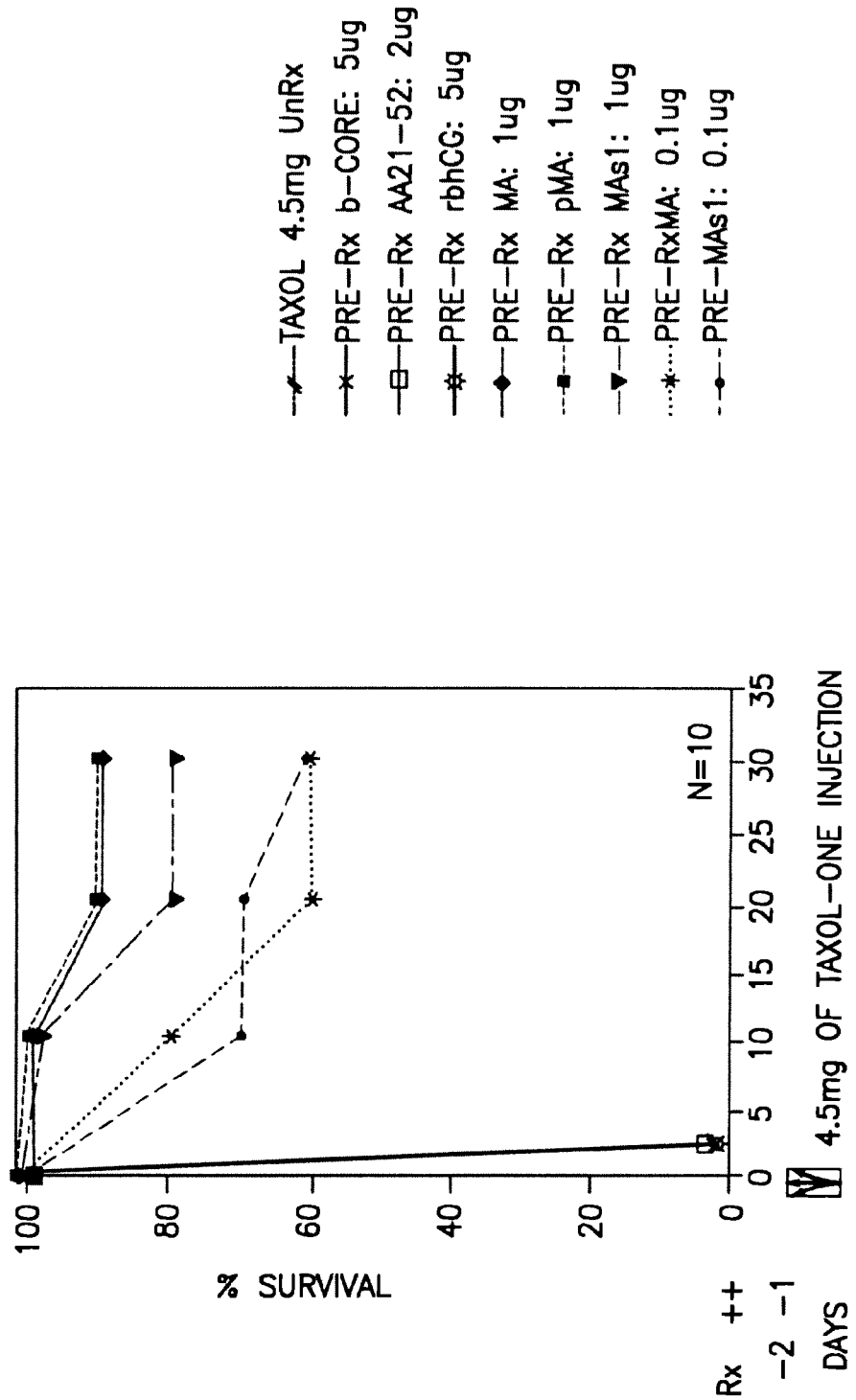
Figure 11B:
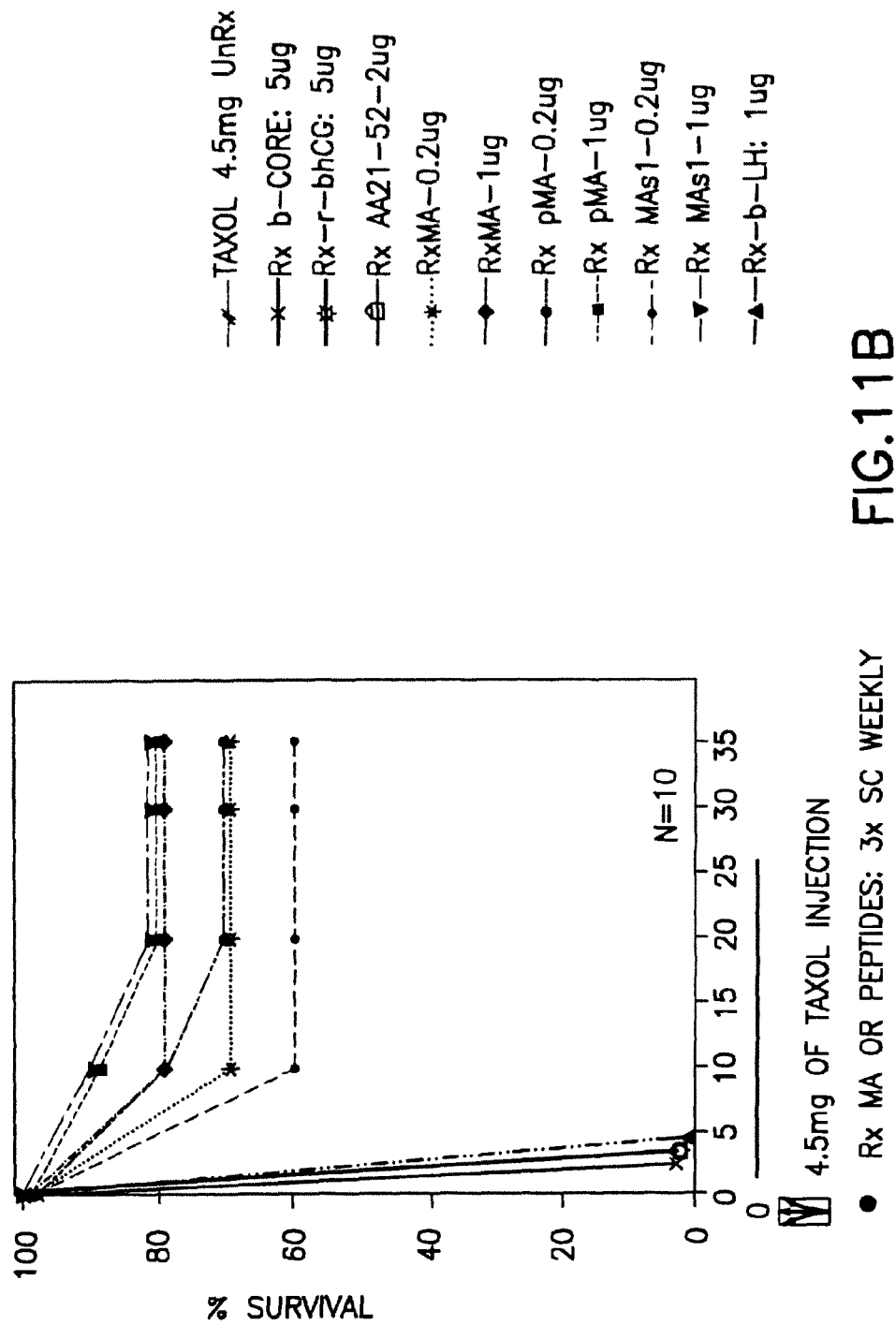
Figures 11C, 11D:
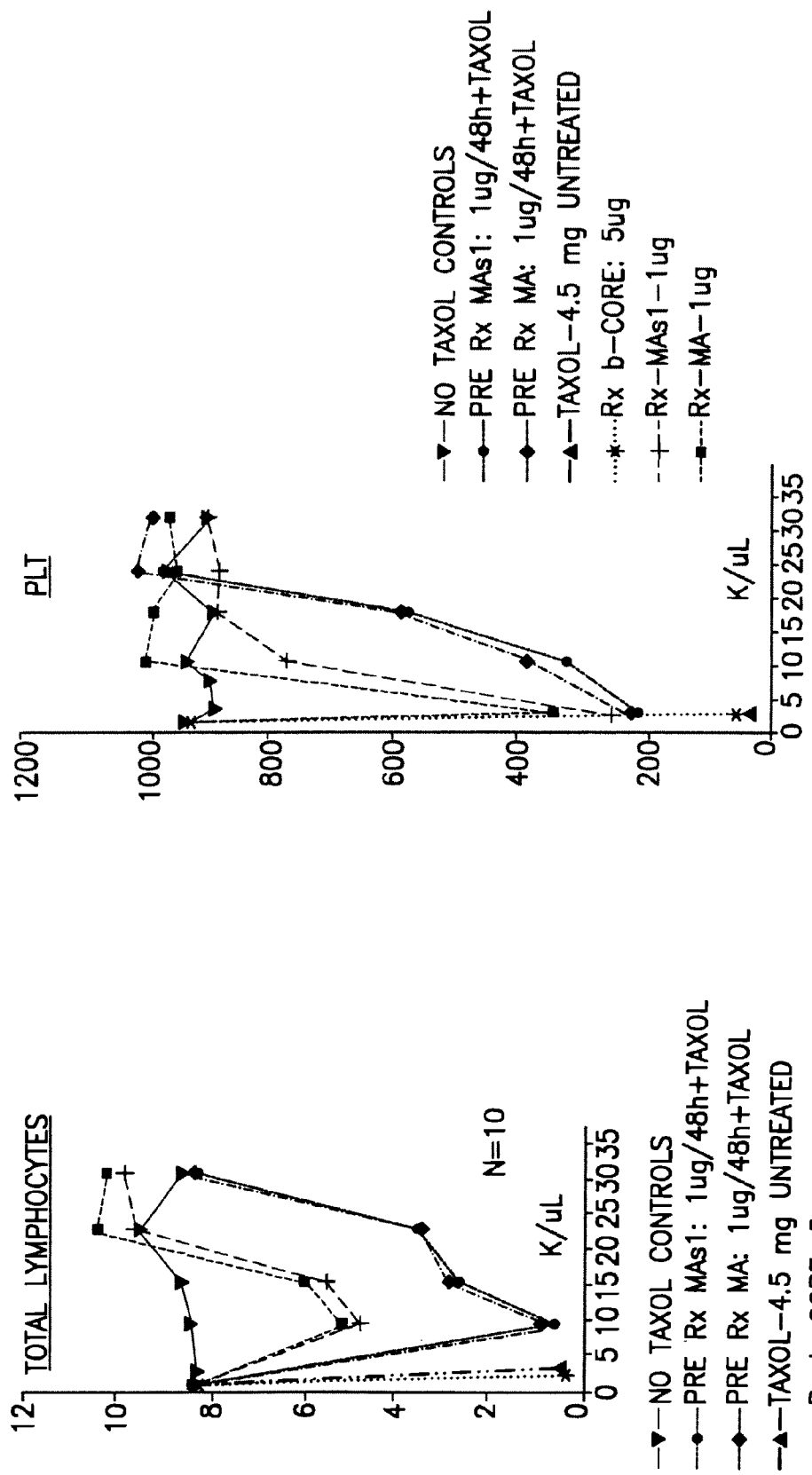

FIGS. 11A and 11B: Rescue of rats from the ultimate lethal effects of high dose paclitaxel (TAXOL™): FIG. 11A shows survival of animals treated prior to administration of paclitaxel; FIG. 11B shows survival of animals undergoing treatment within 24 hours of paclitaxel administration and maintained on 3 weekly injections of 100 ng for four weeks.

Figure 11F:
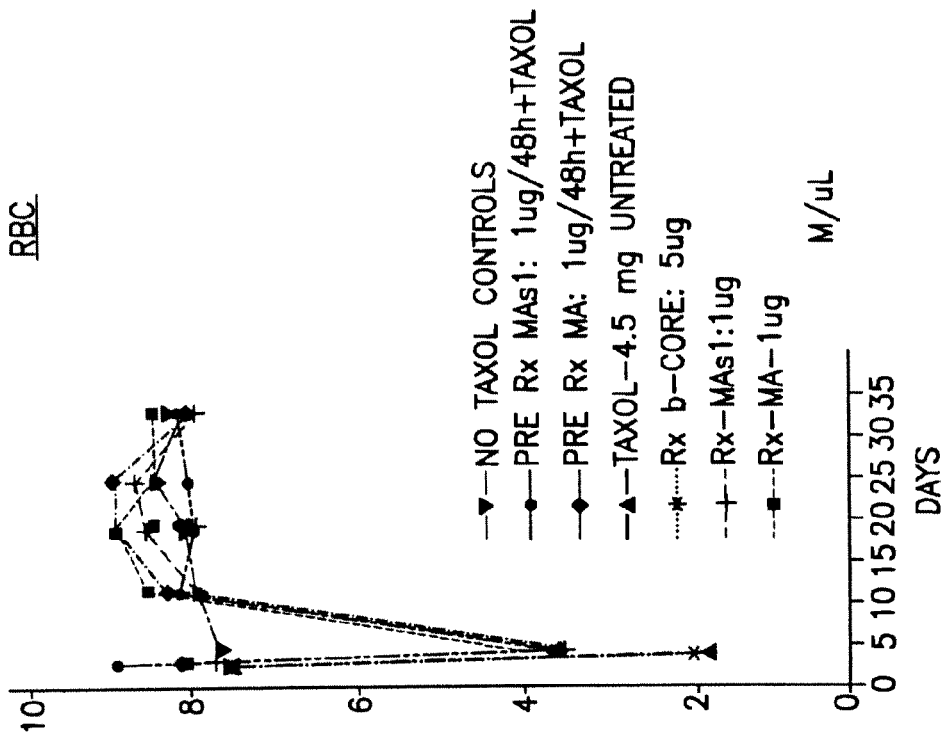
Figure 11E:
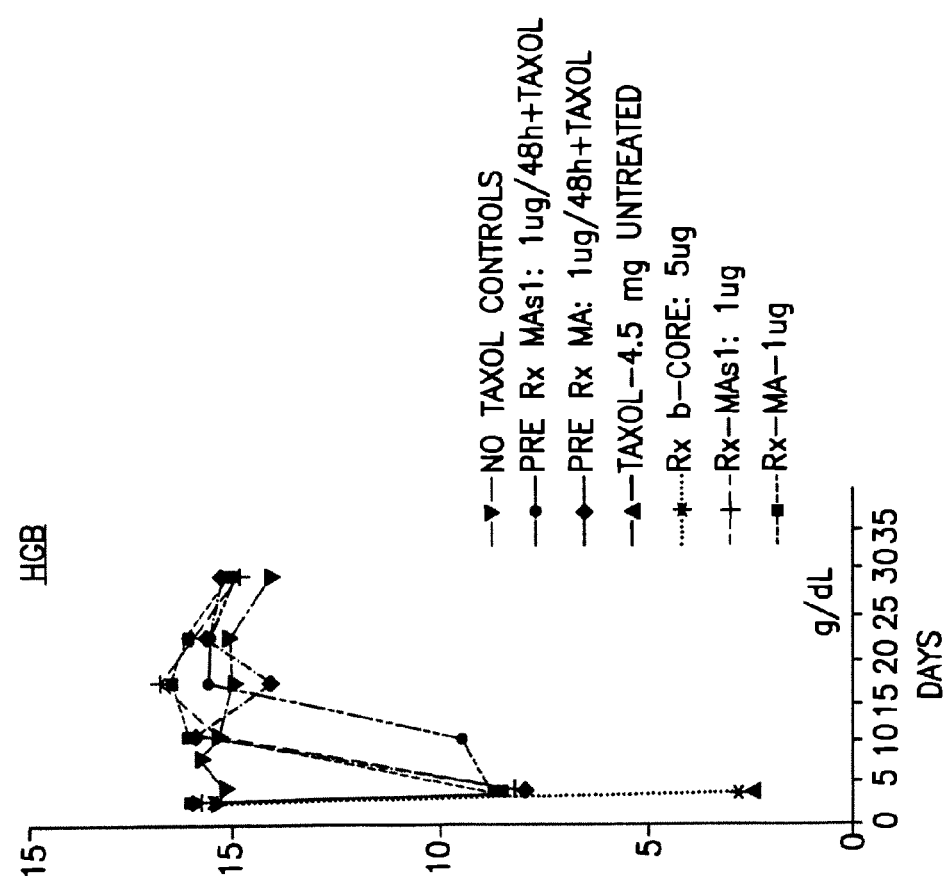
Figures 12A, 12B:
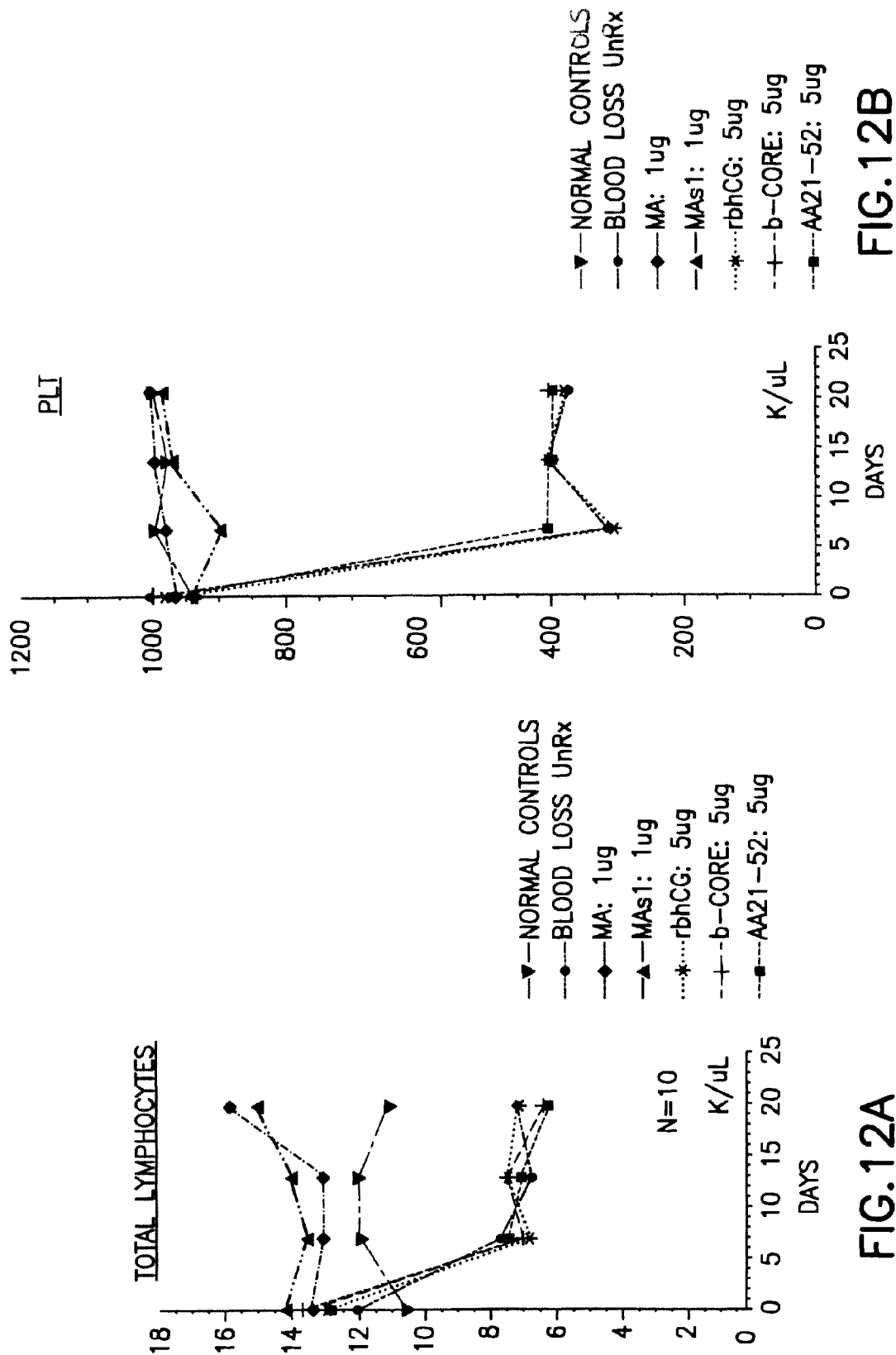
Figure 12D:
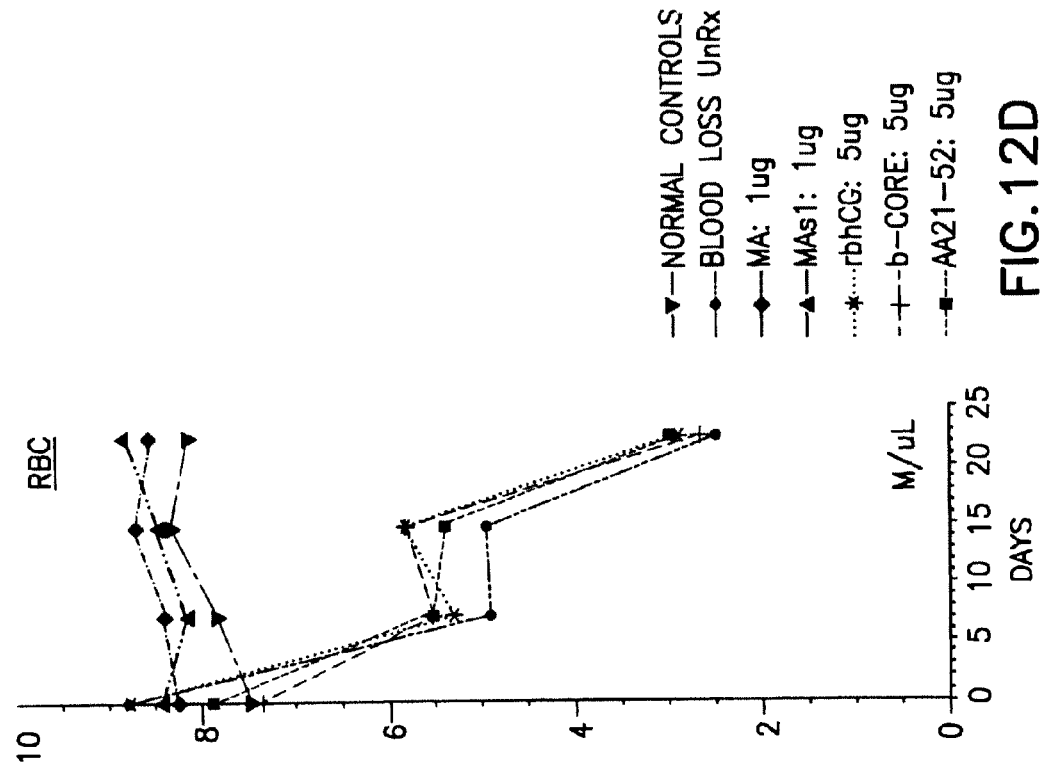
Figure 12C:
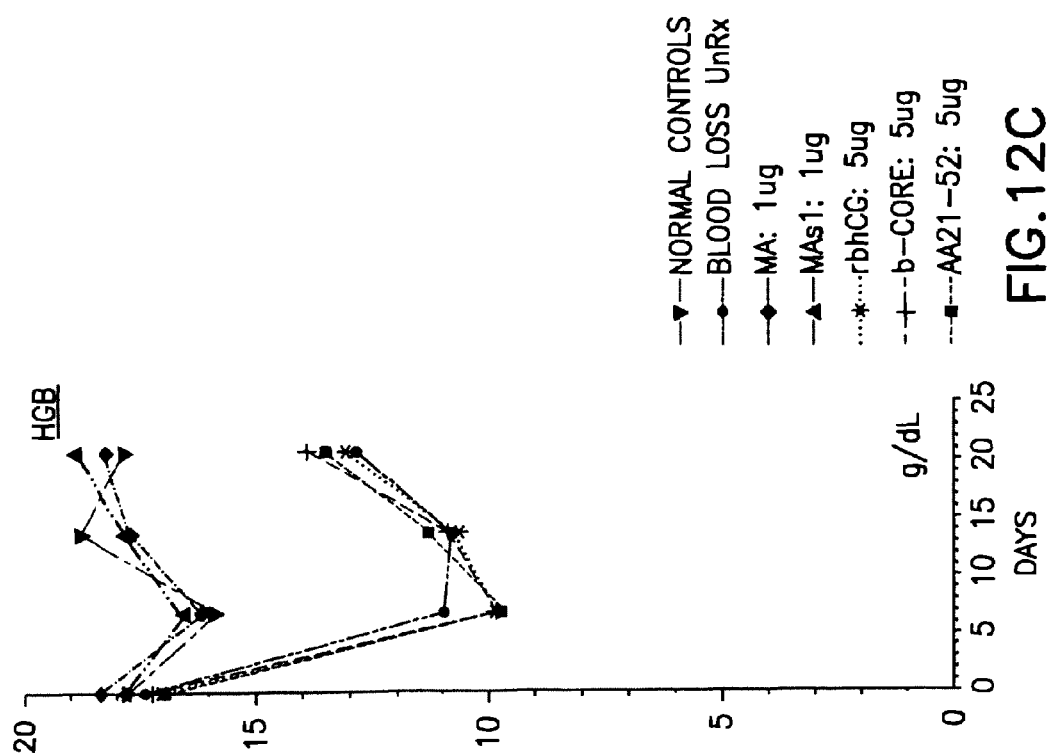
Figure 12E:
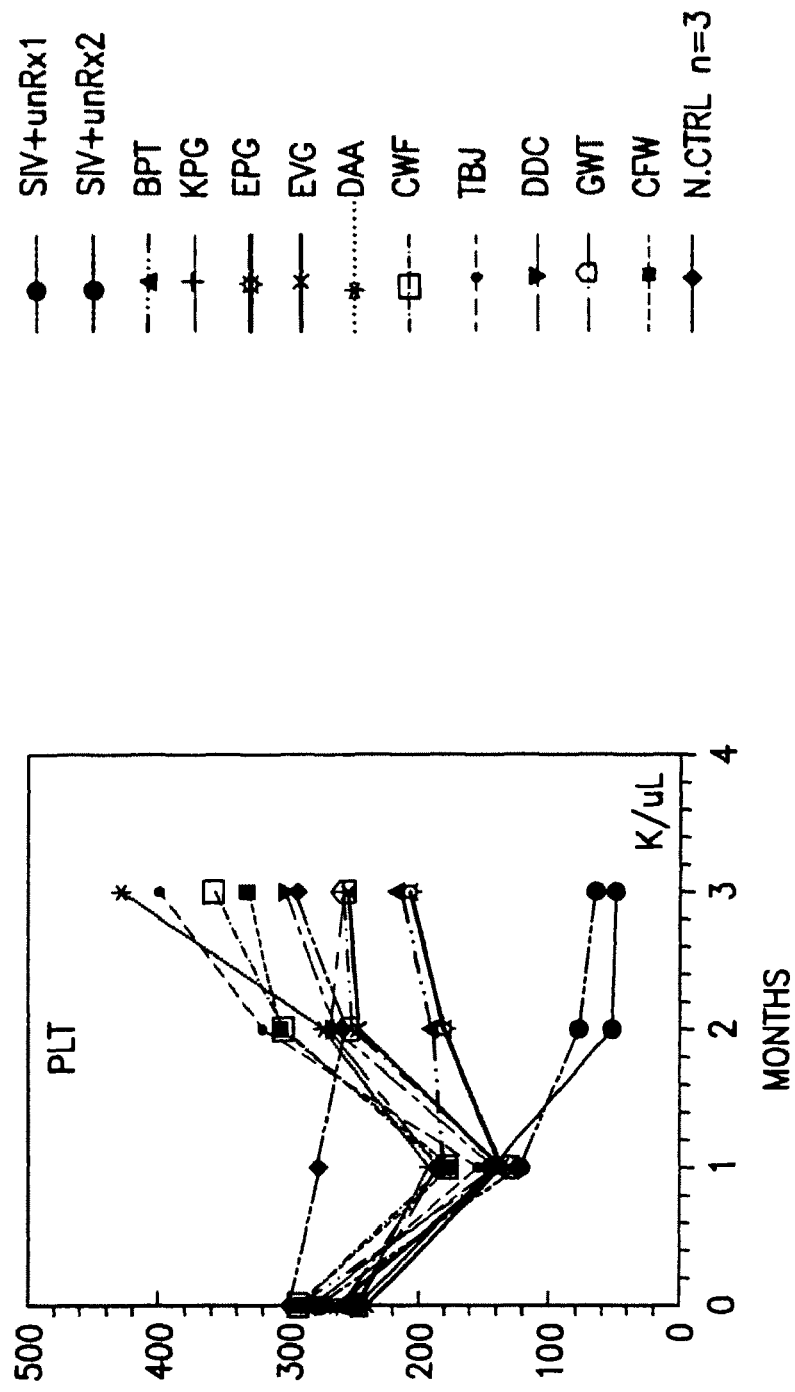
Figure 12F:
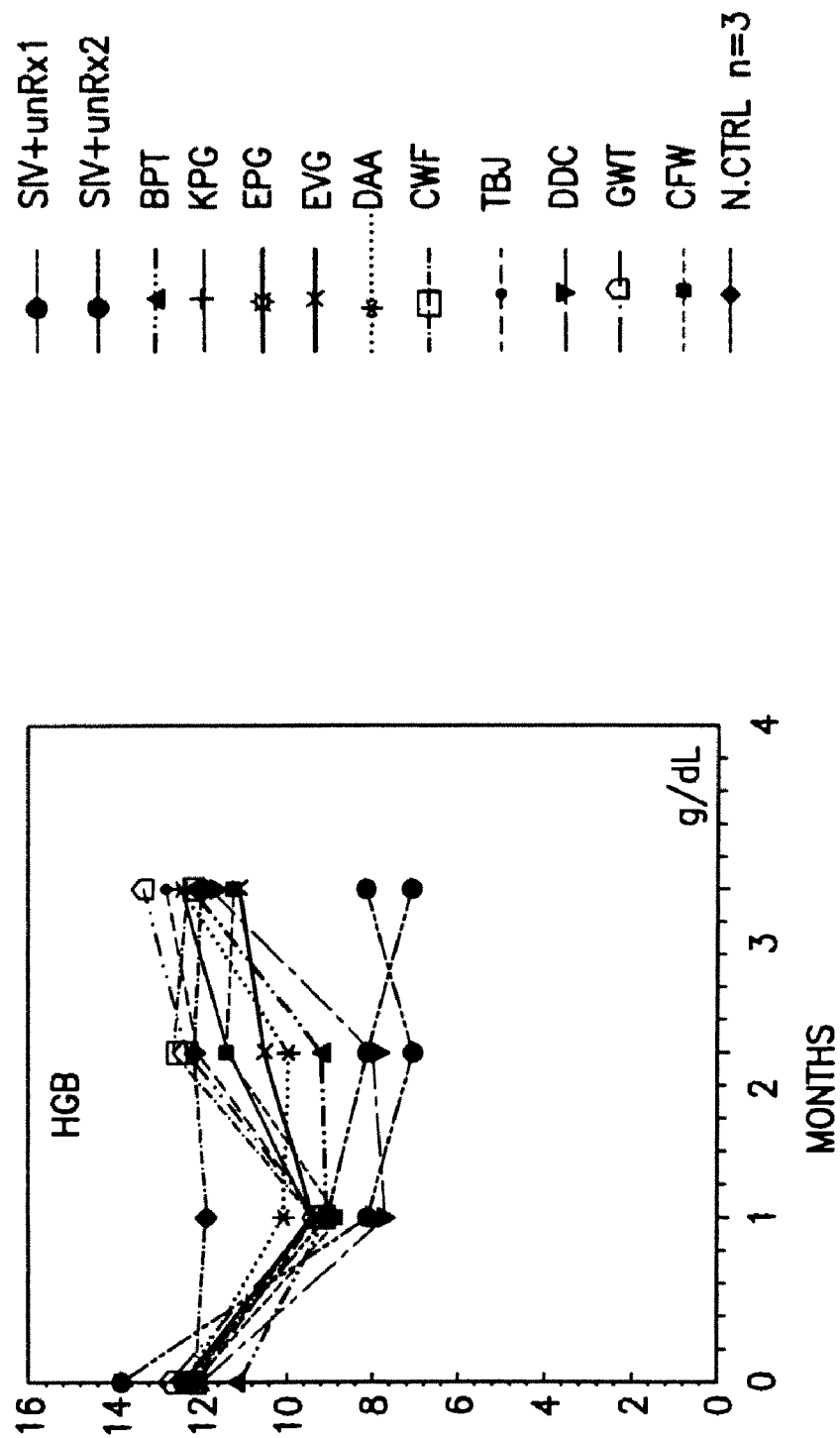
Figure 12G:
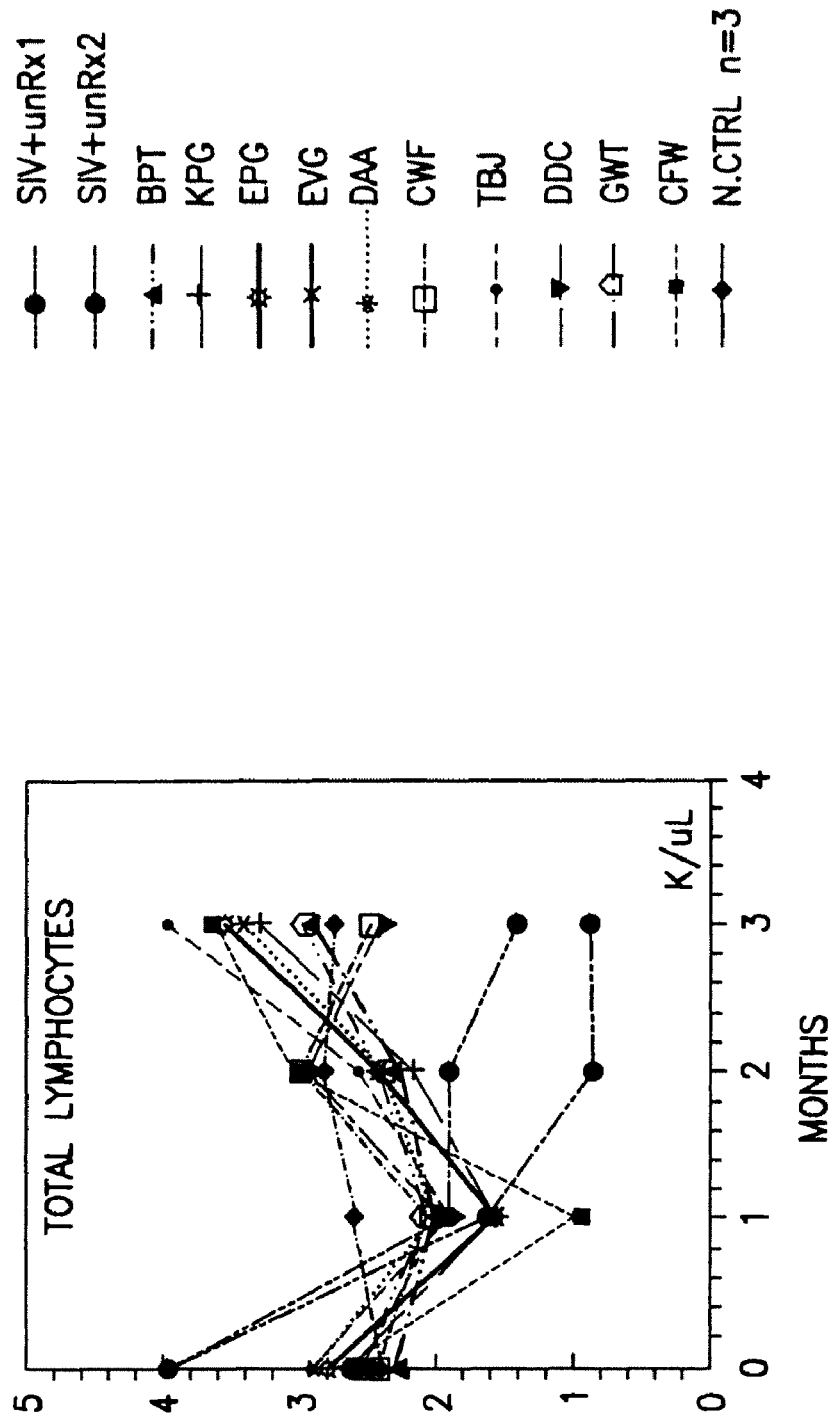
Figure 12H:
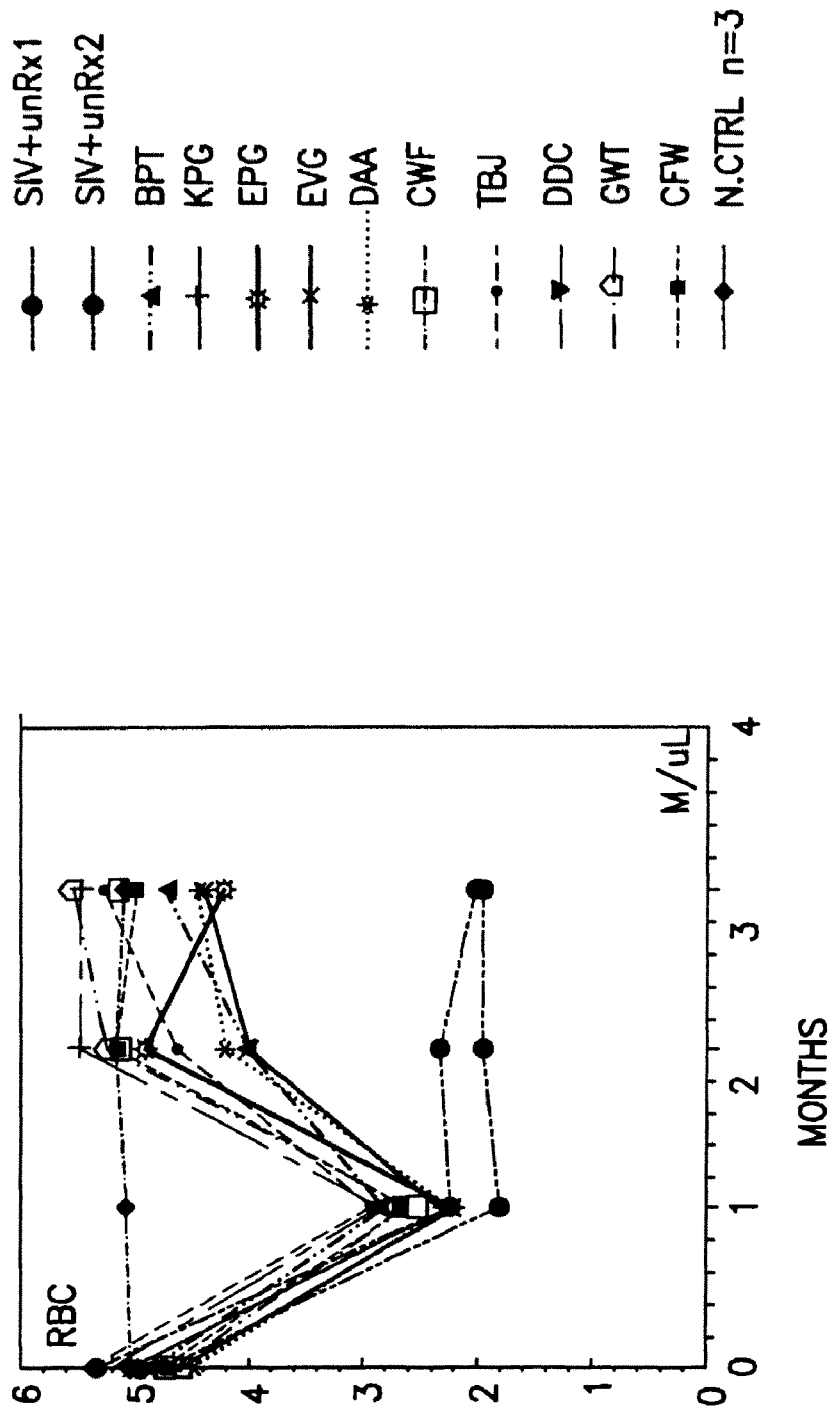
Figure 12I:
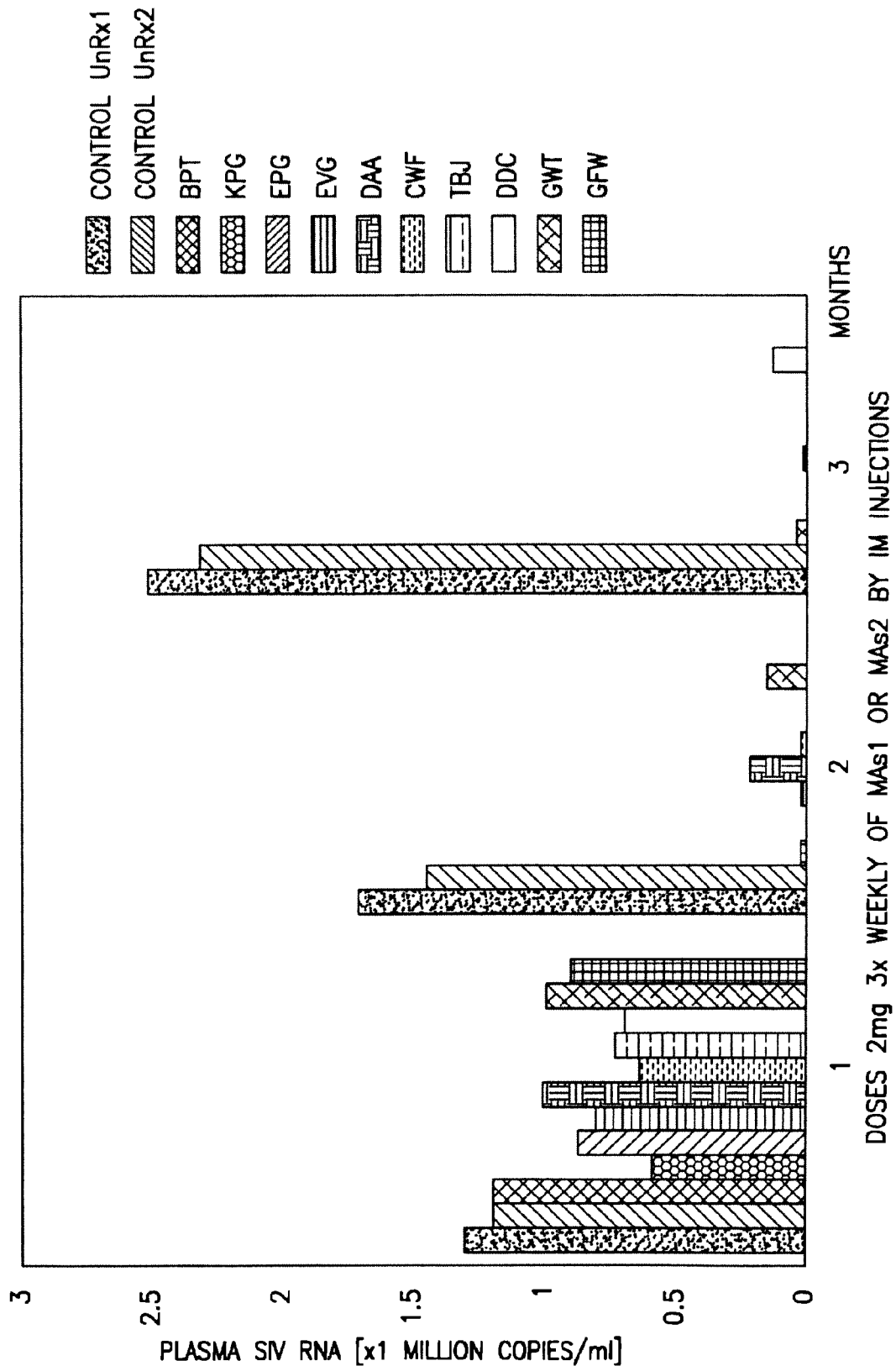

FIGS. 11C, 11D, 11E and 11F: Hematopoietic recovery phase in animals (FIGS. 11A and 11B) for total lymphocytes (FIG. 11C), PLT (FIG. 11D), HGB (FIG. 11E) and RBC (FIG. 11F).

FIG. 12. MA restores hematopoiesis in rats with 40% blood loss.

Panels A-D: Recovery in rats untreated vs. those given i.p. MA or $MA_{S1}$ 24 and 48 hrs after the blood loss (each point represents a mean of 10 animals). MA and $MA_{S1}$ treated animals show a prompt recovery of all peripheral blood cells.

Panels E-H: Blood counts in three monkeys. Each panel illustrates the mean values for the three animals treated with $MA_{S1}$.

Panel I: Shows SIVmac251 viral load in *Macaca mutata*.

Figure 13:
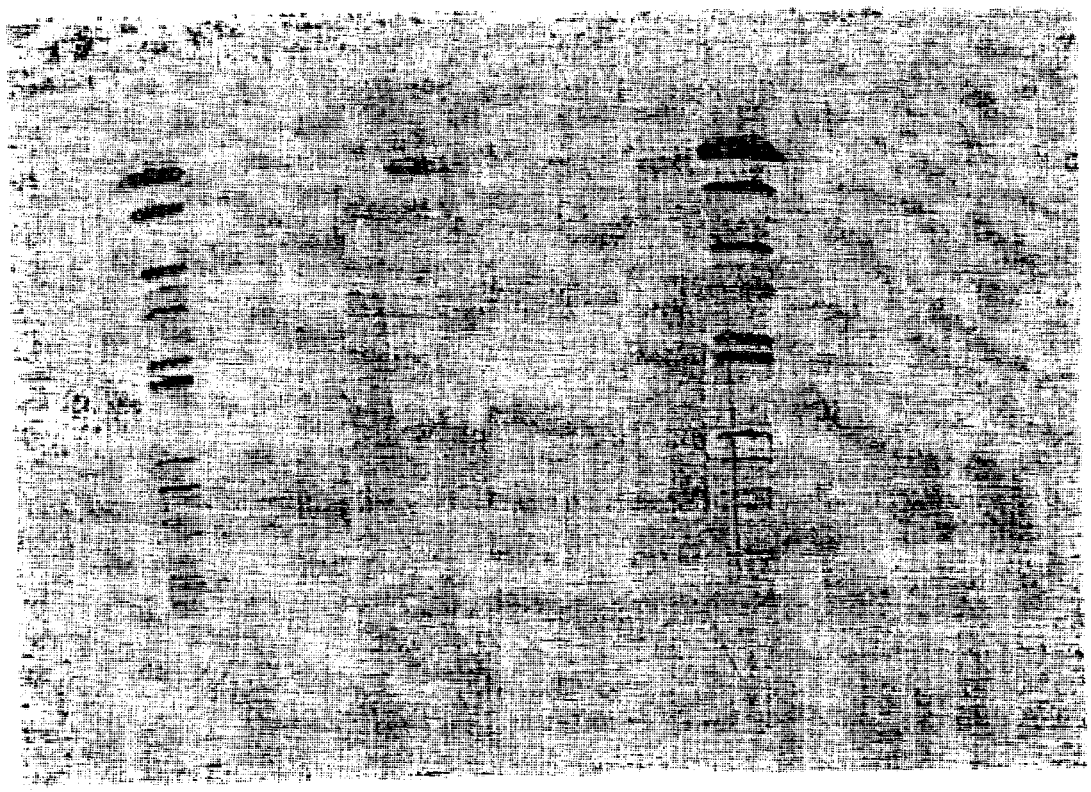

FIG. 13. Silver stained 4-12% Bis-Tris NuPage SDS-PAGE gel.

Column fractions were derived from non-pregnant female urine plus/minus a spike with $MA_{s2}$ (100 ug/L).

Figure 14:
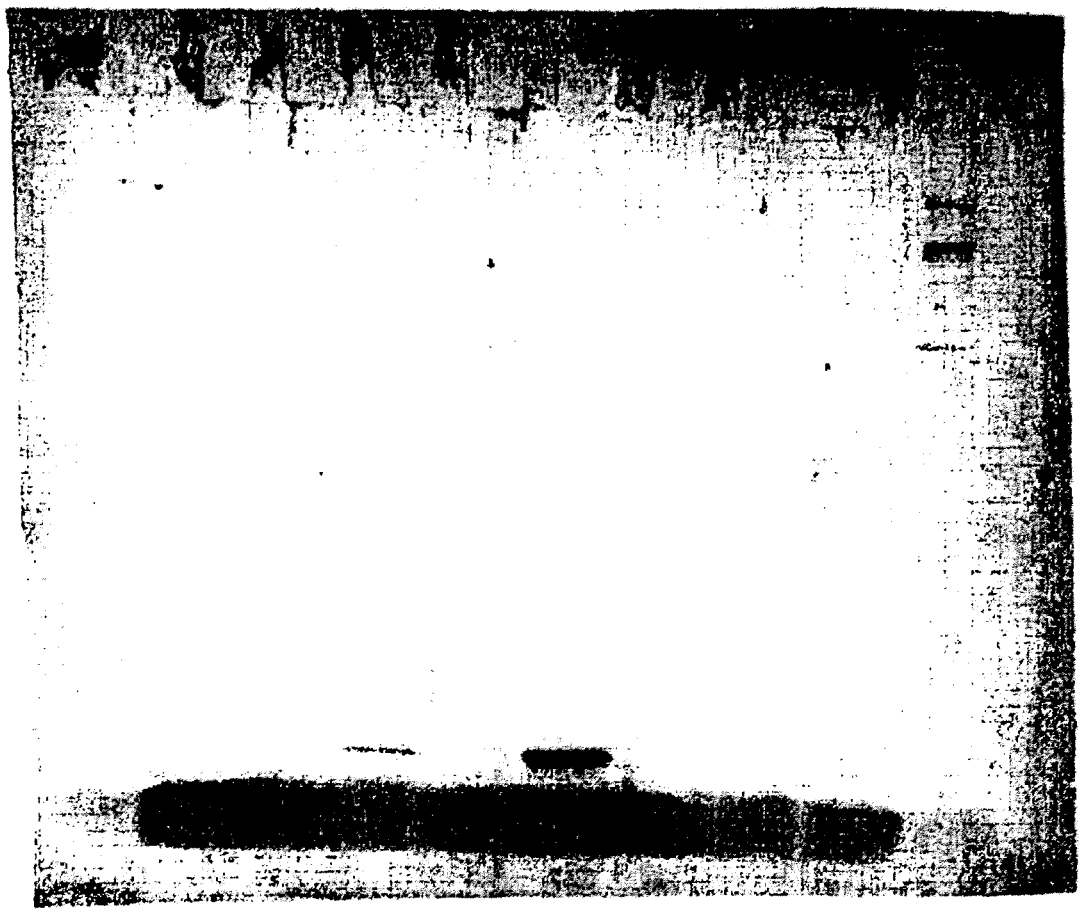

FIG. 14. Western blot of SDS-PAGE showing MA-reactive species.

MA-reactive species only in acid peak (lane 4) and $MA_{s2}$ control (lane 6).

Figure 15:
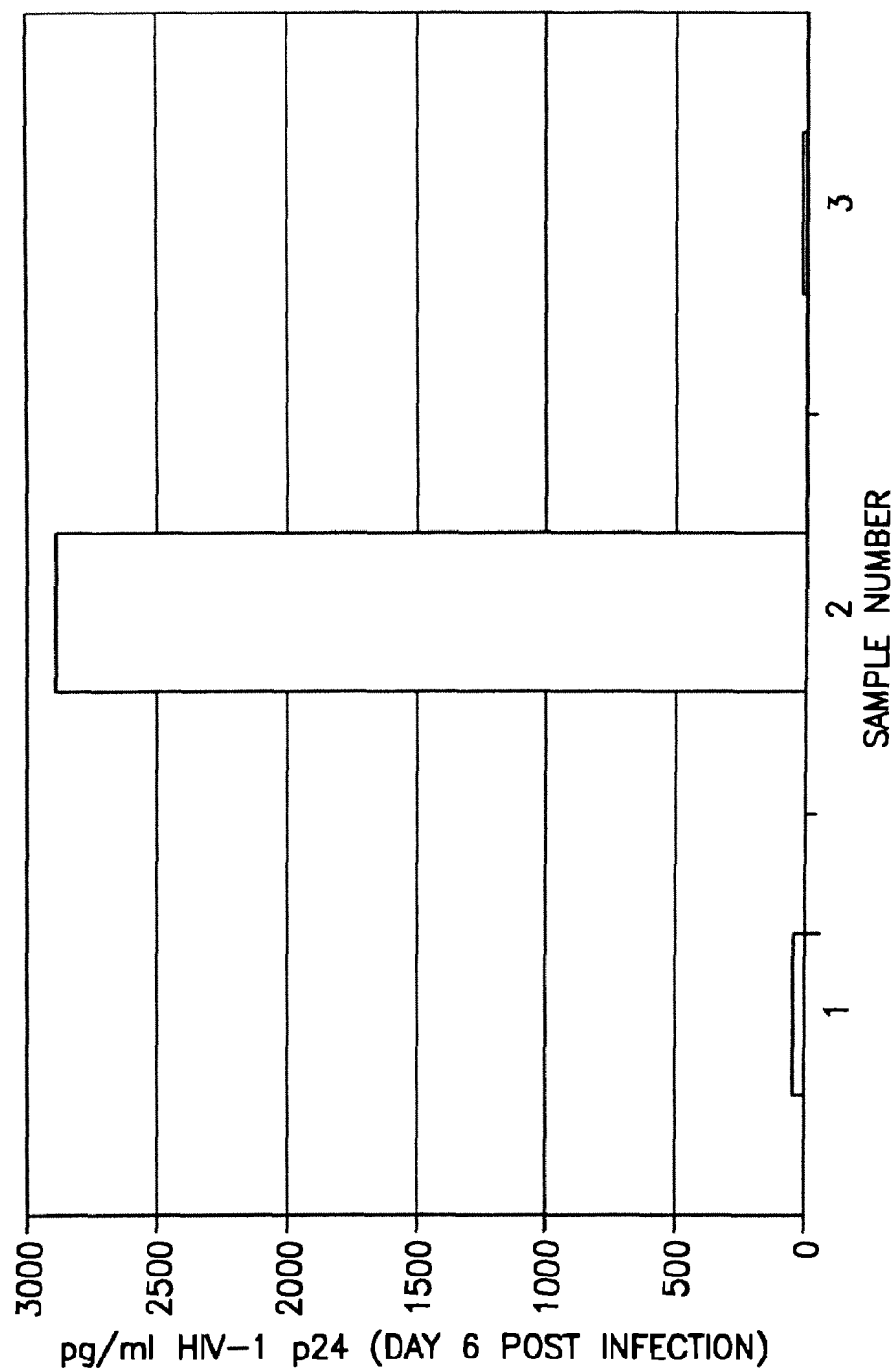

FIG. 15. Anti-MA antibodies remove the anti-viral effect of $MA_{s2}$, resulting in elevated HIV-I p24 production.

Figure 16:
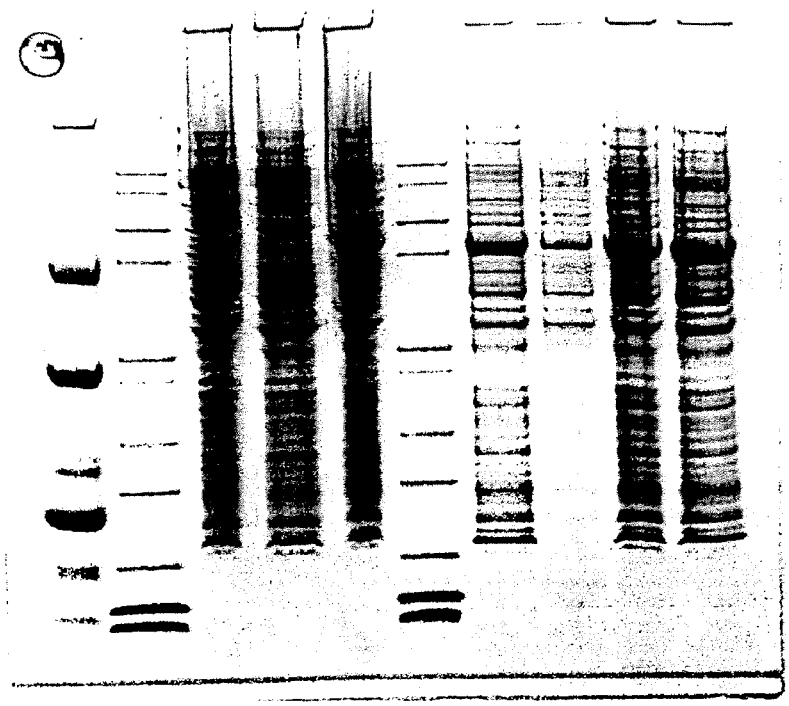
Figure 16:
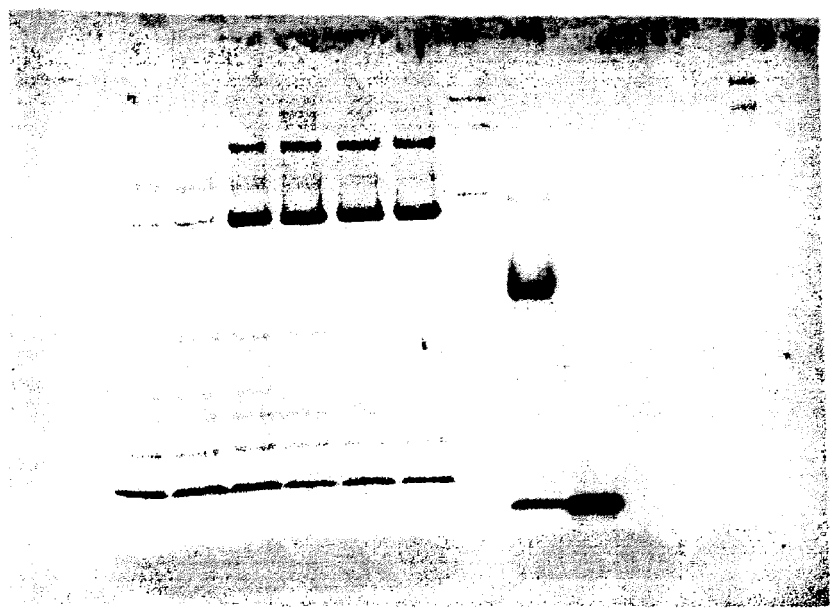

FIG. 16. Coomassie stained gel and Western blot of test expressions showing α-MA reactive material of the expected size (58 kDa).

Panel A: Coomassie stained gel.
Panel B: Western blot.

Figure 17:
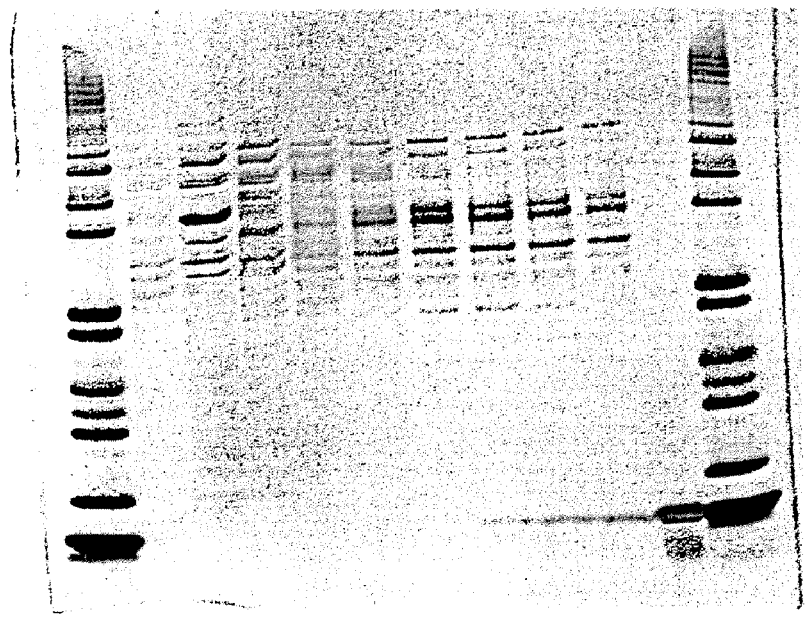
Figure 17:
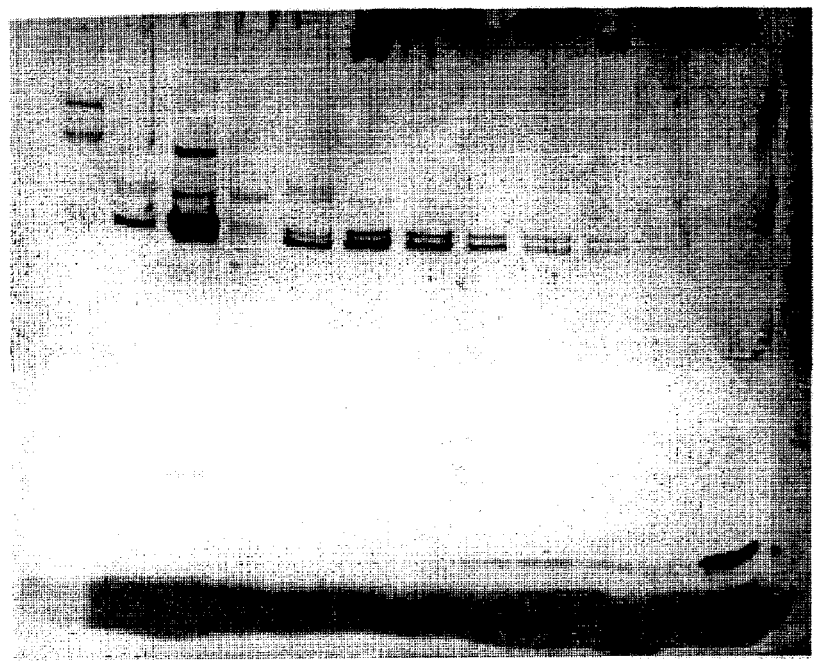

FIG. 17. Silver stained SDS-PAGE and Western blot showing column purification of clone 517.3 expressed Bact:$MA_{s2}$ and immunoreactivity with α-MA antibodies.

Panel A: Silver stained SDS-PAGE.
Panel B: Western blot.

BRIEF DESCRIPTION OF THE SEQUENCE LISTING

The sequences used herein are summarized in Table 1:

| SEQ ID NO: | Name | βhCG AA | Sequence |
|---|---|---|---|
| 1 | β-hCG | 1-145 | Ser Lys Glu Pro Leu Arg Pro Arg Cys Arg Pro Ile Asn Ala Thr Leu Ala Val Glu Lys Glu Gly Cys Pro Val Cys Ile Thr Val Asn Thr Thr Ile Cys Ala Gly Tyr Cys Pro Thr Met Thr Arg Val Leu Gln Gly Val Leu Pro Ala Leu Pro Gln Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys Gln Cys Ala Leu Cys Arg Arg Ser Thr Thr Asp Cys Gly Gly Pro Lys Asp His Pro Leu Thr Cys Asp Asp Pro Arg Phe Gln Asp Ser Ser Ser Ser Lys Ala Pro Pro Pro Ser Leu Pro Ser Pro Ser Arg Leu Pro Gly Pro Ser Asp Thr Pro Ile Leu Pro Gln |
| 2 | MA | 55-89 | Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys Gln |
| 3 | pMA | 55-92 | Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys Gln Cys Ala Leu |
| 4 | $MA_{S1}$ | 62-76 | Val Arg Phe Glu Ser Ile Arg Leu Pro Gly Cys Pro Arg Gly Val |
| 5 | $MA_{S2}$ | 58-87 | Asn Tyr Arg Asp Val Arg Phe Glu Ser Ile Arg Leu Pro Gly Cys Pro Arg Gly Val Asn Pro Val Val Ser Tyr Ala Val Ala Leu Ser |
| 6 | $MA_{S3}$ | 55-89 | Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys Gln |
| 7 | $MA_{S5}$ | 68-74 | Arg Leu Pro Gly Cys Pro Arg |
| 8 | $MA_{S9}$ | A::70-73::G | Ala Pro Gly Cys Pro Gly |
| 9 | $MA_{S10}$ | 69-74 | Leu Pro Gly Cys Pro Arg |
| 10 | $MA_{S11}$ | 69-73::Q | Leu Pro Gly Cys Pro Gln |

-continued

| | | | |
|---|---|---|---|
| 11 | β-hCG 55-88 | 55-88 | Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys |
| 12 | β-hCG 55-90 | 55-90 | Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys Gln Cys |
| 13 | β-hCG 55-91 | 55-91 | Val Val Cys Asn Tyr Arg Asp Val Arg Phe Glu Ser Ile Arg Leu Pro Gly Cys Pro Arg Gly Val Asn Pro Val Val Ser Tyr Ala Val Ala Leu Ser Cys Gln Cys Ala |
| 14 | β-hCG 55-74 | 55-74 | Val Val Cys Asn Tyr Arg Asp Val Arg Phe Glu Ser Ile Arg Leu Pro Gly Cys Pro Arg |
| 15 | β-hCG 6-37 | 6-37 | Arg Pro Arg Cys Arg Pro Ile Asn Ala Thr Leu Ala Val Glu Lys Glu Gly Cys Pro Val Cys Ile Thr Val Asn Thr Thr Ile Cys Ala Gly Tyr |
| 16 | β-hCG 6-38 | 6-38 | Arg Pro Arg Cys Arg Pro Ile Asn Ala Thr Leu Ala Val Glu Lys Glu Gly Cys Pro Val Cys Ile Thr Val Asn Thr Thr Ile Cys Ala Gly Tyr Cys |
| 17 | β-hCG 6-39 | 6-39 | Arg Pro Arg Cys Arg Pro Ile Asn Ala Thr Leu Ala Val Glu Lys Glu Gly Cys Pro Val Cys Ile Thr Val Asn Thr Thr Ile Cys Ala Gly Tyr Cys Pro |
| 18 | β-hCG 6-40 | 6-40 | Arg Pro Arg Cys Arg Pro Ile Asn Ala Thr Leu Ala Val Glu Lys Glu Gly Cys Pro Val Cys Ile Thr Val Asn Thr Thr Ile Cys Ala Gly Tyr Cys Pro Thr |
| 19 | SAT$_{A1}$ | 45-57 | Leu Gln Gly Val Leu Pro Ala Leu Pro Gln Val Val Cys |
| 20 | SAT$_{A2}$ | C::45-57 (circularized) | Cys Leu Gln Gly Val Leu Pro Ala Leu Pro Gln Val Val Cys |
| 21 | SAT$_{A3}$ | C::45-47::R::49-57 | Cys Leu Gln Gly Arg Leu Pro Ala Leu Pro Arg Val Val Cys |
| 22 | SAT$_{A4}$ | N/A | Cys Arg Leu Pro Gly Leu Pro Arg Cys |
| 23 | SAT$_B$ | 109-119 | Thr Cys Asp Asp Pro Arg Phe Gln Asp Ser Ser |

Peptides other than β-hCG:

| SEQ ID NO: | Name | Sequence |
|---|---|---|
| 24 | choriogonadotropin β-chain precursor - horse | Met Glu Thr Leu Gln Gly Leu Leu Leu Trp Met Leu Leu Ser Val Gly Gly Val Trp Ala Ser Arg Gly Pro Leu Arg Pro Leu Cys Arg Pro Ile Asn Ala Thr Leu Ala Ala Glu Lys Glu Ala Cys Pro Ile Cys Ile Thr Phe Thr Thr Ser Ile Cys Ala Gly Tyr Cys Pro Ser Met Val Arg Val Met Pro Ala Ala Leu Pro Ala Ile Pro Gln Pro Val Cys Thr Tyr Arg Glu Leu Arg Phe Ala Ser Ile Arg Leu Pro Gly Cys Pro Pro Gly Val Asp Pro Met Val Ser Phe Pro Val Ala Leu Ser Cys His Cys Gly Pro Cys Gln Ile Lys Thr Thr Asp Cys Gly Val Phe Arg Asp Gln Pro Leu Ala Cys Ala Pro Gln Ala Ser Ser Ser Lys Asp Pro Pro Ser Gln Pro Leu Thr Ser Thr Ser Thr Pro Thr Pro Gly Ala Ser Arg Arg Ser Ser His Pro Leu Pro Ile Lys Thr Ser |
| 25 | lutropin β-chain precursor - sheep | Met Glu Met Leu Gln Gly Leu Leu Leu Trp Leu Leu Leu Gly Val Ala Gly Val Trp Ala Ser Arg Gly Pro Leu Arg Pro Leu Cys Gln Pro Ile Asn Ala Thr Leu Ala Ala Glu Lys Glu Ala Cys Pro Val Cys Ile Thr Phe Thr Thr Ser Ile Cys Ala Gly Tyr Cys Leu Ser Met Lys Gln Val Leu Pro Val Ile Leu Pro Pro Met Pro Gln Arg Val Cys Thr Tyr His Glu Leu Arg Phe Ala Ser Val Arg Leu Pro Gly Cys Pro Pro Gly Val Asp Pro Met Val Ser Phe Pro Val Ala Leu Ser Cys His Cys Gly Pro Cys Arg Leu Ser Ser Thr Asp Cys Gly Gly Pro Arg Thr Gln Pro Leu Ala Cys Asp His Pro Pro Leu Pro Asp Ile Leu Phe Leu |
| 26 | lutropin β-chain precursor - pig | Met Glu Met Leu Gln Gly Leu Leu Leu Trp Leu Leu Leu Ser Val Ala Gly Val Trp Ala Ser Arg Gly Pro Leu Arg Pro Leu Cys Arg Pro Ile Asn Ala Thr Leu Ala Ala Glu Asn Glu Ala Cys Pro Val Cys Ile Thr Phe Thr Thr Ser Ile Cys Ala Gly Tyr Cys Pro Ser Met Val Arg Val Leu Pro Ala Ala Leu Pro Pro Val Pro Gln Pro Val Cys Thr Tyr Arg Glu Leu Ser Phe |

-continued

| | | |
|---|---|---|
| | | Ala Ser Ile Arg Leu Pro Gly Cys Pro Pro Gly Val Asp Pro<br>Thr Val Ser Phe Pro Val Ala Leu Ser Cys His Cys Gly Pro<br>Cys Arg Leu Ser Ser Ser Asp Cys Gly Gly Pro Arg Ala Gln<br>Pro Leu Ala Cys Asp Arg Pro Leu Leu Pro Gly Leu Leu Phe<br>Leu |
| 27 | lutropin β-chain precursor - dog | Leu Gln Gly Leu Leu Leu Trp Leu Leu Leu Ser Val Gly Gly<br>Val Trp Ala Ser Arg Gly Pro Leu Arg Pro Leu Cys Arg Pro<br>Ile Asn Ala Thr Leu Ala Ala Glu Asn Glu Ala Cys Pro Val<br>Cys Ile Thr Phe Thr Thr Thr Ile Cys Ala Gly Tyr Cys Pro<br>Ser Met Val Arg Val Leu Pro Ala Ala Leu Pro Pro Val Pro<br>Gln Pro Val Cys Thr Tyr His Glu Leu His Phe Ala Ser Ile<br>Arg Leu Pro Gly Cys Pro Pro Gly Val Asp Pro Met Val Ser<br>Phe Pro Val Ala Leu Ser Cys Arg Cys Gly Pro Cys Arg Leu<br>Ser Asn Ser Asp Cys Gly Gly Pro Arg Ala Gln Ser Leu Ala<br>Cys Asp Arg Pro Leu Leu Pro Gly Leu Leu Phe Leu |
| 28 | lutropin β-chain precursor - bovine | Met Glu Met Phe Gln Gly Leu Leu Leu Trp Leu Leu Leu Gly<br>Val Ala Gly Val Trp Ala Ser Arg Gly Pro Leu Arg Pro Leu<br>Cys Gln Pro Ile Asn Ala Thr Leu Ala Ala Glu Lys Glu Ala<br>Cys Pro Val Cys Ile Thr Phe Thr Thr Ser Ile Cys Ala Gly<br>Tyr Cys Pro Ser Met Lys Arg Val Leu Pro Val Ile Leu Pro<br>Pro Met Pro Gln Arg Val Cys Thr Tyr His Glu Leu Arg Phe<br>Ala Ser Val Arg Leu Pro Gly Cys Pro Pro Gly Val Asp Pro<br>Met Val Ser Phe Pro Val Ala Leu Ser Cys His Cys Gly Pro<br>Cys Arg Leu Ser Ser Thr Asp Cys Gly Gly Pro Arg Thr Gln<br>Pro Leu Ala Cys Asp His Pro Pro Leu Pro Asp Ile Leu Phe<br>Leu |
| 29 | luteinizing hormone β-subunit - *Rattus norvegicus* | Met Glu Arg Leu Gln Gly Leu Leu Leu Trp Leu Leu Leu Ser<br>Pro Ser Val Val Trp Ala Ser Arg Gly Pro Leu Arg Pro Leu<br>Cys Arg Pro Val Asn Ala Thr Leu Ala Ala Glu Asn Glu Phe<br>Cys Pro Val Cys Ile Thr Phe Thr Thr Ser Ile Cys Ala Gly<br>Tyr Cys Pro Ser Met Val Arg Val Leu Pro Ala Ala Leu Pro<br>Pro Val Pro Gln Pro Val Cys Thr Tyr Arg Glu Leu Arg Phe<br>Ala Ser Val Arg Leu Pro Gly Cys Pro Pro Gly Val Asp Pro<br>Ile Val Ser Phe Pro Val Ala Leu Ser Cys Arg Cys Gly Pro<br>Cys Arg Leu Ser Ser Ser Asp Cys Gly Gly Pro Arg Thr Gln<br>Pro Met Thr Cys Asp Leu Pro His Leu Pro Gly Leu Leu Leu<br>Phe |
| 30 | luteinizing hormone β-subunit precursor - cat | Met Glu Met Leu Gln Gly Leu Leu Leu Leu Trp Leu Leu Leu<br>Leu Asn Val Gly Gly Val Trp Thr Ser Arg Glu Pro Leu Arg<br>Pro Leu Cys Arg Pro Ile Asn Ala Thr Leu Ala Ala Glu Asn<br>Glu Ala Cys Pro Val Cys Val Thr Phe Thr Thr Thr Ile Cys<br>Ala Gly Tyr Cys Pro Ser Met Met Arg Val Leu Pro Ala Ala<br>Leu Pro Pro Val Pro Gln Pro Val Cys Thr Tyr Arg Glu Leu<br>Arg Phe Ala Ser Val Arg Leu Pro Gly Cys Pro Pro Gly Val<br>Asp Pro Val Val Ser Phe Pro Val Ala Leu Ser Cys Arg Cys<br>Gly Pro Cys Arg Leu Ser Ser Ser Asp Cys Gly Gly Pro Arg<br>Ala Gln Pro Leu Ala Cys Asp Arg Pro Pro Leu Pro Gly Leu<br>Leu Phe Leu |
| 31 | β-chain of human LH | Met Glu Met Leu Gln Gly Leu Leu Leu Leu Leu Leu Leu Ser<br>Met Gly Gly Ala Trp Ala Ser Arg Glu Pro Leu Arg Pro Trp<br>Cys His Pro Ile Asn Ala Ile Leu Ala Val Glu Lys Glu Gly<br>Cys Pro Val Cys Ile Thr Val Asn Thr Thr Ile Cys Ala Gly<br>Tyr Cys Pro Thr Met Met Arg Val Leu Gln Ala Val Leu Pro<br>Pro Leu Pro Gln Val Val Cys Thr Tyr Arg Asp Val Arg Phe<br>Glu Ser Ile Arg Leu Pro Gly Cys Pro Arg Gly Val Asp Pro<br>Val Val Ser Phe Pro Val Ala Leu Ser Cys Arg Cys Gly Pro<br>Cys Arg Arg Ser Thr Ser Asp Cys Gly Gly Pro Lys Asp His<br>Pro Leu Thr Cys Asp His Pro Gln Leu Ser Gly Leu Leu Phe<br>Leu |

DETAILED DESCRIPTION OF THE INVENTION

The inventors have identified specific therapeutic polypeptides with a molecular mass of about 3.8 kDa, generally referred to herein as MA peptides. The inventors have also designed and made smaller forms (truncated at C-terminal and N-terminal ends), which mimic the therapeutic activities of the MA peptides. The inventors have confirmed the identity of the native MA peptides by preparing synthetic peptides encompassing the same sequences. Previous work by the inventors had indicated activities in the 3-5 kDa range but also in a higher molecular weight range approximating 17 kDa.[61]

However, with the purification schemes employed here, no activity was found at 17 kDa. This may be explained by the presence in the earlier samples of MA that was to bound to other structures or multimers of MA.

8.1 MA Peptides

The inventors have isolated MA (SEQ ID NO: 2) and pMA (SEQ ID NO: 3) from native sources of hCG. MA was previously referred to in an earlier U.S. Patent Application No. 60/147,825 as a "pregnancy peptide" or "PP." MA (SEQ ID NO: 2) and pMA (SEQ ID NO: 3) exhibit various advantageous pharmacological activities as more fully discussed below. MA (SEQ ID NO: 2) corresponds to amino acids 55-89 of β-hCG (SEQ ID NO: 1), and pMA corresponds to amino acids 55-92 of β-hCG (SEQ ID NO: 1).

The inventors have also designed the following synthetic mimetics of the MA peptides: $MA_{S1}$ (SEQ ID NO: 4); $MA_{S2}$ (SEQ ID NO: 5); $MA_{S3}$ (SEQ ID NO: 6); $MA_{S5}$ (SEQ ID NO: 7); $MA_{S9}$ (SEQ ID NO: 8); $MA_{S10}$ (SEQ ID NO: 9); and $MA_{S11}$ (SEQ ID NO: 10). A similar set of peptides with utility according to the practice of the invention are β-hCG 55-90 and β-hCG 55-91 (SEQ ID NOS: 11 and 12), i.e., MA with one or two C-terminal extensions, respectively, from the β-hCG amino acid sequence.

MA (SEQ ID NO: 2); pMA (SEQ ID NO: 3); $MA_{S1}$ (SEQ ID NO: 4); $MA_{S2}$ (SEQ ID NO: 5); $MA_{S3}$ (SEQ ID NO: 6); $MA_{S5}$ (SEQ ID NO: 7); $MA_{S9}$ (SEQ ID NO: 8); $MA_{S10}$ (SEQ ID NO: 9); $MA_{S11}$ (SEQ ID NO: 10); β-hCG 55-88 (SEQ ID NO: 11); β-hCG 55-90 (SEQ ID NO: 12) and β-hCG 55-91 (SEQ ID NO: 13) are collectively referred to herein as the "MA peptides."

The invention also provides functional equivalents of the MA peptides, as described more fully in Section 8.2. The group consisting of MA peptides and functional equivalents, but excluding full-length β-hCG, is referred to herein as the "therapeutic polypeptides." The therapeutic polypeptides also preferably exclude the native form of the full length native glycosylated β-core of β-hCG.

In one aspect of the invention, a therapeutic polypeptide is provided in a substantially pure form. The therapeutic polypeptide is preferably greater than about 90% free of contaminating polypeptides, more preferably greater than about 99% free of contaminating polypeptides, still more preferably, greater than about 99.9% free of contaminating polypeptides. In a preferred embodiment, the purified therapeutic polypeptide lacks all contaminating proteins. The therapeutic polypeptide is preferably provided at a pharmaceutically acceptable level of purity.

8.2 Functional Equivalents

The functional equivalents of the invention exclude the complete β-chain of hCG (SEQ ID NO: 1) and preferably exclude the β-hCG (SEQ ID NO: 1) 57-93 peptide. In one aspect of the invention, the inventors' previously discovered polypeptides and polypeptides comprising such peptides are excluded from the functional equivalents of the invention, e.g., Satellin A1 (SEQ ID NO: 18); the Satellin A1 branched peptide: β-hCG 45-57 [Leu-Gln-Dab(Pro)-Val-Leu-Pro-Dab (Pro)-Leu-Pro-Gln-Val-Val-Cys (see SEQ ID NO: 18, for primary sequence), where "Dab" represents diaminobutyric acid, and Dab(Pro) indicates a proline peptide-bonded to the amino side chain of Dab], the Satellin A2 circularized peptide [β-hCG 45-57 (SEQ ID NO: 19) with a cysteine residue added to the N-terminus, circularized via a disulfide bond between the cysteine residues], and the Satellin B peptide (SEQ ID NO: 22), as well as β-hCG (SEQ ID NO: 1) 109-145, 47-55, 48-56, 45-57 fused to 109-119, and 45-57 in combination with 109-119. The following peptides are also preferably excluded from the functional equivalents of the invention: β-hCG (SEQ ID NO: 1) 41-53, 41-54, 42-53, 42-53, 43-53, 44-53, 44-57, 45-53, 45-54, 45-55, 45-56, 45-57, 45-58, 46-53, 47-53, 47-54, 47-56, 47-58, 48-145, 58-145, and 109-119. However, these previously discovered peptides may be included in various method and formulation aspects of the invention, as discussed in more detail below.

The functional equivalents of the invention retain some or all of the corresponding biological activity of the corresponding peptide fragments with native amino acid sequences, and preferably exhibit enhanced activity.

8.2.1 Rationally Designed Polypeptides

The functional equivalents include rationally designed peptides. The inventors have identified several repeated patterns within the β-hCG sequence and its active fragments that have permitted successful prediction by the inventors of smaller active fragments (i.e., fragments comprising some or all of the therapeutic activity of MA) of MA and other peptides derived from β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31) that possess some or all of the therapeutic activities of MA. The repeated patterns include SH3 motifs, PDZ motifs, myristoylation sites and phosphorylation sites.

Src-homology 3 (SH3) domains generally consist of sequences of approximately 60 amino acid residues generally forming two small β sheets that bind to each other at right angles. Ligands for SH3 domains include peptides with short proline-rich motifs, especially the PxxP motif, where P stands for proline and x stands for any other amino acid. Activation of SH3 domains mediates the formation of signaling complexes. SH3 binding motifs are typically 7-9 amino acids in length at their core structure. The SH3 domain is involved in cell-to-cell communication and in signal transduction from the cell surface to the nucleus. An SH3 binding interaction is responsible for the complexing of the proto-oncogene Vav to Grb-2, found only in hematopoietic cells. An SH3 interaction is also responsible for activation of Ras in abnormal cells resulting in apoptosis; in normal cells, the same interaction induces proliferation. This multi-action pathway has also been reported to play a role in embryogenesis.

PDZ domains are modular protein-protein interaction domains that are specialized for binding to specific C-terminal peptide sequences and to other PDZ domains. Many proteins contain multiple PDZ domains, thereby allowing them to function as multivalent scaffolds for organizing large protein complexes. PDZ proteins recognize the consensus sequence X-S/T-X-V/I, where x is any amino acid and S is serine, T is threonine, V is valine and I is isoleucine.

Various proteins in signal transduction pathways are myristoylated, and myristoylation is involved in the membrane interactions of various proteins. The intermediate hydrophobic nature of the modification plays an important role in the reversible membrane anchoring of these proteins. Protein myristoylation is also involved in protein-protein interactions, which are regulated by the interplay between ptotein phosphorylation and membrane phospholipds.

Phosphorylation is the addition of a phosphate to an organic compound, such as glucose to produce glucose monophosphate, typically through the action of phosphorylase or kinase. Phosphorylation at particular sites on proteins can trigger an SH3 mediated activity or activate and/or inhibit the activity of a cyclin-CDK complex.

The following motifs are present in the beta chain of hCG:
SH3 domain motifs: β-hCG 4-7, 50-53, 70-73, 124-129, 141-144
PDZ domain motifs: β-hCG 30-33, 41-44, 139-142
myristoylation sites: β-hCG 22-27, 47-52, 71-76
phosphorylation sites: β-hCG 66-68, 94-99, 109-112, 120-122

The following motifs are present in the beta chain precursor of horse coriogonadotropin:
SH3 domain motifs: 24-27, 44-47, 70-73, 90-93, 142-145
PDZ domain motifs: 50-53, 59-62, myristoylation sites: 16-21, 91-96
phosphorylation sites: 78-80, 78-81, 86-88, 137-139, 137-140, 157-159, 158-161, The following motifs are present in the beta chain precursor of sheep lutropin:
SH3 domain motifs: 24-27, 70-73, 90-93, 133-136
PDZ domain motifs: 50-53
myristoylation sites: 17-22, 91-96, 121-126
phosphorylation sites: 60-62, 78-81, 86-88, 116-119

The following motifs are present in beta chain of rat lutropin:
SH3 domain motifs: 24-27, 70-73, 91-94, 133-136
PDZ domain motifs: 15-18, 50-53, 59-62
myristoylation sites: 91-96, 121-126
phosphorylation sites: 78-80, 78-81, 86-88, 107-109, 116-119

The following motifs are present in the beta chain precursor of pig lutropin:
SH3 domain motifs: 24-27, 70-73, 90-93, 133-136
PDZ domain motifs: 50-53, 59-62
myristoylation sites: 17-22, 91-96, 121-126
phosphorylation sites: 78-80, 78-81, 86-88, 116-119

The following motifs are present in the beta chain of bovine leutropin precursor:
SH3 domain motifs: 24-27, 70-73, 90-93, 133-136
PDZ domain motifs: 50-53
myristoylation sites: 17-22, 91-96, 121-126
phosphorylation sites: 60-62, 78-81, 86-88, 116-119

The following motifs are present in the beta chain of dog leutropin precursor:
SH3 domain motifs: 21-24, 67-70, 86-90, 130-133
PDZ domain motifs: 47-50, 56-59
myristoylation sites: 13-18, 88-93, 118-123
phosphorylation sites: 75-78, 83-85, 104-106, 113-116

The following motifs are present in the beta chain of cat leutropin precursor:
SH3 domain motifs: 26-29, 72-75, 92-95, 135-138
PDZ domain motifs: 52-55
myristoylation sites: 18-23, 93-98, 123-128
phosphorylation sites: 22-24, 22-25, 80-82, 80-83, 109-111, 118-121

The following motifs are present in the beta chain of human leutropin precursor:
SH3 domain motifs: 24-27, 71-74, 91-94
PDZ domain motifs: 51-54
myristoylation sites: 16-21, 42-47, 91-96
phosphorylation sites: 78-80, 78-81, 86-88, 107-109, 114-117, 116-119

Based on the observations presented herein, the inventors have established the following guidelines to for peptide selection:
peptides are preferably at least 5 amino acid residues in length; and
peptides preferably include one motif from each of the following groups:
Group A: SH3 and PDZ domain motifs
Group B: phosphorylation and myristoylation domain motifs Synthesis and screening of the peptides may be accomplished using assays described herein or otherwise known in the art.

Preferred sites are found in mammalian LH or CG, preferably from β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31).

Accordingly, the present invention provides a rationally designed polypeptide comprising at least one amino acid segment selected from the group consisting of SH3 and PDZ domain motifs; and at least one amino acid segment selected from the group consisting of phosphorylation and myristoylation domain motifs ("rationally designed polypeptides").

In conjunction with a Group A motif the Group B motif is preferably positioned no more than 20 AA residues from the Group A motif in either direction (i.e., towards the N terminus or towards the C terminus) from the Group A motif. The sequence of the Group B motif preferably begins no more than 20 amino acid residues from the N or C terminus of the Group A motif.

Where the Group A motif is an SH3 and the Group B motif is a phosphorylation site the amino acid sequence of the phosphorylation site preferably begins no more than 10 amino acid residues from the N or C terminus of the SH3 region.

In a preferred embodiment, the group A motif is an SH3 motif and sequences contiguous with the SH3 motif include other proline residues adjacent to the SH3 motif.

In a preferred embodiment, the phosphorylation site is separated from the SH3 motif by no more than 5 amino acid residues, more preferably no more than 3 amino acid residues, most preferably no more than 1 amino acid. In other words, there are preferably no more than 5 amino acid residues separating the phosphorylation site from the SH3 motif, more preferably no more than 3 amino acid residues, most preferably no more than 1 amino acid residue.

Where the Group A motif is an SH3 motif and the Group B motif is a myristoylation motif the myristoylation motif is preferably separated from either the N or C terminus of the SH3 motif by no more than 15 amino acid residues, more preferably no more than 10 amino acid residues, most preferably no more than 5 amino acid residues.

In a preferred embodiment, the Group A motif is an SH3 motif, and the Group B motif is a myristoylation motif, the myristoylation motif is immediately adjacent to with the SH3 motif, i.e., no amino acid residues separate the two motifs.

In one embodiment of the invention, the rationally designed polypeptide contains more than one Group A motif with one Group B motif.

In another embodiment of the invention the rationally designed polypeptide contains more than one Group A motif with more than one Group B motif.

In an embodiment of the invention the rationally designed polypeptide contains one Group A motif with more than one Group B motif.

In a preferred embodiment, the rationally designed polypeptide comprises at least one amino acid segment selected from the group consisting of β-hCG 4-7, 50-53, 70-73, 124-129, 141-144, 30-33, 41-44, and 139-142; and at least one amino acid segment selected from the group consisting of β-hCG 22-27, 47-52, 71-76, 66-68, 94-99, 109-112, and 120-122. Both components of the rationally designed polypeptides are suitably provided in a continuous segment of the foregoing CG and LH chains. For example, one group of rationally designed polypeptides includes β-hCG 6-37, 6-38, 6-39 and 6-40 (SEQ ID NOS: 13, 14, 15 and 16), each of which includes a myristoylation site (22-27) and a PDZ domain (30-33).

In an embodiment the rationally designed polypeptide comprises a sequence selected from hCG 1-39, 1-29, 1-35, 41-54, 66-76, 93-130, 93-131, 93-132, 93-135, 93-144, 93-145, 41-54 linked to 55-92, 41-54 linked to 59-89, or 41-54 linked to 55-76.

In another preferred embodiment, the rationally designed polypeptide comprise a myristoylation and/or an SH3 domain selected from the group consisting of the HUSI-II polypeptide,[62] β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31).

The rationally designed peptides are preferably at least 5 and less than 100 amino acid residues in length, more preferably at least 5 and less than 50, and more preferably at least 5 and less than 25, still more preferably at least 5 and less then 20, and most preferably at least 5 and less than 15 amino acid residues in length.

One or more rationally designed polypeptides may be provided as component(s) of a fusion polypeptide, as discussed in section 8.2.3. Derivatives and analogues are also provided, as discussed in section 8.2.4. The segments of the fusion need not be contiguous on the native polypeptide, i.e., the segments may come from disparate positions of the native polypeptide.

In a related aspect, the invention also provides methods using the HUSI-II polypeptide,[63] β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31) and fragments of these polypeptides. The data presented herein are consistent with the proposition that the HUSI-II polypeptide and fragments thereof will exhibit the same therapeutic efficacies as the therapeutic polypeptides. Thus, while the ensuing discussion speaks in terms of the therapeutic polypeptides, the discussion is also applicable to the HUSI-II polypeptide,[64] β-hCG (SEQ ID NO: 1), horse β CG (SEQ ID NO: 24), sheep β LH (SEQ ID NO: 25), pig β LH (SEQ ID NO: 26), dog β LH (SEQ ID NO: 27), bovine β LH (SEQ ID NO: 28), rat β LH (SEQ ID NO: 29), cat β LH (SEQ ID NO: 30), and human β LH (SEQ ID NO: 31) and fragments of these polypeptides. Preferred fragments are those comprising or consisting of the SH3 motif and its flanking residues. Highly preferred fragments are AA-40-46, 40-60, 40-59, 40-58, 40-66, 40-67, 40-68. Moreover, in another highly preferred embodiment, the fragment includes the SH3 motif and the myristoylation site. Moreover, the invention includes fusion peptides which may comprise one or more fragments of HUSI-II, and may optionally comprise heterologous amino acid sequences.

8.2.2 Polypeptides Containing MA Peptides

Where the therapeutic polypeptides are larger peptides that comprise MA peptides corresponding to amino acid sequences found in β-hCG (SEQ ID NO: 1), such therapeutic polypeptides preferably lack amino acid residues from the β-hCG sequence (SEQ ID NO: 1) that are contiguous to the MA peptide sequence, i.e., the extensions of the MA peptides are preferably not coextensive with the corresponding contiguous amino acids from β-hCG (SEQ ID NO: 1). Moreover, the therapeutic polypeptides of the invention do not include a polypeptide consisting of full-length human β-hCG (SEQ ID NO: 1).

In one aspect of the invention, the inventors' previously discovered polypeptides and polypeptides comprising such peptides are excluded from the therapeutic polypeptides of the invention, e.g., Satellin A1 (SEQ ID NO: 18); the Satellin A1 branched peptide: β-hCG 45-57 [Leu-Gln-Dab(Pro)-Val-Leu-Pro-Dab(Pro)-Leu-Pro-Gln-Val-Val-Cys (see SEQ ID NO: 18, for primary sequence), where "Dab" represents diaminobutyric acid, and Dab(Pro) indicates a proline peptide-bonded to the amino side chain of Dab], the Satellin A2 circularized peptide [β-hCG 45-57 (SEQ ID NO: 19) with a cysteine residue added to the N-terminus, circularized via a disulfide bond between the cysteine residues], and the Satellin B peptide (SEQ ID NO: 22), as well as β-hCG (SEQ ID NO: 1) 109-145, 47-55, 48-56, 45-57 fused to 109-119, and 45-57 in combination with 109-119. The following peptides, previously identified by the inventors, are also preferably excluded from the therapeutic polypeptide of the invention: β-hCG (SEQ ID NO: 1) 41-53, 41-54, 42-53, 42-53, 43-53, 44-53, 44-57, 45-53, 45-54, 45-55, 45-56, 45-57, 45-58, 46-53, 47-53, 47-54, 47-56, 47-58, 48-145, 58-145, and 109-119. However, these previously discovered peptides may be included in various method and formulation aspects of the invention, as discussed in more detail below.

8.2.3 Fusion Polypeptides, Branched and Circularized Polypeptides

The functional equivalents of the invention include fusion polypeptides comprising two or more polypeptide segments covalently linked together. The polypeptide segments of the fusion polypeptides may include any combination of the following: MA peptides, functional equivalents, and heterologous polypeptides. For example, a fusion polypeptide of the invention may consist of two or more MA peptides joined end-to-end by a peptide bond. As another example, one or more MA peptides may be joined at the amino and/or carboxy terminus of a heterologous polypeptide, and/or joined to one or more side chains of one or more amino acid residues within the heterologous polypeptide to form branches (discussed more fully below). Fusion polypeptides of the invention may also include additional MA peptides and/or heterologous polypeptides as branches. The polypeptide segments of the fusion proteins may or may not be contiguous to one another (i.e., an intervening sequence may be present). The polypeptide segments of the fusion polypeptides may also be linked by hydrocarbon linkages.

A therapeutic polypeptide may be joined at its amino- or carboxy-terminus via a peptide bond to another therapeutic polypeptide. The invention also provides fusion polypeptides comprising one or more therapeutic polypeptides joined to one or more heterologous polypeptides. The heterologous polypeptides may be selected from the group which comprises heterologous protein or peptide therapeutics, and other pharmacologically active polypeptides.

In a specific embodiment, the derivative is a fusion protein comprising a therapeutic polypeptide joined at its amino or carboxy-terminus to a chemokine (or active fragment, analogue, or derivative thereof). Preferred chemokines are those which are therapeutically useful in the treatment of HIV-infected subjects. For example, the chemokine may be selected from the group consisting of MIP-1α, MIP-1β and RANTES.[65] The chimeric polypeptide may be produced by recombinant expression of a nucleic acid encoding the fusion protein (comprising a MA peptide coding sequence joined in-frame to a coding sequence for a different protein).

A therapeutic polypeptide of the invention may also be provided as a component of a fusion protein comprising a targeting agent. For example, the targeting agent may be an antibody, preferably a monoclonal antibody. In a specific embodiment, the therapeutic polypeptide is linked to an antibody which targets a specific cancer, such as prostate cancer, to facilitate contact between the therapeutic polypeptide and the cancer cells. In another embodiment, the antibody has specificity for specific blood cells, such as cells expressing CD34. In this manner, specific cells can be targeted for the proliferation-inducing effects of the therapeutic polypeptides of the invention.

Where the therapeutic polypeptide is linked to a targeting agent, the fusion polypeptide may also comprise other therapeutics, such as a nucleic acid, gene, peptide, toxin, or a radioactive molecule for tagging or to induce death in the target cell.

One or more polypeptide segments may be covalently bound to one or more side chains of another of the polypeptide segments, thereby forming a branched polypeptide. For example, one or more MA peptides may be covalently bound to one or more side chains of a heterologous polypeptide, thereby forming a branched polypeptide in which each MA peptide forms a branch, which is linked to the heterologous polypeptide at a side chain. Conversely, one or more heterologous polypeptides may be joined as branch(es) to one or more side chains of an MA peptide. One or more intervening amino acid residues (e.g., an amino acid chain forming a flexible polymer) may also be present between the branches and the base sequence.

The functional equivalents of the invention also include branched analogs. The branched analogs are analogous to the branched polypeptides described in the preceding paragraph with the exception that branching is facilitated by one or more amino acid substitutions or insertions with amino acid(s) or amino acid analog(s) having a free amino- or carboxy-side chain. The side chain(s) may each form a peptide bond with a sequence of one or more amino acids, e.g., a sequence of one or more prolines.

The functional equivalents also include circularized polypeptides. Circularized polypeptides may be formed, e.g., by disulfide bond formation. Where necessary, a cysteine residue may be added to the therapeutic polypeptide to facilitate disulfide bond formation. For example:
one or more native amino acid residues from the therapeutic polypeptide, e.g., an MA peptide, is replaced with cysteine;
one or more cysteines is inserted between native residues of the therapeutic polypeptide, e.g., inserted between native residues of an MA peptide; and/or
one or more cysteines is added at one or both ends of the therapeutic polypeptide, e.g., added at one or both ends of an MA peptide sequence.

The therapeutic polypeptides can also be linked to a suitable targeting agent or delivery vector to direct the therapeutic polypeptides to a desired site of action.

In one aspect a therapeutic polypeptide is linked to a monoclonal antibody, such as an antibody specific for a tumor marker such as a monoclonal antibody against prostate specific antigen (PSA), or a marker over-expressed in a tumor. The monoclonal antibody delivers the therapeutic polypeptide directly to the site of a tumor expressing PSA, e.g., to the site of a primary prostate lesion or a metastasis. This allows the polypeptide to be concentrated at the tumor site to increase its activity, i.e., inducing apoptosis and/or exerting anti-angiogenic activity.

In a specific embodiment the therapeutic peptides are linked to an antibody that recognizes a cell surface marker or receptor. In a preferred embodiment, the antibody is CD34 for targeting MA to stem cells.

In another specific aspect the therapeutic polypeptide is linked to a monoclonal antibody specific to a viral protein. In a preferred aspect the therapeutic polypeptides is linked to a monoclonal antibody against an HIV protein. This allows the therapeutic peptide to be delivered directly to HIV expressing cells targeting its action.

8.2.4 Derivatives of the MA Peptides

The derivatives of the MA peptides can comprise substitutions, additions or deletions that provide for therapeutically effective molecules. In one aspect of the invention, the derivatives have a primary amino acid sequence of a therapeutic polypeptide, except that functionally equivalent amino acid residues are substituted for residues within the sequence. Such derivatives retain some or all of the bioactivity of the corresponding therapeutic polypeptide, preferably a therapeutically significant degree of activity.

One or more amino acid residues of a therapeutic polypeptide can be substituted by another amino acid of a similar polarity that acts as a functional equivalent, resulting in a silent alteration. Conservative substitutions for an amino acid within the therapeutic polypeptide may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a preferred embodiment the therapeutic polypeptides of the invention are modified to increase their hydrophobicity in order to enhance their penetration into the cell through the cell membrane. This can be accomplished by the addition of one or more hydrophobic amino acid residues at either the amino terminus, carboxyl terminus or within the amino acid sequence of the therapeutic polypeptide. The therapeutic polypeptide can also have one or more hydrophobic residues within its sequence replacing non-hydrophobic residues. The typical hydrophobic residues include but are not limited to alanine, leucine, isoleucine, valine, proline, phenylalanine, tryptophan and methionine.

Functional equivalents can be chemically synthesized.[66] For example, peptides can be synthesized by solid phase techniques, cleaved from the resin, and purified by preparative high performance liquid chromatography (HPLC).[67] Functional equivalents of MA peptides can also be synthesized using a peptide synthesizer. The composition of the synthetic peptides may be confirmed by amino acid analysis or sequencing.[68] Synthetic production of the therapeutic polypeptides is discussed more fully in 8.4.1.

Functional equivalents of the MA peptides can be prepared by chemical peptide synthesis or by recombinant production from a nucleic acid encoding the derivative. A nucleic acid encoding the derivative can be prepared by various techniques known in the art in light of the instant disclosure. For example, such a nucleic acid may be prepared by mutation of a nucleic acid encoding the corresponding therapeutic polypeptide. Various techniques for mutagenesis are commonly practiced in the art, e.g., chemical mutagenesis, in vitro site-directed mutagenesis, etc.[69] Recombinant production of the therapeutic polypeptides is discussed more fully in 8.4.2.

The functional equivalents of the invention may also comprise various nonclassical amino acids. For example, the functional equivalents include therapeutic polypeptides with any one or more of the following alterations:
one or more native amino acid residues from the therapeutic polypeptide, e.g., an MA peptide is replaced with a non-classical amino acid residue;
one or more non-classical residues is inserted between native residues of the therapeutic polypeptide, e.g., inserted between native residues of an MA peptide; and
one or more non-classical residues is added at one or both ends of the therapeutic polypeptide, e.g., added at one or both ends of an MA peptide sequence.

Examples of non-classical amino acids include: D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Also included within the scope of the invention are derivatives comprising therapeutic polypeptides, which have been differentially modified during or after synthesis, e.g., by benzylation, glycosylation, acetylation, phosphorylation, amidation, PEGylation, derivatization by known protecting/blocking groups, proteolytic cleavage, linkage to an antibody molecule or other cellular ligand, etc. In one embodiment, the therapeutic polypeptides are acetylated at the N-terminus and/or amidated at the C-terminus. In another embodiment, the derivatives are conjugated to polymers, e.g., polymers known in the art to facilitate oral delivery, decrease enzymatic degradation, increase solubility of the polypeptides, or otherwise improve the chemical properties the therapeutic polypeptides for administration to humans or other animals. The polymers may be joined to the therapeutic polypeptides by hydrolyzable bonds, so that the polymers are cleaved in vivo to yield the active therapeutic polypeptides.

Any of numerous chemical modifications may be carried out by known techniques, including but not limited to acetylation, formylation, oxidation, reduction; metabolic synthesis in the presence of tunicamycin, etc.

In a preferred embodiment the therapeutic polypeptides of the invention are produced in reverse order, substituting D-amino acids for the naturally occurring L-amino acids in order to increase stability and in vivo half-life on the polypeptide. In this embodiment, the amino-terminus amino acid of the therapeutic polypeptide becomes the carboxy-terminus amino acid and the carboxy-terminus amino acid becomes the amino-terminus amino acid.

8.3 Antibodies

The invention also includes monoclonal and polyclonal antibodies having binding affinity for one or more of the therapeutic polypeptides of the invention. The term "antibodies" as used herein is broadly construed to include (1) monoclonal and polyclonal antibodies which bind to one or more therapeutic polypeptides of the invention, as well as humanized analogues of such antibodies and active fragments of such antibodies which bind to one or more of the therapeutic polypeptides, and (2) antibodies which bind to the variable regions of the foregoing antibodies, humanized analogs and active fragments.

The antibodies can be manufactured by a wide variety of known methods. As an example, antibodies may be produced by immunizing a host animal by injection with MA peptides. Examples of suitable animals include goats, sheep, donkeys, horses, hamsters, chickens, rabbits, mice, rats, etc. Antibody production may be performed according to a variety of methods known in the art. In a preferred embodiment, antibodies are raised against therapeutic polypeptides fused to a carrier protein, such as keyhole limpet hemocyanin (KLH), bovine serum albumin (BSA) or ovalbumin (OVA). The antibodies may, for example, be obtained from tissue culture supernatants and/or cell lysates, ascite fluid, serum, plasma and/or whole blood.

Once obtained, the antibodies may be cleaved to provide F(Ab)2 and/or F(AB) fragments while still maintaining the activity of the uncleaved antibodies. Antibodies can be immobilized on resins, added in solution or coated on other solid support surfaces.

Antibodies of the invention can be used in a variety of assays, for example, enzyme linked immunosorbent assay (ELISA), Western blot, and immuno-PCR assays, and are also useful in solution or solid phase affinity quantification/ qualification. In a preferred embodiment the assay is an ELISA.

In one aspect of the invention, two or more of the antibodies are used together in an in vitro assay for the quantification or qualitative analysis of a therapeutic polypeptide species. In a specific embodiment, one antibody is a monoclonal antibody to the therapeutic polypeptide and one antibody is a polyclonal antibody to the therapeutic polypeptide. In a related embodiment, the antibodies are both monoclonal antibodies recognizing different epitopes of a therapeutic polypeptide.

Various adjuvants may be employed in the production of antibodies of the invention, to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. For preparation of monoclonal antibodies, any technique that provides for the production of antibody molecules by continuous cell lines in culture may be used. For example, the hybridoma technique originally developed by Kohler and Milstein,[70] as well as the trioma technique, the human B-cell hybridoma technique,[71] and the EBV-hybridoma technique to produce human monoclonal antibodies.[72] Monoclonal cells lines can then be screened for binding to the particular MA peptides peptides using the purified species in any type of immunoassay available in the art.[73] The antibodies are preferably monoclonal antibodies.

It will be recognized by one of skill in the art that the antibodies of the invention have a wide range of uses, e.g., in the isolation, qualitative characterization, and quantification of MA peptide; isolation, qualitative characterization, and quantification of natural and synthetic functional equivalents of the MA peptide; as well as the isolation, qualitative characterization, and quantification of immunologically cross-reactive materials derived from other biological sources e.g., primate, rodent, ovine, porcine and ovoid species.

The antibodies of the invention are useful for monitoring serum levels of the therapeutic polypeptides by methods known in the art. Antibodies to the therapeutic polypeptides are also useful for tracking delivery of the therapeutic polypeptides. The antibodies of the invention can be linked to a suitable tag to allow visualization of sites where the antibodies have accumulated, e.g., where they have bound to the therapeutic peptides or other polypeptides. In one aspect of the invention, tagged antibodies are administered to a subject to identify the site of accumulation or expression of the therapeutic polypeptides.

Analysis of compounds using the antibodies of the invention may be accomplished in biological fluids and physiological buffers. Moreover, the antibodies may be immobilized by attachment to a suitable support structure according to known methods for isolation and purification of the MA peptide.

The antibodies of the invention are also useful for in vivo therapeutic administration and manipulation of naturally occurring levels of MA or pMA peptide, as well as in vitro analysis of production levels, location and species, study of pharmacokineticaly relevant levels of therapeutic polypeptides of the invention, half-life and in vivo distribution, degradation, manipulation and sites of production, depot and action. In this regard, the antibodies of the invention may be bound to agents having affinity for target tissues. Conversely, the antibodies themselves are usefully employed in the targeting of therapeutics to MA peptide-reactive sites, blocking of activity in vitro or in vivo, modification of solution kinetics, and a wide variety of other uses that would be apparent to one of skill in the art.

In one aspect of the invention, one or more antibodies of the invention is administered to a subject to block the activity of a therapeutic polypeptide or to block the activity of cancer-produced hCG or a cancer-produced fragment of hCG (e.g., β-core).

Moreover, the antibodies of the invention are useful for identifying functional domains, folding patterns, sequence and in investigating the effects of in vivo/in vitro post-translational modifications on solubility of MA and pMA. The antibodies of the invention also find a variety of uses in the investigation of solubility, physio-chemical, biological, stability, degradation and structural characteristics of the therapeutic polypeptides.

The antibodies of the invention are useful in the detection and purification of MA peptides. The antibodies of the invention may be linked to a variety of accessory molecules to aid in purification, analysis, assay characteristics, as well as to improve targeting, tracking and biological half-life, depoting, location, and cofactor use. For example, antibodies can be tagged by known methods with markers, such as with radioactive markers, fluorescent markers, chemiluminescent markers or affinity tags, such as biotin.

The antibodies of the invention provide a significant advantage in the purification of MA peptides. Techniques used by the inventors in the initial stages of this work included size separation methodologies, i.e., SDS-PAGE, gel permeation chromatography, size-exclusion centrifugation and membrane separations, and non-specific charge effects, i.e., cation and anion exchange chromatography, and RP-HPLC. The ability to isolate the MA peptides using antibody-driven methods is a significant advance over these original methods.

The antibodies of the invention are useful in qualitative and quantitative assays for the presence of natural, synthetic and modified MA peptide-derived sequences and also for immunologically cross-reactive materials derived from other biological sources i.e., primates, rodents, ovine, porcine and ovoid species. Examples of suitable sources include urine, serum, plasma and whole-blood collected from suitably qualified donors, tissue sections, biopsy samples bacterial/tissue culture supernantants/lysates prepared from transfected/transformed cell cultures, and partially purified materials derived from these sources.

The described antibodies can be utilized in the purification of synthetic and natural MA peptides and/or functional derivatives from synthetic and natural sources. Examples of suitable starting materials include, but are not limited to urine, serum, plasma and whole-blood collected from suitably qualified donors, tissue sections, biopsy samples bacterial/tissue culture supernantants/lysates prepared from transfected/transformed cell cultures, and partially purified to materials derived from these sources.

In a specific embodiment antibodies to a therapeutic polypeptide are immobilized to a support such as a silica or sepharose bead in order to isolate the therapeutic peptide. Antibodies may be positioned in a therapeutic polypeptide manufacturing system (e.g., downstream from an incubator where a therapeutic polypeptide is being produced by recombinant organisms) for isolating the therapeutic polypeptide. Examples of suitable production methods include chemical synthesis, expression in a suitable recombinant expression vector/host cell culture systems, and isolation from urine, serum or plasma (e.g., urine, serum or plasma produced by a recombinant organism).

The antibodies may be manipulated according to various techniques known in the art to achieve alteration of soluble material concentrations, complexing material so as to reduce or enhance half-life in solute, complexing to neutralize or otherwise modify activity against target entities, modification of biological target.

The antibodies of the invention are also useful for the production of anti-idiotype antibodies, which will mimic the therapeutic activities of the therapeutic polypeptides described herein.

The antibodies of the invention also find use as immunogens in suitable animal species (e.g., rat, mouse or rabbit) to produce an anti-idiotype antibody that mimics the activity of a therapeutic polypeptide. In a preferred aspect, the immunogen is a monoclonal antibody that, upon incubation with a therapeutic polypeptide, inactivates one or more of the therapeutic activities of the therapeutic polypeptide.

8.4 Preparation of Therapeutic Polypeptides

The therapeutic polypeptides can be prepared by any means known in the art, for example, by known synthetic or recombinant techniques. MA and pMA may be isolated from native sources of hCG, such as early pregnancy urine.

8.4.1 Preparation of Therapeutic Polypeptides by Synthetic Methods

As an example, the therapeutic polypeptides can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperidine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. In the first coupling step in peptide synthesis, the resin can be allowed to swell to effect more efficient coupling by increasing the time of mixing in the initial DMF washes to three 15-minute washes rather than three 30 second washes.

After synthesis, the peptide can be cleaved from the resin as follows: (1) washing the peptide-resin three times for 30 seconds with DMF; (2) removing the Fmoc protective group on the amino terminus by washing two times for 15 minutes in 20% piperidine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% trisopropysilane with the peptide-resin for two hours, then filtering the peptide in the cleavage cocktail away from the resin, and precipitating the peptide out of solution by addition of two volumes of ethyl ether.

To isolate the peptide, the ether-peptide solution can be allowed to sit at −20° C. for 20 minutes, then centrifuged at 6,000×G for 5 minutes to pellet the peptide. The peptide can be washed with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

Branched derivatives of the therapeutic polypeptides may be prepared by any method known in the art for covalently linking any naturally occurring or synthetic amino acid to any naturally occurring or synthetic amino acid in a peptide chain. The amino acid residue to which the branch is attached preferably has a side chain group able to react with the amino or carboxyl group at a terminus of the branch, so that the branch may be covalently bound to the peptide chain.

Examples of amino acids with a free amino side chain group include diaminobutyric acid, lysine, arginine, ornithine, diaminopropionic acid and citrulline. Such amino acids can be incorporated into a peptide so that an amino acid can form a branch therewith, for example, by forming a peptide bond to the free amino side group, from that residue.

Examples of amino acids with a free carboxyl side chain group include glutamic acid, aspartic acid and homocitrulline. Such amino acids can be incorporated into polypeptide (e.g., the therapeutic polypeptide) so that an amino acid can form a branch therewith, for example, by forming a peptide bond to the free carboxyl side group, from that residue.

The amino acid from which the branch is formed can be linked to a side chain group of an amino acid in the peptide chain by any type of covalent bond. Preferred bonds include peptide bonds, ester bonds and disulfide bonds. Amino acids capable of covalently bonding to a branch may also be substituted for residues within the MA peptide sequence.

As an example, branched peptides can be prepared as follows: (1) the amino acid to be branched from the main peptide chain can be prepared as an N-α-tert-butyloxycarbonyl-protected (Boc-protected) amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12 N HCl in a 1 liter separatory funnel, and allowing the phases to separate, saving the bottom aqueous layer and re-extracting the top layer two more times with 200 ml 0.12 N HCl; (4) the solution containing the peptide can be dehydrated by adding 2-5 grams magnesium sulfate, filtering out the magnesium sulfate, and evaporating the remaining solution to a volume of about 2-5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared in an analogous manner, using is the N-F-moc coupled form of the amino acid or amino acid analog.

The therapeutic polypeptides or functional equivalents of the invention can also be prepared as cyclic polypeptides. For example, in a segment containing a first cysteine residue, a second cysteine residue may be inserted or substituted for a different amino acid residue in the segment, and a disulfide bond may be formed between the first and second cysteine residues. In a related method, the therapeutic polypeptide comprises at least two cysteine residues, disulfide bond is formed between two of the cysteine residues. The therapeutic polypeptides may also be modified as necessary by inserting one or more cysteine residues between two other (preferably non-cysteine) amino acid residues; coupling at least one cysteine residue at an end of the therapeutic polypeptide; or replacing at least one non-cysteine amino acid residue with a cysteine residue. Suitable modifications are those which do not eliminate the therapeutic efficacy of the therapeutic polypeptide.

Cyclic polypeptides may also be formed by establishing a disulfide bond between two cysteine residues or by an amide linkage. Disulfide bridge formation can be achieved by (1) dissolving the purified polypeptide at a concentration of between 0.1.-0.5 mg/ml in 0.01 M ammonium acetate, pH 7.5; (2) adding 0.01 M potassium ferricyanide to the dissolved polypeptide dropwise until the solution appears pale yellow in color and allowing this solution to mix for 24 hours; (3) concentrating the cyclized polypeptide to 5-10 ml of solution, repurifying the peptide by reverse phase-high pressure liquid chromatography (RP-HPLC) and finally lyophilizing the peptide. If the polypeptide to be cyclized does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge.

In another approach, cyclic peptides are obtained by establishing an amide linkage. The amide linkage can be established by various methods known in the art. In one method, an allyl-protected amino acid, such as aspartate, glutamate, asparagine or glutamine, can be incorporated into the peptide as the first amino acid, and then the remaining amino acids coupled onto the allyl-protected amino acid. The allyl protective group can be removed by mixing the peptide-resin with a solution to of tetrakistriphenylphosphine palladium (0) in a solution of chloroform containing 5% acetic acid and 2.5% N-methylmorpholine. The peptide resin can be washed with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperidine in DMF, and washed with DMF. The activator mix, N-methylmorpholine and HBTU in DMF, can be brought onto the column and allowed to couple the free amino terminal end to the carboxyl group generated by removal of the allyl group to cyclize the peptide. The peptide can be cleaved from the resin as described in the general description of chemical peptide synthesis above. The peptide can be purified by reverse phase-high pressure liquid chromatography (RP-HPLC). When the peptide to be cyclized does not contain an allyl-protected amino acid, an allyl-protected amino acid can be introduced into the sequence of the peptide at the amino-terminus, carboxy-terminus or internally, to permit the peptide to be cyclized.

The nucleic acid can be constructed by ligating the appropriate nucleic acid sequences encoding the desired amino acid sequences in the proper coding frame. The nucleic acid can be induced to express the chimeric product by standard methods. Alternatively, the chimeric product may be made by protein synthetic techniques, e.g., by use of a peptide synthesizer.

8.4.2 Preparation of Therapeutic Polypeptides by Recombinant Expression Techniques The therapeutic polypeptides of the invention can also be obtained by recombinant expression techniques.[74] Examples of recombinant expression systems that may be suitably employed in the production of the therapeutic polypeptides of the invention include prokaryotic cell systems, eukaryotic cell systems and artificial expression systems.

An expression vector for expressing a nucleic acid sequence encoding a therapeutic polypeptide can be introduced into a cell for expression of the therapeutic polypeptide. In a preferred embodiment, the nucleic acid is DNA. The vector can remain episomal or become chromosomally integrated, as long as it can be transcribed in the host cell to produce the desired RNA. Vectors can be constructed by standard recombinant DNA technology methods. Vectors can be plasmid, viral, or others known in the art, used for replication and expression in, eukaryotic or prokaryotic cells.

For prokaryotic production, any expression vector that is functional in the selected prokaryotic host cell may be used, provided that the vector contains all of the necessary nucleic acid components or elements to ensure expression of the therapeutic polypeptide. Typically, the vector will contain a promoter, an origin of replication element, a transcriptional termination element, a ribosome binding site element, a polylinker region for inserting the nucleic acid encoding the polypeptide to be expressed, and a selectable marker element.

The promoter may be homologous (i.e., from the same prokaryotic species and/or strain as the host cell), heterologous (i.e., from a source other than the prokaryotic host cell species or strain), or synthetic. As such, the source of the promoter may be any unicellular prokaryotic or eukaryotic organism, any vertebrate or invertebrate organism, or any plant, provided that the promoter is functional in, and can be regulated by, the host cell. The more preferred promoters of this invention are inducible promoters, such as those of bacteriophage lambda origin, i.e., lambda promoters, the T5 promoter or the T7 promoter, bacterial promoters such as lac, tac (a composite of the trp and lac promoters), trp, and tna.

The promoter nucleic acid sequences useful in this invention may be obtained by any of several methods well known in the art. Typically, promoters useful herein will have been previously identified by mapping and/or by restriction endonuclease digestion and can thus be isolated from the proper tissue source using the appropriate restriction endonucleases. In some cases, the promoter may have been sequenced. For those promoters whose DNA sequence is known, the promoter may be synthesized using the methods described above for nucleic acid synthesis or cloning. Where all or only portions of the promoter sequence are known, the promoter may be obtained using PCR and/or by screening a genomic library with suitable oligonucleotide and/or promoter sequence fragments from the same or another species. Once isolated, the promoter may optionally be sequenced and prepared synthetically.

Where the promoter sequence is not known, a fragment of DNA containing the promoter may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, QIAGEN™ column or other methods known to the skilled artisan. Selection of suitable enzymes to accomplish this purpose will be readily apparent to one of ordinary skill in the art.

An origin of replication is typically a component of commercially available prokaryotic expression vectors. The origin of replication aids in the amplification of the vector in a host cell. Amplification of the vector to a desirable copy number (e.g., a number which results in maximum production of the therapeutic polypeptide and effective maintenance of the plasmid in the cell culture) can, in some cases, be important for optimal expression of the therapeutic polypeptide. If the vector of choice does not contain an origin of replication site, one may be chemically synthesized based on a known sequence, and ligated into the vector.

A transcription termination element is typically located 3' to the end of the Polypeptide coding sequence and serves to terminate transcription of the polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

Selectable marker genes encode proteins necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; (c) supply critical nutrients not available from complex media; or (b) result in fluorescence or other observable qualities. Preferred selectable markers are the kanamycin resistance gene, the ampicillin resistance gene, and the tetracycline resistance gene.

A ribosime binding site element may also be present. This element, commonly called the Shine-Dalgarno sequence, facilitates translation initiation of a mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Delgarno sequences have been identified, each of which can be readily synthesized using methods set forth above.

All of the elements set forth above, as well as others useful in this invention, are well known to the skilled artisan and are described, for example, in Sambrook et al.,[75] Berger et al.[76] and other references.[77]

For eukaryotic expression, any promoter known to be effective in the cells in which the vector will be expressed can be used to initiate expression of the therapeutic polypeptide. Suitable promoters may be inducible or constitutive. Examples of suitable eukaryotic promoters include the SV40 early promoter region,[78] the promoter contained in the 3N long terminal repeat of Rous sarcoma virus,[79] the HSV-1 (herpes simplex virus-1) thymidine kinase promoter,[80] the regulatory sequences of the metallothionein gene,[81] etc., as well as the following animal transcriptional control regions, which exhibit tissue specificity and have been utilized in transgenic animals: elastase I gene control region (active in pancreatic acinar cells);[82] insulin gene control region (active in pancreatic beta cells),[83] immunoglobulin gene control region (active in lymphoid cells),[84] mouse mammary tumor virus control region (active in testicular, breast, lymphoid and mast cells),[85] albumin gene control region (active in liver cells),[86] alpha-fetoprotein gene control region (active in liver cells),[87] alpha 1-antitrypsin gene control region (active in liver cells),[88] beta-globin gene control region (active in erythroid cells),[89] myelin basic protein gene control region (active in oligodendrocyte cells in the brain),[90] myosin light chain-2 gene control region (active in skeletal muscle cells),[91] and gonadotropin releasing hormone gene control region (active in cells of the hypothalamus).[92]

The therapeutic polypeptides of the invention can be prepared for secretion using recombinant DNA technology. This may be accomplished by creating a nucleic acid construct wherein the DNA encoding the therapeutic polypeptide is attached at its 5' end to a naturally occurring or synthetic DNA sequence encoding a signal peptide. For secretion, the signal peptide sequence selected must be one that is recognized by, and therefore capable of being processed by, the host cell into which this construct is to be inserted and expressed. Thus, for example, a signal peptide obtained from a naturally secreted bacterial polypeptide can be attached to a polypeptide from a source such as human tissue thereby creating a hybrid precursor polypeptide that can be synthesized in, and secreted from, those bacterial (and other prokaryotic) cell species that recognize and are able to process the signal peptide. The hybrid construct can be introduced into the host cell to provide the host cell with the capability of manufacturing and secreting the therapeutic polypeptide.

In one aspect of the invention, a mammal is genetically modified to produce the therapeutic polypeptide in its milk. Techniques for performing such genetic modifications are described in U.S. Pat. No. 6,013,857, issued Jan. 11, 2000, for "Transgenic Bovines and Milk from Transgenic Bovines." The genome of the transgenic animal is modified to comprise a transgene comprising a DNA sequence encoding a therapeutic polypeptide operably linked to a mammary gland promoter. Expression of the DNA sequence results in the production of the therapeutic polypeptide in the milk. The therapeutic polypeptide may then be isolated from milk obtained from the transgenic mammal (e.g., using a column comprising an antibody which binds to the therapeutic polypeptide). The transgenic mammal is preferably a bovine species.

8.4.3 Preparation of MA (SEQ ID NO: 2) and pMA (SEQ ID NO: 3) and Other Native MA Peptides by Isolation from Native hCG Sources The MA peptides can be prepared from certain native sources of hCG. Native preparations (i.e. derived from naturally occurring sources and not recombinantly produced) of hCG and β-hCG preparations can be obtained from a variety of sources. Both hCG and β-hCG are commercially available (e.g., Sigma Chemical Company) and hCG is commercially available in a form suitable for therapeutic use in humans (e.g., from Fujisawa, Wyeth-Ayerst Laboratories (APL™), Organon, Inc. (PREGNYL™) and Serono Laboratories, Inc. (PROFASIT™)). MA peptides are also present in the urine of women most abundantly in their first trimester of pregnancy ("human early pregnancy urine"). Other sources include, but are not limited to, urine from women in the second and third trimesters of pregnancy, urine from patients with proteinuria, urine from patients having hCG secreting tumors or other cancer patients, from pituitary glands, and from urine of post-menopausal women MA peptide can be isolated and/or partially purified from native sources of hCG. For example, the inventors have isolated MA peptide from human early (i.e. first trimester) pregnancy urine. Other native sources of hCG include, but are not limited to, urine from women in the second and third trimester of pregnancy, urine from proteinuria patients (both pregnant women with preeclampsia and patients with nephrotic syndromes), urine from patients with hCG-secreting tumors, cultures of hCG-producing cells (e.g., trophoblasts[93]) and pituitary glands.

MA peptide can be isolated and/or partially purified using conventional techniques, such as affinity chromatography. For example, antibodies prepared against MA peptide can be used to prepare an affinity chromatography column that can be used to purify the polypeptides by well-known techniques.[94] Antibodies, either polyclonal or, preferably, monoclonal, with specificity for MA peptide can be generated by the methods described herein or by other methods known in the art.[95]

Fractions of human early pregnancy urine or other source of MA can be assayed for the presence of the MA peptide species using a monoclonal antibody specific for the MA peptides. The assay can be performed by known methods. For example, an immunoradiometric assay (IRMA) can be used.[96] Briefly, the IRMA assay is performed by adsorbing an antibody against the MA peptides onto the surface of wells of a microtiter plate by incubation in a coating buffer (0.2 M sodium bicarbonate, pH 9.5) overnight at 4° C. The residual non-specific binding sites are blocked by the addition of a 1% bovine serum albumin solution (with 0.1% sodium azide) to the wells for 3 hours at room temperature, and the wells of the microtiter plate are then washed with deionized water. An aliquot of the fraction in assay buffer (0.01 M sodium phosphate, 0.15 M NaCl, 0.01 M EDTA, 0.1% sodium azide, 0.1% bovine γ-globulin, pH 7.4) is incubated in the wells for 24 hours at room temperature. The sample is then removed and the wells washed with deionized water. A solution of a second antibody specific for the MA peptide, which antibody has been iodinated with $I^{125}$, (approximately 40,000 cpm/well) is incubated in the wells for 24 hours at room temperature. The iodinated antibody solution is removed and the wells washed five times with deionized water. The level of radioactivity in each well is then determined in a scintillation counter which can measure γ-irradiation.

In an alternative embodiment, MA peptides can be obtained by proteolysis of β-hCG (SEQ ID NO: 1) followed by purification using standard techniques such as chromatography (e.g., HPLC), electrophoresis, etc. Moreover, MA peptides and fragments thereof can be obtained by treating the β-core of β-hCG to remove the residual sugar residues and treating β-hCG to break 6-40 away from 55-89 and treating the deglycosylated beta core to break the 6-40 and 55-92 apart.

8.5 Therapeutic Methods

The therapeutic polypeptides of the invention have multiple therapeutic and diagnostic uses, as more fully described in the ensuing sections. It will be appreciated that the therapeutic polypeptides of the invention may be administered to a specific subject for any one or more of the therapeutic uses discussed herein. The therapeutic methods of the invention include administration of the therapeutic polypeptides of the invention, as well as administration of a nucleic acid encoding a therapeutic polypeptide and/or a functional equivalent thereof. The therapeutic polypeptides of the invention may also be administered as components of cells transformed to express the therapeutic polypeptides of the invention. The therapeutic polypeptides may be expressed with signal peptides, directing excretion of the polypeptides and/or functional equivalents from the cells. The signal peptides may be enzymatically cleaved upon excretion to provide free therapeutic polypeptides. The therapeutic polypeptides may also be administered by means which cause a subject's own cells to express the polypeptide from the subject's native genome. In all of the therapeutic methods of the invention, the therapeutic polypeptide is administered in a therapeutically effective amount.

The therapeutic methods of the invention may all include administration of multiple therapeutic polypeptides [e.g., combinations of MA (SEQ ID NO: 2); pMA (SEQ ID NO: 3); $MA_{S1}$ (SEQ ID NO: 4); $MA_{S2}$ (SEQ ID NO: 5); $MA_{S3}$ (SEQ ID NO: 6); $MA_{S5}$ (SEQ ID NO: 7); $MA_{S9}$ (SEQ ID NO: 8); $MA_{S10}$ (SEQ ID NO: 9); and $MA_{S11}$ (SEQ ID NO: 10)] in a regimen that may or may not include other therapeutic agents.

Moreover, the therapeutic methods of the invention may also include administration of other β-hCG (SEQ ID NO: 1) fragments either alone, or in a therapeutic regimen that also includes administration of one or more therapeutic polypeptides of the invention—though in a preferred embodiment, use of such fragments without also using a therapeutic polypeptide of the invention is excluded from the therapeutic methods of the invention. Preferred fragments of β-hCG, which are not therapeutic polypeptides of the invention, are those with demonstrated anti-HIV, anti-cancer and/or prohematopoietic efficacy. Such polypeptides and peptide fragments are specifically described in U.S. Pat. Nos. 5,968,513 and 5,997,871; U.S. patent application Ser. Nos. 09/220,415 and 08/709,948; and International Patent Publications PCT/US97/11209 and PCT/US97/11202; the entire disclosure of each of these patents/applications is incorporated herein by reference. Examples include β-hCG fragments consisting of amino acid sequences 41-54, 45-54, 47-53, 45-57, and 109-119 of β-hCG (SEQ ID NO: 1), as well as 45-57::109-119, 110-119::45-57, and 47-57::108-119. Preferred β-hCG therapeutics include the Satellins, e.g.:

Satellin A1: β-hCG 45-57 [Leu-Gln-Gly-Val-Leu-Pro-Ala-Leu-Pro-Gln-Val-Val-Cys (SEQ ID NO: 18);

branched Satellin A1: β-hCG 45-57 [Leu-Gln-Dab(Pro)-Val-Leu-Pro-Dab(Pro)-Leu-Pro-Gln-Val-Val-Cys (see SEQ ID NO: 18 for primary sequence)], where "Dab" represents diaminobutyric acid, and Dab(Pro) indicates a proline peptide-bonded to the amino side chain of Dab);

circularized Satellin A2: β-hCG 45-57 with a cysteine residue added to the N-terminus, circularized via a disulfide bond between the systeine residues [Cys-Leu-Gln-Gly-Val-Leu-Pro-Ala-Leu-Pro-Gln-Val-Val-Cys (SEQ ID NO: 19)]; and Satellin B: β-hCG 109-119 [Thr-Cys-Asp-Asp-Pro-Arg-Phe-Gln-Asp-Ser-Ser (SEQ ID NO: 22).

8.5.1 Treatment of Retrovirus Infections

The invention provides for the treatment of diseases and disorders associated with retrovirus infections in a subject. The method generally comprises administering to a subject infected with a retrovirus a therapeutically effective amount of one or more therapeutic polypeptides of the invention to treat or prevent the infection.

In a central embodiment of the invention, the therapeutic polypeptides are used to treat or prevent HIV infection. The anti-HIV activity of MA peptides has been demonstrated in both in vivo and in vitro studies. In vitro cell culture studies conducted by the inventors show that at least one anti-HIV property exhibited by the MA peptides is the inhibition of HIV replication.

In HIV transgenic mice and rats, MA peptides suppress HIV expression and prevent death. When MA peptides are administered to nursing mice, the homozygous transgenic pups develop normally as compared to placebo-treated pups, which fail to develop and then die within two weeks of birth.

In monkeys, crude fractions of MA peptides reduce SIV viral load and prevent AIDS-like disease, increas $CD4^+$ T cell counts, promote weight gain and improve bone marrow function.

The invention provides for treatment or prevention of diseases and disorders associated with retroviral infection by a method that comprises administering to an infected subject one or more therapeutic polypeptides of the invention. For example, MA peptides exhibit properties that are useful in reversing the bone marrow dysplasia seen in AIDS patients.

The therapeutic polypeptides can also be used to prevent the progression of HIV infection to AIDS or to treat a subject with AIDS. In one aspect of the invention, the therapeutic polypeptides of the invention are administered to an HIV-infected subject having a T cell count that is below 500.

The therapeutic polypeptides of the invention also exhibit properties that are useful in the treatment of individuals acutely exposed to HIV (e.g., rape or inadvertent needle sticks). In such cases, one or more therapeutic polypeptides of the invention can be administered to prevent the establishment of an HIV infection following an initial inoculation event. Administration of a multi-drug regimen of anti-HIV therapeutics following such an inoculation event is known to be useful in reducing the probability of establishing an active HIV infection. The therapeutic polypeptides can be used as a component of such a multi-drug "day after" treatment, to reduce the probability that an HIV infection will become established.

The therapeutic polypeptides can be administered in a monotherapeutic treatment regimen, e.g., a therapeutic polypeptide can be administered alone in the treatment of HIV without also administering other anti-HIV therapeutics. Alternatively, one or more therapeutic polypeptides can be administered as component(s) of a multi-drug regimen, which includes one or more other anti-HIV compounds. Examples of other anti-HIV compounds that can be used in such multi-drug regimens include: protease inhibitors (e.g., CRIXIVAN™ (indinavir); FORTOVASE™ and INVIRASE™ (saquinavir); NORVIR™ (ritonavir); and VIRACEPT™ (nelfinavir)); non-nucleoside reverse transcriptase inhibitors (e.g., RESCRIPTOR™ (delavirdine); SUSTIVA™ (efavirenz); and VIRAMUNE™ (nevirapine)); and nucleoside reverse transcriptase inhibitors (e.g., VIDEX™ (didanosine, also known as DDI); EPIVIR™ (lamivudine, also known as 3TC); ZERIT™ (stavudine, also known as d4T); HIVID™ (Zalcitabine, also known as DDC); RETROVIR™ (zidovudine, also known as AZT or ZDV); and COMBIVIR™ (lamivudine and zidovudine)).

A multi-drug regimen may also include multiple therapeutic polypeptides of the present invention [e.g., combinations of MA (SEQ ID NO: 2); pMA (SEQ ID NO: 3); $MA_{S1}$ (SEQ ID NO: 4); $MA_{S2}$ (SEQ ID NO: 5); $MA_{S3}$ (SEQ ID NO: 6); $MA_{S5}$ (SEQ ID NO: 7); $MA_{S9}$ (SEQ ID NO: 8); $MA_{S10}$ (SEQ ID NO: 9); $MA_{S11}$ (SEQ ID NO: 10); β-hCG 55-88 (SEQ ID NO: 11); β-hCG 55-90 (SEQ ID NO: 12); β-hCG 55-91 (SEQ ID NO: 13); β-hCG 55-74 (SEQ ID NO: 14); β-hCG 6-37 (SEQ ID NO: 15); β-hCG 6-38 (SEQ ID NO: 16); β-hCG 6-39 (SEQ ID NO: 17); and β-hCG 6-40 (SEQ ID NO: 18)

and/or their functional equivalents] in a regimen that may or may not include other anti-HIV compounds.

A multi-drug regimen may also include therapeutic agents for treating various side effects of HIV-infection or AIDS, such as therapy for treating opportunistic infections and/or malignancies. For example, a multi-drug therapeutic regimen may include antibiotics for bacterial infections, chemotherapy and/or radiation therapy for malignancies, and/or ativiral treatments for opportunistic viral infections (e.g., treatments for Cytomegalovirus, Herpes zoster, and/or Herpes simplex infection).

Moreover, the therapeutic polypeptides of the invention may be administered with other β-hCG (SEQ ID NO: 1) fragments, and/or polypeptides comprising such fragments, with demonstrated anti-HIV, anti-cancer and/or pro-hematopoietic efficacy.

The therapeutic polypeptides are also useful in combination with one or more chemokines, functional equivalents of chemokines, and/or genes encoding chemokines or their functional equivalents. Examples of suitable cytokines include macrophage-derived chemokine, monocyte chemotactic protein 1, monocyte chemotactic protein 2, monocyte chemotactic protein 3, monocyte chemotactic protein 4, activated macrophage specific chemokine 1, macrophage inflammatory protein 1 alpha, macrophage inflammatory protein 1 beta, macrophage inflammatory protein 1 gamma, macrophage inflammatory protein 1 delta, macrophage inflammatory protein 2α, macrophage inflammatory protein 3α, macrophage inflammatory protein 3β, regulated upon activation, normal T cell expressed and secreted (and its variants), I-309, EBI1-ligand chemokine, pulmonary and activation regulated chemokine, liver and activation-regulated chemokine, thymus and activation regulated chemokine, eotaxin (and variants), human CC chemokine 1, human CC chemokine 2, human CC chemokine 3, IL-10-inducible chemokine, Liver-expressed chemokine, 6Ckine, exodus 1, exodus 2, exodus 3, thymus-expressed chemokine, secondary lymphoid tissue chemokine, lymphocyte and monocyte chemoattractant, monotactin, chemokine-related molecule, myeloid progenitor inhibitory factor-1, myeloid progenitor inhibitory factor-2, stromal cell-derived factor 1α, stromal cell-derived factor 1β, B-cell-attracting chemokine 1, HuMIG, H174, Interferon-stimulated T-cell α-chemoattractant, interleukins, IP-10, platelet factor 4, growth-regulated gene-α, growth-regulated gene-β, growth-regulated gene-γ, neutrophil-activating protein 2, ENA-78, granulocyte chemotactic protein 2, lymphotactin, fractalkine/neurotactin, viral chemokines and functional equivalents of the foregoing chemokines. Other specific examples of suitable components Steel factor (SLF) and adult PB plasma. Preferred factors are those which cause proliferation or, less preferably, differentiation of cells that are CFU-GEMM or earlier cells, e.g., IL-3 and GM-CSF. Preferred chemokines include C-C type chemokines, such as RANTES, MIP-1α, MIP-1β and MDC.

A preferred embodiment of the invention relates to methods of using one or more therapeutic polypeptides of the invention for treatment or prevention of HIV infection, preferably HIV-1 infection, in a human subject. In a specific embodiment, one or more therapeutic polypeptides of the invention is administered to a subject with a set of one or more conditions which does not include a cancer which secretes hCG or hCG fragments to treat or prevent HIV infection in the subject. In another specific embodiment, one or more therapeutic polypeptides of the invention is used for the treatment or prevention of HIV infection in a human subject with a set of one or more conditions that does not include Kaposi's sarcoma (KS). In the treatment of HIV infection, the therapeutic polypeptides of the invention can be used to prevent or slow progression of HIV infection to AIDS in a human subject, or to treat a human subject with AIDS.

In another aspect the therapeutic polypeptide is administered to an infant born to an HIV infected mother in order to reduce the risk of HIV infection in the newborn and to increase weight gain and blood cell development. Moreover, the therapeutic polypeptides may also (or alternatively) be administered to the HIV-infected mother, before or during birth of the infant, to reduce the risk of HIV infection in the newborn. In a preferred embodiment, one or more therapeutic polypeptides are administered to an HIV infected mother to prevent wasting, promote hematopoiesis and to reduce the risk of infecting the unborn. In a specific embodiment only one or more therapeutic polypeptides is administered, i.e., therapeutic polypeptide(s) in the absence of other anti-HIV, anti-wasting and/or pro-hematopoietic therapeutic agents. In an additional embodiment the therapeutic polypeptides are administered as part of a multi-drug therapy regimen.

The therapeutic polypeptides of the invention are also useful in the treatment of retroviral infection in non-human animals. For example, one or more therapeutic polypeptides of the invention is suitably administered, alone or in combination with one or more other pharmaceutical agents in a therapeutically effective amount, to (1) a horse species (e.g., *Equus caballus*) to treat or prevent an infection and/or symptoms associated with equine infectious anemia virus; (2) a bovine species (e.g., *Bos taurus* or *Bos indicus*) to treat or prevent the infection and/or symptoms associated with bovine immunodeficiency virus; (3) an *Ovis* species to treat or prevent the infection and/or symptoms associated with visna virus; or (4) a feline species to prevent the infection and/or symptoms associated with feline immunodeficiency virus and/or feline leukemia virus (FELV).

8.5.2 Treatment of Non-HIV Viral Infection

The therapeutic polypeptides are also useful in the treatment or prevention of viral diseases other than HIV. In this embodiment, the therapeutic polypeptides are suitably administered to a subject to slow or stop the progression of viral diseases, such as hepatitis and herpes infection. In one aspect of the invention, the therapeutic polypeptides of the invention are administered to a subject infected with both HIV and hepatitis C to directly combat the virus and/or to combat symptoms of the infection. The therapeutic polypeptide can be used in a monotherapeutic treatment regimen or in combination with other anti-viral compounds in a multi-drug regimen.

To assess the utility of treating a subject infected with a virus, one skilled in the art can evaluate the anti-viral activity of any of the therapeutic polypeptides in any in vitro system as described herein or as otherwise known in the art. After demonstration of in vitro activity, or if in vitro testing systems are not available, the therapeutic polypeptides may also evaluated in animal models, e.g., as described herein, or in any of a variety of known in vitro assays.

To effect treatment or prevention, one or more therapeutic polypeptides of the invention is administered to a subject, either alone or in combination with another drug, or drugs for the prevention and/or treatment of an infection, symptoms of an infection, and/or conditions resulting from an infection by a virus, such as hepatitis C virus, herpesvirus 1, herpesvirus 4, is encephalomyocarditis virus (EMCV), rubella virus and influenza virus. In a related embodiment, one or more therapeutic polypeptides of the invention is administered to a subject, either alone or in combination with one or more other therapeutic agents for the prevention and/or treatment of viral meningitis.

8.5.3 Treatment of Bacterial Infections

The therapeutic polypeptides can be administered alone or in combination with another drug or drugs. The effectiveness of treating a specific bacterial infection in a subject can be assessed by in vitro and/or in vivo methods available in the art. The bacterial infection may be an intracellular bacterial infection and/or an extracellular bacterial infection.

In a preferred embodiment, the therapeutic polypeptides are administered either alone or in combination with another drug or drugs to a subject to treat or prevent infection with *Treponema pallidum* (i.e., a subject with syphilis).

*Helicobacter pylori*, the causative agent of gastric ulcers, may also be treated or prevented by administration of a therapeutic polypeptide of the invention, either alone or in combination with one or more other therapeutic agents. In a preferred embodiment, the therapeutic polypeptide is delivered in combination with Flagil, Amoxycylin and/or a drug to reduce production of acid such as ranitidine (e.g., ZANTAC™), famotidine (e.g., PEPCID™ or omeprazole (e.g., PRILOSEC™).

The therapeutic polypeptides of the invention are also suitably employed in the treatment or prevention infection with *Escherichia coli* and/or infection with *Mycobacterium tuberculosis*.

8.5.4 Treatment of Wasting Syndromes

The inventors have discovered that MA peptides mediate a significant reversal in wasting syndromes. For example, the empirical work undertaken by the inventors has demonstrated reversal in wasting associated with HIV infection, as well as wasting associated with various malignancies.

The invention provides a method for treating wasting syndromes comprising administering a therapeutically effective amount of one or more therapeutic polypeptides to a subject with a wasting syndrome.

The methods are applicable to the treatment of any disease or disorder characterized by an undesired loss of body cell mass. For example, the therapeutic polypeptides are useful in the treatment of: wasting associated with viral infection, such as HIV-associated wasting; wasting associated with bacterial infection or other types of infection or sepsis; cachexia associated with cancer, chemotherapy, and/or radiation therapy; wasting associated with chronic cardiovascular disease; wasting caused by exposure to toxic substances; and wasting associated with diarrhea and other gastrointestinal disorders.

In a preferred embodiment, one or more therapeutic polypeptides of the invention is administered to treat or prevent a wasting syndrome associated with HIV infection. In a related embodiment, one or more therapeutic polypeptides of the invention is administered to treat or prevent a wasting syndrome associated with cancer.

The therapeutic polypeptides of the invention may also be administered to treat and/or prevent chronic diarrhea and/or its associated effects.

8.5.5 Treatment of Hematopoietic Deficiencies

The invention also relates to therapeutic methods for treating or preventing hematopoietic deficiencies. MA promotes both in vivo and in vitro hematopoiesis of multiple lineages, e.g., T-cells, erythrocytes, granulocytes, platelets, and macrophages, of mice, rats, monkeys, and human bone marrow. MA can rescue lethally irradiated animals and restore their blood counts to normal, even when administered before or after exposure to radiation (e.g., 24 hours after the radiation exposure). Equally remarkable, MA protects against side effects of cancer chemotherapy (TAXOL™ (paclitaxel)) at lethal doses, and facilitates recovery of acutely bled rats and monkeys. None of these hematopoietic effects have been observed with pure native glycosylated β-core, β-hCG, α-hCG, hCG scrambled MA (see SCRAM I and SCRAM II in Table 1), nor with a variety of synthetic peptides corresponding to many other regions of β-hCG.

The methods of the invention for treating hematopoietic deficiency can be employed in the treatment of any disease or disorder in which increased amounts of hematopoietic cells are desirable. Examples include disorders associated with reduced numbers of one or more hematopoietic cell types. The treatment methods of the invention comprise administering to a subject with a hematopoietic deficiency a therapeutically effective amount of one or more therapeutic polypeptides of the invention.

The invention also provides methods for expansion of hematopoietic cells in vitro by contact with a therapeutic polypeptide of the invention. In a related aspect, the invention provides for treatment or prevention of hematopoietic cell deficiencies by administering hematopoietic cells, the numbers of which have been increased in vitro by contact with a therapeutic polypeptide of the invention.

The therapeutic polypeptides are useful in treating conditions characterized by failure or dysfunction of normal blood cell production and maturation. Examples of such conditions include aplastic anemias, cytopenias and hypoproliferative stem cell disorders. These disorders entail failure of stem cells in bone marrow to provide normal numbers of functional blood cells.

Aplastic anemias result from the failure of stem cells to give rise to the intermediate and mature forms of red cells, white cells, and platelets. While red cell production is usually most seriously affected, a production of other mature blood cell elements, such as white cells and/or platelets is also relatively common. The majority of these anemias are acquired during adult life and are not related to any apparent genetic predisposition. About half of these acquired anemias arise in the absence of any obvious causative factor such as exposure to poisons, drugs or disease processes that impair stem cell function; these are termed idiopathic aplastic anemias. The remaining cases are associated with exposure to an extremely diverse array of radiation, chemotherapy, chemicals and drugs and also occur as a consequence of viral infections, such as HIV infection, and after pregnancy.

Other specific types of aplastic anemias, which may be treated by administration of the therapeutic polypeptides, include agranulocytosis and thrombocytopenia, in which the major deficiency lies in particular white cells and in platelet production, respectively. These non-red blood cell deficiencies are also often associated with HIV infection. Idiopathic Thrombocytopenic Purpura (ITP), a severe platelet deficiency is also associated with HIV infection. Additionally, agranulocytosis may be associated with autoimmune syndromes such as systemic lupus erythematosus (SLE) or with other infections, such as neonatal rubella.

In addition, immune deficiencies that are the primary or secondary result of infection by pathogenic microorganisms can be treated by administration of one or more of the therapeutic polypeptides. For example, immune deficiencies caused by microbes that are intracellular pathogens of hematopoietic cells can be treated by providing new hematopoietic cells. In one aspect of the invention, these new hematopoietic cells are generated by contacting hematopoietic stem and/or progenitor cells in vitro with the therapeutic polypeptides to cause proliferation of the cells. Examples of microbes which cause such immune deficiencies include gram-negative bacilli such as *Brucella* or *Listeria*; *Mycobacterium tuberculosis*, *Mycobacterium leprae*; parasites such as

*Plasmodium* and *Leishmania*; and fungi (such as those that cause pneumonia and other lethal infections secondary to immunodeficiencies).[97]

The therapeutic polypeptides can be administered to a subject to treat a cytopenia associated with HIV infection. The hematopoietic deficiencies associated with HIV infection include reduction in CD4+ T cells and other lymphocytes, red blood cells, platelets, specifically ITP, and neutrophils.

In one aspect of the invention, HIV-infected subjects are treated by contacting hematopoietic stem and/or progenitor cells in vitro with one or more therapeutic polypeptides; the resulting hematopoietic cells can then be directly infused into the subject in need of treatment. The cells can be obtained from the subject or from a suitable donor. Hemeotopoetic deficiency can also be treated by directly administering one or more therapeutic polypeptides or functional equivalents to the subject in need of treatment.

In one aspect of the invention, hematopoietic deficiency is treated by administering autologous hematopoietic cells (obtained from the subject or its identical twin) to the subject after in vitro expansion. This embodiment may also be employed as a step in a gene therapy protocol. For example, nucleic acid(s) of interest (e.g., comprising a gene(s) which provides a function desired in a subject) can be introduced into hematopoietic cells, before or after expansion of the cells by contact with one or more therapeutic polypeptides. Cell subpopulations can be isolated for use, before or after expansion in vitro. For example, blood cells can be isolated and expanded, and optionally also differentiated, in vitro, followed by introduction of all or a therapeutically effective portion of the cells (e.g, purified platelets, red blood cells, lymphocytes, etc.) into a subject.

Hematopoeitic deficiencies that can be treated by the therapeutic polypeptides can be generally divided into five broad categories. These categories should not be understood to be all-inclusive, as conditions not within these categories may be treatable using the therapeutic polypeptides of the invention. First are diseases resulting from a failure or dysfunction of normal blood cell production and maturation (i.e., aplastic anemia, cytopenias and hypoproliferative stem cell disorders). The second group includes neoplastic, malignant diseases in the hematopoietic organs (e.g., leukemia and lymphomas). The third group of disorders comprises disorders found in subjects with a broad spectrum of malignant solid tumors of non-hematopoietic origin. Induction of hematopoietic cell proliferation or administration of replacement hematopoietic cells in these subjects serves as a bone marrow rescue procedure, which is provided to a subject following otherwise lethal chemotherapy or irradiation of the malignant tumor. The fourth group of diseases consists of autoimmune conditions; in subjects affected with these conditions the hematopoietic cells serve as a source of replacement of an abnormal immune system. The fifth group of diseases comprises a group of genetic disorders which can be corrected by infusion of hematopoietic stem cells, preferably syngeneic, which prior to transplantation have undergone gene therapy.

In one aspect of the invention, the disease or disorder results from a failure or dysfunction of normal blood cell production and maturation. For example, the therapeutic polypeptides of the invention are useful in the treatment of hyperproliferative stem cell disorders, aplastic anemia, pancytopenia, agranulocytosis, thrombocytopenia, red cell aplasia, Blackfan-Diamond syndrome due to drugs, radiation, or infection, and idiopathic anemia.

The therapeutic polypeptides of the invention are also useful in the treatment of hematopoietic malignancies, such as acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, and non-Hodgkin's lymphoma.

Furthermore, the therapeutic polypeptides of the invention are useful in the treatment of immunosuppression in subjects with malignant, solid tumors, such as malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma and lymphoma.

The therapeutic polypeptides of the invention are also useful in the treatment of autoimmune diseases, such as rheumatoid arthritis, diabetes type I, chronic hepatitis, multiple sclerosis and systemic lupus erythematosus.

Moreover, the therapeutic polypeptides of the invention are usefully employed in the treatment of anemias resulting from various genetic (congenital) disorders, such as congenital anemias, familial aplastic anemia, Fanconi's syndrome, Bloom's syndrome, pure red cell aplasia (PRCA), dyskeratosis congenita, Blackfan-Diamond syndrome, congenital dyserythropoietic syndromes I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phosphate dehydrogenase) deficiency, pyruvate kinase deficiency, congenital erythropoietin sensitivity deficiency, sickle cell disease and trait, hemoglobinemias, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis and congenital leukocyte dysfunction syndromes.

In a preferred aspect, one or more therapeutic polypeptides of the invention is used to treat a disease resulting from a failure or dysfunction of normal blood cell production and maturation, such as an aplastic anemia, a cytopenia or a hypoproliferative stem cell disorder.

The therapeutic polypeptides also promote the in vitro growth of all hematopoietic progenitors in human cord blood and bone marrow, as well as bone marrow of other animals, such as monkeys, rats, digs, cats, pigs, sheep, cattle and horses.

The therapeutic polypeptides are also useful as radioprotective and/or chemoprotective agents. In animal studies (mouse and rat), in which animals were treated with a lethal dose of radiation or chemotherapy, administration of a single dose of a therapeutic polypeptide either 24 hours before or 24 hours after the lethal dose significantly increased survival time. Animals treated with a single dose of therapeutic polypeptide survived for 15-18 days, compared to survival times of 3-4 days for untreated animals. More dramatically, when radiation or chemotherapy-treated animals received MA peptides every other day for two weeks, the animals survived and their blood cell counts returned to normal within 28-30 days. In contrast, lethally exposed animals who did not receive MA peptides died in 3-4 days.

The present invention therefore provides methods of treating subjects before, during or after exposure to radiation to protect blood cells and other cells and/or increase blood cell counts, the methods comprising administering one or more therapeutic polypeptides of the invention to the subject before and/or during and/or after exposure to the radiation. The therapeutic polypeptides are preferably administered in an amount sufficient to decrease the recovery time of subjects administered chemotherapy or radiation. In cases of accidental exposure to chemical agents or radiation, the therapeutic polypeptides are preferably administered in an amount sufficient to decrease the recovery time or, in cases of lethal exposure, to lengthen survival time and/or to improve the likelihood of survival of the subject so exposed. Administration of the therapeutic polypeptides of the invention permits increased dosing of radiation and/or chemotherapy, thereby enabling more aggressive therapy with less harm to the subject.

The invention also provides methods for treating subjects who have sustained or may be expected to sustain blood loss. MA (SEQ ID NO: 2) promotes blood cell formation in animal models (monkeys and rats) where blood loss was induced. In an animal (monkey and rat) bled by ⅓ to ½ its blood volume, treatment with MA peptides increases survival rates, while also reducing the time necessary to restore normal blood counts. This surprising discovery is consistent with the conclusion that the therapeutic polypeptides of the invention are useful in trauma settings, where massive blood loss has occurred. The invention thus provides a method for increasing survival rates, reducing complications and/or reducing recovery times comprising administering one or more therapeutic polypeptides of the invention to a subject who has sustained blood loss, such as a trauma victim.

The therapeutic polypeptides of the invention have utility in any medical condition or circumstance in which a subject has sustained a medically important amount (i.e., an amount which is detrimental to the health of the subject) of blood loss. In such cases, the therapeutic polypeptides of the invention are administered to assist in the restoration of normal blood counts. For example, the therapeutic polypeptides of the invention may be administered in surgical settings to reduce dependency on heterologous blood transfusions. The therapeutic polypeptides of the invention may also be administered prior to surgery to induce hematopoiesis and thereby increase blood cell counts, thus reducing or eliminating the need for blood transfusions during or after surgery.

The therapeutic polypeptides of the invention may also be administered to a subject before and/or after blood loss (e.g., anticipated blood loss, such as donation of blood or planned surgery) to reduce the severity of or eliminate the adverse effects of blood loss. The therapeutic polypeptides may be administered to induce production of excess blood cells, so that sufficient amounts of blood may be removed and stored for transfusions that may become necessary during or after anticipated blood loss.

In a related aspect of the invention one or more of the therapeutic polypeptides is delivered to a donor of a blood cell component or bone marrow to decrease the time necessary for cell counts to return to normal level following such donation to decrease the time between successive donations of cells.

The therapeutic polypeptides can also be administered to eliminate and/or reduce the need for or increase the efficacy of a blood or bone marrow transfusion in trauma or non-trauma settings. The therapeutic polypeptides can be administered in trauma settings where blood loss threatens a subject's health. Administration of the therapeutic polypeptides can be used to reduce or eliminate the need for blood transfusions. For example, administering one or more therapeutic polypeptides during or after a blood transfusion can reduce the time required to restore normal blood cell counts and function. Such administration can limit the need for additional transfusions, and/or reduce complications associated with blood loss as well as those associated with blood transfusion. Administration one or more of the therapeutic polypeptides of the invention can therefore increase survival rates and reduce recovery time.

In a specific embodiment the therapeutic peptides are made available to military forces in combat settings. The therapeutic peptides are then administered at the first threat of biological and/or chemical exposure to reduce or prevent damage to the bone marrow and circulating blood cells. The therapeutic peptides are preferably administered as soon as practicable after an injury to promote hematopoiesis and to reduce the risk of infections.

The therapeutic polypeptides are suitably delivered with one or more other pro-hematopoietic agents to promote hematopoiesis, in vitro or in vivo. As an example MA can be administered with erythropoietin to a subject or applied ex-vivo with erythropoietin to cells to increase the numbers of red cells. In a specific embodiment MA is provided as a component of a pharmaceutical formulation which also comprises the other agent.

Examples of pro-hematopoietic agents that can be formulated with or administered with MA to promote hematopoiesis can be identified by one skilled in the art using assays as described herein and/or by any other assay known in the art to quantify or otherwise characterize hematopoietic production.

In one aspect one or more therapeutic polypeptides is administered with one or more cytokines, preferably a growth or differentiation factor.

In a preferred embodiment MA is formulated with erythropoietin and administered to a subject to increase numbers of red cells in a subject presenting with renal failure.

In another preferred embodiment MA is formulated with colony stimulating factor and administered to a subject to increase the numbers of white cells.

One or more of the therapeutic polypeptides may also be added to stored blood to extend the viability of the collected blood product and to increase the time the product can be used for transfusion into a subject. In one aspect, the therapeutic polypeptide is added to a blood collection vessel prior to collection of the blood.

One or more of the therapeutic polypeptides of the invention may also be administered to a subject who has been, or may have been, exposed to an infectious agent. Such administration will promote hematopoiesis and improve the subject's immune response to the infectious agent. In a preferred embodiment, the therapeutic polypeptides are administered to a subject prior to, during and/or after possible exposure to an infectious agent as a result of traveling to an area known to be endemic for infectious agents.

In a related aspect of the invention, the therapeutic polypeptides may be administered to a subject to enhance normal physiological functioning. As an example, the therapeutic polypeptides may be administered to a high altitude climber to increase red blood cells. The therapeutic polypeptides may be administered to a subject to enhance athletic performance.

8.5.6 Expansion of Stem and Progenitor Cells

The invention provides a method for the expansion of stem and/or progenitor cells. Stem cells and progenitor cells can be expanded ex-vivo and/or in vivo by contacting the cells with a therapeutic polypeptide of the invention. One or more therapeutic polypeptides of the invention may be administered as a component of a therapeutic regimen with other pharmaceutical agents to induce proliferation and/or differentiation of stem and/or progenitor cells into desired cell types and in sufficient numbers prior to implantation in a subject.

Stem and/or progenitor cells may, for example, be isolated from a subject's own organ system or from a donor and expanded ex-vivo prior to implantation in a subject. In a preferred embodiment, stem or progenitor cells are isolated from the bone marrow of a subject or a donor. As an alternative, the therapeutic polypeptide can be directly administered to a subject to promote expansion of stem and progenitor cells in vivo.

Stem cells are also suitably isolated from cord blood at birth and then expanded by contacting with a therapeutic polypeptide and stored for future use by the donor or by another subject. Isolated stem cells may also be frozen prior to expansion and thawed for expansion as needed.

In one embodiment, one or more therapeutic polypeptides is applied to stem cells and/or progenitor cells with one or more cytokine(s) to increase cell numbers and to stimulate differentiation and/or migration. Examples of cytokines that can be usefully combined with a therapeutic polypeptide of the invention include EGF, FGF-2, IL-2, GM-CSF, G-CSF, EPO, IGF and TGF. Preferred cytokines are those which induce the proliferation and/or differentiation of stem and/or progenitor cells. Cytokines and other pharmaceutical agents useful in the expansion, differentiation and/or migration of stem and progenitor cells can be identified by combining them with the therapeutic polypeptide and screening them using any in vitro and/or in vivo assay known in the art.

The stem cells may also be embryonic stem cells. In a specific embodiment, the therapeutic polypeptide is utilized to increase numbers of stem and progenitor cells giving rise to cartilage cells, bone cells, fat cells, muscle cells, neural cells (e.g., astrocytes), and/or cells of the hematopoietic system.

The therapeutic polypeptides may also be applied to stem and/or progenitor cells giving rise to neural cells to provide neural cells for treating a subject presenting with Parkinson's, Alzheimer's disease, multiple sclerosis, stroke and/or injuries to the neural system.

The therapeutic polypeptides are usefully administered to a subject to increase numbers of stem and/or progenitor cells giving rise to pancreatic islet cells (in vivo or in vitro) for the treatment of diabetes.

The therapeutic polypeptides are also suitably administered to a subject who has sustained an injury to a bone, such as a broken bone, to promote healing.

One or more therapeutic polypeptides of the invention may be brought into contact with stem and/or progenitor cells, either in vivo or in vitro, to increase number of stem and/or progenitor cells giving rise to heart, smooth and/or skeletal muscle.

In a preferred embodiment, the therapeutic polypeptide is administered to a subject to maintain or increase the numbers of stem and/or progenitor cells to slow the aging process and its associated complications.

8.5.7 Treatment of Cancer

The invention further relates to methods for treating and/or preventing cancer. The methods comprise administration of one or more therapeutic polypeptides of the invention in an amount sufficient to treat and/or prevent cancer. Like the crude hCG preparations discussed in Section 4, MA and pMA induce apoptotic death of human cancer cells in vitro and in vivo, e.g., Kaposi's sarcoma, other sarcomas, carcinomas of the breast, prostate, lung, pancreas, brain, and kidney, and some hematopoietic tumors as well as carcinomas, melanomas, and sarcomas of rodents.

The pharmacological properties of the MA peptides are consistent with their efficacious use in cancer therapy.

Examples of activities of MA peptides useful in cancer therapy include:
 induction of apoptisis of cancer cells;
 promotion of hematopoiesis;
 protection of bone marrow, blood and/or other cells from side effects of chemotherapy and/or radiation therapy;
 direct boosting of the immune system;
 induction of anti-angiogenesis; and
 reversal of wasting associated with cancer.

The therapeutic polypeptides are useful in the treatment of Kaposi's sarcoma (KS). MA peptides kill KS cells in vitro and block tumor formation when such tumor cells are transplanted into immune deficient mice. As described more fully in Section 9, systemic or intralesional inoculation with MA peptides induces apoptosis of KS cells.

The therapeutic polypeptides are also useful in the treatment of brain, breast, lung, pancreas, prostate, renal and hematopoietic cancers. The MA peptides exhibit anti-cancer activity against brain, breast, lung, pancreas, prostate, and renal cancers as well as in some hematopoietic cancers grown in vivo as xenotransplants in immune deficient mice. The same range of activity is seen with cultured human tumor cells.

Examples of cancers treatable by the methods of the invention include: KS, brain, breast, lung, pancreas, prostate, and renal cancer, and hematopoietic malignancies.

In a specific embodiment the therapeutic polypeptides are administered to a subject suffering from a cancer that secretes hCG or one of its subunits.

The therapeutic polypeptides are also useful in the ongoing treatment of diagnosed and treated cancer patients to prevent reoccurrence of disease, and in preventing the spread of a malignancy in a dormant cancer, such as the spread of prostate cancer.

The therapeutic polypeptides of the invention are useful as a monotherpay or in combination with other therapies including radiation or chemotherapy. Moreover, one or more therapeutic polypeptides of the invention is usefully administered as a component of a cancer vaccine composition to boost the immune response to a cancer vaccine and optionally to induce apoptosis and/or angiogenesis.

The therapeutic polypeptides are also usefully employed in the treatment of leukemias. Specific leukemias which may be treated using the therapeutic polypeptides of the invention include, for example, acute leukemia, such as acute lymphocytic leukemia and acute myelocytic leukemias (e.g., myeloblastic, promyelocytic, myelomonocytic, monocytic and erythroleukemia), and chronic leukemia (e.g., chronic myelocytic (granulocytic) leukemia and chronic lymphocytic leukemia).

The therapeutic polypeptides of the invention are usefully employed in the treatment of polycythemia vera, lymphoma (e.g., Hodgkin's disease and non-Hodgkin's disease), multiple myeloma, Waldenstrom's macroglobulinemia, and heavy chain disease.

Additionally, the therapeutic polypeptides of the invention are useful in the treatment of solid tumors, including sarcomas and carcinomas, such as fibrosarcoma, myxosarcoma, liposarcoma, chondrosarcoma, osteogenic sarcoma, chordoma, angiosarcoma, endotheliosarcoma, lymphangiosarcoma, Kaposi's sarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and virally-induced cancers.

In specific embodiments, a therapeutic polypeptide of the invention is used in the treatment of neoplasms, such as gestational trophoblastic tumor, testicular germ cell tumor, adenocarcinoma, virally induced cancers, as well as cancer of the bladder, pancreas, cervix, lung, liver, ovary, colon, prostate and/or stomach.

One or more therapeutic polypeptides of the invention may be administered to a subject as a treatment for neuroblastoma or carcinoma of the ovary or stomach.

One or more therapeutic polypeptides of the invention may be administered to a subject as a treatment for Kaposi's sarcoma or carcinoma of the breast, lung, prostate, or kidney (renal).

In one aspect of the invention, one or more therapeutic polypeptides of the invention is administered in conjunction with other cancer therapy, such as chemotherapy (e.g., treatment with tamoxifen, adriamycin, etoposide, bleomycin, vincristine, vinblastine, doxorubicin, paclitaxel and/or docetaxal). Examples of other suitable antineoplastics for use in combination therapies with the therapeutic polypeptides of the invention include: adrenocorticotrophic hormones (e.g., corticotropin); antibiotic antineoplastics (e.g., plicamycin); miscellaneous antineoplastics (e.g., gallium nitrate); bone resorption suppression agents (e.g., etidronate disodium and pamidronate disodium); and glucocorticoids (e.g., adrenal cortex; betamethasone; budesonide; cloprednol; cortisone acetate; cortivazol; deflazacort; dexamethasone; fluprednisolone; hydrocortisone; hydrocortisone acetate; hydrocortisone cypionate; hydrocortisone hemisuccinate; hydrocortisone sod phosphate; hydrocortisone sod succinate; meprednisone; methylprednisolone; methylprednisolone acetate; methylprednisolone hemisucc; methylprednisolone sod succ; paramethasone acetate; prednisolone; prednisolone; prednisolone acetate; prednisolone hemisuccinate; prednisolone Na Met-Sul-Benz; prednisolone sod phosphate; prednisolone sod succinate; prednisone; prednylidene; prednylidene).

The therapeutic polypeptides of the invention are also useful for treating premalignant conditions to prevent progression to a neoplastic or malignant state (e.g., the malignant disorders listed above). Such prophylactic or therapeutic use is indicated in conditions known or suspected of preceding progression to neoplasia or cancer. Preferred conditions for treatment according to this aspect of the invention include those characterized by non-neoplastic cell growth, such as hyperplasia, metaplasia, or most particularly, dysplasia.[98] Prophylactic treatment is also warranted where the subject is determined to have a genetic predisposition to a cancer. As an example, such a determination may be made by identification of a mutation that predisposes the subject to a cancer, e.g., using the BRCA1 test (Myriad Genetics, Salt Lake City).

Hyperplasia is a form of controlled cell proliferation involving an increase in cell number in a tissue or organ without significant alteration in structure or function. As an example, endometrial hyperplasia often precedes endometrial cancer.

Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium.

Dysplasia is frequently a forerunner of cancer and is found mainly in the epithelia; it is the most disorderly form of non-neoplastic cell growth, involving a loss in individual cell uniformity and abnormal changes in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively, or in addition to, the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of one or more therapeutic polypeptides of the invention. Examples of characteristics of a transformed phenotype include morphology changes, looser substratum attachment, loss of contact inhibition, loss of anchorage dependence, protease release, increased sugar transport, decreased serum requirement, expression of fetal antigens, etc.

In other embodiments, a subject who exhibits one or more of the following predisposing factors for malignancy is treated by administration of an effective amount of one or more therapeutic polypeptides of the invention: a chromosomal translocation associated with a malignancy (e.g., the Philadelphia chromosome for chronic myelogenous leukemia, t(14;18) for follicular lymphoma, etc.); familial polyposis or Gardner's syndrome (possible forerunners of colon cancer); benign monoclonal gammopathy (a possible forerunner of multiple myeloma); and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome).[99]

The therapeutic polypeptides of the invention are also usefully administered to a human subject to prevent progression of prostate, breast, colon, lung, pancreatic, uterine cancer, melanoma or sarcoma.

Hyperproliferative malignant stem cell disorders, as well as non-hematopoietic malignancies, can be treated with chemotherapy or radiation therapy along with rescue of hematopoietic cells by direct in vivo administration of one or more therapeutic polypeptides of the invention. Such conditions may also br treated by administration of hematopoietic cells induced to proliferate by contacting the cells in vitro with one or more therapeutic polypeptides of the invention.

Hyperproliferative stem cell disorders are currently treated by, inter alia, chemotherapy and, when feasible, allogeneic bone marrow transplantation. However, allogeneic HLA identical sibling bone marrow rarely available. Moreover, transplantation is associated with various complications, such as immunodeficiency and graft versus host disease. Induction of hematopoietic cell proliferation in vivo or provision of autologous hematopoietic stem and progenitor cells expanded by administration of one or more therapeutic polypeptides of the invention in vitro permits hematopoietic reconstitution in subjects lacking suitable allogeneic donors and eliminates the risks of graft versus host disease arising from allogeneic marrow transplantation.

The therapeutic polypeptides of the invention are usefully employed in vitro to induce proliferation in hematopoietic cells which are then administered to a subject who has undergone, and/or will undergo, chemotherapy or radiation therapy for treatment of cancer or an immunological disorder. In another embodiment, one or more therapeutic polypeptides of the invention is directly administered to a subject who has undergone, and/or will undergo, chemotherapy or radiation therapy for treatment of cancer or an immunological disorder.

Radiation therapy and chemotherapy (e.g., radiation therapy and chemotherapy associated with cancer therapy) commonly result in damage to bone marrow and/or blood cells. One or more therapeutic polypeptides of the invention can be administered to a subject before, during and/or after chemotherapy or radiation therapy to prevent, limit and/or control hematopoietic damage or dysfunction. Administration of one or more therapeutic polypeptides of the invention before, during and/or after chemotherapy and/or radiation therapy will reduce damage to the bone marrow and circulating blood cells. Such administration may thereby reduce the need for blood and bone marrow transfusions, and eliminate or reduce the risks associated with such transfusions (e.g., the risk of contracting an infectious disease such as HIV or hepatitis from a donor). Such administration can enable the use of more aggressive radiation therapy than would be tolerated by a subject in the absence of the pro-hematopoietic effects of the therapeutic polypeptides of the invention.

8.5.8 Treatment of Impaired Immune Function and Autoimmune Conditions

The therapeutic polypeptides can also be administered to a subject before, during and/or after chemotherapy or radiation therapy to prevent, limit or control hematopoietic or other cell damage or dysfunction and thereby reduce or eliminate the risks of infection and bleeding disorders, increase survival rates and reduce recovery time.

The inventors have surprisingly discovered that the MA peptides exhibit anti-angiogenic effects in animal systems. Accordingly, the therapeutic polypeptides are useful to prevent or reduce pathological angiogenesis, e.g., in subjects with cancer, macular degeneration, Crohn's disease or glaucoma. Direct treatment of a subject with one or more therapeutic polypeptides of the invention can prevent, limit or reduce medically detrimental angiogenesis.

Many chronic inflammatory and degenerative diseases are characterized by autoimmunity. Examples of such autoimmune disorders include rheumatoid arthritis and other inflammatory osteopathies, diabetes type I, chronic hepatitis, multiple sclerosis, and systemic lupus erythematosus.

Autoimmune disorders are often treated by lymphoid irradiation. Administration of one or more therapeutic polypeptides of the invention, and/or cells produced by in vitro exposure to one or more therapeutic polypeptides of the invention can be used to repopulate the hematopoietic system after radiotherapy.

Anti-inflammatory drugs, such as steroids, retard inflammatory cells, which are activated by autoreactive T cells. However, such drugs do not prevent self-recognizing T cells from activating new inflammatory cells. A more direct approach to treating autoimmune diseases requires eradication of T cells by irradiation of the lymphoid tissues, and repopulation of the subject's hematopoietic system by administering stem cells from the unirradiated bone marrow. The rationale for this approach is that the formation of new populations of mature T cells from bone marrow stem cells may result in absence of T cells that have reactivity to self-specific antigens. This procedure, called total lymphoid irradiation (TLI), has been used to treat intractable rheumatoid arthritis.[100] Clinical trials have shown that in the majority of otherwise intractable cases, joint disease is significantly alleviated for at least 2-3 years. The major drawback to such treatment is failure of stem cells in the bone marrow to efficiently repopulate the hematopoietic system, resulting in infections and bleeding disorders.

Other researchers have studied the use of TLI as an alternative to cytotoxic drugs for treatment of SLE.[101] Studies of the use of TLI to treat intractable SLE have shown that this treatment alleviates disease activity but is severely limited by failure of bone marrow stem cells to rapidly and efficiently repopulate the hematopoietic system after irradiation.

The therapeutic polypeptides of the invention can be administered to promote proliferation of pluripotential stem cells and other hematopoietic cells to increase the success of TLI therapy. Additionally, hematopoietic stem and progenitor cells can be isolated from the subject before treatment or obtained from a suitable donor, induced to proliferate in vitro, and then introduced into the subject after TLI treatment to repopulate the hematopoietic system. Alternatively, hematopoietic stem and progenitor cells can be isolated from the subject prior to therapy or obtained from a suitable donor and infused into the patent and expanded in vivo by direct administration of one or more therapeutic polypeptides of the invention. Thus, the therapeutic polypeptides of the invention can be administered to promote proliferation of the remaining hematopoietic cells to increase the success of TLI therapy. Additionally, hematopoietic stem and progenitor cells can be isolated from the subject before treatment, induced to proliferate ex vivo and then introduced into the subject after TLI treatment to repopulate the hematopoietic system.

The therapeutic polypeptides may also be delivered to a subject undergoing radiation and/or chemotherapy for the treatment of a cancer to prevent damage to the oral and/or gastrointestinal tract. Damage to the cells lining the oral cavity and the gastrointestinal tract add greatly to the discomfort of patients undergoing anti-cancer therapy and greatly increases the risk of loss of weight and fungal infections.

Subjects with impaired immune function are prone to infections, such as fungal infections. Impairment of immune function can be associated with a variety of causes, such as cancer therapy (e.g., radiation and/or chemotherapy), stress to or reduction in the capacity of the hematopoietic system, and infections (e.g., viral and/or bacterial infections). Administration of one or more therapeutic polypeptides of the invention to such persons can reduce the risk of developing fungal infections. The therapeutic polypeptides are also usefully administered to a subject presenting with a fungal infection to eliminate the infection.

The therapeutic polypeptides of the invention are suitably administered to a subject presenting with a fungal infection to eliminate or reduce the severity of such infection. The therapeutic peptide(s) may, for example, be administered locally by direct inoculation into the site of infection or topically to the site of infection. The therapeutic peptide(s) may also be administered systemically to eliminate or reduce the severity of the infection and/or to prevent the spreading of the infection to uneffected tissue.

The therapeutic polypeptides are also usefully administered to a subject with a wound or burn. One or more therapeutic polypeptides may be administered to a subject who has sustained a burn or laceration to reduce inflammation, promote hematopoiesis, and/or to reduce the risk of infection. For example, one or more of the therapeutic polypeptides may be topically or systemically applied to the site of a wound or burn in order to reduce inflammation, reduce the risk of infection and to promote healing.

In another embodiment, one or more of the therapeutic polypeptides is administered to a subject to reduce inflammation of the cornea and/or to promote development of new corneal tissue.

In one aspect of the invention, the therapeutic polypeptides are administered to a subject who has an infection to boost the subject's capacity to combat the infection. The therapeutic polypeptides may be administered in conjunction with antibiotics to combat infection.

8.5.9 Treatment Methods Employing Gene Therapy Techniques

The invention provides gene therapy methods that employ the therapeutic properties of the therapeutic polypeptides. In the gene therapy aspects of the invention, therapy is effected by administering to a subject genetic material comprising a nucleic acid sequence encoding a therapeutic polypeptide. The therapeutic polypeptide is then expressed in the subject, thereby mediating a therapeutic effect. For a general treatment of gene therapy, see Lemoine, ed., *Understanding Gene Therapy*.[102]

The invention provides treatment methods comprising administering to a subject a nucleic acid comprising a nucleotide sequence encoding one or more therapeutic polypeptides of the invention. The gene therapy methods of the invention are usefully employed in the treatment of any of the diseases and conditions described herein (e.g., see Sections 4.1, 4.2, 4.3, 4.4, 8.5.1, 8.5.4, 8.5.5 and 8.5.7). For example, such methods are usefully employed in the treatment and/or prevention HIV infection, wasting, cancer, and/or hematopoietic deficiency.

The invention provides a nucleic acid for use in gene therapy methods. The nucleic acid encodes one or more therapeutic polypeptides of the invention. The nucleic acid is preferably provided as a component of an expression vector that produces the therapeutic polypeptide in a suitable host cell.

The nucleic acid may also be provided as a component of an expression cassette, for insertion into an expression vector. The nucleic acid comprises a promoter operably linked to a nucleic acid sequence coding for a therapeutic polypeptide. The promoter may be inducible or constitutive and is optionally tissue-specific.

The nucleic acid sequence encoding the therapeutic polypeptide and encoding any other desired sequences may be flanked by regions that promote homologous recombination at a desired site in the genome, thus providing for intrachromosomal expression of the therapeutic polypeptide.[103]

Delivery of the nucleic acid into a subject may be either direct, in which case the subject is directly exposed to the nucleic acid or nucleic acid-carrying vector, or indirect, in which case, cells are first transformed with the nucleic acid in vitro, then administered to the subject. These two approaches are known, respectively, as in vivo and ex vivo gene therapy.

In a specific embodiment, the nucleic acid is directly administered in vivo, where it is expressed to produce the encoded product. Delivery can be accomplished by any of numerous methods known in the art. For example, the nucleic acid can be included as a component of an appropriate nucleic acid expression vector and administered by an intracellular delivery method. Examples of suitable intracellular delivery methods include infection using a defective or attenuated retroviral or other viral vector,[104] direct injection of naked DNA, microparticle bombardment (e.g., a gene gun; Biolistic, Dupont), coating with lipids or cell-surface receptors or transfecting agents, encapsulation in liposomes, microparticles, or microcapsules, or linkage to a peptide which is known to enter the cell or nucleus (e.g., by administering it in linkage to a ligand subject to receptor-mediated endocytosis[105]), which can be used to target cell types specifically expressing the receptors, etc. In a specific embodiment, the nucleic acid can be targeted in vivo for cell-specific uptake and expression, by targeting a specific receptor.[106] In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated by homologous recombination within host cell DNA for expression.[107] For a recent review of non-viral gene therapy, see Ledly, "Nonviral Gene Therapy The Promise of Genes as Pharmaceutical Products."[108]

In a specific embodiment, the gene therapy methods employ a viral vector that comprises a nucleic acid sequence encoding one or more therapeutic polypeptides of the invention. For example, the viral vector may comprise a retroviral vector.[109] Suitable retroviral vectors are those which have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a subject. More detail concerning retroviral vectors can be found in Boesen et al.[110] which describes the use of a retroviral vector to deliver the mdr1 gene to hematopoietic stem cells in order to make the stem cells more resistant to chemotherapy.[111]

Adenoviruses may also be suitably employed in gene therapy methods of the invention. Adenoviruses naturally infect respiratory epithelia and are therefore especially attractive vehicles for delivering genes to respiratory epithelia. Other targets for adenovirus-based delivery systems are liver, the central nervous system, endothelial cells, and muscle. Adenoviruses have the advantage of being capable of infecting non-dividing cells. Kozarsky and Wilson,[112] present a review of adenovirus-based gene therapy. Bout et al.[113] demonstrated the use of adenovirus vectors to transfer genes to the respiratory epithelia of rhesus monkeys. Other instances of the use of adenoviruses in gene therapy can be found in Rosenfeld et al.;[114] and Mastrangeli et al.[115]

Adeno-associated virus (AAV) and Herpes virus vectors are also suitably employed in the gene therapy methods of the invention.[116] For recent reviews of viral vecotors in gene therapy, see Smith, "Viral Vectors in Gene Therapy";[117] Amalfitano, et al., "Isolation and characterization of packaging cell lines that coexpress the adenovirus E1, DNA polymerase, and preterminal proteins: implications for gene therapy";[118] Hitt et al., "Human Adenovirus Vectors for Gene Transfer into Mammalian Cells";[119] Ali et al. "The use of DNA viruses as vectors for gene therapy"; [120] Yeh et al. "Advances in adenoviral vectors: from genetic engineering to their biology";[121] Robbins et al., "Viral Vectors for Gene Therapy."[122]

DNA and/or RNA encoding the therapeutic polypeptides can be administered to a subject by introduction of the specific DNA or RNA sequence in a live bacterial delivery system as is described for DNA in U.S. Pat. No. 5,877,159, Mar. 2, 1999. titled "Method for Introducing and Expressing Genes in Animal Cells and Live Invasive Bacterial Vectors for use in the Same."

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. Cells that have taken up and are expressing the transferred gene are then isolated. The isolated cells may then be delivered to the subject.

In an ex vivo gene therapy method, the vector comprising the nucleic acid encoding one or more therapeutic polypeptides of the invention may be introduced into a cell in vitro, prior to administration in vivo of the resulting recombinant cell. Such introduction can be carried out by any method known in the art. Examples of suitable methods include transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells[123] and may be used in accordance with the invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, recombinant blood cells (e.g., hematopoietic stem or progenitor cells) are administered intravenously. Epithelial cells can be injected, e.g., subcutaneously, or recombinant skin cells (e.g., keratinocytes) may be applied as a skin graft onto the subject. The amount of cells envisioned for use depends on the desired effect, subject state, etc., and can be determined by one skilled in the art.

In an embodiment in which recombinant cells are used in gene therapy, a nucleic acid sequence coding for therapeutic polypeptides of the invention or functional equivalents thereof is introduced into the cells such that it is expressible by the cells or their progeny. The recombinant cells are then administered in vivo where they will produce the therapeutic polypeptides to provide the desired therapeutic effect. In a specific embodiment, stem or progenitor cells, preferably hematopoietic stem or progenitor cells, are used. Any stem and/or progenitor cells which can be isolated and maintained in vitro are suitable for use in accordance with this embodiment of the invention.

In a preferred aspect of the invention, hematopoietic cells (preferably hematopoietic stem and progenitor cells) are administered to a subject. Prior to such administration, the cells are induced to proliferate with one or more therapeutic polypeptides of the invention and genetically manipulated to stably incorporate a heterologous gene capable of expression by their progeny cells. This particular aspect of the invention is highly useful in the treatment of diseases and disorders affecting cells of hematopoietic lineage. In one embodiment, hematopoietic reconstitution with such recombinant hematopoietic cells can be used in the treatment of genetic disorders of the hematopoietic system. Such genetic disorders include but are not limited to those described herein.

Genetic deficiencies or dysfunctions of hematopoietic cells can be treated by supplying recombinant stem and progenitor cells to a subject. In a specific embodiment, subjects having hematopoietic cells which lack a gene or have a mutant gene, can be provided stem and progenitor cells that comprise a functional counterpart of the deficient gene. Examples of genes that can be usefully employed in this embodiment of the invention include genes for hemoglobin or for enzymes which mediate the synthetic pathway for hemoglobin. Such genes are useful in the treatment of anemias, such as β-thalassemia and sickle-cell syndrome.

In another specific embodiment, subjects with infections by pathogenic microorganisms which occur in or affect a hematopoietic cell lineage can be treated with recombinant hematopoietic cells. Such recombinant hematopoietic cells can comprise a heterologous gene which is expressed as a product which ameliorates disease symptoms, is toxic to the pathogen without undue detriment to the host, or which interferes with the pathogen's life cycle, etc. Examples of infectious agents that cause infections treatable with recombinant stem cells according to this embodiment of the invention include lymphotropic viruses such as HIV; gram-negative bacilli such as *Brucella* or *Listeria; Mycobacterium tuberculosis; Mycobacterium leprae*; parasites, such as *Plasmodium* and *Leishmania*; and fungi (such as those that cause pneumonia and other lethal infections secondary to immunodeficiencies).[124]

The invention also provides stem or progenitor cells that express a sequence that is "anti-sense" to the nucleic acid of a hematopoietic cell pathogen. An antisense polynucleotide, which is complementary to the pathogen's RNA or DNA, can hybridize to and inactivate all or a critical component of such RNA or DNA. For example, the antisense preferably inhibits the expression of a protein or peptide that is critical to the pathogen's life cycle.

Recombinant hematopoietic cells can be used in the treatment of HIV infection. Recombinant stem and progenitor cells which express an antisense nucleic acid that is complementary to a critical region (e.g., the long-terminal repeat or polymerase sequence) of the HIV genome[125] can be used for in the treatment of HIV infection.

A nucleotide encoding a sequence which is complimentary to a sequence encoding MA (SEQ ID NO: 2) (MA antisense) may be administered as a treatment for cancers.

8.5.10 Use of the Therapeutic Polypeptides in Vaccines

The prohematopoietic effects of the MA peptides are consistent with the conclusion that the therapeutic polypeptides of the invention are usefully administered to a subject to enhance the subject's immune response to an antigen, particularly a vaccine. Accordingly, the invention provides a method for enhancing the efficacy of a vaccine. This method comprises administering one or more therapeutic polypeptides of the invention to a subject with an antigen against which an immune response is desired. The therapeutic polypeptides of the invention are also useful in modulating Th1 vs Th2 immune response.

The therapeutic polypeptides of the invention may be administered with the antigen and/or within a time period before and/or after administration of the antigen. The window during which the therapeutic polypeptides of the invention may be administered (in relation to the administration of the antigen) is any time during which the administration of the therapeutic polypeptides of the invention enhances the subject's immune response to the antigen. Enhancement of the immune response is determined by comparison with a subject receiving an identical dose of the antigen in the absence of the therapeutic polypeptide.

The efficacy of a vaccine can also be enhanced by administering to a subject a nucleic acid comprising a nucleotide sequence encoding the therapeutic polypeptide. The nucleic acid can be administered with an antigen against which an immune response is desired. Alternatively, the nucleic acid can be administered with a second nucleic acid comprising a nucleotide sequence encoding an antigen against which an immune response is desired, such that the therapeutic polypeptide and the antigen are expressed in a coordinated manner upon introduction into a suitable cell. Additionally, one or more nucleotide sequences encoding one or more therapeutic polypeptides of the invention and one or more nucleotide sequences encoding one or more antigens, against which an immune response is desired, may be provided on the same nucleic acid.

8.5.11 Other Treatment Methods

The therapeutic polypeptides are usefully added as component of part of the fluid to allow a sperm and egg to fuse for the purpose of implantation to promote fertilization and growth of the embryo. In a specific embodiment, one or more of the therapeutic polypeptides is administered to a subject prior to and/or during and/or after implantation of an embryo to promote retention and development of the placenta and embryo.

The therapeutic polypeptides of the invention are usefully administered to a subject who has sustained an injury to the spinal cord, nerves or the brain to reduce inflammation and to promote growth of stem cells and nerve tissue and ultimately to reduce neural damage and the resulting effects of such damage.

The inventors have also observed that humans exhibit a feeling of wellbeing and increased libido when administered the therapeutic polypeptides of the invention. Accordingly, administration of one or more of the therapeutic polypeptides of the invention to a subject to induce such a feeling of wellbeing and/or to increase libido forms another aspect of the invention. In a related embodiment the therapeutic polypeptide is administered to a subject in order to treat impotence.

Further examples of diseases which may be treated using the therapeutic polypeptides of the invention include osteopetrosis, myelosclerosis, acquired hemolytic anemias, acquired immunodeficiencies, infectious disorders causing primary or secondary immunodeficiencies, bacterial infections (e.g., Brucellosis, Listeriosis, tuberculosis, leprosy), parasitic infections (e.g., malaria, Leishmaniasis), fungal infections, disorders involving disproportions in lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving, immune mechanisms, Wiskott-Aldrich Syndrome and alpha 1-antitrypsin deficiency.

In another aspect of the invention, one or more therapeutic polypeptides is administered to a woman in perimenopause or menopause to prevent or treat osteoporosis.

8.5.12 In Vitro Preparation of Hematopoietic Cells

The invention provides methods for inducing hematopoietic stem and progenitor cells to proliferate. Sources for such cells are known in the art and include, for example, bone marrow, fetal and neonatal blood (preferably from the umbilical cord and/or placenta), peripheral blood, neonatal thymus, and neonatal spleen. Suitable cells also include cryopreserved cells, cell lines, and long-term cell cultures derived from the foregoing sources. Preferred cells are mammalian cells, e.g., dog, cat, sheep, rat, cow, horse, primate, monkey, and most preferably, human.

Techniques for obtaining such stem and progenitor cells are well known in the art. For example, in one particular embodiment, human bone marrow cells can be obtained from the posterior iliac crest by needle aspiration.[126] Neonatal blood can be obtained at birth by direct drainage from the umbilical cord and/or by needle aspiration from the delivered placenta at the root and at distended veins.[127] Fetal blood can be obtained, e.g., by taking it from the fetal circulation at the placental root with the use of a needle guided by ultrasound,[128] by placentocentesis,[129] by fetoscopy,[130] etc.

Methods of the invention which comprise contacting hematopoietic stem and/or progenitor cells (or other hematopoietic cells) with one or more therapeutic polypeptides of the invention have already been described. Such methods can be carried out on unseparated, partially separated, or purified cell populations. The methods are usefully employed before and/or after cryopreservation (and thawing) or in vitro culturing of such cell populations. Moreover, the methods may also be employed before and/or after introduction of a recombinant gene, and any other desired manipulations of the cells. In a preferred aspect, samples (e.g. bone marrow or adult blood or neonatal blood) can be subjected to physical and/or immunological cell separation procedures to enrich for hematopoietic stem and progenitor cells. For example, such separation procedures may be carried out prior to culturing in the presence of a therapeutic polypeptide of the invention to induce proliferation of the cells.

Various procedures for enriching for stem and progenitor cells are known in the art. For example, suitable procedures include equilibrium density centrifugation, velocity sedimentation at unit gravity, immune rosetting and immune adherence, counterflow centrifugal elutriation, T lymphocyte depletion, and fluorescence-activated cell sorting, alone or in combination. Procedures have been reported for the isolation of very highly enriched populations of stem/progenitor cells. U.S. Pat. No. 5,061,620 dated Oct. 29, 1991 discloses a method for isolation of human hematopoietic stem cells. Several groups have purified murine CFU-S using slightly different procedures.[131] Studies using human[132] or murine[133] fetal liver cells have yielded highly enriched progenitor cells with up to 90% of them being colony forming cells for multi-, erythroid-, and granulocyte-macrophage lineages. CFU-E have also been very highly enriched.[134] Purification of adult mouse marrow CFU-GM with cloning efficiencies of up to 99% in semi-solid medium has been accomplished by pretreatment of mice three days prior to sacrifice with cyclophosphamide, density separation of cells on Ficoll-Hypaque, and counterflow centrifugal elutriation.[135] The resulting fraction of cells contained no detectable CFU-GEMM, BFU-E or CFU-MK, but up to 10% of the cells formed CFU-S measured at day 12. These procedures, or modifications thereof, can be used.

Human stem and progenitor cells are present in the nonadherent, low density, T-lymphocyte-depleted fraction of bone marrow, spleen, and adult and cord blood cells. Low density (density less than 1.077 gm/cm$^3$) cells can be separated by use of Ficoll-Hypaque (Pharmacia Fine Chemicals, Piscataway, N.J.) or Percol.[136] In this procedure, the mature cells of the granulocytic series, which are not needed for transplantation, are removed in the dense fraction that goes to the bottom of the tube. An adherence/nonadherence separation protocol can also be used for enrichment of hematopoietic stem and progenitor cells.

It is also possible to use cell separation procedures that entail immunological recognition of cells. Stem and progenitor cells can be isolated by positive or negative selection using antibodies that recognize antigenic determinants on the surface of cells. One means is to separate the cells by using monoclonal antibodies that recognize cell surface determinants on these cells, in conjunction with separation procedures such as fluorescence-activated cell sorting or panning.[137] Human hematopoietic stem and progenitor cells contain antigenic determinants that are not present on all other cells. These antigenic determinants can be used in antibody selection protocols for enrichment purposes. Such antigens include, for example, those known to be present on human stem/progenitor cells,[138] as well as those used to distinguish progenitors of the granulocyte-macrophage lineage,[138] and others known in the art.[140]

The numbers of the hematopoietic stem and/or progenitor cells (or precursor cells thereof) may be expanded by exposing the cells or contacting them with a composition comprising a therapeutic polypeptide of the invention time sufficient to obtain the desired number of cells. Preferably the cells are contacted while under appropriate culture conditions for a period of time which ranges from 1 to 21 or, more preferably, from 7 to 21 days.

The composition comprising the therapeutic polypeptides of the invention, to which the stem and progenitor cells are exposed, may comprise other growth factors (i.e., polypeptides that stimulate cell division) and/or cytokines or cell culture materials. Examples of suitable growth factors include but are not limited to heregulin (ERG), insulin, insulin-like growth factors I and II (IGF-I and IGF-II), epidermal growth factor (EGF), insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), fibroblast growth factor (FGF), transforming growth factors alpha and beta (TGF-alpha and TGF-beta), hepatocyte growth factor (HGF), and nerve growth factor (NGF). Examples of suitable cytokines include macrophage-derived chemokine, monocyte chemotactic protein 1, monocyte chemotactic protein 2, monocyte chemotactic protein 3, monocyte chemotactic protein 4, activated macrophage specific chemokine 1, macrophage inflammatory protein 1 alpha, macrophage inflammatory protein 1 beta, macrophage inflammatory protein 1 gamma, macrophage inflammatory protein 1 delta, macrophage inflammatory protein $2\alpha$, macrophage inflammatory protein $3\alpha$, macrophage inflammatory protein $3\beta$, regulated upon activation, normal T cell expressed and secreted (and its variants), I-309, EBI1-ligand chemokine, pulmonary and activation regulated chemokine, liver and activation-regulated chemokine, thymus and activation regulated chemokine, eotaxin (and variants), human CC chemokine 1, human CC chemokine 2, human CC chemokine 3, IL-10-inducible chemokine, Liver-expressed chemokine, 6Ckine, exodus 1, exodus 2, exodus 3, thymus-expressed chemokine, secondary lymphoid tissue chemokine, lymphocyte and monocyte chemoattractant, monotactin, chemokine-related molecule, myeloid progenitor inhibitory factor-1, myeloid progenitor inhibitory factor-2, stromal cell-derived factor $1\alpha$, stromal cell-derived factor $1\beta$, B-cell-attracting chemokine 1, HuMIG, H174, Interferon-stimulated T-cell $\alpha$-chemoattractant, interleukins, IP-10, platelet factor 4, growth-regulated gene-$\alpha$, growth-regulated gene-$\beta$, growth-regulated gene-$\gamma$, neutrophil-activating protein 2, ENA-78, granulocyte chemotactic protein 2, lymphotactin, fractalkine/neurotactin, viral chemokines and functional equivalents of the foregoing chemokines. Other specific examples of suitable components include Steel factor (SLF) and adult PB plasma. Preferred factors are those which cause proliferation or, less preferably, differentiation of cells that are CFU-GEMM or earlier cells, e.g., IL-3, GM-CSF.

The stem and/or progenitor cells are preferably contacted with the therapeutic polypeptide(s) and/or functional equivalent(s) of the invention during cell culture. Thus, the therapeutic polypeptide is preferably added to the cell culture medium being used to culture the hematopoietic stem and/or progenitor cells.

The cells may be cultured by any method known in the art. Examples of suitable methods for culturing the cells include growing cells in culture dishes, test tubes, roller bottles, bioreactors (perfusion system machines wherein cells are grown on a surface with continual perfusion by medium; e.g., as sold by Aastrom Biosciences, Inc., Ann Arbor, Mich.), etc. Various protocols have been described for the in vitro growth of cord blood or bone marrow cells.[141] Such procedures, or modifications thereof, may be employed in the methods of the invention. The cell culture medium is preferably supplemented to contain an effective concentration of one or more therapeutic polypeptides of the invention. Culturing may also be achieved by using any of a variety of cross-flow filter culturing systems known in the art.

Progeny cells of hematopoietic stem and progenitor cells can be generated in vitro. Such differentiated progeny cells can be therapeutically useful. For example, in one embodiment of this aspect of the invention, hematopoietic stem cells and/or CFU-GEMM progenitor cells, can be induced to differentiate into platelets. Such platelets can be used, for example, for infusion into a subject with thrombocytopenia (e.g., a subject with HIV-associated ITP or a subject undergoing radiation and/or chemotherapy for cancer).

In another embodiment, granulocytes can be generated in vitro prior to infusion into a subject. One or more of the hematopoietic progeny cells can be generated in vitro, allowing for the in vitro production of blood components. The generation of differentiated blood components may be accompanied by expansion of the hematopoietic stem and progenitor cell pool to permit production of a greater quantity of differentiated cells.

Various growth factors can be used to promote expansion and/or differentiation of hematopoietic stem and progenitor cells, such as cytokines (growth factors) including, but not limited to, G-CSF, CSF-1, IL-3, IL-5, tumor necrosis factor-$\beta$, and $\alpha$-interferon.

The blood components produced by the methods of the invention have a variety of in vitro uses, e.g., for the production and isolation of hematopoietic cell products such as growth factors, antibodies, etc.

A specific embodiment of the invention relates to a method of increasing the amount of hematopoietic cells, which method comprises contacting in vitro a non-terminally differentiated hematopoietic cell with a composition comprising an amount of a therapeutic polypeptide of the invention effective to increase proliferation of the cell, under conditions suitable and for a time sufficient to increase the numbers of the hematopoietic cell. For example, hematopoietic cell numbers can be increased by contacting a non-terminally differentiated hematopoietic cell (e.g., a cell isolated from bone marrow or blood, adult or fetal or umbilical cord blood) with a composition comprising a therapeutic polypeptide of the invention and culturing the cell for at least ten days.

8.6 Assays for Therapeutic Activity

The ensuing description is described with regard to the assaying of an individual therapeutic polypeptide for therapeutic activity; however, it will be appreciated that the same methods can be used to assay multi-drug combinations that include combinations of the therapeutic polypeptides, and which optionally include other therapeutic compounds. A kit may be provided for any of the following assay methodologies. Such a kit suitably comprises one or more therapeutic polypeptides of the invention along with instructions and/or other reagents and/or supplies for performing the assay.

8.6.1 Assays for Anti-HIV Activity

The invention provides a method for screening therapeutic polypeptides of the invention for anti-HIV activity. The assay comprises assaying the therapeutic polypeptides of the invention for the ability to inhibit HIV replication or expression of HIV RNA or protein. In one specific embodiment, the therapeutic polypeptide of the invention is assayed by a method comprising: (1) contacting HIV-1-infected cultured hematopoietic cells with one or more therapeutic polypeptides to of the invention, and (2) measuring HIV-1 p24 antigen levels in the cells. The measured HIV-1 p24 antigen levels in the cells is preferably compared to a corresponding group of cells for which the contacting step has not been performed. A lower level of HIV-1 p24 antigen levels in the contacted cells indicates that the therapeutic polypeptide has anti-HIV activity.

The therapeutic polypeptide of the invention may also be assayed by a method comprising: (1) contacting HIV-1-infected cultured hematopoietic cells with one or more therapeutic polypeptides of the invention; (2) measuring the activity of a reporter gene product expressed from a construct in which the HIV-1 LTR is operably linked to the reporter gene; and (3) comparing the measured expression of the reporter gene in the contacted cells with the levels in cells not contacted with the therapeutic polypeptide of the invention. A lower level in the contacted cells indicates that the therapeutic polypeptide has anti-HIV activity.

A therapeutic polypeptide of the invention may also be assayed by a method comprising measuring HIV-1 derived RNA transcripts or HIV-1 antigen levels in HIV-1 transgenic mice administered the therapeutic polypeptide. The measured transcript or antigen levels in the mice which have been administered the therapeutic polypeptide of the invention may be compared with the levels in mice not administered the therapeutic polypeptide of the invention. A lower level of transcript or antigen in mice to which the therapeutic polypeptide of the invention was administered indicates that the therapeutic polypeptide has anti-HIV activity.

The therapeutic polypeptides of the invention may also be assayed by a method comprising measuring SIV p27 antigen levels in the peripheral blood mononuclear cells of SIV infected monkeys. A lower level of SIV p27 antigen in monkeys administered the therapeutic polypeptide of the invention indicates that the therapeutic polypeptide has anti-HIV activity.

A therapeutic polypeptide of the invention in vitro can be assayed by examining the effect of the therapeutic polypeptide on HIV replication in cultured cells. Briefly, cultured hematopoietic cells (e.g., primary PBMCs, isolated macrophages, isolated CD4+ T cells or cultured 119 human T cells) are acutely infected with HIV-1 using titers known in the art to acutely infect cells in vitro, such as $10^5$ TCID$_{50}$/ml. Then, appropriate amounts of the therapeutic polypeptide are added to the cell culture media. Cultures are assayed 3 and 10 days after infection for HIV-1 production by measuring levels of p24 antigen using a commercially available ELISA assay. Reduction in p24 antigen levels over levels observed in untreated controls indicates the therapeutic polypeptide is effective for treatment of HIV infection.

Additionally, assays for HIV-1 LTR driven transcription are useful for testing the efficacy of therapeutic polypeptides of the invention. Such assays employ a reporter gene, i.e., a gene with a detectable protein or RNA product. A preferred reporter gene is the gene for chloramphenicol acetyltransferase (CAT). The reporter gene is cloned into a DNA plasmid construct, so that the transcription of the reporter gene is driven by the HIV-1 LTR promoter. The resulting construct is then introduced by transfection, or any other method known in the art, into a cultured cell line. A preferred cell line is the human CD4+ T cell line HUT 78. After exposure of the transformed cells to the therapeutic polypeptide, transcription from the HIV-1 LTR is determined by measurement of CAT activity using techniques which are routine in the art. Reduction in HIV-1 LTR driven transcription demonstrates utility of the therapeutic polypeptide for treatment and/or prevention of HIV infection.

Exemplary tests in animal models are described briefly as follows: First, a therapeutic polypeptide of the invention is administered to mice transgenic for HIV-1 (e.g., mice which have integrated molecular clone pNL4-3 containing 7.4 kb of the HIV-1 proviral genome deleted in the gag and pot genes).[142] Skin biopsies taken from the mice are tested for HIV-1 gene expression by RT-PCR (reverse transcription-polymerase chain reaction) or for HIV-1 antigen expression, such as expression of gp120 or NEF, by immunostaining. Additionally, the mice are examined for reduction in the cachexia and growth retardation usually observed in HIV-1 transgenic mice.[143]

The efficacy of therapeutic polypeptides of the invention can also be determined in SIV infected rhesus monkeys.[144] The rhesus monkeys are preferably infected with SIV$_{mac251}$, which induces a syndrome in the experimentally infected monkeys that is very similar to human AIDS.[145] Monkeys can be infected with cell free SIV$_{mac251}$, for example, with virus at a titer of $10^{4.5}$ TCID$_{50}$/ml. Infection is monitored by the appearance of SIV p27 antigen in PBMCs. Utility of the therapeutic polypeptide is characterized by normal weight gain, decrease in SIV titer in PBMCs and/or an increase in CD4+ T cells.

Once the therapeutic polypeptide has been tested in vitro, and also preferably in a non-human animal model, the utility of the therapeutic polypeptide can be determined in human subjects. The efficacy of treatment with a therapeutic polypeptide can be assessed by measurement of various parameters of HIV infection and HIV associated disease. Specifically, the change in viral load can be determined by quantitative assays for plasma HIV-1 RNA using quantitative RT-PCR[146] or by assays for viral production from isolated PBMCs. Viral production from PBMCs is determined by co-culturing PBMCs from the subject with H9 cells and subsequent measurement of HIV-1 titers using an ELISA assay for p24 antigen levels.[147] Another indicator of plasma HIV levels and AIDS progression is the production of inflammatory cytokines such as IL-6, IL-8 and TNF-α; thus, efficacy of the therapeutic polypeptide can be assessed by ELISA tests for reduction of serum levels of any or all of these cytokines.

Administration of the therapeutic polypeptide can also be evaluated by assessing changes in CD4+ T cell levels, body weight, or any other physical condition associated with HIV infection or AIDS or AIDS Related Complex (ARC). Reduction in HIV viral load or production, increase in CD4+ T cell or amelioration of HIV-associated symptoms demonstrates utility of a therapeutic polypeptide for administration in treatment/prevention of HIV infection.

8.6.2 Assays for Anti-Wasting Activity

The invention provides a method for screening a therapeutic polypeptide of the invention for anti-wasting activity. Such method generally comprises assaying the preparation for the ability to promote weight gain in an animal model that exhibits a wasting syndrome.

In one specific embodiment, the therapeutic polypeptide of the invention is screened by a method comprising: (1) administering the therapeutic polypeptide of the invention to an offspring of an HIV-1 transgenic mouse; (2) measuring the weight of the offspring; and (3) comparing the weight of the offspring therapeutic polypeptide of the invention with the weight of an offspring not so exposed. A greater weight in the exposed offspring indicates that the preparation has anti-wasting activity. The same method can be employed using an SIV infected monkey.

Any animal model in which wasting occurs can be used. Exemplary tests in animal models are described briefly as follows: First, a therapeutic polypeptide of the invention is assayed in mice transgenic for HIV-1 (e.g., mice which have integrated molecular clone pNL4-3 containing 7.4 kb of the HIV-1 proviral genome deleted in the gag and pol genes).[148] These mice exhibit cachexia and growth retardation.[149] Reversal of the cachexia and growth retardation in the HIV transgenic mice is consistent with a conclusion that the therapeutic polypeptide is useful for treating or preventing wasting syndromes.

Similarly, the efficacy of therapeutic polypeptide of the invention can be assayed in SIV infected rhesus monkeys.[150] The rhesus monkeys are preferably infected with $SIV_{mac251}$, which induces a syndrome in experimentally infected monkeys that is very similar to human AIDS and results in weight loss in the infected monkeys.[151] Specifically, monkeys are infected with cell free $SIV_{mac251}$, for example, with virus at a titer of $10^{45}$ $TCID_{50}$/ml and SIV infection is monitored by the appearance of SIV p27 antigen in PBMCs. An increase in the weight of infected monkeys administered the therapeutic polypeptide of the invention indicates that the therapeutic polypeptide of the invention has utility in the treatment of wasting syndrome.

Compounds for use in therapy are preferably tested in suitable animal model systems prior to testing in humans, including but not limited to rats, mice, chicken, cows, monkeys, rabbits, etc. For in vivo testing, prior to administration to humans, any animal model system known in the art may be used.

Once the therapeutic polypeptide of the invention has been tested in a non-human animal model, the utility of the therapeutic polypeptide of the invention can be determined in human subjects. Improvement in wasting syndrome, i.e. and increase in body cell mass, can be assessed by any well known clinical techniques available in the art. Examples of suitable techniques include measuring body weight, determining total body potassium content, determining intracellular water volume, bioelectrical impedance analysis, anthropometrics and determining total body nitrogen content.[152] Therapeutic polypeptides of the invention which increase body weight or cell mass are concluded to have utility in treating wasting syndrome.

8.6.3 Assays for Anti-Cancer Activity

The invention provides a method for screening a therapeutic polypeptide of the invention for anti-cancer activity. The method comprises assaying the therapeutic polypeptide of the invention for the ability to inhibit the survival or proliferation of malignant cells.

In one embodiment, the preparation is screened by a method comprising: (1) contacting malignant cells with the therapeutic polypeptide of the invention; (2) measuring the survival or proliferation of malignant cells; and (3) comparing the survival or proliferation of the cells contacted with the therapeutic polypeptide of the invention with the survival or proliferation of cells not so contacted (e.g., cells contacted with a control). A lower level of survival or proliferation in the contacted cells indicates that the preparation has anti-cancer activity. Examples of suitable cells are those which are derived from or display characteristics associated with a malignant disorder.

Cells may also be screened for the ability of a therapeutic polypeptide of the invention to convert cells having an abnormal phenotype to a more normal cell phenotype. For example, suitable cells may include pre-neoplastic or pre-malignant cells. A more normal phenotype in the contacted cells indicates that the preparation has anti-cancer activity.

Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc.[153]

A therapeutic polypeptide of the invention may also be assayed the ability to inhibit Kaposi's Sarcoma cell proliferation or promote Kaposi's Sarcoma cell apoptosis. The therapeutic polypeptide of the invention may be screened by a method comprising measuring proliferation or colony formation in cultured KS Y-1 or KS-SLK cells contacted with the therapeutic polypeptide of the invention. Contacted cells are compared with cells which have not been contacted with the therapeutic polypeptide of the invention. A lower level of proliferation or colony formation in the contacted cells indicates that the preparation has anti-Kaposi's Sarcoma activity.

A therapeutic polypeptide of the invention can be tested for efficacy in the treatment or prevention of Kaposi's sarcoma (1) by any the method described herein; (2) by the Lunardi-Iskandar et al.[154] method; and/or (3) by any other method known in the art. Briefly, KS cell lines, KS Y-1 (Ibid.) or KS-SLK,[155] which will produce malignant tumors in immunodeficient mice, are used to perform in vitro proliferation and clonogenic assays.[156] Methods for performing such assays are well known in the art. A therapeutic polypeptide of the invention that reduces proliferation or colony formation in the cultured cells can be used in the methods of the invention for treatment or prevention of KS.

The method may also comprise measuring apoptosis in a Kaposi's Sarcoma tumor in an immunodeficient mouse. Kaposi's Sarcoma tumors may be induced by injection with KS Y-1 or KS-SLK cells. Following exposure to the therapeutic polypeptide of the invention, the degree of apoptosis in the tumor of a mouse which has been exposed to the therapeutic polypeptide of the invention may be compared with the degree of apoptosis in a mouse with a tumor in a mouse not so exposed. A higher in level of apoptosis in the tumor of the exposed mouse indicates that the therapeutic polypeptide of the invention has anti-Kaposi's Sarcoma activity.

In vitro assays can be used to determine whether administration of a specific therapeutic polypeptide of the invention is indicated in a specific subject. For example, the invention provides in vitro cell culture assays. A tissue sample obtained from a subject is grown in culture and exposed to or otherwise administered a therapeutic polypeptide of the invention. The effect of the therapeutic polypeptide of the invention upon the tissue sample is observed. In one embodiment, where the subject has a malignancy, a sample of cells from the malignancy is plated out or grown in culture. The cells are then exposed to a therapeutic polypeptide of the invention. A therapeutic polypeptide which inhibits survival or growth of the malignant cells is selected for therapeutic use in vivo.

Many assays standard in the art can be used to assess such survival and/or growth. For example, cell proliferation can be assayed by measuring $^3$H-thymidine incorporation, by direct cell count, by detecting changes in transcriptional activity of known genes such as proto-oncogenes (e.g., fos, myc) or cell cycle markers. Cell viability can be assessed by trypan blue staining. Cell differentiation can be assessed visually based on changes in morphology, etc.

In various specific embodiments, in vitro assays can be carried out with representative cells of cell types involved in a subject's specific disorder, to determine if a therapeutic polypeptide has a desired effect upon such cell types.

In other specific embodiments, the in vitro assays described supra can be carried out using a cell line, rather than a cell sample derived from the specific subject to be treated. The cell line is preferably derived from or displays characteristic(s) associated with the malignant, neoplastic or pre-neoplastic disorder desired to be treated or prevented, or is derived from the cell type upon which an effect is desired, according to the invention.

Efficacy of a therapeutic polypeptide can also be determined by administration of the a therapeutic polypeptide or functional equivalent to immunodeficient mice injected with either the KS-Y-1 or KS-SLK cells, which cause tumor formation in the mice. The degree of apoptosis and angiogenesis of tumor cells after treatment with the therapeutic polypeptide is measured. Apoptosis is detected by staining fixed tissue samples from the tumor for the presence of cells with DNA fragmentation. For example, this detection is accomplished by treating tissue slides from formalin-fixed tumors with terminal deoxynucleotide transferase for extension of DNA ends (3' hydroxyl ends) and incorporation of digoxigenin-11-dUTP. Anti-digoxigenin antibody conjugated with the enzyme peroxidase allows detection of apoptotic cells that stain brown whereas viable cells stain blue. An increase in KS tumor cell apoptosis and a decrease in angiogenesis indicates that the therapeutic polypeptide has utility in treatment of KS.

A therapeutic polypeptide can also be assessed in clinical trials in human subjects presenting with KS or any other cancer. To test the efficacy of the therapeutic polypeptide in KS patients, either local, i.e. intralesional, or systemic administration of the therapeutic polypeptide can be used. Tumors can be examined physically for regression in response to administration of the therapeutic polypeptide. Additionally, tissue biopsies can be taken from the tumors and examined for apoptosis, as described above.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

8.6.4 Assays for Pro-Hematopoietic Activity

The invention provides a method for testing a therapeutic polypeptide for pro-hematopoietic activity. The therapeutic polypeptide is preferably tested in vitro, and then in vivo for the desired therapeutic or prophylactic activity, prior to use in humans. Any in vitro or in vivo assay known in the art to measure a pro-hematopoietic effect may be used. For example, suitable assays include those which measure the ability to induce hematopoietic cell proliferation in vitro or production of one or more hematopoietic cell types in vivo.

A specific embodiment provides a method for screening a therapeutic polypeptide for pro-hematopoietic activity, the method comprising assaying the preparation for the ability to induce an increase in hematopoietic cell numbers. The preparation may be screened by a method comprising measuring the number of colonies formed from hematopoietic stem or progenitor cells. The number of colonies formed from cells contacted with the therapeutic polypeptide is compared with the number of colonies formed from cells not so contacted. A higher number of colonies formed from the contacted cells indicates that the preparation has pro-hematopoietic activity.

In one embodiment, the cells are $CD4^+$ T cells in an SIV infected monkey. The monkey is exposed to the therapeutic polypeptide. The number of $CD4^+$ T cells in the monkey, which has been exposed to the therapeutic polypeptide, with the number of CD4+ T cells in a monkey not so exposed. A higher number of $CD4^+$ T cells in the exposed monkey indicates that the preparation has pro-hematopoietic activity.

The effect of the therapeutic polypeptide can also be measured on proliferation of hematopoietic cells in vitro. For example, hematopoietic cells may be cultured for an appropriate amount of time, such as 5 to 20 days and preferably 10 days, in the presence of (or otherwise exposed to) the therapeutic polypeptide of the invention. Colony assays are then performed to determine the number of colonies formed in comparison to the number of colonies formed by cells cultured in the absence of the therapeutic polypeptide of the invention. For example, hematopoietic progenitor cells can be isolated from bone marrow or cord blood, seeded in methylcellulose in the presence of absence of the therapeutic polypeptide, and then colony numbers determined after 10 days of culture. An increase in colony numbers in cells contacted with the therapeutic polypeptide of the invention indicates that the therapeutic polypeptide of the invention has activity in inducing proliferation of hematopoietic cells. Thus, for example, depending on the progenitor cell desired to be assayed, CFU-GM, CFU-GEMM, etc., assays can be performed using this method.

A therapeutic polypeptide of the invention can also be tested in vivo for the ability to increase numbers of hematopoietic cells. Preferably, the therapeutic polypeptide of the invention is tested in animal models of hematopoietic disorders before testing them in human subjects. For example, a therapeutic polypeptide can be tested in rhesus monkeys infected with SIV, particularly $SIV_{mac251}$ (as described above). Blood or bone marrow of the infected monkeys can be examined for an increase in $CD4^+$ T cells or any other hematopoietic cell type for which the monkey is deficient. An increase in numbers of the hematopoietic cell demonstrates that the therapeutic polypeptide is useful for treating diseases and disorders associated with hematopoietic deficiencies. Any animal model of an anemia can be similarly used for testing.

A therapeutic polypeptide of the invention can be tested in human subjects, preferably after tests in vitro and/or in vivo in an animal model. The subjects tested may be affected by hematopoietic deficiencies. Such deficiencies may include deficiencies associated with HIV infection such as anemia, neutropenia, thrombocytopenia, or $CD4^+$ T cell lymphocyte deficiency. In such cases, the therapeutic polypeptide of the invention may be screened for activity in increasing numbers of hematopoietic cells for which the subject is deficient. Briefly, the therapeutic polypeptide is administered, for example by intramuscular injection two to three times per week, to the subject presenting with the hematopoietic deficiency. The subject's blood or bone marrow is assayed before and after treatment with the therapeutic polypeptide for an increase in the hematopoietic cell numbers. A therapeutic polypeptide of the invention that causes an increase in hematopoietic cell numbers is useful for treatment of diseases and disorders associated with hematopoietic deficiencies.

Assays for hematopoietic cell proliferation in the blood or bone marrow can be accomplished by any method well known in the art. For example, blood can be drawn and blood cell numbers can be determined by routine clinical laboratory tests for red blood cells, platelets, neutrophils, lymphocytes, etc. Additionally, colony assays on isolated bone marrow can be performed to assess increases in stem or progenitor cells.

For example, bone marrow can be sampled and bone marrow cells evaluated for stem and progenitor cell colony formation. Briefly, cells are seeded in methylcellulose, cultured for 12 to 14 days, and then scored for colony formation where aggregates containing more than 50 cells are counted as a colony.[157] Bone marrow progenitors that can be evaluated by this colony assay include, but are not limited to, CFU-Mix, BFU-e and CFU-GM.

As an alternative to colony assays for detection and quantitation of stem and/or progenitor cells, immunological detection methods can be employed, based on the antigens expressed by the particular cell type (see, e.g., the relevant discussion hereinabove).

8.7 Therapeutic Compositions and Methods of Administration

The invention provides methods of treatment and prevention by administration to a subject in need of such treatment of a therapeutically or prophylactically effective amount of one or more therapeutic polypeptides of the invention. The subject is preferably an animal, including, but not limited to, animals such as monkeys, cows, pigs, horses, chickens, cats, dogs, etc., and is preferably a mammal, and most preferably human. In a specific embodiment, the subject is a human not afflicted with a cancer which secretes hCG or hCG fragments and, more particularly, not afflicted with KS.

Various delivery systems are known and can be used to administer therapeutic polypeptides of the invention. For example, suitable systems include: encapsulation in liposomes, microparticles and/or microcapsules; recombinant cells capable of expressing the therapeutic polypeptide; receptor-mediated endocytosis;[158] plasmids encoding one or more therapeutic polypeptides; viral vector delivery systems, etc. The therapeutic polypeptides can be delivered in a vesicle, in particular a liposome.[159]

Methods of introduction include but are not limited to intradermal, intramuscular, intraperitoneal, intravenous, subcutaneous, intranasal, epidural, and/or oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection. An intraventricular catheter may be used to facilitate intraventricular injection, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. For example, local administration may be achieved by topical application, by injection, by means of a catheter, by means of a suppository, or by means of an implant, the implant being of a porous, non-porous, or gelatinous material, including membranes, such as sialastic membranes, or fibers.

In yet another embodiment, the therapeutic polypeptide can be delivered in a controlled release system. A pump may be used as needed.[160] Polymeric materials may also be employed in a controlled release system, according to methods known in the art.[161] In yet another embodiment, a controlled release system can be placed in proximity of the therapeutic target, thus requiring only a fraction of the systemic dose.[162] Other controlled release systems are discussed in the review by Langer.[163]

In a specific embodiment a nucleic acid encoding one or more therapeutic polypeptides of the invention is administered by gene therapy methods as described herein, or as otherwise known in the art.

The pharmaceutical compositions comprise a therapeutically effective amount of one or more therapeutic polypeptides of the invention, and a pharmaceutically acceptable carrier.

The term "carrier" refers to a diluent, adjuvant, excipient, or vehicle with which the therapeutic polypeptide is administered to a subject. Examples of suitable pharmaceutical carriers are described in "Remington's Pharmaceutical Sciences" by E. W. Martin. Such compositions will contain a therapeutically effective amount of one or more therapeutic polypeptides of the invention, preferably in purified form, together with a suitable amount of carrier so as to provide the form for proper administration to the subject. The formulation should suit the mode of administration. In a preferred embodiment, the composition is formulated in accordance with routine procedures as a pharmaceutical composition adapted for intravenous administration to human beings. The compositions may also be formulated for vetrinary use.

Examples of suitable pharmaceutical carriers include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides.

Oral formulation can include standard carriers such as pharmaceutical grades of mannitol, lactose, starch, magnesium stearate, sodium saccharine, cellulose, magnesium carbonate, etc.

Typically, compositions for intravenous administration are solutions in sterile isotonic aqueous buffer. Where necessary, the composition may also include a solubilizing agent and a local anesthetic such as lignocaine to ease pain at the site of the injection.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutic polypeptides of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic polypeptide(s) and/or functional quivalent(s) of the invention that will be effective in the treatment of a particular disorder or condition depends on various factors and can readily be determined by one of skill in the art using standard clinical techniques with reference to the instant disclosure. For example, dosage amounts will depend on the nature of the disorder or condition. In vivo and/or in vitro assays may optionally be employed to help predict optimal dosage ranges. Effective doses may also be extrapolated from dose-response curves derived from the in vitro and in vivo experiments described herein. In general, the dose for administration to a human is 0.01 to 5.0 mg/24-48 hours, preferably 0.1-4 mg/24-48 hours, more preferably 0.25 to 2.5 mg/24-48 hours. In non-human animals preferred dosages are 0.00014 to 0.071 mg/kg/24-48 hours, more preferably 0.0014 to 0.057 mg/kg/24-48 hours, most preferably 0.0036 to 0.036 mg/kg/24-48 hours. These ranges will vary depending on the route of administration, the seriousness of the disease or disorder, the size of the subject, and other factors known in the art.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

Except as specifically described herein, methods used in the ensuing examples have been previously published.[164]

9.1 Isolation and Characterization of the MA Peptides

The active factor was isolated and purified from three sources with similar results:
a 2 day freshly collected sample of urine from women in early (first trimester) pregnancy kept at 4° without any additions, and used almost immediately after collection;
urine collections made over several weeks from women in early pregnancy and stored at −80° with sodium azide; and
commercial preparations of hCG pre-tested for activity.
9.1.1 Preparation of MA Peptides from Urine
Three different sources of the therapeutic polypeptides, previously shown to contain all the biological activities previously described in the filing, were used for the starting materials: A. Commercial hCG preparations. B. 24 hr urine collection from 2 different volunteers in the first trimester of pregnancy [3-4 weeks] and processed after storage at 4° C. without any preservative. C. Two-week urine collection from two women in first their trimester of pregnancy stored at −80° C. with sodium azide [1 g/l] as preservative.°

A). Commercials hCG preparations: APL (Wyeth Ayerst), Pregnyl (Organon) and CG10 (Sigma) contain mixtures of peptides (i.e. α+β hCG, free α hCG, free β hCG, β core, nicked β hCG and unknown cleavage or degraded β hCG peptides). 10 vials of commercials grade hCG-CG10 [10.000 IU/vials~1 mg of total proteins], APL [20.000 IU/vials~2 mg of total proteins] or Pregnyl [10.000 IU/ml~1 mg of total proteins] were dissolved in PBS without Ca2+ Mg2+ [10.000 IU/1 ml of PBS, pH 7.2] and were ultra-filtered and concentrated using three steps of size exclusions: 30 kDa, 10 kDa and 3 kDa of Macrocep [Pall Gelman Laboratory, Ann Arbor, Mich., USA]. Macrosep macro-concentrators provide rapid and convenient concentration, purification and desalting of small volume biological samples. A starting sample of 15 ml can be concentrated to 0.5 ml within [centrifugation at 1000 to 5000 g, typically for 30-90 minutes].

Retentate and filtrate at each step were tested for biological activity (i.e. anti-HIV-1, anti-Tumor and hematopoiesis). The material was then purified on a SUPERDEX™ peptide column HR 10/30 column run on HPLC (size exclusion from 100-7000 Da, Pharmacia). Concentrate sample load volume was 0.5 ml. Samples after HPLC were analyzed on SDS page gel [non-reducing conditions] and also by an agarose gel technique.[165] The gels showed major bands [silver staining] at approximately >3 [Pp1~MA] and >6 kDa [Pp2~pMA]. The gels were divided into seven 0.5 cm sections, each section was then electro-eluted (Hoefer GE 200 eluter, Pharmacia), using eluter buffer (BIO-RAD, CA), and tested for biological activity after removal of SDS and desalting. The eluted material was analyzed by MALDI-TOF mass spectrometry or SELDI using the matrix: CHCA and SA. Sample was also further purified by either DEAE or direct reverse phase [C18] column chromatography. Purity was again confirmed by MALDI-TOF mass spectrometry or SELDI. Purified samples were then sequenced utilizing N-terminal sequencing by Edman degradation.

B) From 24 hr collections of urine from two different volunteers in the early first trimester of pregnancy [~3-4 weeks] we proceeded within days after storage at 4° C. without any preservatives. Fifty ml/tube [1 L~20 tubes] of urine were centrifuged at 1000 g for 30 min, the supernatant was collected and the pellets were discarded. The pooled supernatants were then filtered through a 0.45 micron membrane filter [DS0200, Nalgene, Rochester, N.Y.]. One L of urine was processed at a time and 10 runs were pooled because of equipment limitations. 1 L of fresh urine yielded about 10 ug of Maternin. The material was then processed as described above starting with the 30 kDa, then the 10 kDa and finally the 3 kDa cutoff Pall Filtron Macrocep [PALL Gelman Laboratory, Ann Arbor, Mich.]. C) Two-week collections of urine from 2 different women in their first trimester of pregnancy were stored at −80° C. with sodium azide [1 g/l] as a preservative. The frozen urine was thawed and the pH was adjusted to 7.2-7.4 with sodium hydroxide and allowed to sediment for 1 hour at room temperature. Approximately 75% of the supernatant was decanted and the remaining supernatant was centrifuged to remove sediment and added to the rest of the supernatant. The supernatant was then filtered through a 0.45 filter [DS0200, Nalgene, Rochester, N.Y.]. From that point on the frozen urine was processed as described above FIG. 1, Panel A illustrates the peak fractions on HPLC-superdex peptide column chromatography, which followed stepwise size fractionation utilizing filters of varying size porosity and was followed by either porous DEAE or reverse phase (C18) column chromotography.

Active peaks were pooled for SDS PAGE analysis. The activities on SDS PAGE (Panel B) migrated as two distinct bands, the size of which are only crude estimates in view of their low molecular weights, but in general they ran with markers of about 4-6 kDa and 3-4 kDa for the larger and smaller polypeptides respectively. These samples were electroeluted and analyzed. In other experiments, affinity columns of polyclonal antibodies to the purified bioactive polypeptides were used.

After the urine samples were centrifuged at 1000 g for 30 min, the pellet was discarded, and the supernatant then filtered through a 0.45 micron filter to further remove particulate. The hCG preparations were simply dissolved in PBS. The purification scheme employed a series of microcep size exclusion filters: 30 kDa, 10 kDa, and 3 kDa. The activities were recovered in the 30 and 10 kDa filtrates but were retained with the 3 kDa. The active fractions were lyophilized, dissolved in 2.5 ml of $H_2O$, and 0.5 ml aliquots were applied in series five times to an HPLC-superdex (HR10/30) peptide column (range 100-7000 Da) with PBS. The peak activities (FIG. 1, Panel A) were pooled, lyophilized, and the samples dissolved in $H_2O$. One microgram was then applied to each lane of SDS polyacrylamide or agarose slab gels for electrophoresis. The gels showed major bands (silver staining) at approximately 4-6 kDa and 3-4 kDa (FIG. 1, Panel B). The gels were divided into seven 0.5 cm sections, each section electroeluted with a Hoefer GE 200 eluter (Pharmacia) using eluter buffer (Bio Rad, Ca.), and assayed after removal of the SDS with SDS removal kit (Pierce Co., Ill.) and removal of salt (Bio Rad, desalting kit). The activities migrated precisely with these bands.

For generating larger amounts of MA, 20 or more lanes were used and the area corresponding to known size of MA were electroeluted and pooled. One microgram of material from each band region was inoculated i.m. into male NZW rabbits every 2 days for 10 days with Freund's adjuvant. After 10 weeks sera was collected and tested by immunoblotting.

The polyclonal antibodies so generated reacted with homologous antigen and gave reactivity with crude hCG preparations known to contain MA activity and with sera from early pregnancy but had no cross reactivity with pure hCG, β-hCG, α-hCG, native glycosylated β-core (FIG. 2). There was little cross reactivity by Western blot between MA and pMA, but cross reactivities were found on ELISA (not shown).

These polyclonal antibodies were then used in an affinity column as part of a larger scale purification scheme. In addition, neither the 6 kD nor the 3-4 kDa polypeptide had reactivity with various monoclonal antibodies to β-hCG, (B108) or with three monoclonal antibodies (B-201, B-204, and B-210) to the native glycosylated β-core (FIG. 2) (the β-core antibodies were generously supplied by Dr. S. Birken, Columbia University). Purification form commercial hCG preparations followed similar procedures.

MoAbs were generated by injecting 6 week-old BALB/C with 300 ug of MA or pMA in Freund's adjuvant by the I.P. route. Repeated immunizations were done every few weeks for 6 months. At peak Ab titer (measured by ELISA), spleens were removed and splenocytes fused with NS1 plasmacytoma cells (6). Hybrid clones were selected for specificity of reactions in limiting dilution cultures, injected I.P. into nude mice and the ascites fluid collected after 3 weeks. The MoAbs were then purified by column chromatography (ref). Fractions containing the activity and single H and L chains, as shown by Comassie blue staining of SAS-AGE, were pooled. Isotyping was with isostrips (mouse isotyping kit, Roche).

Assays were performed with 1 ug of Ab and 10 ug of antigen electrophorese on a 10-20% acrylamide denaturing gel by electroblotting onto a nitrocellulose membrane (Bio-Rad). Blots were blocked with nonfat dry milk on TBS-tween 20 for 1 hr at room temperature, incubated with the indicated MoAb (5 to 10 ug) for 3 hrs, washed extensively with 1% TBS, and then incubated with a 1:1000 dilution of horseradish peroxidase-conjugated secondary antibody (Sigma) for 1 hr. Blots were washed with TBS and developed using the enhanced chemiluminesence method (Amersham) or by immunoblot kits (Bio-Rad). In addition polyclonal antibodies (Po-Ab) were also prepared. One ug of purified MA or pMA with 0.5 ml Freund's complete adjuvant were injected i.p. into 4 kg New Zealand male rabbits, and the sera were collected 2½ months later.

MA peptides were tested for their sensitivity to proteolytic enzymes as well as for thermosensitivity. Peptides were incubated with pronase, trypsin or chymotrypsin in PBS for 1 h at 37° C. The active material was protease-sensitive and lipase-(Sigma kit) and glycosidase-(Bio Rad kit) resistant. Proteolytic enzyme treatment eliminated the inhibitory effect of MA peptides in both the KS and human carcinoma (prostate and breast) clonogenic assays as well as in the HIV-1 replication assays as measured by HIV p24 ELISA. The purified material resisted boiling for 3 min but was destroyed after boiling 1 hr. Purity was estimated by the above gel procedures (Panel B), mass spectroscopy using MALDI-TOF and a CHCA matrix (Panel C), and N-terminal sequence analysis by Edman degradation (Panel A insert), and the sequence identity was confirmed by peptide synthesis (Panel D) with demonstrable reproducibility of bioactivities.

These analyses revealed that the material which migrated at 3-4 kDa was a polypeptide of size varying from 30 to 35 AA. The molecular masses correspond to 3.33 kDa to 3.8 kDa. The variation in size appears to be the result of variable C-terminal cleavage. However, the most frequently isolated polypeptide with these activities was the 35-mer identical to β-hCG AA 55-89, and smaller forms were identical but with varying degrees of C-terminal truncation. We named these polypeptides MA. The polypeptide of about 4-6 kDa contained the MA sequences but linked to other yet to be defined sequences. We tentatively refer to the larger polypeptide as pro-MA (pMA). The conclusion that MA is the active material was proven by demonstrating all of the biological activities with synthetic versions of MA as well as with more truncated forms. We note that MA activity is susceptible to 4° C. storage in water and to freeze thawing. Reproducible results were best obtained when the peptides were used soon after dissolving in aqueous solutions.

After isolation and confirmation of activity the material was sent to two independent laboratories for sequencing. N-terminal protein sequence analysis was performed by automated Edman degradation as well as on a combination of mass spectroscopy and Edman degradation.

9.1.2 Synthetic Production of MA peptides

MA (SEQ ID NO: 2) and derivatives of MA were produced synthetically by solid-phase synthesis using an automated synthesizer employing Fmoc and, t-Butyl, on a Wang resin.

Nα-Fmoc-protected amino acids (10 equivalents) were added sequentially using HTBU (O-Benzotriazole-N,N,N', N'-tetramethyl-uronium hexafluorophosphate) and N-methylmorpholine as coupling reagents. Side chain protected Nα-Fmoc amino acids were purchased from AnaSpec. The side chain is Trityl for Cys and Gln, t-Butyl for Asp, Thr, Ser and Pbf (pentamethyldihydrobenzofuran-5-sulfonyl). Peptides were deprotected and cleaved from the resin using reagent B for two hours. Peptides were purified to >95% by reverse-phase HPLC.

Isolated sequenced MA (SEQ ID NO: 2) is 35 AA residues in length. The inventors have produced synthetic peptides that exhibit the activities of MA (SEQ ID NO: 2). One active peptide, $MA_{S1}$ (SEQ ID NO: 4) is only 15 AA acid residues in length. Another, $MA_{S2}$, (SEQ ID NO: 5) is 30 AA residues in length.

The following designations will be used for the polypeptides (experimental and various controls) used in the work described herein:

pMA (SEQ ID NO: 3): natural peptide 38 amino acids in length;

MA (SEQ ID NO: 2): natural peptide 35 amino acids in length;

$MA_{S1}$ (SEQ ID NO: 4): MA synthetic peptide 15 amino acids in length;

$MAs_{S2}$ (SEQ ID NO: 5): MA synthetic peptide 30 amino acids in length;

$MA_{S3}$ (SEQ ID NO: 6): MA synthetic peptide 35 amino acids in length (same sequence as MA, but $MA_{S3}$ is the synthetic version as opposed to MA, which is the isolated version);

CP: control peptide 32 amino acids in length, consisting of AA 21-52 of β-hCG (SEQ ID NO: 1);

CR 127: highly purified native hCG; and beta core: purified hCG beta core (a well known and substantiated degradation product of the beta chain of hCG, consisting of an N-terminal polypeptide of the beta chain: AA 6-42 joined by a disulfide bridge to a C-terminal polypeptide formed also from β-hCG (SEQ ID NO: 1): AA 55-92 with AA 43-54 having been removed).

9.2 Anti-Cancer Effects of MA

The anti-tumor activities of MA were assessed in several in vitro and in vivo systems using published methods.[166] In vitro studies were with a wide variety of human tumor cell lines as well as short-term cultures of cells from biopsy samples obtained from tumors. The assays included effects of MA on colony formation, cell number and viability (trypan blue), and apoptosis. Four measures of microscopy were used. In vivo studies included the effects of MA on tumors induced in immunodeficient mice by xenotransplanted various human neoplastic cells, spontaneous neoplasms of immuno-competent mice and rats, and a few standard tumors in immuno-competent mice. Representative examples are presented.

9.2.1 MA Selectively Kills Human Tumor Cells In Vitro

Since the crude active hCG preparations[167] and partially purified fractions[168] were previously shown to inhibit growth of KS tumor cells, the effects of native, synthetic full-length, and various truncated forms of MA were all first tested on KS cells. The procedures used were as previously described.[169] A dose-dependent inhibition of colony formation was observed. At concentrations of approximately 30 nM there was 60-80% inhibition (FIG. 3, Panel A) and evidence (DNA laddering and Annexin V staining) of marked apoptosis (FIG. 3, Panel B).

For colony formation assays (Panel A): Cells ($5 \times 10^5$/ml) were seeded in modified Eagle's medium supplemented with 10% FCS, 10% conditioned medium form PHA stimulated human lymphocytes, 2 mM glutamine in 0.8% V/V methylcellulose with or without various treatments in a final volume of 1.0 ml. Then 0.1 ml aliquots were seeded in 96 well flat bottom microtest plates and incubated at 37° C. in 5% $CO_2$ in air for 7 days. Aggregates containing 50 cells or more were scored as colonies. The results show a representative experiment and are mean of triplicate values.

For Annexin V assays (Panel B): $5 \times 10^5$ cells were seeded in triplicate on 24 gelatin coated wells in conditions as described for Panel A and treated with the indicated test materials. After 3 days the cells were dislodged from their monolayers by gentle pipetting with cell dissociation buffer (Life Technologies), counted after trypan blue staining and aliquots examined for Annexin V staining by indirect IFA (ref).

Studies of the anti-tumor cell effects of MA were extended to other carcinomas, melanoma, some hematopoietic tumors, and carcinomas of the colon, prostate, breast, lung, brain, pancreas, and kidney-using cell lines from these tumors. In all cases a dose dependent inhibition of growth (FIG. 3, Panel A) and induction of apoptosis (FIG. 3, Panel B) was again obtained, illustrated here only for studies with carcinomas of the prostate and breast. Less than 30 nM native and synthetic MA, including the truncated forms, produced near maximum effects. Many more types of tumor cells were studied utilizing other assays (see below).

More extensive studies of the effects of MA and with truncated synthetic forms of MA ($MA_S$) on a wide range of other human tumor cells were carried out using three-dimensional confocal microscopy. Cells were cultured and then seeded onto gelatinized glass chamber slides and incubated 24 hrs with the various test materials. The slides were then fixed with formalin and treated serially with Triton X-100 (0.01%) for 10 min at 25°, 0.4 ug/ml fluorescein isothiocyanate (FITC)-labeled Phalloidin (Sigma Chem. Co.) at room temperature for 30 min to bind actin, washed with PBS and the DNA stained with Propidium iodide (PI) (0.5 ug.ml) (Sigma Chemical Co.), for 15 min. The stained slides were washed and mounted on slow fade (Molecular Probes, Inc., Eugene, Oreg.) and examined through a dual emission filter XF53 (Omega, Inc., Brattlesboro, Va.) by fluorescent microscopy. In some experiments only DNA staining was performed. In these instances Triton X-100 was not used. The slides were stained with PI and examined for cell morphology and chromatin degradation under 3D confocal microscopy.

Figure 4A:
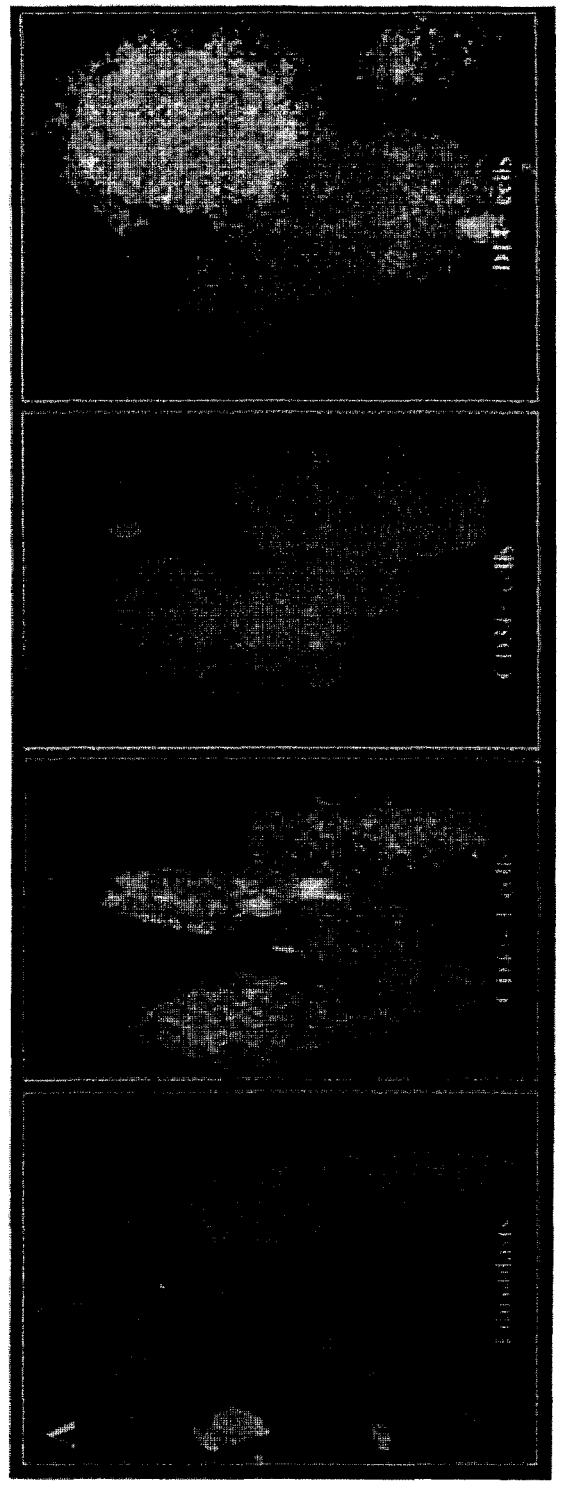
Figure 4B:
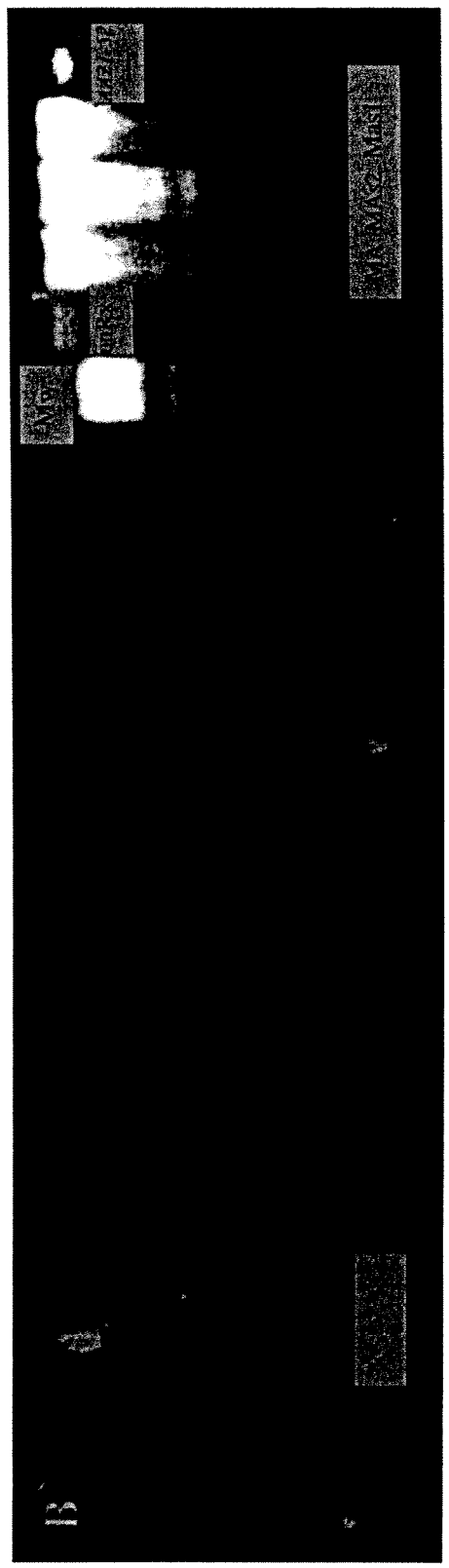
Figure 4C:
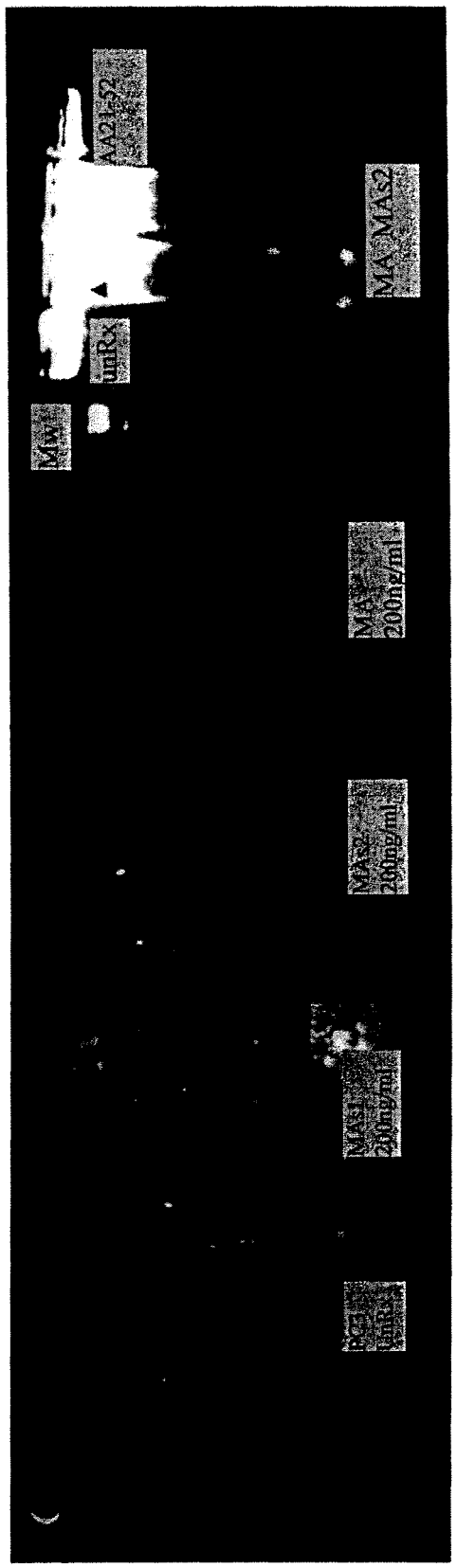
Figure 4D:
Figure 4E:
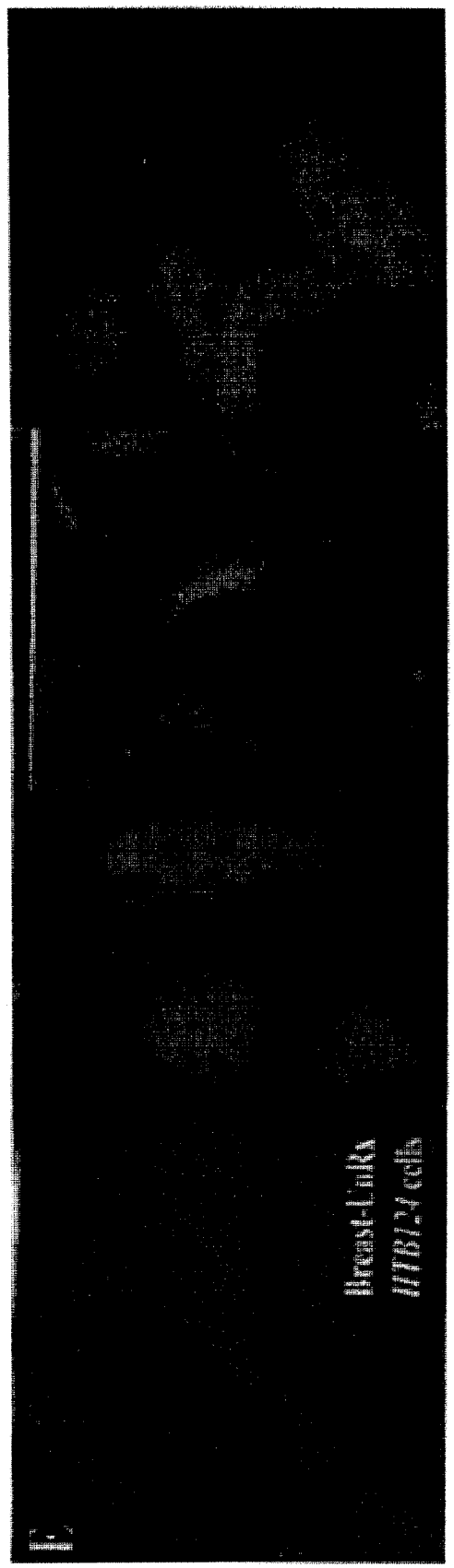
Figure 4F:
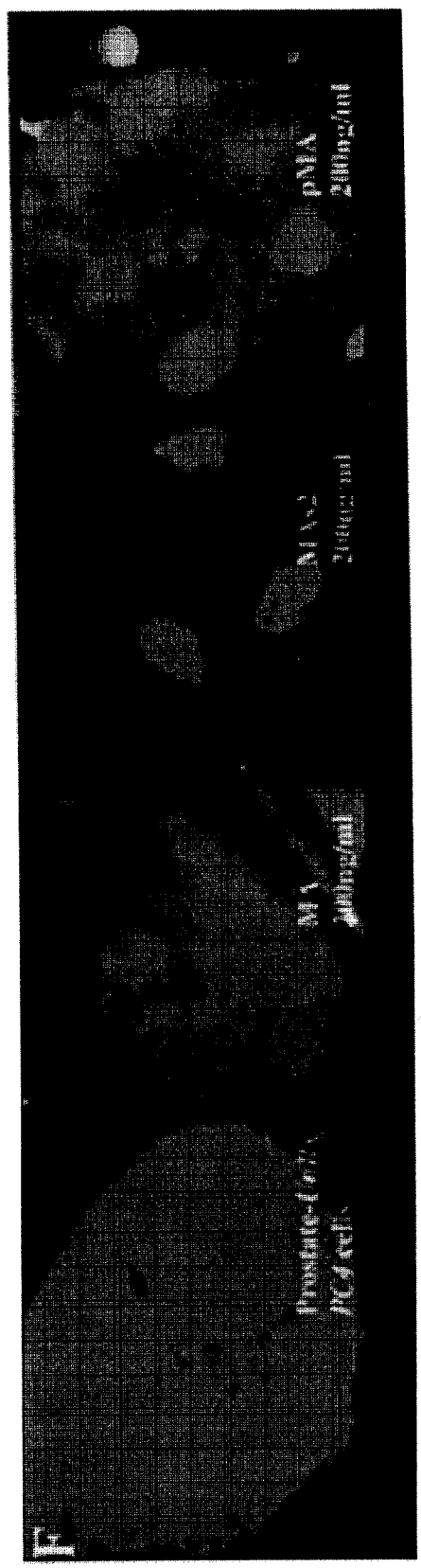
Figure 4G:
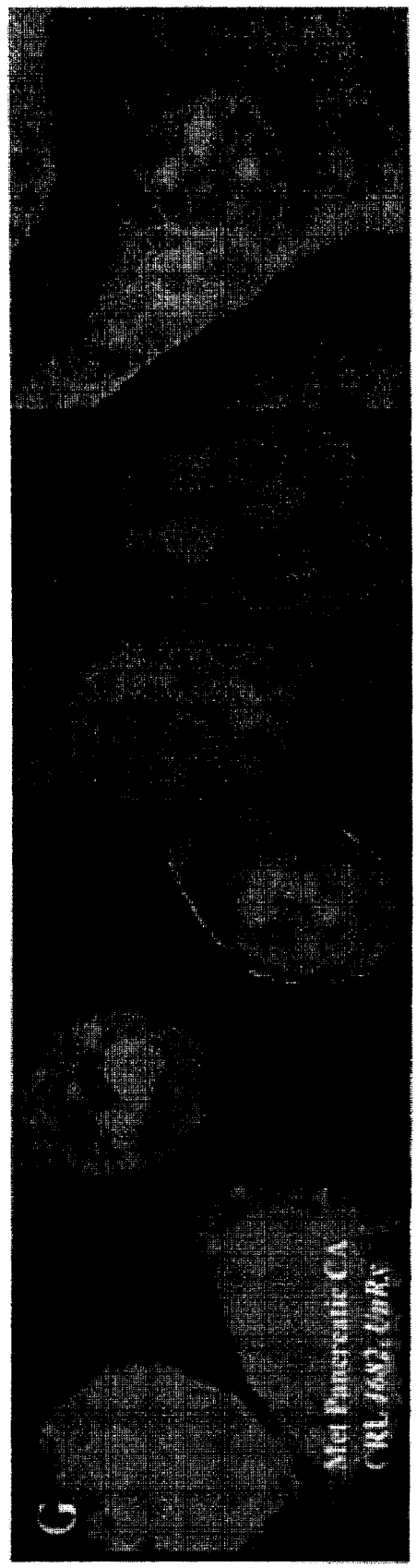
Figure 4H:
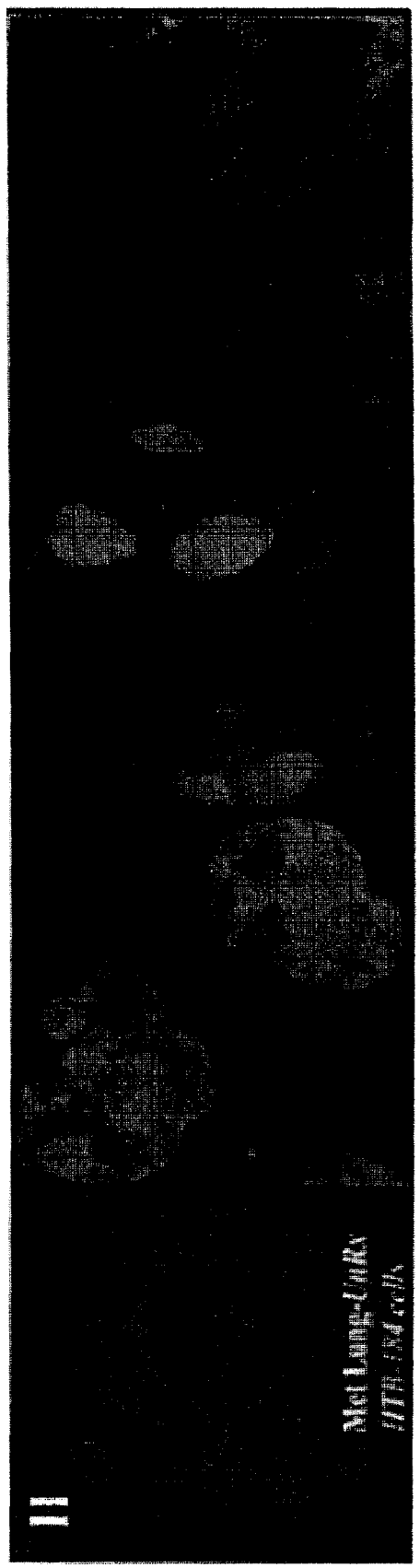
Figure 4:
Figure 4K:
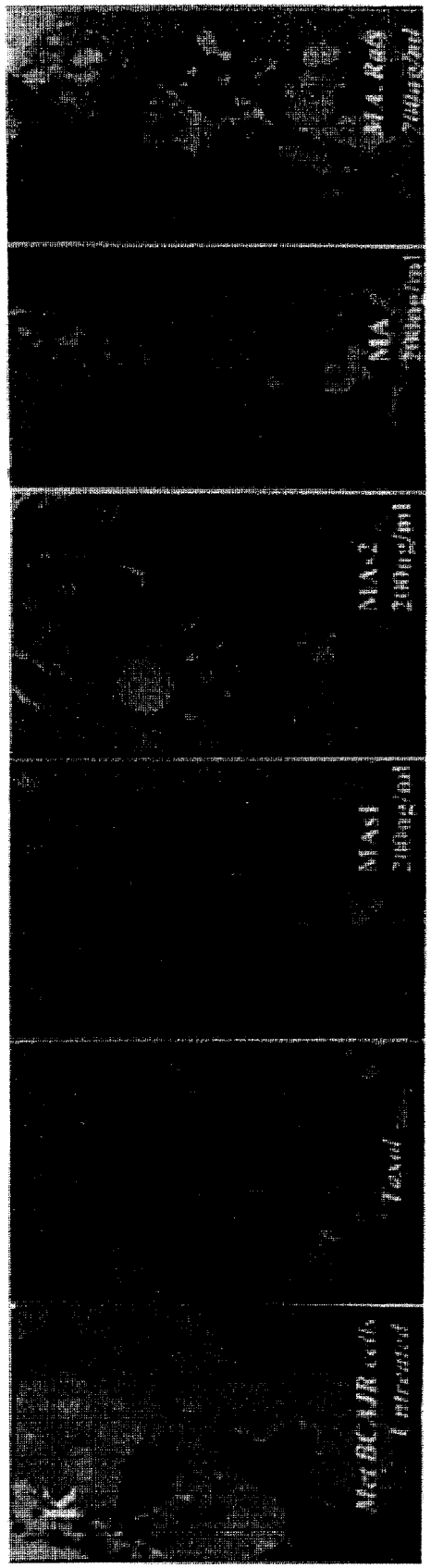

These results provided morphological conformation of the induction of apoptosis of almost all tested human tumor cells by MA. Prominent nuclear pyknotic changes were observed with all tumor cells (FIG. 4, Panels B through K; Panel A shows normal cells). Untreated cells (first line) show normal morphology. The confocal microscopy results also verified the specificity of MA in killing tumor cells. Concentrations of MA (2000 ng/ml which are 10× higher than needed for inducing apoptosis of tumor cells) had no effect on the morphology of primary human fibroblasts, cord blood derived CD34+ cells, PBMC derived CD4+ T cells, or macrophages (FIG. 4, Panel A).

To be certain that this specificity for tumor cells was not simply the consequences of a difference between cycling and non-cycling cells, the following cell-types were also used: proliferating human normal fibroblasts, endothelial cells (HUVEC), and PHA-stimulated lymphocytes. Again, no inhibition of growth or evidence of apoptosis was observed. In fact, MA actually promoted growth of some of these cells.

Moreover, 200 ng/ml of MA, $MA_{S1}$ (a synthetic 15-mer lacking the first 7 AA and last 13AA of MA), and $MA_{S2}$ (a synthetic 30-mer lacking the first 3AA and last 2AA of MA) induced apoptosis of:

KS Y-1 cells: provided by NIH (Panel B);

other sarcoma cell lines: fibrosarcoma 4TB166, and Ewing's sarcoma from ATCC (not shown);

two prostate carcinoma cell lines: PC3 and PC4 (Panels C and F);

gliobastoma: HTB16/ATCC (Panel D);

carcinoma of the breast: HTB124/ATCC (Panel E);

carcinoma of the pancreas: CRL 1682/ATCC (Panel G);

carcinoma of the colon: CRL 1682 (not shown);

carcinoma of the lung: HTB184/ATCC (Panel H); and carcinoma of the kidney: HTB46/ATCC (Panel I);
melanoma: HTB67/ATCC (not shown); and
some leukemia and lymphoma cell lines: HUT78/ATCC, DAVDI, HG, SULTAN, T-cell lymphoma (not shown).

9.2.2 MA Inhibits Growth and Induced Apoptosis in Primary Human Cancer Cells

Because cell lines might be more susceptible to growth inhibition and apoptosis, the effects of MA on short-term cultured human tumor cells were investigated. The cells were obtained from biopsied specimens and immediately cultured (primary cultures). The results were similar to the results with tumor cell lines. MA inhibited growth and induced apoptosis at similar concentrations to those concentrations that inhibited growth and induced apoptosis of neoplastic cell lines. FIG. 3, Panels A and B are representative results with primary breast and prostate carcinomas respectively. These pro-apoptotic effects of MA on human tumor cells were with 10% serum rather than the lower concentrations sometimes used to make cells more susceptible to apoptosis.

More extensive studies of primary human tumor cells were carried out utilizing confocal microscopy. Primary neoplastic cells from metastatic carcinomas of the breast, prostate, lung (small cell carcinoma), colon, and kidney were examined to determine if these results were limited to neoplastic cell lines or whether MA would induce morphological changes reflecting apoptosis in primary human tumor cells.

With the exception of the kidney carcinoma, which was a biopsy sample direct from the tumor, the samples were from pleural effusions which developed after metastasis to the lung. The breast, prostate, and colon carcinomas were freshly obtained and immediately cultured, whereas the lung and kidney carcinomas went through 22 and 18 passes respectively before they were used in these studies. All cells were examined after 3 days culture in the presence or absence of MA (200 ng/ml) or other treatments. Rapid induction of apoptosis was observed with all the primary carcinomas. FIG. 4, Panels J and K show representative examples using prostate (PCANJ) and breast (BCAJR) carcinomas. pMA was also effective in the same molar concentration range as MA (see Panels F and I for examples).

Polypeptides with MA activity were also isolated from sera and urine of mice and rats in early pregnancy. Though these polypeptides have not yet been sequenced, they exhibit the full range of activity as human MA. An illustrative example is shown with rat MA (MA•R) in the induction of apoptosis of the primary human prostate (PCANJ) and breast carcinoma (BCAJR) cells (FIG. 4, Panels J and K, last row). Taxol (5 ug/ml) was used as a positive control (see Panels J and K, fourth row). A large number of other control polypeptides were negative in these and all other assays. Most importantly, no inhibition of growth or induction of apoptosis was observed with equimolar or 5 to 10× greater concentrations of purified native hCG (CR127), recombinant hCG, rβ-hCG, α-hCG, or the native glycosylated β-core with any of the neoplastic cells. Other hCG synthetic peptides also tested negative. These included: β-hCG 21-52 (FIGS. 3 and 4), 6-39; and 9-119.

9.2.3 MA Kills Human Tumor Cells In Vivo

Both native and synthetic MA also inhibited growth (between 60% and 100%) and promoted apoptosis of tumors in vivo. In the first set of experiments, MA was tested against tumors formed by xenotransplantation of various human carcinoma and sarcoma cells in immunodeficient mice. After allowing the tumors to develop for 7 to 10 days, treatment was initiated by I.P. injection with 200 ng (about 60-100 pmoles)/day for seven days. FIG. 5, Panel A illustrates a typical result with prostate carcinoma (PC3), and Panel B shows results for KC cells (KS Y-1). The inhibitory effects were dose-dependent and found with both native and synthetic MA and pMA. At the dose range of 60-100 pmoles there was over 70% inhibition of tumor size. Increasing the concentration to 300-500 ng/day (about 100-200 pmoles) and treating for 2 to 3 weeks lead to complete tumor regression. Three different synthetic forms of MA were used: full length ($MA_{S3}$) and the previously described $MA_{S1}$ and $MA_{S2}$ (Panel C). With equivalent and higher molar concentrations, there was no effect of pure hCG (CR127) (150 pmoles), pure β-hCG (rhCG) (140 pmoles), αhCG (200 pmoles), or pure native glycosylated β-core (150 to 400 pmoles) (FIG. 5, Panel C), nor with a wide variety of control peptides derived from β- and α-hCG chains. However, inhibition was obtained with some lots of crude preparations of hCG (APL, Wyeth-Ayrest) and β-hCG (CG10, Sigma) (FIG. 5, Panel C), as we have previously reported,[170] which is expected, since MA can be isolated from these commercial preparations. The anti-tumor effects were observed when therapy was initiated 1 week after the start of tumor formation when tumor size had reached approximately 0.2×0.2 mm (about 30-50% of their maximum size in untreated animals). Similar to the in vitro studies, the mechanism of tumor inhibition was by rapid induction of apoptosis (FIG. 5, Panels A and B) as determined by APO-TAG staining.

It is possible that an anti-angiogenic effect of MA also contributes to tumor inhibition, since light microscopic examination of the thin sections of the tumors revealed reduction in blood vessel formation. However, whether this effect is direct, and in turn facilitates tumor destruction by diminished blood supply or is a consequence of primary tumor cell killing is not settled because a rapid induction of tumor cell apoptosis may prevent release of angiogenic factors such as VEGF.

Thus, all the anti-tumor activity may rest on the capacity of MA to directly induce apoptosis of the tumor cells as observed in vitro. In either event, MA has potent, broad, and specific killing effects on human cancer cells in vitro and in vivo with experimental models encompassing both mesenchymal derived tumors (the sarcomas and some hematopoietic tumors) and epithelial carcinomas (prostate, breast, lung, pancreas, colon, brain, and renal), producing no evident cytotoxic effects on normal human cells, even at higher concentrations. However, MA did not inhibit growth and kill all kinds of tumor cells. For example, it had no effect on HTLV-I induced adult T-cell leukemia nor some β-cell lymphomas.

9.2.4 MA Inhibits Mouse and Rat Spontaneous Tumorigenesis

As shown, MA killed a wide variety of human tumor cells in vitro and in vivo killed xenotransplanted human tumors in immune deficient mice. We wanted to be certain that the in vivo results would not be limited to immune deficient mice. We were also curious to see whether MA effected rodent tumors because we had evidence that indicated that MA would cross species barriers in that human MA could affect mouse cells and rodent MA (MA•R) could affect primate and rodent cells. Therefore, we tested the effects of MA on:

spontaneous fibrosarcomas which developed in three older FVB/N mice; and spontaneous breast carcinomas which developed in three older Sprague-Dawley rats.

The tumors were recognized and treated after different stages of development. Samples of the tumor cells were grown in short-term culture and when treated with MA underwent rapid apoptosis. Treatment of the mouse fibrosarcomas with MA for 2 weeks led to complete abolishment of the tumor in two of three animals (tumor size less than 0.5 cm in diameter) (FIG. 6, Panel A). Partial regression was observed in one animal first treated with MA when the sarcoma progressed to about 1 cm. However, no further growth was noted in the subsequent 8 weeks of the study.

Similar results were obtained with the spontaneous mammary carcinomas of rats. Treatment of one rat with a tumor of approximately 3×3 cm led to complete tumor regression (FIG. 6, Panel B). Two other rats with breast carcinomas of about 4×5 cm showed partial tumor regression after 2 weeks of therapy with MA and no further growth during the subsequent 8 weeks of the study.

9.2.5 MA Inhibits Tumorigenesis in Standard Mouse Models (B16 Melanoma and Lewis Lung Carcinoma).

B16 melanoma and Lewis lung (LL) carcinoma cells were first shown to be susceptible to the pro-apoptotic effects of MA (FIG. 6, Panels C and D) at the same dose range used with cultured human tumor cells. The tumor cells grown in standard culture conditions were used to generate metastatic cancers in pathogen-free 6-8 week old C57/BL mice (Charles River). In one set of experiments, the animals were treated with $MA_{S1}$ or $MA_{S2}$ at two doses, 0.1 ug or 1.0 ug either in a pre-treatment protocol (two subcutaneous inoculations 24 and 48 hrs before transplanting the tumor cells). In a second set of experiments after establishment of widespread metastasis (day 7 and day 14), the animals (5 per group) were treated daily for 14 days with the same low (0.1 ug) and high (1.0 ug) dose of $MA_{S1}$ or $MA_{S2}$. The results demonstrate a potent pro-apoptotic effect of MA on neoplastic cells in vivo.

9.3 Anti-HIV Effects of MA

The following sections describe empirical work demonstrating the anti-HIV effects of MA peptides.

9.3.1 MA Suppresses HIV-1 and SIV In Vitro

The effect of native and synthetic MA on HIV-1 infection in vitro was evaluated using PHA and Il-2 stimulated primary peripheral blood cells (PBMC), CD4+ T-cells enriched fractions from PBMC, and CD14+ macrophage enriched fractions. Infection was with HIV-1 IIIB (PBMC and CD4+ T-cells), HIV-1 Ba-L (macrophages), and two primary HIV-1 isolates not passaged in any cell line (PBMC). As illustrated in FIG. 7, a dose dependent inhibition of virus (IIIB and Ba-L) production was observed as determined by p24 levels in the extracellular fluid. Virus production was inhibited 50% with both native and synthetic MA at about 30 nM. Similar inhibition curves were obtained with the primary HIV-1 isolates. No inhibition of HIV replication occurred with pure native hCG (CR127), βhCG, native glycosylated β-core or with β-hCG synthetic peptide AA 21-52 (FIG. 7) nor with scrambled MA peptides at equimolar or higher concentrations. It is important to emphasize that accurate in vitro assays of the effects of MA on chronic HIV production in cell lines such as 119 or CEM are not possible because of the cytotoxic effect of MA on these tumor cell lines. MA also inhibited $SIV_{MAC\ 251}$ infection of rhesus macaque PBMCs.

9.3.2 MA Suppresses HIV-1 In Vivo in HIV-1 Transgenic Mice

In vivo effects of MA were also examined in:
HIV-1 transgenic mice;
a newly developed HIV-1 transgenic rat model; and
$SIV_{MAC\ 251}$ infected rhesus macaques.
Methods used were previously described by Kestler et al. and Letvin et al.[171]

The transgenic mice contain 5.1 kb of the HIV-1 proviral genome, lacking gag and pol genes and 2.3 kb of vector.[172] The newly developed transgenic rat contains the same HIV-1 sequences and vector. In both birth weights and features, the homozygous animals are born with normal weight and gross appearance, but in untreated animals shortly after birth, high levels of env and regulatory genes are expressed promptly correlating with failure to develop, cachexia, hyperkeratosis, immune abnormalities, kidney and CNS lesions, and early mortality (death of >90% by 10 days of age).

Twenty-four hours after birth the mothers were either inoculated subcutaneously daily for 10 days or received an implanted osmotic pump delivering 30-150 pmoles of either native or synthetic MA or pMA. Various control polypeptides were used at equimolar or vast molar excess. The newborn pups were then allowed to feed from the foster mother breast milk over the entire period. Since the animals are at risk from needle inoculation, breastfeeding was the chosen route for MA administration.

Animals feeding from mothers inoculated with 30-150 pmoles of MA, $MA_S$ or pMA survived (FIG. 8, Panels A and C), quadrupled their weight over the ten day period (Panel A, and left of Panel C), and when sacrificed for post-mortem examination their tissues showed marked inhibition of viral expression[173] (FIG. 8, Panel C, right side).

In these experiments total RNA was extracted from samples of skin $RNA_{206}$ 10 days after birth of MA treated and untreated mice. One ug of RNA was reverse transcribed into cDNA using random hexamer primer and MMTV reverse transcriptase (Life Technologies, Inc.) in a final vol. Of 30 ul. Three ul of each reaction was used for PCR amplification of the HIV-1 gene sequences (env, tat, nef, and rev) as described (ref), and glyceraldehyde 3-phosphate dehydrogenase (GAPDH) was amplified from each sample for normalization. After 25 cycles, 10% of the products were resolved by electrophoresis on 2% agarose gels, transferred to nitrocellulose membranes by Southern blotting, and hybridized to fluorescein isthiocyanate-labeled oligonucleotide probes complementary to internal sequences of the amplicons (ref). Bound probes were detected by chemiluminescence (Amersham) and relative mRNA levels determined by densitometry after normalization with GAPDH mRNA levels.

The marked decrease in detectable HIV-1 RNA transcripts was confirmed for HIV-1 proteins gp120 and Nef by in situ histochemistry.

Similarly, treatment with 300 IU of crude preparations of hCG (APL or CG-10), both of which also contain MA as an impurity, were also protective. In contrast, mothers treated with an irrelevant β-hCG peptide (AA 21-52) or with purified native (CR127) rhCG, pure β-hCG, native glycosylated β-core, or control peptides (AA 21-52) had pups with full disease in that 10 of 10 mice were dead by day 10 (Panel B), and their tissues showed a high expression of HIV-1 env and regulatory genes like untreated controls. Animals reared from mothers receiving the low dose (30 pmoles) of MA had greater survival than control or untreated animals, but the results were not as impressive in that about 50% eventually died (after 2 mos). An extremely low amount of MA, approximating only 100 pmoles, as an intact polypeptide or a biologically active degradation product, is able to enter lactating ducts of the mother, and cross the mucosal surface of the gastrointestinal tract of the newborn pup, sufficiently distribute throughout body tissues, and maintain adequate biological activity to block HIV-1 gene expression and restore normal development of the mice. An alternative possibility is that MA is able to induce a factor in the mother mouse which accomplishes this feat.

In these experiments total RNA was extracted from samples of skin $RNA_{206}$ 10 days after birth of MA treated and untreated mice. One ug of RNA was reverse transcribed into cDNA using random hexamer primer and MMTV reverse transcriptase (Life Technologies, Inc.) in a final vol. Of 30 ul.

Three ul of each reaction was used for PCR amplification of the HIV-1 gene sequences (env, tat, nef, and rev) as described (ref), and glyceraldehyde 3-phosphate dehydrogenase (GAPDH) was amplified from each sample for normalization. After 25 cycles, 10% of the products were resolved by electrophoresis on 2% agarose gels, transferred to nitrocellulose membranes by Southern blotting, and hybridized to fluorescein isthiocyanate-labeled oligonucleotide probes complementary to internal sequences of the amplicons (ref). Bound probes were detected by chemiluminescence (Amersham) and relative mRNA levels determined by densitometry after normalization with GAPDH mRNA levels.

These results also indicate that the in vivo anti-HIV effects involve mechanisms in addition to that involved in the inhibition of HIV-1 infection in vitro, since the concentrations required in vivo are less than those required in vitro in these models. It is of interest that LH had a slight effect (FIG. 8). We speculate that analogous to some hCG commercial preparations, the activity of LH is due to a polypeptide present in preparations as an impurity. It is likely that this hypothetical polypeptide will be homologous to MA and accounts for this activity in sera and urine of rodents in early pregnancy since rodents do not have CG genes.

9.3.3 MA Suppresses HIV-1 In Vivo in HIV-1 Transgenic Rats

Because of the extraordinary effects of MA in the mouse modes, we were concerned that the results might be peculiar to the model. Consequently, an HIV-1 transgenic rat model was developed. An additional advantage of the rat model is the larger size of the animals, enabling direct inoculation of MA into the developing pups rather than therapy being indirect (the lactating mother) and limited to the lactation phase. Thus, the transgenic rats can be followed and treated much longer.

Like the transgenic mice, the transgenic rats contain HIV-1 provirus PNNL 4-3, again deleted in gag/pol, and also develop hyperkeratosis. Additionally, they develop tissue fibrosis, inflammatory changes, and some histopathology more similar to human AIDS than in the mouse model, but unlike the HIV-1 transgenic mice the effect is usually not lethal. The changes correlate with expression of HIV-1 proteins. The transgenic rats are more fully described in copending U.S. patent application Ser. No. 09/058,113, by Bryant et al., filed Apr. 9, 1998, entitled "HIV Transgenic Animals and Uses Therefor," the entire disclosure of which is incorporated herein by reference.

Inoculation (subcutaneous) of a 250-300 gm mother with 300 pmoles of MA for 10 days began after birth of the pups. As in the mouse model, pups were breastfed during this period, but their larger size and non-lethality of the provirus for these animals allowed longer term direct subcutaneous inoculation with MA. The MA-treated rats survived, developed normally, and had markedly reduced transgene expression.

It is obvious that these HIV-1 transgenic animals do not reflect an HIV natural infection in several major respects, such as the lack of inclusion of any step in the infectious process prior to provirus integration and the lack of specific human cellular factors involved such as, for example, in the intranuclear transcriptional events involving Tat. However, this model was important for the following reasons: (1) though not all-inclusive in providing targets for inhibition of HIV, nonetheless, the HIV-1 transgenics do contain the HIV-1 LTR elements, several of the HIV protein biosynthetic events, and the proteolytic processing and viral maturation steps in the HIV replication cycle, one or more of which may have been targeted by MA; (2) independent from any discussion of the utility of these models for exploring a new HIV inhibitor, the transgenic studies clearly demonstrate that MA is able to have profound in vivo effects at very low concentrations; (3) the results show that MA is either able to survive harsh conditions or induce other factors which achieve the biological effects; and (4) the HIV-1 transgenic mouse assay proved to be the most sensitive and accurate method for following the purification of MA.

9.3.4 SIV Infected Monkeys

Certain strains of SIV produce an AIDS-like illness in susceptible monkeys. Among them $SIV_{MAC\ 251}$ induces disease in rhesus monkeys similar to AIDS in humans only with much greater rapidity.[174] Therapy with purified MA of 3 monkeys with end-stage disease infected 13-14 mos earlier was initiated when the animals were losing weight, highly viremic (plasma virus 0.5 to $3 \times 10^6$ copies of SIV RNA/ml by NASBA), and developing pancytopenia. Methods used were as previously described by Kestler et al. and Letvin et al.[175] Treatment of these monkeys with end-stage AIDS with MA at 0.2 mg/kg dose 3 times weekly produced no significant change in SIV titer over 6 mos. observation period. However, in this period none of the 3 animals died. In contrast, most untreated animals died by this period. Though the limitation of animal number precludes strong conclusions related to survival. The beneficial effect of MA in these end-stage animals was indicated by the stabilization and in some instances even increase in weight and T-cell number.

Far more impressive were experiments performed soon after infection (3 weeks). In these experiments, crude urinary preparations containing MA, but not crude fractions lacking MA, were inoculated subcutaneously. Using a $10^{4.5}$ $TCID_{50}$ of cell free $SIV_{mac\ 251}$, the characteristic rise in SIV p27, reduction of CD4+ T-cells, and weight loss, which occurred in the untreated animals, was prevented in MA treated animals. The untreated animals died before 6 mos. The treated animals were maintained for 7 mos. without weight loss, with normal CD4+ T-cell counts, and barely detectable plasma p27 (less than 5 ng/ml in contrast to over 200 ng/ml in control animals). However, stopping therapy led to rapid onset of virus production and development of AIDS-like disease.

9.4 Pro-Hematopoietic Effects of MA

Preliminary experiments in monkeys treated with MA showed an increase in peripheral blood T-cells.[176] Though no other blood cells were measured in those experiments we speculated that MA might have a pro-hematopoietic effect which could be a factor on the very low concentrations required for some of its in vivo effects, particularly the effects on HIV-1 transgenic rodents. Consequently, we tested the effects of MA on hematopoiesis using methods described by Lunardi-Iskandar et al.[177] The assays first included in vitro effects of MA on various blood cell precursors. Three types of in vivo tests were also carried out. The in vivo tests were based on the effects of MA to rescue:

lethally irradiated rats and mice;
    rats treated with lethal doses of a cancer chemotherapeutic agent (taxol) which suppresses the bone marrow; and
    acutely bled but otherwise normal rats and monkeys.

9.4.1 MA Promotes Multi-Lineage Hematopoiesis In Vitro

Hematopoietic colony formation assays with bone marrow or cord blood of normal human volunteers and bone marrow of monkeys, rats, and mice were utilized. The assays are conventional measurements of the number of progenitors for erythrocytes, granulocytes, macrophages, platelets, and T-cells. The culture conditions included growth factors that would give near optimum growth for the particular lineage.

These factors included Il-3, PHA-lymphocyte conditioned medium, erythropoietin (EPO), Il-6, and GM-CSF. The number of colonies developing in methylcellulose reflects the number of progenitor cells, and the percent increase is a measure of the effect of different polypeptides to increase colony number above the maximum obtained with the indicated known growth factors.

An illustrative example of a human bone marrow derived culture is shown in FIG. 9. There was no significant effect above background with equimolar or higher concentrations of rβ-hCG, native glycosylated β-core, and control peptides or pure hCG. However, concentrations ranging from 10-500 ng/ml (approximately 3-150 nM) of both native MA and $MA_{S1}$, $MA_{S2}$, and $MA_{S3}$ promoted an increase in colony number in a dose-dependent manner reaching a maximum of 60-80% increase at 30-150 nM (FIG. 9) for all hematopoietic progenitors. We observed similar results when the source of hematopoietic precursors were: human cord blood, rhesus macaque bone marrow, and rat and mouse bone marrow. Thus, like the anti-tumor and anti-viral results, the multi-lineage pro-hematopoietic effects of MA crosses several species. MA promotes CFU-GEMM (FIG. 9, Panel A) which includes precursors of granulocytes, red blood cells, and macrophages; BFU0e, (FIG. 9, Panel B) which are red blood cell precursors; CFU-GM (FIG. 9, Panel C) which include myeloid (granulocyte) and macrophage precursors; and T-CFC, (FIG. 9, Panel D) which are cells capable of forming colonies of T-cells. The latter is a less conventional assay, and details on the methods involved are described elsewhere.[178]

These in vitro results prompted us to determine whether MA could produce significant effects in vivo on blood cell formation. To this end we carried out several kinds of experiments which utilized either lethally irradiated rats and mice, animals given chemotherapeutic (anti-cancer drugs) agents which have toxic and at high doses lethal side effects due to bone marrow suppression, and severely acutely bled animals, and we determined the effects of short-term (1 or 2 subcutaneous injections) pre-treatment with MA or continuous (3×/week) treatment for a few weeks beginning after the traumatic event.

9.4.2 Treatment with MA Rescues Lethally Irradiated Rats and Mice

In order to determine in vivo relevance of the prohematopoietic effects of MA treated rats and mice under several conditions of bone marrow suppression. First, the effects of native MA and pMA and of the synthetic 15-mer $MA_{S1}$ were treated for their capacity to reduce or prevent the effects of lethal doses of gamma irradiation. Pre-experiments showed that 7Gy of total body radiation were 100% lethal within 5 days with bone marrow hypoplasia causing a rapid decline in PBMCs. MA, pMA, $MA_{S1}$, and various control polypeptides were given 48 and 24 hrs before, during, or 24 hrs after radiation. The animals treated prior to radiation received either 100 ng vs. 1 ug (rats) or 50 ng vs. 500 ng (mice) as 2 subcutaneous injections. Control animals were untreated or treated with pure hCG (CR127), rβ-hCG, native glycosylated β-core, or β-AA 21-52. Like the untreated animals, rats (FIG. 10, Panel A) and mice treated 24 and 48 hrs prior to radiation with hCG or with control polypeptides all died before day 5. However, 100% of the pretreated animals survived at least 25 days. Those treated with the higher dose of native MA survived longest. A typical result is shown in FIG. 10, Panel A. Survival varied from 60-95% at day 15.

Similar experiments were carried out in mice and rats treated at the time of radiation with therapy maintained for 4 weeks by systemic treatment 3×/week with either 100, 500, or 100 ng. All animals treated at the higher dose of MA and pMA (about 150 pmoles) or $MA_{S1}$ (300 pmoles) survived, and 100% of these animals continue to thrive (now over 100 days) (FIG. 10, right panel). Extraordinary promotion of survival was also seen at the lowest doses of MA (30 pmoles) and $MA_{S1}$ (about 50 pmoles) results in 80% survival. It is not yet possible to determine the precise molar dose of pMA because of less certainty on its full-length sequence. All control animals died within 5 days, including those treated with the closely related native glycosylated β-core (400 pmoles).

To ascertain that the MA effect did promote hematopoiesis in these animals we examined the bone marrow for cellularity and colony formation and determined peripheral blood counts. The bone marrow of the radiated animals show severe hypocellularity and the capacity to form colonies is reduced to near zero. As illustrated in FIG. 10, Panel C, the blood of control non-irradiated rats had 5 to 6 K/ul total lymphocytes, $7-8 \times 10^6$ red blood cells/ul and a hemoglobin content of 14-15 g/dL. After radiation these were reduced to near zero (lymphocytes), about $3 \times 10^6$/ul (red cells), and 6 g/dL (hemoglobin) by day 5. MA treatment produced a rapid rise, presumably prior to the effect of the radiation on hematopoiesis, followed by a precipitous fall in these values but significantly less than in untreated animals. Importantly, within one week the fall in blood cells was followed by a hematopoietic recovery phase, and by days 20 to 30 the recovery was complete. Similarly, bone marrow blood cell progenitors returned to normal and histology showed marked increased in cellularity.

These results suggest that MA may be useful in protection against radiation injury and may allow higher doses of radiotherapy for cancer. Although the rescue of lethally irradiated animals is most likely mediated chiefly by the pro-hematopoietic effects of MA, the MA treated animals also showed little or no gastrointestinal distress. Thus, the effect of MA could be peculiar to radiation injury (radioprotective) rather than a broad effect on growth promotion of primitive progenitor cells that might extend even to the gastrointestinal tract. Therefore, we sought an in vivo pro-hematopoietic effect in a different experimental setting. We chose a chemotherapy-induced bone marrow suppression model because the information obtained might also be clinically useful in that if MA protected against these side effects, MA might reduce and even prevent side effects of chemotherapy and as in the case of chemotherapy, it might allow uses of higher doses in order to reach optimum cancer killing by the chemotherapeutic agent. Additionally, MA itself is anti-tumorigenic as shown.

9.4.3 MA Protects Against the Side Effects of Chemotherapy

We selected taxol as the chemotherapeutic agent because it is one of the most effective and widely used anti-tumor agents and because at high doses it can have serious toxic effects on bone marrow. Sprague-Dawley rats were given taxol in large lethal doses, 4.5 mg in one I.P. inoculation. This amount lead to bone marrow cytotoxicity, resultant blood cell deficiencies, and death of the rats in less than 5 days. Bone marrow suppression can also be a side effect of the clinical use of taxol.[179] As in the radiation experiments, either MA, pMA, $MA_{S1}$, or various polypeptide controls were given subcutaneously only in two doses 24 and 48 hrs before taxol treatment or were given 3 times/week for 4 weeks. A representative experiment (FIG. 11, upper panels) shows the rescue of the rats from the ultimate lethal effects of the high dose taxol. Sixty-percent (low dose) or 80-90% (higher dose) of pretreated animals survived when given MA, $MA_{S1}$, or pMA. In animals in which therapy was maintained 28 days with low (100 ng) or high (1000 ng) doses of MA, $MA_{S1}$, or pMA, there was 100% survival on day 5 reducing to about 60% (low dose) and 80% (high dose) maintained at this level with the animals appearing healthy now at day 80, similar to the radiation experiments. Again, no effect was obtained with pure hCG, rβ-hCG, native glycosylated β-core, control peptides, or LH even at high doses, e.g., 5000 ng of native glycosylated β-core. Like untreated animals, these rats were all dead before day 5.

Taxol treated rats showed a 70% to greater than 90% reduction of their peripheral blood counts (lower panels). Total lymphocytes (A), platelets (B), hemoglobin (C), and red cells (D) within a few days of receiving the one inoculation of the high dose MA or $MA_{S1}$ show striking rise in number (blood counts were not performed on the pMA-treated animals). The animals pretreated 2 days with MA or $MA_{S1}$ but not maintained longer rebounded by day 15 with platelets, RBC, and hemoglobin returning to normal and above by day 20. Total lymphocytes remain low somewhat longer. These animals treated with MA or $MA_{S1}$ after taxol but maintained on therapy (3 weekly inoculations) recovered more rapidly, including total lymphocytes, which also returned to normal levels by day 20. The radiation and taxol experiments involved responses to MA after a highly traumatic incident. We wished next to study its effects in a more physiological setting.

9.4.4 MA Peptides Rescue Acutely Bled Rats

To delineate the effects of MA on hematopoiesis in the absence of any external bone marrow suppression, blood (35-40% of total blood volume) was removed from five Sprague-Dawley rats by intracardiac puncture. FIG. 12, Panels A-D shows the recovery in rats untreated vs. those given i.p. MA or $MA_{S1}$ 24 and 48 hrs after the blood loss (each point represents a mean of 10 animals). MA and $MA_{S1}$ treated animals show a prompt recovery of all peripheral blood cells. FIG. 12, Panels E-G shows blood counts in three monkeys. Each panel illustrates the mean values for the three animals treated with $MA_{S1}$. Thus, MA and related derivatives have potent pro-hematopoietic effects.

9.5 Inactivity of β-Core

For several reasons it was important to unambiguously eliminate the native glycosylated hCG β-core as a significant contributor to the multiple effects described here for MA. First, because of the relatedness of MA to a major part of the C-terminal polypeptide of the native glycosylated β-core there was a possibility of copurification. Second, because one report claims an in vitro inhibitory effect of native glycosylated β-core on KS tumor cells, though these effects were limited to cell culture studies, and oddly the inhibitory effect on tumor cells was reported to be specific for KS.[180] Third, because of the interesting speculation that since the native glycosylated β-core of hCG is present in relative abundance in urine and its N-polypeptide (β6-42) has some homology to PDGF it may have biological function independent of hCG.[181] In other words, there has been a search for some function of this relatively abundant peptide, and good reasons to suspect it might have been the factor accounting for these activities.

However, we have demonstrated that:
homogenously purified native glycosylated β-core had none of the biological activities ascribed here to MA;
that MA was separated from β-core during purification;
native glycosylated β-core is found in relative abundance in urine but only in very low amounts in sera of early pregnancy,[182] whereas MA is demonstrable in both by bioassays, serological tests, and purification;
the hCG β-core is not present in rodents, whereas biological and serological activities of MA were found in mice and rats;
antibodies made against purified MA did not bind pure native glycosylated β-core but did bind MA and neutralized MA biological activities both from purified and cruder preparations derived from serum and urine of pregnant women as well as from some commercial hCG preparations;
three monoclonal antibodies to native glycosylated β-core did not react with MA nor inhibit these biological activities;
the PDGF related sequences contained in the native glycosylated β-core AA 6-42 N-terminal polypeptide are not part of MA, and despite the interesting homology to PDGF, peptide 6-42 had none of the activities described here; and
most important, there was no evidence of the complete native glycosylated β-core in either pMA or MA by AA sequencing and by mass spectroscopy.

9.6 Summary of Active and Inactive Peptides

Table 2 summarizes active and inactive peptides according to the work presented herein:

| Active Petides | Non-Active Peptides |
| --- | --- |
| Native MA Sequence AA 55-89 from β-hCG: MA: 1 ---------------------------------------------- VVCNYRDVRFESIRLPGCPRGVNPVVSYA VALSCQ -----------35 (SEQ ID NO:2) | β-core: Full length native glycosylated-AA 6-40 & 55-92<br>MA $_{S6}$: AAPGCPAA (SEQ ID NO: 32) |
| $MA_{S1}$[MA synthetic peptide: AA 8-22]: VRFESIRLPGCPRGV (SEQ ID NO: 4) | MA $_{S7}$: PILP (SEQ ID NO: 33) |
| $MA_{S2}$[MA synthetic peptide: AA 4-33]: NYRDVRFESIRLPGCPRGVNPVVSYAVALS (SEQ ID NO: 5) | MA $_{S8}$: LPGCRR (SEQ ID NO: 34) |
| $MA_{23}$[MA synthetic peptide: AA 1-35]: VVCNYRDVRFESIRLPGCPRGVNPVVSYA VALSCQ (SEQ ID NO: 6) | MA $_{S12}$: PGCP (SEQ ID NO: 35) |
| $MA_{S5}$[MA synthetic peptide: AA 14-20]: RLPGCPR (SEQ ID NO: 7) | MA $_{S13}$: PALP (SEQ ID NO: 36) |
| $MA_{S9}$: APGCPG (SEQ ID NO: 8) | MA $_{S14}$: APGCPA (SEQ ID NO: 37) |
| $MA_{S10}$: LPGCPR (SEQ ID NO: 9) | MA $_{S15}$: AAGCAPR (SEQ ID NO: 38) |
| $MA_{S11}$: LPGCPQ (SEQ ID NO: 10) | MA $_{S16}$: ALGCLR (SEQ ID NO: 39) |
| $SAT_{42}$: CLQGVLPALPQVVC (SEQ ID NO: 20) | MA $_{S17}$: LPAAPR (SEQ ID NO: 40) |
| $SAT_{43}$: CLQGRLPALPRVVC (SEQ ID NO: 21) | MA $_{S18}$: LPRRPR (SEQ ID NO: 41) |
| $SAT_{44}$: CRLPGLPRC (SEQ ID NO: 22) | MA $_{S19}$: LPPPPR (SEQ ID NO: 42) |
| | MA $_{S20}$: CPAAPC (SEQ ID NO: 43) |

-continued

| Active Petides | Non-Active Peptides |
|---|---|
| | MA$_{S21}$: NPGCPR (SEQ ID NO: 44) |
| | β-hCG AA 1-20, AA 21-52, AA 6-16, AA 88-92, AA 8-34, AA 93-100, AA 74-95, AA 34-49, AA 125-145, AA 100-110, AA 93-100, AA 134-144, AA 100-112, AA 6-21 and AA 6-28 |
| | Scram 1: QCSLAVAYSVVPNVGRPCGPL-RISEFRVDRYNCVV (SEQ ID NO: 45) |
| | Scram 2: SYAVALQRGVNPVVCAANYRD-VRFESIRL (SEQ ID NO: 46) |

9.7 Toxicity Studies

In the concentration ranges and over the time periods reported here we observed no cytopathogenicity of MA on normal cells in vitro. These cells included human, primate, and rodent bone marrow, PBMCs, and human CD4+ T-cells, CD8+ T-cells, CD34+ cells, and macrophages enriched from normal PBMCs, as well as normal human endothelial cells and fibroblasts. Cytotoxicity was assessed by 3H-thymidine incorporation, trypan blue staining, cell numbers, and morphological examination by light and confocal microscopy. Hematopoiesis was not only unimpaired it was promoted. Consequently, we studied the effects of higher concentrations (up to 10× the effective concentrations) of MA and found no evident cytotoxicity. Similarly, we observed no evident toxic side effects in animal studies grossly or by blood counts. These studies were chiefly performed with rats and mice, but also included rhesus macaques treated with 0.2 mg/kg for several months. Like the in vitro results, hematopoiesis was not impaired but instead enhanced.

9.8 Anti-MA Antibodies

Polyclonal and monoclonal antibodies to MA were raised according to the methods of Harlow et al.[183] and de St Groth et al.,[184] respectively. Antigens were synthetic peptides 58-87 and 68-74×2 coupled to keyhole limpet hemocyanin (KLH).[185]

58-87: NH$_2$-NYRDVRFESIRLPGCPRGVNPV-VSYAVALSC-COOH (SEQ ID NO: 47)

68-74 (2×): NH$_2$-RLPGCPRRLPGCPRC-COOH (SEQ ID NO: 48)

Antibodies to other MA peptides and other therapeutic polypeptides of the invention may be prepared using the same method. For example, the following antigens may be prepared by the same method 77-88: NH$_2$-NPVVSYAVALSC-COOH (SEQ ID NO: 49)

62-81: NH$_2$-VRFESIRLPGCPRGVNPVVS-COOH (SEQ ID NO: 50)

9.9 Characterization of Monoclonal Antibodies Raised Against MA Peptides

Antigens listed are synthetic except for 55-92 (derived from beta-core), β-core (hCG β-core isolated from pregnant female urine), BSA (bovine serum albumin), PP2 (native pMA), Preg (crude MA-enriched fraction from pregnant female urine). NT=not tested.

Antibody Characterization

| | | | | | Antigen | | | | | | | | | | |
|---|---|---|---|---|---|---|---|---|---|---|---|---|---|---|---|
| | | | | | ELISA (Antigen Coated on plate) | | | | | | | Western | | | |
| Antibody | Source | M/P | type | Tit/C | MA$_{s2}$ 1 | 5887 1 | 6281 2 | 68742 5 | 55-92 0.2 | β Core 0.5 | BSA 20 mg | PP2 | MA$_{s2}$ 2 | PP2 2.67 | Preg 6.4 | β Core 2 |
| 5887-1E7 | IHV | m-B/c | G1/2b | 1 mg | − | − | − | − | − | − | − | NT | +/− | + | + | + |
| 5887-2D12 | IHV | m-B/c | G1/k | 1.5 mg | − | − | − | − | − | − | − | NT | NT | NT | NT | NT |
| 5887-13G6 | IHV | m-B/c | G1/k | 570 ug | +/− | + | + | − | − | +/− | − | − | + | + | + | + |
| 5887-15E7 | IHV | m-B/c | G3/k | 400 ug | − | − | − | − | − | − | − | NT | NT | NT | NT | NT |
| 5887-18G5 | IHV | m-B/c | G1/k | 860 ug | − | − | − | − | − | − | − | NT | NT | NT | NT | NT |
| 5887-1B2 | IHV | m-BD | G1/k | 500 ug | ++ | ++ | − | − | + | + | − | ++ | + | + | + | + |
| 5887-1H3 | IHV | m-BD | G2b/I | 1.5 mg | ++ | ++ | − | − | + | − | − | NT | NT | NT | NT | NT |
| 5887-2D11 | IHV | m-BD | G1/k | 840 ug | + | + | + | − | − | − | − | + | + | + | + | + |
| 5887-3F3 | IHV | m-BD | G2b/k | 800 ug | + | + | + | − | − | − | − | +/− | + | + | + | + |
| 5887-10F12 | IHV | m-BD | G1/k | 600 ug | + | + | + | − | − | − | − | +/− | + | +/− | + | + |
| 5887-13A4 | IHV | m-BD | G1/k | 600 ug | +/− | + | + | − | − | − | − | ++ | + | + | + | + |
| 68742-18C9 | IHV | m-B/c | G1/k | 800 ug | − | − | − | − | − | − | − | NT | − | +/− | + | + |

Conc used (ELISA = ug/ml, Western = ug/lane)

9.10 Immunopurification Using Antibodies

The inventors have successfully employed the antibodies of the invention in the immunopurification of MA peptides from biological fluids and for qualitative detection of MA peptides.

FIG. 13 shows silver stained 4-12% Bis-Tris NuPage SDS-PAGE gel (Invitrogen/Novex) of column fractions derived from non-pregnant female urine plus/minus a spike with MA$_{s2}$ (100 ug/L). An MA$_{s2}$-sized band is only seen in the plus spike acid peak lane (4$^{th}$ from right) and MA$_{s2}$ control (lane 6). Gel is displayed upside down so low Mr material is at top. Lanes R to L as displayed: (1) Novex Mark 12 Mr; (2) Urine+ MAs2 column FT; (3) Pk-1 (shoulder); (4) Pk-2 (acid peak), (5) Pk-3 (salt peak), (6) MA$_{s2}$ standard; (7) Urine-MA$_{s2}$; (8) Pk-1 (acid peak); (9) Pk-2 (salt peak); (10) Novex Mark 12 Mr.

FIG. 14 shows Western blot of SDS-PAGE showing MA-reactive species only in acid peak (lane 4) and MA$_{s2}$ control (lane 6). Antibody used was a 1:500 dilution from a mix (1:1 ratio) of sera from 2 rabbits both immunized with the 5887-KLH antigen. Rabbits used were identified as AP-2032 and IHV-5887. Rabbit antibodies were visualized with KPL Goat-anti-Rabbit-AP (1:1000) and BCIP/NBT. Gel was loaded exactly as on previous page but is displayed right side up. Lanes L to R as displayed: 1, Novex Mark 12 Mr, 2, Urine+MAs2 column FT, 3, Pk-1 (shoulder), 4, Pk-2 (acid peak), 5, Pk-3 (salt peak), 6, MAs2 std, 7, Urine-MAs2, 8, Pk-1 (acid peak), 9, Pk-2 (salt peak), 10, Novex Mark 12 Mr.

9.11 Use of Anti-MA Monoclonal Antibodies to Neutralize the Anti-HIV-I Effect of the MA Peptide In Vitro Anti-MA antibodies, or control (anti-MDC) antibodies were added to an HIV-I infection assay to determine if they could inhibit the anti-viral activity of the MA peptide. As shown in lane 2 of FIG. 15 anti-MA antibodies remove the anti-viral effect of MA$_{s2}$, resulting in elevated HIV-I p24 production. In comparison, addition of a control antibody (lane 1) shows no effect and results in continued full-inhibition of HIV-I p24 production as seen in the MAs2 treated lane (3).

9.12 Bacterial Production of MA Peptides

A bacterial-optimized DNA sequence encoding the MA$_{S2}$ sequence was designed with 5' NcoI and 3' SapI restriction sites and methionine on the N-terminal end. Complementary oligonucleotides were constructed and a synthetic gene assembled in vector pTYB3 (New England Bioloabs). N-terminal fused MA$_{s2}$ sequence was DNA sequenced to confirm the sequence and integrity of the intein fusion C-terminal to the MA sequences. Test expressions revealed band of size desired by SDS-PAGE (silver stain) and Western. Expression and cleavage of material, using NEB supplied protocol (only changes were addition of 40 ug/ml pMSF, 5 mM MgCl$_2$ and 40 ug/ml DnaseI to lysis buffer), produced a band of correct size (Silver stain of SDS-PAGE) and immunological reactivity (Western vs pc-Ab)-data not shown.

Bacterial optimized MA sequence:
5'-CATGAAATACCGTGATGT-
GCGTTTTGAAAGCATTCGTCTGCCGGGT-
TGTCCGCGCGGTGTG-AATCCGGTTGTGAGC-
TACGCGGTTGCGCTGAGCTGC-3' (SEQ ID NO: 51)

The utilization of the intein cleavage system results in production of a pure species without addition of external proteases or detergents that could affect determinations of biological activity if not 100% removed.

Optimized gene can be expressed as existing N-terminal fusion or as a C-terminal fusion. CNBr can be used to cleave the added N-terminal Met resulting in release of previously defined MA$_{S2}$ sequence.

This gene construct has been used here in a single expression system (Impact T7, New England Biolabs) but has been designed so that it can readily be moved into other systems. For example, a suitable system could involve the use of a C-teminal fusion protein to increase production levels (e.g., through depoting in inclusion bodies or use of a stronger promoter) while minimizing internal methionines. Fusion protein purified from such as system could then be treated with CNBr to release the MA$_{s2}$ peptide without the currently present Met.

FIG. 16, Panel A shows a Coomassie stained gel and Panel B shows a Western blot of test expressions showing α-MA reactive material of the expected size (58 kDa). Lanes: 1, vector cntl (516.1), 2-6 induced lysates 517.1-517.5, 7, Novex Mk12 Mr, 8, Pregnin, 9, MA$_{S2}$ cntl, 10-11 buffer cntl, 12, Novex Mk12 Mr.

FIG. 17a shows silver stained SDS-PAGE and FIG. 17b a Western blot showing column purification of clone 517.3 expressed Bact:MA$_{s2}$ and immunoreactivity with α-MA antibodies. SDS-PAGE lanes: 1, Novex Mk12 Mr, 2, uninduced, 3, induced pre column, 4, column FT, 5-10 column eluate fractions 1-6 (2 ml ea), 11, MAs2 control, 12, Novex Mk12 Mr. Western lanes: 1, Novex Mk12 Mr, 2, uninduced, 3, induced lysate, 4, column FT, 5-11 column fractions 2-8 (2 ml ea), 12, MAs2 control.

9.13 Extensive Proliferation Ex Vivo, Long Term Cultures [LTC-IC] and Self Renewal of Human Primitive Hematopoietic Stem Cells from Cord Blood/Bone Marrow or Peripheral Blood in the Presence of MA Polypeptides Hematopoietic tissues contain a small population of primitive, stem cells capable of self-renewal and generating committed progenitors of the different myeloid and lymphoid compartments. In semisolid assays, hematopoietic progenitors in the presence of specific growth factors proliferate and differentiate to produce mature cells. In this system, depending on the combination of growth factors, different classes of multipotent committed progenitors CFU-GM, FRU-e, CFR-GEMM, T-CFC and CFU-Mk with high differentiation but negligible self-renewal capacity are used. Early progenitor/stem cells may also be used.

In the human system, a long-term culture-initiating assay (LTC-IC) can be used to detect cells that can generate myeloid clonogenic cells (CFC/colony forming cells) in long-term cultures for a minimum of 5 weeks. Bone marrow stromal was produced by culturing 107 fresh BM-MNC in a T25 flash for at least 2 weeks in 5 mL stromal medium; 12.5% horse [HS] and 12.5% fetal calf serum [FCS]; both from hyclone [Logan, Utah], Iscove's modified Dulbecco's medium [IMDM, GIBCO-BRL], 2-mercaptoethanol [Sigma, st. Louis, Mo.], $10^{-6}$ mol/L hydrocortisone [Sigma] and penicillin/streptomycine.

One or 2 days before co-cultures, bone marrow stroma was irradiated with 15Gy and plated at $7 \times 10^3/cm^2$ in 24-well plates to form pre-established stromal layers for the long-term cultures. Limiting dilution was 1 to 1000 CD34+ bone marrow/cord blood cells and equivalent aliquots, i.e., limiting dilutions of the cells grown in long-term cultures stroma-free cultures after 2 to 20 weeks were seeded on top of the irradiated bone marrow stroma in culture medium containing IMDM, 12.5% HS, 12.5% FCS, 2-mercaptoethanol, and $10^{-6}$ mon-hydrocortisone for 5 weeks LTC-IC assay period. Non-adherent cells were removed from the cultures, combined with the corresponding trypsinized adherent cells, washed and assayed for colony forming units (CFU-Cs) in methyl-cellulose medium containing 1.3% methylcellulose (Fluka Chemilka Biochemika, buck\hs, Switzerland), 30% FCS, EPO (3 U/ml), IL-3 (20 ng/ml), G-CSF (20 ng/ml), GM-CSF (20 ng/ml) and KL (c-kit, 50 ng/ml). These cultures were incubated at 37° C. and colonies were scored 2 to 3 weeks later. LTC-IC enumeration was based on the number of CFU-C scored in the limiting assays [LDA] and another technique.

Stroma-free long-term cultures were performed as follows. 2 to 10×10³ CD34+/CD34⁻CD38⁻ from bone marrow/CB/PBMC cells were cultured in quadrutriplicate flat bottomed 24 well plates in 1 ml to of IMDM supplemented with 10% FCS and the following cytokines: IL-3 (10 ng/ml), IL-6 (10 ng/ml), KL [c-kit 50 ng/ml, FL (50 ng/ml) and TPO (10 U/ml), which added, alone or in combination of two or more factors, to each series of microwells twice a week. The wells were grown at 37° C. and share a number of features with in vivo murine long-term repopulating cells. These include assay for cobblestone areas colony forming cells (CAFC), high proliferative potentials colony-forming cells (HPP-CFC), CFU-GEMM, CFU-Bl (blast colony forming units). Results were as shown in Table 2 (LTC-IC or stroma-free culture after 3 mos):

| CD34+,CD38−cells from human BMMC | CFU-Mixed | CFU-GM | BFU-e | T-CFC |
|---|---|---|---|---|
| 1. Control LTC without stroma; untreated (n = 3) | 4 ± 2 | 64 ± 6 | 50 ± 7 | 64 ± 8 |
| 2. LTC-IC untreated (n = 3) | 2 ± 1 | 28 ± 5 | 15 ± 6 | 19 ± 23 |
| 3. LTC stroma free; treated with MA (n = 3) | 13 ± 3 | 198 ± 11 | 161 ± 8 | 199 ± 10 |

Additional results were as follows for 1, 2, and 3 (respectively) as identified in the above table:
CD34+ cells: 52, 42, and 77.71%
CFU-GM: 25, 15, and 27% of CD14; and 14, 12 and 22% of CD68
Rx $MA_{S1}$: 35% of CD1 and 27% of CD68
Rx MA: 30, 17 and 38% of CD14; and 21, 14 and 29% of CD68
T colonies Rx MA
  CD3+/CD4+: 38, 28 and 46%
  CD3+/CD8+: 32, 29 and 49%

These results demonstrate that the therapeutic polypeptides of the invention are usefully applied with chemokines known to cause differentiation of stem cells, in order to facilitate improved yields of differentiated cells.

9.14 MA Peptides Improve Engraftment of Ex Vivo Expanded Hematopoietic Progenitor Cells The inventors also investigated the effect of MA on engraftment of human bone marrow stem cells [CD34+, CD38⁻ cells, long term cultures after 4 mos, and stromal free cultures] ex vivo expanded hematopoietic progenitor cells in Rats irradiated [Sprague DAwley, 450 Rad] and immunodeficient mice [SCID or BNX-XID mice].

Measurement of short-term hematopoietic reconstitution kinetics and long term repopulating ability. Just prior to implantation, SCID, BNX-XID-immunodeficient mice and Sprague Dawley rats were exposed to 450 rad total body γ-irradiation. The aim was to determine whether human B, T, and myeloid cells will be detected in the blood circulating after 10⁶ of human bone marrow long term culture: CD34+, CD38⁻ (HBMLTC-CD34+/APL: 68% are CD34+, CD38⁻ cells but HBMLTC-CD34+/MA were implanted into the irradiated rats and mice's spleen. One month after implantation, virtually all of the circulating cells in the peripheral blood of rats or mice were human cells. In contrast, the control immunodeficient mice [BNX-XID or SCID mice] or rats irradiated and implanted with fresh untreated human CD34+ cells did not produce human CD4+ T-cells: 0%, CD14+ cells: 0% and CD34+ cells: 0% (N=3). But the SCID and BNX-XID immunodeficient mice were repopulated by the cultured, treated human cells.

The following table illustrates the effect on engraftment of ex vivo expanded hematopoietic progenitor cells:

| CD34+, CD38+ cells from human BMMC | | Rat S. Dawley [irradiated 450 RAD (n = 3)] | SCID Mice | BNX-XID Mice |
|---|---|---|---|---|
| 1. LTC without stroma treated with APL 300 IU (n = 3) | CD4 | 2% | 0% | 1% |
| | CD14 | 3% | 5% | 2% |
| | CD34 | 48% | 40% | 39% |
| 1. LTC stroma-free treated with MA 500 ng/ml (n = 3) | CD4 | 1% | 2% | 3% |
| | CD14 | 1% | 2% | 1% |
| | CD34 | 40% | 38% | 37% |

9.15 Discussion

Although rodents do not produce an exact homologue of CG, it is likely that the active factor in sera of mice is derived from a sequence similar to the MA peptides, since similar biological activities were found in sera of mice and rats selectively during early pregnancy. Partial purification showed that this murine factor followed patterns similar to human MA. Moreover, specific antibody to human MA bound to a factor from mouse and rat sera and urine from early pregnancy but not proteins of non-pregnant female rodents or male rodents.

The fact that murine β-LH contains sequences 60% homologous to MA, including some common structural motifs, is consistent with a conclusion that murine MA is derived from their β-LH.

MA is a small cationic polypeptide which contains cysteine residues at positions 3, 18 and 34 that could give rise to intra-peptide disulfide bridges favoring its stabilization. As a component of β-hCG the MA sequence is a major portion of the third β-hairpin loop.[188] However, the free form is not likely to retain secondary structure, and various truncated forms with elimination of CYS-3 are as active as the full length form. MA contains a polyproline II (PPII) sequence RL-PGCP-R (SEQ ID NO: 7) which is related to a repeated $PX_2P$ motif present in five places in β-hCG[189] and is found in LH, and as described by Lapthorn et al.,[190] comprises the β-hairpin structure in β-hCG flanked by β-strands. The sequence fits the motif of 7-8 AAN SH3 binding PPII helix sequences found in adapter molecules involved in amplification of tyrosine protein kinase signaling pathways. Adjacent to the MA polyproline II sequence, the N-terminal side is a PKC phosphylation site, SIR. The polyproline II motif and phosphorylation sites may provide the most important clues on the mechanisms of which MA exerts its effects. In view of its pro-hematopoietic effects on normal blood cell precursors, the possibilities of interactions with the SH3 sequences of Grb2 and Vav merit noting, since Vav-Grb2 interactions are known to be involved in embryonic development of the hematopoietic system,[191] and Vav is expressed only in hematopoietic cells.[192] Similarly, major hematopoietic effects, such as marked enhancement of the capacity of erythropoietin and Il-I to induce activation of signal pathways, are mediated by Crk L by a Ras-dependent mechanism.[193] Crk L is also an SH3 containing adapter protein which could be affected by MA.

In view of MA's pro-apoptotic activity, the Ras-GAP interaction is another possible target, since very recently Leblanc et al. have reported that inhibition of their linkage in vitro with antibodies directed against —SH3 promotes tumor cell apoptosis.[194] An HIV gene product, Nef, contains three related SH3 sequences. Its natural SH3 target was recently identified by Renkema et al.[195] as a p21 activated kinase 2 (PAK2). Since Nef promotes HIV replication, it is possible that the anti-HIY effects of MA are mediated through interference with Nef-PAK2 interactions. Moreover, since PAK2 is activated by pro-apoptotic caspases, it is possible that MA apoptotic and pro-hematopoietic effects also involves interactions with SH3 of PAK2 or related kinases. Finally, the 7-mer RLPGCPR (SEQ ID NO: 7) sequence of MA is identical to the PPII sequence of inhibitors of the serine proteinases, the acrosyn trypsin inhibitor precursor, also by interactions with SH3 regions.[196] Inhibition of regulatory proteinases could, of course, have major influences on cell growth and differentiation.

Our results are consistent with the interpretation that MA is a natural product rather than an hCG degradation form occurring during laboratory purification, e.g.:
   consistency in the isolation of very closely related polypeptides with the bioactivities by different methods;
   consistency of finding the multiple biological activities in the crudest preparations from urine and sera; and
   immunoassays which distinguish MA from β-core, hCG, α- and β-hCG, yet showing reactivity with some crude hCG preparations and urinary concentrates, which contain all the activities described here, and these materials are only minimally handled in the laboratory virtually precluding their genesis from laboratory manipulations.

Though the evidence suggests that MA is naturally occurring, as opposed to a laboratory-derived degradation product, the questions of its tissue of origin and mechanism by which it is generated are not answered. Since several human tumors and cell lines produce hCG and/or its subunits[197] and even β-core in the absence of the hCG or its subunits,[198] it is possible that MA is produced by any number of tissues. However, it is far more likely that MA is made by the trophoblast, since its production is limited to early pregnancy and the trophoblast is the source of hCG and both α- and β-chains.[199] However, some other tissues have been found to produce hCG and β-hCG at low levels and even different forms of β-core with no known function.

Several purifications of MA have generally led to the 35-mer (β-hCG 55-89) sequence with a molecular mass of 3,864. However, in some instances MA peptides have been as small as 30-mer, as illustrated by the mass spectroscopy shown in FIG. 21, corresponding to β-hCG 55-84. The pMA sequence contains the full length C-terminal polypeptide (β-hCG 55-92) of (β-core. This 38-mer terminates at a known peptide cleavage size and is routinely generated in the formation of the β-core. Thus pMA could be a precursor of MA. The most obvious pathway is hCG→β-hCG→β-core→pMA→MA or more immediately from β-hCG, since the free subunit is also independently produced by the trophoblast[200] and by some human tumors.[201] There is evidence that β-core can be produced in the absence of β-hCG,[202] which may suggest that β-core can arise from novel mRNAs, and alternate splicing has been described from some β-hCG RNAs.[203] Thus, it is possible that MA could arise directly from β-core or even from its own alternate spliced transcript. Since MA inhibits growth of tumor cells, the observations that some human tumors produce β-hCG and even β-core and show no growth inhibition also favor the interpretation of a more direct origin of MA. It is of interest in this regard that among the several related glycoprotein hormones and growth factors only the β-chain of hCG is polygenic. Six β-hCG genes or related sequences have been described which cluster on chromosome 19,[204] and some are known to produce novel transcripts by alternative splicing.[205] "Improperly" folded β-hCG products are known to be secreted.[206] MA could be one such polypeptide.

MA does not bind the hCG receptor. Saturation of cells with pure hCG did not affect the biological activity of MA added later to these cells. In this regard, unusual β-hCG gene transcripts have been known for several years,[207] and as noted above, among the several related heterodimeric glycoprotein hormones, only β-hCG has multiple genes. In addition, the β-hCG subunit is produced during early pregnancy.[208] These findings suggest a role for one or more of these genes independent of hCG function.

Although neither β-hCG or any of its degradation products significantly bind to the hCG receptor,[209] several alternative spliced transcripts for the receptor are known which are developmentally timed,[210] making it feasible that one or more of these transcripts may encode receptors specific for certain β-hCG fragments. MA may be derived in this manner and may utilize one of these receptors.

MA may have important physiological functions in the developing embryo. This view is supported by that finding MA activities are selectively expressed in an early embryonic period in both rodents and humans. One function could be selective cell killing, for instance in the known early selective killing of syncytiotrophoblasts with concomitant cytotrophoblast proliferation[211] or in the subsequent molding of tissues, while concomitantly promoting the development of blood forming cells in the embryo. The finding that MA and smaller synthetic forms have major biological effects in vivo, coupled with several structural features such as its β-hairpin structure, are reminiscent of the in vitro hormone mimicry effects of created small peptides with β-hairpin structure recently described by Wrighton et al and Linah et al.[212] These groups made peptide libraries and screened them for binding to known receptors such as the erythropoietin (EPO) receptor, and surprisingly found very small peptides not homologous to EPO, which had remarkable activities. On the other hand, we do not know whether there is an MA receptor, and MA does not mimic the effects of hCG, its parentally related hormone.

It is also possible that MA can enter cells in the absence of specific receptors and directly mediate intracellular signaling by SH3 interactions and/or protease inhibition as described above. Alternatively MA could exert a direct effect on cell membranes affecting channeling. In this context it is intriguing to view MA as a possible component of the natural or innate defense mechanisms helping to compensate for the reduction in the mother's adaptive immune system in order to prevent fetal rejection. MA is a proline-containing, small polypeptide with cysteine residues and β-hairpin-β-strand configurations and can kill some cells and inhibit an enveloped virus (HIV). These structural and functional features are reminiscent of some selectively mammalian defensins,[213] which may have anti-microbial activity, kill cells, or both by disrupting cell membranes. The N-terminal region of MA also has perforin-related sequences, a molecule which, though not homologous to defensins can similarly lead to membrane disruption and cell death.[214]

REFERENCES

Various patent and non-patent references have been cited throughout the text. The entire disclosure of each of these references, specifically including, but not limited to the following references, is incorporated herein by reference.

[1] Lunardi-Iskandar, et al., 1994, *Nature,* 375:64-68.
[2] Gallo et al., 1996, *N. Engl. J. Med.,* 335(17):1261-9.
[3] Gallo et al., 1998, *J. Human Vir.,* 1(4):185-186.
[4] See U.S. Pat. No. 5,968,513 and application Ser. Nos. 08/709,925, 08/709,948, 09/220,415.
[5] Bourinbaiar, A. S., and Nagomy, R., 1992, *FEMS Microbiology Letters* 96:27-30.
[6] Bourinbaiar, A. S., and Nagomy, R., 1992, *FEBS Letters* 309:82-84.
[7] U.S. Pat. No. 4,880,626.
[8] 1995, *The Lancet* 346:118-119.
[9] Bourinbaiar, A. S., and Lee-Huang, S., 1995, *Immunology Letters* 44:13-17.
[10] 1995, *Nature* 375:64-68 and PCT Publication No. WO96/04008.
[11] See WO 97/49721 (Methods of Treatment of Wasting Syndrome Based on Administration of Derivatives of Human Chorionic Gonadotropin); WO 97/49432 (Treatment and Prevention of Cancer by Administration of Derivatives of Human Chorionic Gonadotropin); WO 97/49418 Methods of Promoting Hematopoiesis Using Derivatives of Human Chorionic Gonadotropin); and WO 97/49373 (Treatment and Prevention of HIV Infection by Administration of Derivatives of Human Chorionic Gonadotropin).
[12] Y. Lunardi-Iskandar et al, *Nature Medecine* 4, 428 (1998)
[13] S. A. Griffiths, T. A. Bramley, G. S. Menzies, and D. J. Adams, *Molec. Cell Endocrinol.* 134, 69 (1997).
[14] S. Lee-Huang et al, *PNAS* 96, 2678 (1999).
[15] A. Albini et al, *AIDS* 11, 713 (1997).
[16] S. Lee-Huang et al, *PNAS* 96, 2678 (1999).
[17] A. S. Bourenbaiar and R. Nagomy, *FEBS Lett.* 309, 82 (1992).
[18] Z. Kachra et al., *Endocrinol.* 138, 4038, 1997.
[19] S. Lee-Huang et al, *PNAS* 96, 2678 (1999).
[20] Y. Lunardi-Iskandar et al, *Nature Medecine* 4, 428 (1998)
[21] Z. Kachra et al., *Endocrinol.* 138, 4038, 1997.
[22] Teich, N., et al., 1984, RNA Tumor Viruses, Weiss, R., et al., eds., CSH-Press, pp. 949-956.
[23] Barre-Sinoussi, F., et al., 1983, *Science* 220:868-870; Gallo, R., et al., 1984, *Science* 224:500-503.
[24] Barre-Sinoussi, F., et al., 1983, *Science* 220:868-870; Gallo, R., et al., 1984, *Science* 224:500-503.
[25] Clavel, F., et al., 1986, *Science* 233:343-346; Guyader, M., et al., 1987, *Nature* 326:662-669.
[26] Hammarskjold, M., & Rekosh, D., 1989, *Biochem. Biophys. Acta* 989:269-280.
[27] Mitsuya, H., et al., 1991, *FASEB J.* 5:2369-2381.
[21] Mitsuya, H., et al., 1991, *Science* 249:1533-1544.
[29] Perelson, A. S., et al., 1996, *Science* 15:1582-1586.
[30] Smith, D. H., et al., 1987, *Science* 238:1704-1707.
[31] Daar, E., et al., 1990, *Proc. Natl. Acad. Sci. USA* 87:6574-6579.
[32] Schooley, R., et al., 1990, Ann. Int. Med. 112:247-253; Kahn, J. O., et al., 1990, Ann. Int. Med. 112:254-261; Yarchoan, R., et al., 1989, Proc. Vth Int. Conf. on AIDS, p. 564, MCP 137.
[33] Erickson, J., 1990, Science 249:527-533.
[34] Paul, W. E., 1994, Cell 82:177; Bolognesi, D. P., 1993, Semin. Immunol. 5:203.
[35] Cocchi, F, et al., 1995, Science 270:1811-1815.
[36] Barin et al., 1985, Science 228:1094-1096.
[37] See for example, Ivanoff, L., et al., U.S. Pat. No. 5,141,867; Saith, G., et al., WO92/22,654; Shafferman, A., WO91/09,872; Formoso, C., et al., WO90/07,119.
[38] For review, see Broxmeyer, H. E., 1983, "Colony Assays of Hematopoietic Progenitor Cells and Correlations to Clinical Situations," CRC Critical Reviews in Oncology/Hematology 1:227-257.
[39] Lajtha, L. G., 1979, Differentiation 14:23.
[40] Lajtha, L. G. (Rapporteur), 1979, Blood Cells 5:447.
[41] Lunardi-Iskandar, Y. et al., 1989, *J. Clin. Invest* 83:610-615; Louache, F. et al., 1992, *Blood* 180:2991-2999.
[42] Ballem, P. J. et al., 1992, *N. Engl. J. Med.* 327:1779.
[43] Berchtold, P. and Wenger, M., 1993, *Blood* 81:1246; Ballem, P. J. et al., 1987, *J. Clin. Invest.* 80:33.
[44] For a general discussion of hematological disorders and their causes, see, e.g., "Hematology" in Scientific American Medicine, E. Rubenstein and D. Federman, eds., Volume 2, chapter 5, Scientific American, New York (1996).
[45] See Pillow, R. P., et al., 1966, *N. Engl. J. Med.* 275:94-97; Thomas, E. D., et al., Feb. 5, 1972, *The Lancet,* pp. 284-289.
[46] Nothdurtt, W., et al., 1977, *Scand. J. Haematol.* 19:470-481; Sarpel, S. C., et al., 1979, *Exp. Hematol.* 7:113-120; Ragharachar, A., et al., 1983, *J. Cell. Biochem. Suppl.* 7A:78; Juttner, C. A., et al., 1985, *Brit. J. Haematol.* 61:739-745; Abrams, R. A., et al., 1983, *J. Cell. Biochem. Suppl.* 7A:53; Primmer, O., et al., 1985, *Exp. Hematol.* 13:891-898.
[47] Reiffers, J., et al., 1986, *Exp. Hematol.* 14:312-315; Goldman, J. M., et al., 1980, *Br. J. Haematol.* 45:223-231; Tilly, H., et al., Jul. 19, 1986, *The Lancet,* pp. 154-155; see also To, L. B. and Juttner, C. A., 1987, *Brit. J. Haematol.* 66: 285-288, and references cited therein.
[48] Korbling, M., et al., 1986, *Blood* 67:529-532.
[49] Hershko, C., et al., 1979, *The Lancet* 1:945-947; Ochs, H. D., et al., 1981, *Pediatr. Res.* 15:601.
[50] Weinroth et al., 1995, *Infectious Agents and Disease* 4:76-94; Kotler and Grunfeld, 1995, *AIDS Clin. Rev.* 96:229-275.
[51] Kotler et al., 1985, *Am J. Clin. Nutr.* 42:1255-1265; Cahill, 1970, *N. Engl. J. Med.* 282:668-675.
[52] Kotler at al., 1989, *Am. J. Clin. Nutr.* 50:444-447; Heymsfield et al., 1982, *Am. J. Clin. Nutr.* 36:680-690.
[53] Kotler and Grunfeld, 1995, *AIDS Clin. Rev.* 96:229-275; Weinroth et al., 1995, *Infectious Agents and Disease* 4:76-94.
[54] For review, see Robbins and Angell, 1976, *Basic Pathology,* 2d Ed., W.B. Saunders Co., Philadelphia, pp. 68-122.
[55] Lunardi-Iskandar, Y., et al., 1995, *Nature* 375:64-68; Friedman-Kien, A. E., et al., 1981, *J. Am. Acad. Dermatol.* 5:468-473.
[56] Nakamura, S., et al., 1988, *Science* 242:426-430; Ensoli, B., et al, 1989, *Science* 243:223-226; Salahuddin, S. Z., et al., 1988, *Science* 242:430-433; Masood, R., et al., 1994, *AIDS Res. Hum. Retroviruses* 10:969-976; Lunardi-Iskandar, Y., et al., 1995, *JNCI* 88:450-454.
[57] Lunardi-Iskandar, Y., et al., 1995, *JNCI* 87:974-981; Delli-Bovi, P., et al., 1986, *Cancer Res.* 46:6333-6338; Siegal, B., et al., 1990, *Cancer* 65:492-498; Yunis, J. J., 1983, *Science* 221:227-236; Popescu, N. C., et al., 1995, *JNCI* 88:450-454.
[58] Chak, L. Y., et al., 1988, *J. Clin. Oncol.* 6:863-7; Evans, L. M., et al., 1991, *J. Immunother.* 10:39-50; Kovas, J., et al., 1990, *Ann. Intern. Med.* 112:812-21; Gelmann, E. D., et al., 1987, *Am. J. Med.* 82:456-62; Gill, P. S., et al., 1991, *Am. J. Med.* 90:427-33; Gill, P. S., et al., 1990; *Am. J. Clin. Oncol.* 13:315-9; Gill, P. S., et al., 1994, *AIDS* 8:1695-9.
[59] Kovas, J., et al., 1990, *Ann. Intern. Med.* 112:812-21; Gill, P. S., et al., 1991, *Am. J. Med.* 90:427-33; Gill, P. S., et al., 1994, *AIDS* 8:1695-9.

[60] Burstein, "Angiogenesis and Cancer: From the Bench to the Bedside" http://www.medscape.com/medscape/cno/1999/ASCO/Story.cfm?story_id=621. See also Kerbel et al., "Preclinical and clinical aspects of anti-angiogenic strategies to treat cancer [Scientific Symposia 2]." American Society of Clinical Oncology 35th Annual Meeting, Atlanta, 1999.

[61] Y. Lunardi-Iskandar et al, Nature Medecine 4, 428 (1998).

[62] Fink et al., 1990, *FEBS*, 270(1,2)222-224.

[63] Fink et al., 1990, *FEBS*, 270(1,2)222-224.

[64] Fink et al., 1990, *FEBS*, 270(1,2)222-224.

[65] For amino acid sequences of these chemokines see Shall, 1991, *Cytokine* 3:165-183.

[66] See, e.g., Merrifield, 1963, *J. Amer. Chem. Soc.* 85:2149-2156.

[67] E.g., see Creighton, 1983, Proteins, Structures and Molecular Principles, W.H. Freeman and Co., N.Y., pp. 50-60.

[68] E.g., the Edman degradation procedure; see Creighton, 1983, Proteins, Structures and Molecular Principles, W.H. Freeman and Co., N.Y., pp. 34-49.

[69] Hutchinson, C., et al., 1978, *J. Biol. Chem.* 253:6551), use of TAB™ linkers (Pharmacia).

[70] 1975, Nature 256:495-497.

[71] Kozbor et al., 1983, Immunology Today 4:72.

[72] Cole et al., 1985, in Monoclonal Antibodies and Cancer Therapy, Alan R. Liss, Inc., pp. 77-96.

[73] See, e.g., Erlich et al., 1985, Am. J. Reprod Immunol. Microbiol. 8:48.

[74] See, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II.

[75] Molecular Cloning: A Laboratory Manual, Cold Spring Harbor Laboratory Press, Cold Spring Harbor, N.Y. [1989].

[76] Guide to Molecular Cloning Techniques, Academic Press, Inc., San Diego, Calif. [1987].

[77] Recombinant DNA Laboratory Manual, Academic Press, Inc., San Diego, Calif. [1999]; Baumberg, ed. Prokaryotic Gene Expression (Frontiers in Molecular Biology), Oxford Univ Press [1999].

[78] Bernoist and Chambon, 1981, *Nature* 290:304-310.

[79] Yamamoto et al., 1980, *Cell* 22:787-797.

[80] Wagner et al., 1981, *Proc. Natl. Acad. Sci. USA* 78:1441-1445.

[81] Brinster et al., 1982, *Nature* 296:39-42.

[82] Swift et al., 1984, *Cell* 38:639-646; Ornitz et al., 1986, *Cold Spring Harbor Symp. Quant. Biol.* 50:399-409; MacDonald, 1987, *Hepatology* 7:425-515.

[83] Hanahan, 1985, *Nature* 315:115-122.

[84] Grosschedl et al., 1984, *Cell* 38:647-658; Adames at al., 1985, *Nature* 318:533-538; Alexander et al., 1987, *Mol. Cell. Biol.* 7:1436-1444.

[85] Leder et al., 1986, *Cell* 45:485-495.

[86] Pinkert et al., 1987, *Genes and Devel.* 1:268-276.

[87] Krumlauf et al., 1985, *Mol. Cell. Biol.* 5:1639-1648; Hammer at al., 1987, *Science* 235:53-58.

[88] Kelsey et al., 1987, *Genes and Devel.* 1:161-171.

[89] Mogram et al., 1985, *Nature* 315:338-340; Kollias et al., 1986, *Cell* 46, 89-94.

[90] Readhead et al., 1987, *Cell* 48:703-712.

[91] Sani, 1985, *Nature* 314:283-286.

[92] Mason et al., 1986, *Science* 234:1372-1378.

[93] Okamoto et al., 1998, *Mol Cell Endocrinol.*, 139(1-2):171-178.

[94] See, e.g., Hudson & May, 1986, *Practical Immunology*, Blackwell Scientific Publications, Oxford, United Kingdom.

[95] See, e.g., O'Connor et al., 1994, *Endocrine Reviews* 15:650-683; Krichevsky et al, 1991, *Endocrinology* 128:1255-1264; and Krichevsky et al., 1988, *Endorcrinology* 123:584-593.

[96] Krichevsky et al., 1988, *Endocrinology* 123:584-593.

[97] For a discussion of many of these disorders, see Harrison's Principles of Internal Medicine, 1970, 6th Edition, Wintrobe, M. M., et al., eds., McGraw-Hill, New York, pp. 798-1044.

[98] For review of such abnormal growth conditions, see Robbins and Angell, 1976, *Basic Pathology*, 2d Ed., W.B. Saunders Co., Philadelphia, pp. 68-79.

[99] See Robbins and Angell, 1976, *Basic Pathology*, 2d Ed., W.B. Saunders Co., Philadelphia, pp. 112-113, etc.

[100] Strober, S., et al., 1985, *Annals of Internal Medicine* 102:441-449, 450-458.

[101] Strober, S., et al., 1985, *Ann. Internal Med.* 102:450.

[102] Lemoine, ed. 1999, *Understanding Gene Therapy*, Bios Scientific Publishers.

[103] Koller and Smithies, 1989, *Proc. Natl. Acad. Sci. USA* 86:8932-8935; Zijlstra at al., 1989, *Nature* 342:435-438.

[104] See U.S. Pat. No. 4,980,286.

[105] See e.g., Wu and Wu, 1987, *J. Biol. Chem.* 262:4429-4432.

[106] See, e.g., PCT Publications WO92/06180 dated Apr. 16, 1992 (Wu et al.); WO92/22635 dated Dec. 23, 1992 (Wilson et al.); WO92/20316 dated Nov. 26, 1992 (Findeis et al); WO93/14188 dated Jul. 22, 1993 (Clarke et al), WO93/20221 dated Oct. 14, 1993 (Young); WO99/46278 dated Mar. 12, 1999 (Parks at al.).

[107] Koller and Smithies, 1989, *Proc. Natl. Acad. Sci. USA* 86:8932-8935; Zijlstra at al., 1989, *Nature* 342:435-438.

[108] Ledly, 1995, *Human Gene Therapy* 6:1129-1144.

[109] See Miller et al., 1993, *Meth. Enzymol.* 217:581-599.

[110] 1994, Biotherapy 6:291-302.

[111] Other references illustrating the use of retroviral vectors in gene therapy are: Clowes et al., 1994, *J. Clin. Invest.* 93:644-651; Kiem et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114.

[112] 1993, *Current Opinion in Genetics and Development* 3:499-503.

[113] 1994, *Human Gene Therapy* 5:3-10.

[114] 1991, *Science* 252:431-434; Rosenfeld et al., 1992, *Cell* 68:143-155.

[115] 1993, *J. Clin. Invest.* 91:225-234.

[116] see Walsh et al., 1993, *Proc. Soc. Exp. Biol. Med.* 204:289-300.

[117] Smith, 1995, *Annu. Rev. Microbiol.* 49:807-838.

[118] Amalfitano et al., *Gene Therapy* 4:258-263.

[119] Hitt et al., 1997, *Advances in Pharmacology* 40:137-206.

[120] Ali et al., 1994, *Gene Therapy* 1:367-384.

[121] Yeh et al., 1997, *FASEB* 11:615-623.

[122] Robbins et al., 1998, *Pharmacol. Ther.* 80(1):35-47

[123] See e.g., Loeffler and Behr, 1993, *Meth. Enzymol.* 217:599-618; Cohen et al., 1993, *Meth. Enzymol.* 217:618-644; Cline, 1985, *Pharmac. Ther.* 29:69-92.

[124] For a discussion of many of these disorders, see Harrison's Principles of Internal Medicine, 1970, 6th Edition, Wintrobe, M. M., et al., eds., McGraw-Hill, New York, pp. 798-1044.

[125] Wain-Hobson et al., 1985, *Cell* 40:9-17.

[126] See, e.g., Kodo et al., 1984, *J. Clin. Invest.* 73:1377-1384.

[127] See U.S. Pat. Nos. 5,004,681 and 5,192,553.

[128] Daffos et al., 1985, *Am. J. Obstet. Gynecol.* 153:655-660; Daffos et al., 1983, *Am. J. Obstet. Gynecol.* 146:985.

[129] Valenti, 1973, *Am. J. Obstet. Gynecol.* 115:851; Cao et al., 1982, *J. Med. Genet.* 19:81.

[130] Rodeck, C. H., 1984, in *Prenatal Diagnosis*, Rodeck, C. H. and Nicolaides, K. H., eds., Royal College of Obstetricians and Gynecologists, London.

[131] Visser et al., 1984, *J. Exp. Med.* 59:1576; Nijhof et al., 1984, *Exp. Cell Res.* 155:583; Bauman et al., 1986, *J. Cell Physiol.* 128:133; Lord and Spooncer, 1986, *Lymphokine Res.* 5:59.

[132] Emerson et al., 1985, *J. Clin. Invest.* 76:1286.

[133] Nicola et al., 1981, *Blood* 58:376.

[134] Nijhof et al., 1983, *J. Cell Biol.* 96:386.

[135] Williams et al., 1987, *Exp. Hematol.* 15:243.

[136] Broxmeyer, H. E., 1982, *J. Clin. Invest.* 69:632-642.

[137] Broxmeyer et al., 1984, *J. Clin. Invest.* 73:939-953

[138] Lu et al., 1983, *Blood* 61:250; Winchester et al., 1977, *Proc. Natl. Acad. Sci. U.S.A.* 74:4012; Busch et al., 1987, *Blut* 54:179; Moore et al., 1980, *Blood* 55:682; Keating et al., 1984, *Blood* 64:1159.

[139] Ferrero et al., 1983, *Proc. Natl. Acad. Sci. U.S.A.* 80:4114; Robak et al., 1985, *Leukemia Res.* 9:1023; Ferrero et al., 1986, *Cancer Res.* 46:975.

[140] Leary et al., 1987, *Blood* 69:953; Strauss et al., 1986, *Exp. Hematol.* 14:879; Katz et al., 1985, *Leukemia Res.* 9:191; Katz et al., 1986, *Leukemia Res.* 10:961; Katz et al., 1985, *Leukemia Res.* 9:191; Katz et al., 1986, *Leukemia Res.* 10:961; Bodger et al., 1983, *Blood* 61:1006; Andrews et al., 1986, *Blood* 67:842; Andrews et al., 1986, *Blood* 68:1030; Civin et al., U.S. Pat. No. 4,714,680 dated Dec. 22, 1987; Huang and Terstappen, 1992, *Nature* 360:745-749; Terstappen et al., 1992, *Leukemia* 6:993-1000; Strauss et al., 1986, *Exp. Hematol.* 14:935; Nicola et al., 1980, *J. Cell Physiol.* 103:217; Reisner et al., 1982, *Blood* 59:360; Reisner et al., 1978, *Proc. Natl. Acad. Sci. U.S.A.* 75:2933; Aizawa and Tavassoli, 1986, *Int. J. Cell Cloning* 4:464.

[141] See, e.g. Smith, S, and Broxmeyer, H. E., 1986, *Br. J. Haematol.* 63:29-34; Dexter et al., 1977, *J. Cell. Physiol* 91:335; Witlock and Witte, 1982, *Proc. Natl. Acad. Sci. U.S.A.* 79:3608-3612.

[142] Dickie, P., et al., 1991, *Virology* 185:109-119.

[143] Franks, R. R., et al., 1995, *Pediatric Res.* 37:56-63.

[144] See Letrin, N. L., and King, N. W., 1990, *J. AIDS* 3:1023-1040.

[145] Kestler, H., et al., 1990, *Science* 248:1109-1112.

[146] Van Gemen, B., et al., 1994, *J. Virol. Methods* 49:157-168; Chen, Y. H., et al., 1992, *AIDS* 6:533-539.

[147] Popovic, M., et al., 1984, *Science* 204:497-500.

[148] Dickie, P., et al., 1991, *Virology* 185:109-119.

[149] Franks, R. R., et al., 1995, *Pediatric Res.* 37:56-63.

[150] See Letrin, N. L., and King, N. W., 1990, *J. AIDS* 3:1023-1040

[151] Kestler, H., et al., 1990, *Science* 248:1109-1112

[152] See, e.g., Kotler, D. P. et al., 1985, *Am. J. Clin. Nutr.* 42:1255-65; Ott, M. et al., 1993, *Am. J. Clin. Nutr.* 57:15-19; Miller, T. L. et al., 1993, *Am. J. Clin. Nutr.* 57:588-592.

[153] See Luria et al., 1978, *General Virology*, 3d Ed., John Wiley & Sons, New York pp. 436-446.

[154] 1995, *Nature* 375:64-68.

[155] Siegal, B. et al., 1990, *Cancer* 65:492-498.

[156] See, e.g., Lunardi-Iskandar, Y. et al., 1993, *J. Exp. Med.* 177:741-750.

[157] See, e.g., Lunardi-Iskandar, Y. et al., 1995, *Nature* 375:64-68; Louache, R. et al., 1992, *Blood* 180:2991-2999; Lunardi-Iskandar, Y. et al., 1989, *J. Clin. Invest.* 83:610-615.

[158] See, e.g., Wu and Wu, 1987, *J. Biol. Chem.* 262:4429-4432.

[159] See Langer, *Science* 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.

[160] See Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989).

[161] See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989).

[162] See, e.g., Goodson, in Medical Applications of Controlled Release, supra, vol. 2, pp. 115-138 (1984).

[163] *Science* 249:1527-1533 (1990).

[164] Y. Lunardi-Iskandar et al., *Nature* 375, 64 (1995); Y. Lunardi-Iskandar et al., *Nature Medecine* 4, 428 (1998); P. S. Gill et al., *N. Engl. J. Med.* 335, 1261 (1996); P. Hermans et al, *J. Human Virol.* 1, 82 (1998).

[165] Minjie Wu et al, *Biotechniques* 24:676-678 (1998).

[166] Y. Lunardi-Iskandar et al., *Nature* 375, 64 (1995); P. S. Gill et al., *N. Engl, J. Med.* 335, 1261 (1996); P. Hermans et al, *J. Human Virol.* 1, 82 (1998).

[167] Y. Lunardi-Iskandar et al, *Nature* 375, 64 (1994); P. S. Gill et al, N, Engl, J. Med. 335, 1261 (1996); P. Hermans et al, J. Human Virol. 1, 82 (1998).

[168] Y. Lunardi-Iskandar et al, *Nature Medecine* 4, 428 (1998).

[169] Y. Lunardi-Iskandar et al., *Nature Medecine* 4, 428 (1998); P. S. Gill et al., *N. Engl, J. Med.* 335, 1261 (1996); P. Hermans et al, *J. Human Virol.* 1, 82 (1998).

[170] Y. Lunardi-Iskandar et al, *Nature Medecine* 4, 428 (1998).

[171] Kestler et al., *Science* 248, 1109 (1990); N L. Letvin & N. W. King, *J. Acquir. Immune Defic. Syndr.* 3, 1023 (1990).

[172] H. Kestler et al, *Science* 248, 1109 (1990); N L. Letvin & N. W. King, *J. Acquir. Immune Defic. Syndr.* 3, 1023 (1990).

[174] H. Kestler et al, *Science* 248, 1109 (1990); N L. Letvin & N. W. King, *J. Acquir. Immune Defic. Syndr.* 3, 1023 (1990).

[175] H. Kestler et al, *Science* 248, 1109 (1990); N L. Letvin & N. W. King, *J. Acquir. Immune Defic. Syndr.* 3, 1023 (1990).

[176] Y. Lunardi-Iskandar et al, *Nature Medecine* 4, 428 (1998).

[177] Y. Lunardi-Iskandar et al, *Nature Medecine* 4, 428 (1998).

[178] Y. Lunardi-Iskandar et al, *Clin. Exp. Immun.* 60, 285 (1985) and *Blood* 67, 1063 (1986).

[179] T. Kadota et al, *J. Toxicol Sci* 19, 35 (1994).

[180] A. Albini et al, *AIDS* 11, 713 (1997).

[181] A. J. Lapthorn et al., *Nature* 369, 455 (1994).

[182] A. J. Lapthorn et al., *Nature* 369, 455 (1994).

[183] Antibodies—a laboratory manual, Cold Spring Harbor Laboratory (1988).

[184] Production of monoclonal antibodies: strategy and tactics., J Immunol Methods. 1980; 35(1-2):1-21.

[185] Harlow et al., supra, note 183.

[186] Harlow et al., supra, note 183.

[187] Harlow et al., supra, note 183.

[188] A. J. Lapthorn et al., *Nature* 369, 455 (1994).

[189] K. Talmadge, W. R. Boorstein, and J. C. Fiddes, *DNA* 2, 281 (1983); P. F. Policastro, S. Daniels-McQueen, G.

Carle, and I. Boime, *J. Biol. Chem.* 261, 5907 (1986); Bo, M. and Boime, I. *J. Biol. Chem.* 267, 3179 (1992).

[190] A. J. Lapthorn et al., *Nature* 369, 455 (1994).

[191] F. Ramos-Morales et al., *Oncogene* 11, 1665 (1995); N. Bonnefoy-Berard et al., *Stem Cells* 14, 250 (1996).

[192] F. Ramos-Morales et al., *Oncogene* 11, 1665 (1995); N. Bonnefoy-Berard et al., *Stem Cells* 14, 250 (1996).

[193] Y. Noasaka, A. Arai, N. Miyasaka, and O. Miura, *J. Biol. Chem.* 274, 30154 (1999).

[194] V. Leblanc, I. Delemeau, and B. Tocque, *Oncogene* 18, 4884 (1999).

[195] G. H. Renkema et al., *Current Biol.* 9, 1407 (1999).

[196] E. Fink, C. Heklein-Fink, and M. Eulitz, *FEBS Lett.* 270, 222 (1990).

[197] J. L. Vaitukaitis, *J. Clin. Endocrinol. Metab.* 37, 505 (1973); H. F. Acevedo, Y. J. Tong, and R. J. Hartsock, *Cancer* 76, 1467 (1995); Kardana et al., *Brit. J. Cancer* 58, 281 (1988); E. M. J. Schutter, C. Mulder, G. J. Van Kamp, and P. Kenemans, *Anticancer Res.* 17, 1255 (1997).

[198] P. D. Papapetrou and S. C. Nicopoulu, *Acta Endrocrinol.* 112, 415 (1986); R. Nishimura et al., *Jpn. J. Cancer Res.* 80, 968 (1989); Udagawa et al., *Molec. Cell. Endocrinol.* 139, 171 (1998).

[199] L. A. Cole and S. Birken, *Molec. Endocrinol.* 9, 825 (1988); M. Ozturk et al., *Endocrinol.* 120, 549 (1987).

[200] L. A. Cole and S. Birken, *Molec. Endocrinol.* 9, 825 (1988); M. Ozturk et al., *Endocrinol.* 120, 549 (1987).

[201] J. L. Vaitukaitis, *J. Clin. Endocrinol. Metab.* 37, 505 (1973); H. F. Acevedo, Y. J. Tong, and R. J. Hartsock, *Cancer* 76, 1467 (1995); Kardana et al., *Brit. J. Cancer* 58, 281 (1988); E. M. J. Schutter, C. Mulder, G. J. Van Kamp, and P. Kenemans, *Anticancer Res.* 17, 1255 (1997).

[202] P. D. Papapetrou and S. C. Nicopoulu, *Acta Endrocrinol.* 112, 415 (1986); R. Nishimura et al., *Jpn. J. Cancer Res.* 80, 968 (1989); Udagawa et al., *Molec. Cell. Endocrinol.* 139, 171 (1998).

[203] M. Bo and I. Boime, J. Biol. Chem. 267, 3179 (1992); S. Dimhofer et al., J. Clin. Endocrinol. Metab. 81, 4212 (1996).

[204] K. Talmadge, W. R. Boorstein, and J. C. Fiddes, *DNA* 2, 281 (1983); P. F. Policastro, S. Daniels-McQueen, G. Carle, and I. Boime, *J. Biol. Chem.* 261, 5907 (1986); Bo, M. and Boime, I. *J. Biol. Chem.* 267, 3179 (1992).

[205] M. Bo and I. Boime, J. Biol. Chem. 267, 3179 (1992); S. Dimhofer et al., J. Clin. Endocrinol. Metab. 81, 4212 (1996).

[206] E. Bedows et al., *J. Biol. Chem.* 269, 10574 (1994).

[207] V. Lazar et al., *Cancer Res.* 55, 3735 (1995).

[208] L. Cole, *Clin. Chem.* 43, 2233 (1997).

[209] L Lobel et al, Endocrine 10, 261 (1999).

[210] D. L. Segaloff, *Endocrinol. Rev.* 14, 324 (1993).

[211] C. C. W. Chan, T. T. Lao, A. N. Y. Cheung, *Placenta* 20, 223 (1999).

[212] N. C. Wrighton et al., *Science* 273, 458 (1996); O. Livnah et al., *Science* 273, 464 (1996).

[213] C. P. Hill et al, *Science* 251, 1481 (1991); J. A. Hoffman, F. C. Kafotos, C. A. Janeway, and R. A. B. Ezekowitz, *Science* 284, 1313 (1999).

[214] E. J. Blank, J. A. Trapani, and D. A. Jans, *Immunol. Cell Biol.* 77, 206 (1999).

---

What is claimed is:

1. An isolated polypeptide consisting of SEQ ID NO: 2 or a truncated form of SEQ ID NO: 2 selected from the group consisting of SEQ ID NO: 4, SEQ ID NO: 5, SEQ ID NO: 7 and SEQ ID NO: 9.

2. An isolated polypeptide wherein the polypeptide comprises the amino acid sequence of the MA peptide (SEQ ID NO: 2) with the proviso that the polypeptide does not comprise amino acid extensions corresponding to amino terminus or carboxy terminus amino acid sequences along the β-hCG chain (SEQ ID NO: 1) contiguous to the amino acid sequence of the MA peptide (SEQ ID NO: 2).

3. An isolated polypeptide consisting of a truncated form of SEQ ID NO: 2, wherein the truncated form has 1, 2, 3, 4, 5 or 6 amino acid residues deleted from the amino terminus or carboxy terminus of SEQ ID NO: 2.

4. A fusion polypeptide comprising the polypeptide of claim 1 joined via a covalent bond to a heterologous polypeptide.

5. A fusion polypeptide comprising two or more of the polypeptides of claim 1 joined together via a covalent bond.

6. A pharmaceutical composition comprising the polypeptide of claim 1 in association with a pharmaceutically acceptable carrier.

7. A peptide isolated from early pregnancy urine consisting essentially of the amino acid sequence of MA (SEQ ID NO: 2) with the proviso that the peptide does not comprise amino acid extensions corresponding to amino terminus or carboxy terminus amino acid sequences along the β-hCG chain (SEQ ID NO: 1) contiguous to the amino acid sequence of the MA peptide (SEQ ID NO: 2).

8. A fusion polypeptide comprising the polypeptide of claim 2 joined via a covalent bond to a heterologous polypeptide.

9. A fusion polypeptide comprising two or more of the polypeptides of claim 2 joined together via a covalent bond.

10. A pharmaceutical composition comprising the polypeptide of claim 2 in association with a pharmaceutically acceptable carrier.

11. A fusion polypeptide comprising the polypeptide of claim 3 joined via a covalent bond to a heterologous polypeptide.

12. A fusion polypeptide comprising two or more of the polypeptides of claim 3 joined together via a covalent bond.

13. A pharmaceutical composition comprising the polypeptide of claim 3 in association with a pharmaceutically acceptable carrier.

14. A fusion polypeptide comprising the peptide of claim 7 joined via a covalent bond to a heterologous polypeptide.

15. A fusion polypeptide comprising two or more of the peptides of claim 7 joined together via a covalent bond.

16. A pharmaceutical composition comprising the peptide of claim 7 in association with a pharmaceutically acceptable carrier.

17. An isolated polypeptide consisting essentially of the amino acid sequence of MA (SEQ ID NO: 2) with the proviso that the peptide does not comprise amino acid extensions corresponding to amino terminus or carboxy terminus amino acid sequences along the β-hCG chain (SEQ ID NO: 1) contiguous to the amino acid sequence of the MA peptide (SEQ ID NO: 2).

18. A fusion polypeptide comprising the polypeptide of claim 17 joined via a covalent bond to a heterologous polypeptide.

19. A fusion polypeptide comprising two or more of the polypeptides of claim 17 joined together via a covalent bond.

20. A pharmaceutical composition comprising the polypeptide of claim 17 in association with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,994,278 B1 | Page 1 of 1 |
| APPLICATION NO. | : 09/632831 | |
| DATED | : August 9, 2011 | |
| INVENTOR(S) | : Robert C. Gallo | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1916 days.

Signed and Sealed this
Twenty-seventh Day of March, 2012

David J. Kappos
*Director of the United States Patent and Trademark Office*